US012102672B2

(12) United States Patent
Zitvogel

(10) Patent No.: US 12,102,672 B2
(45) Date of Patent: Oct. 1, 2024

(54) IMMUNOGENIC SEQUENCES FROM A PHAGE TAIL LENGTH TAPE MEASURE PROTEIN, BACTERIA EXPRESSING THE SAME AND THEIR USE IN TREATING A CANCER

(71) Applicants: INSTITUT GUSTAVE ROUSSY, Villejuif (FR); INSTITUT NATIONAL DE LA SANTE ET DE LA RECHERCHE MEDICALE, Paris (FR); UNIVERSITE PARIS-SACLAY, Gif Sur Yvette (FR); CENTRE HOSPITALIER UNIVERSITAIRE DE RENNES, Rennes (FR); UNIVERSITE DE RENNES, Rennes (FR)

(72) Inventor: Laurence Zitvogel, Paris (FR)

(73) Assignees: INSTITUT GUSTAVE ROUSSY, Villejuif (FR); INSTITUT NATIONAL DE LA SANTE ET DE LA RECHERCHE MEDICALE, Paris (FR); UNIVERSITE PARIS-SACLAY, Gif Sur Yvette (FR); CENTRE HOSPITALIER UNIVERSITAIRE DE RENNES, Rennes (FR); UNIVERSITE DE RENNES, Rennes (FR)

( * ) Notice: Subject to any disclaimer, the term of this patent is extended or adjusted under 35 U.S.C. 154(b) by 875 days.

(21) Appl. No.: 16/959,042

(22) PCT Filed: Dec. 21, 2018

(86) PCT No.: PCT/EP2018/086812
§ 371 (c)(1),
(2) Date: Jun. 29, 2020

(87) PCT Pub. No.: WO2019/129753
PCT Pub. Date: Jul. 4, 2019

(65) Prior Publication Data
US 2020/0338189 A1    Oct. 29, 2020

(30) Foreign Application Priority Data
Dec. 29, 2017 (EP) .................. 17306980

(51) Int. Cl.
| | |
|---|---|
| A61K 39/12 | (2006.01) |
| A61K 35/76 | (2015.01) |
| A61K 45/00 | (2006.01) |
| A61P 35/00 | (2006.01) |
| C07K 14/005 | (2006.01) |
| C07K 14/74 | (2006.01) |
| C12N 5/0783 | (2010.01) |
| C12N 15/74 | (2006.01) |
| C12Q 1/02 | (2006.01) |
| C12Q 1/6886 | (2018.01) |
| G01N 33/50 | (2006.01) |
| G01N 33/543 | (2006.01) |
| A61K 39/00 | (2006.01) |

(52) U.S. Cl.
CPC .............. *A61K 39/12* (2013.01); *A61K 35/76* (2013.01); *A61K 45/00* (2013.01); *A61P 35/00* (2018.01); *C07K 14/005* (2013.01); *C07K 14/70539* (2013.01); *C12N 5/0636* (2013.01); *C12N 15/746* (2013.01); *C12Q 1/025* (2013.01); *C12Q 1/6886* (2013.01); *G01N 33/5091* (2013.01); *G01N 33/54306* (2013.01); *A61K 2039/5154* (2013.01); *A61K 2039/523* (2013.01); *C12N 2509/00* (2013.01); *C12N 2795/10321* (2013.01); *C12N 2795/10333* (2013.01); *C12N 2795/10343* (2013.01); *C12Q 2600/106* (2013.01); *C12Q 2600/158* (2013.01); *G01N 2800/52* (2013.01)

(58) Field of Classification Search
CPC ....................................................... A61K 39/12
USPC ....................................................... 424/186.1
See application file for complete search history.

(56) References Cited

U.S. PATENT DOCUMENTS

| | | | | |
|---|---|---|---|---|
| 10,646,521 B2 * | 5/2020 | Zitvogel | ................. | A61P 35/00 |
| 2016/0303172 A1 * | 10/2016 | Zitvogel | ............ | A61K 39/0216 |

FOREIGN PATENT DOCUMENTS

| | | |
|---|---|---|
| WO | 2015/075688 A1 | 5/2015 |
| WO | 2018/115519 A1 | 6/2018 |

OTHER PUBLICATIONS

Aspord et al (Journal of Investigative Dermatology, 2012, 132: 2395-2406).*
Schroeder et al (Crit Rev Biochem Mol Biol, 2018, 53(1): 29-48).*
International Search Report, PCT/EP2018/086812, Mar. 6, 2019.
(Continued)

*Primary Examiner* — Sean E Aeder
(74) *Attorney, Agent, or Firm* — Arrigo, Lee, Guttman & Mouta-Bellum LLP

(57) ABSTRACT

The present invention relates to the field of probiotic adjuvantization of anticancer treatments. In particular, the present invention concerns immunogenic sequences from a prophage present in bacteria identified as efficient adjuvants of cancer treatments. The invention provides bacterial compositions expressing immunogenic sequences from this prophage, immunogenic compositions comprising such sequences and methods using sequences from this prophage, for increasing the anticancer armamentarium.

18 Claims, 68 Drawing Sheets

Specification includes a Sequence Listing.

(56) References Cited

OTHER PUBLICATIONS

Qinqin Bai, et al., "Characterization and genome sequencing of a novel bacteriophage infecting *Streptococcus agalactiae* with high similarity to a phage from *Streptococcus pyogenes*," Arch Virol (2013) vol. 158: 1733-41.

Romain Daillere, et al., "Enterococcus hirae and Barnesiella intestinihominis Facilitate Cyclophosphamide-Induced Therapeutic Immunomodulatory Effects, " Immunity (2016) vol. 45: 931-43.

* cited by examiner

A.
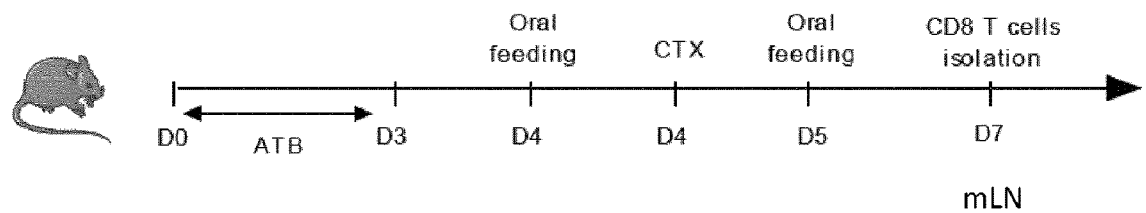
B.
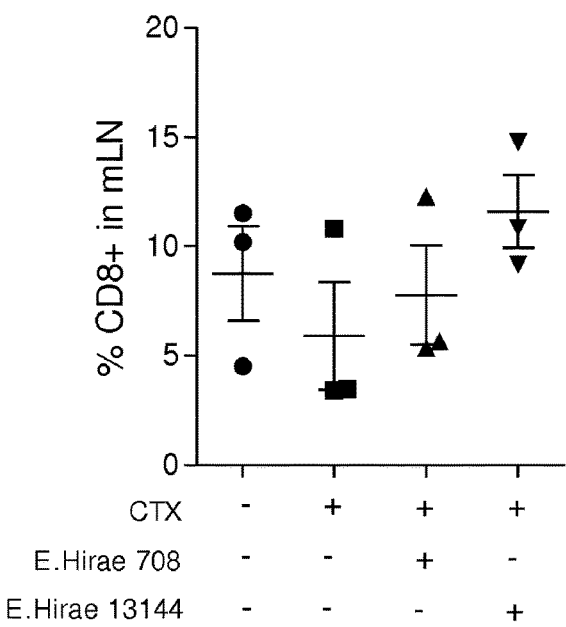
C.
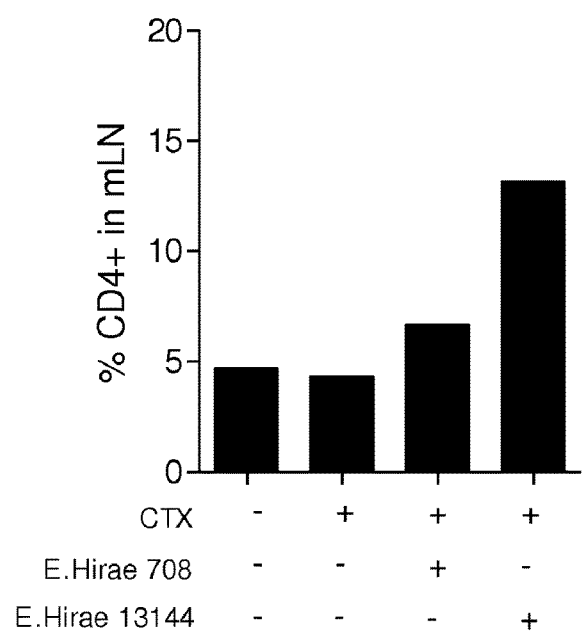
Figure 7A-C

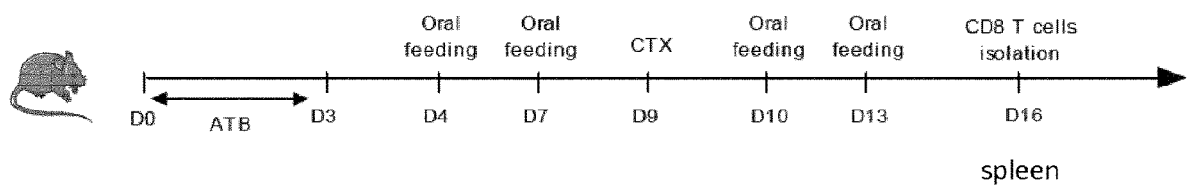
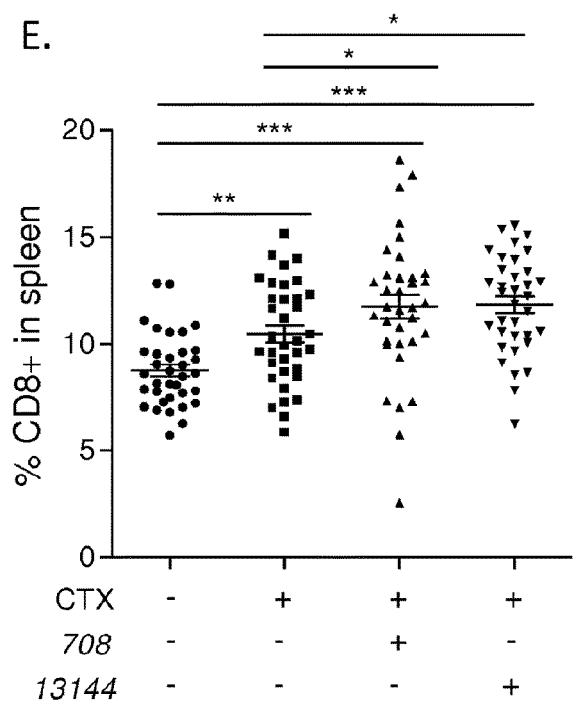
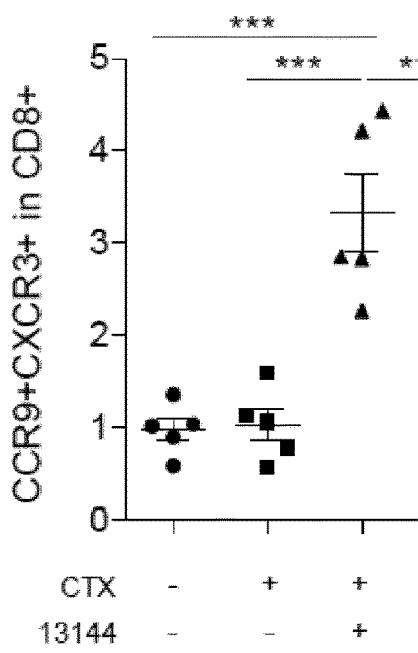
Figure 7D-F

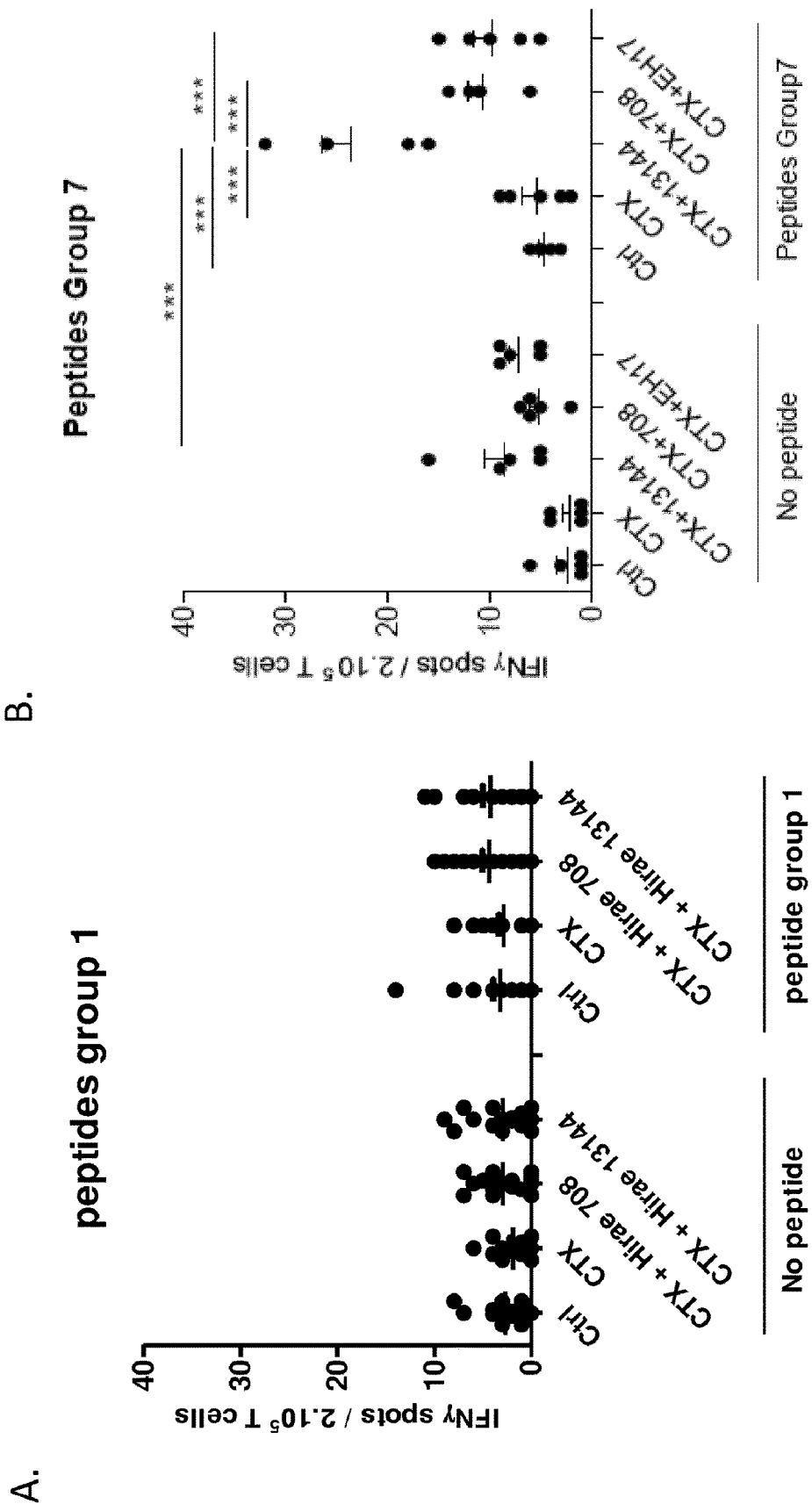
Figure 13A-B

D.

Score = 611 bits (1575), Expect = 0.0, Method: Compositional matrix adjust.
Identities = 314/473 (66%), Positives = 379/473 (80%), Gaps = 3/473 (1%)

```
13144 Query   46  VSGAMKSFGDKTASIGQSIEKVGGSMTKGITLPIAGAVGAVTTAAVKWESAFTGVKKTND  105
                  ++G +    D     G S + +G S+T G+T+PIAGAV AVTTAAVKWESAF GVKKTND
ATCC  Sbjct  133  ITGVINKTSDVLQKAGNSAQNIGTSLTHGVTIPIAGAVTAVTAAVKWESAFAGVKKTND  192

Query  106  EMVDSNGKVIYSYDDLEKGLRDLAKELPTSHEEIAKVAEAAGQLGIKTDKVVGFTKTMID  165
                  E+VDSNG V+YSY DLEKGLRDLAK LP SHEEIA VA AAGQLGI+TD VV FTKTMID
      Sbjct  193  EIVDSNQNVVYSYSDLEKGLRDLAKELPASHEEIAGVAEAAGQLGIQTDNVVSFTKTMID  252

Query  166  MGESTNMSADTAITSLARFANITQMSQDKFSNLGSAIVDLGNNLATTESEITEMGLRLAG  225
                  +GESTNMSA+TA+TS RFANITQMSQ  F  LG+ +VDLGNNLATTESEITEMGLRLAG
      Sbjct  253  LGESTNMSAETAATSFARFANITQMSQKDFERLGAVVVDLGNNLATTESEITEMGLRLAG  312

Query  226  AGKQIGMTEGDIVGFAAALSSVGIEAEAGGSAFSRLMVQMQLATETGVKAFEPLKQAVAI  285
                  AGKQ+GM++ +I+ FAAALSSVGIEA AGG+AFS++M+QMQLA E GV AF  LK
      Sbjct  313  AGKQVGMSQAEIMSFAAALSSVGIEAEAGGTAFSKVMIQMQLAVENGVGAFNQLKNMAEK  372

Query  286  QGVSWEKFVHAVNWGGKELTAVSKQMGVPASELKKLYKEASKASGSLEDFANVTGRTGEE  345
                  QGV W   V+AV GGK L AVSKQMG+ +S+LKK+Y+E K++GSL FA +VTGRT +E
      Sbjct  373  QGVPWVNLVNAVRDGGKSLKAVSKQMGLTSSDLKKMYEETEKSAGSLSSFADVTGRTSDE  432

Query  346  FAELFKSNPSQAMIEFIQGLKDSEKHGISAIKVLDDMGITEVRLRDSLLRAANASDVFEG  405
                  FAELFKSNPSQA+IEFI+GL ++EKHG SAIKVL+DM I EVRLRDSLLRAANAS VFEG
      Sbjct  433  FAELFKSNPSQAIIEFIKGLGNAEKHGTSAIKVLNDMEIKEVRLRDSLLRAANASGVFEG  492

Query  406  AVKRQNEAFNENTALAEEAGKRYGTTESQLKILRGQLNDVAITFGGPLVAALNSAISAAK  465
                  A+KRG +A+ +NTAL +EA KRY TTES++K L+ ++ D+AI  GGP V AL  A+ A+K
      Sbjct  493  AIKRGTKAWEKNTALTDEANKRYETTESKVKALKNEVVDMAIDMGGPFVDALRDALKASK  552

Query  466  PMIEALANMAEAFASADPKTQEFILKMAALAASAGPVLKVFG---KMTSVFGK       515
                  P++E L+  A+AF++  P+ Q+ I+K+ A  A+ GPVLK+ G      S FG+
      Sbjct  553  PLLETLSTAAKAFSNTSPEVQKSIVKLIAWTAAVGPVLKIAGSGASKISTFGQ       605
```

| 13144 | HLA | peptide | Affinity(nM) |
|---|---|---|---|
| | H-2-Kb | TSLARFANI (TMP1) | 7.81 |

| 10815 | HLA | peptide | Affinity(nM) |
|---|---|---|---|
| | H-2-Kb | TSFARFANI | 4.37 |

| 13144 | HLA | peptide | Affinity(nM) |
|---|---|---|---|
| | H-2-Kb | AMIEFIQGL (TMP2) | 31.25 |

| 10815 | HLA | peptide | Affinity(nM) |
|---|---|---|---|
| | H-2-Kb | AIIEFIKGL | 82.63 |

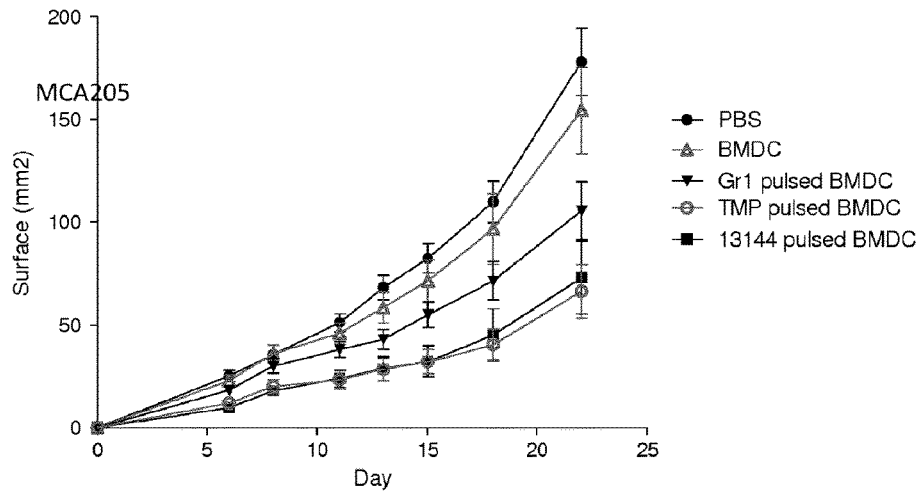
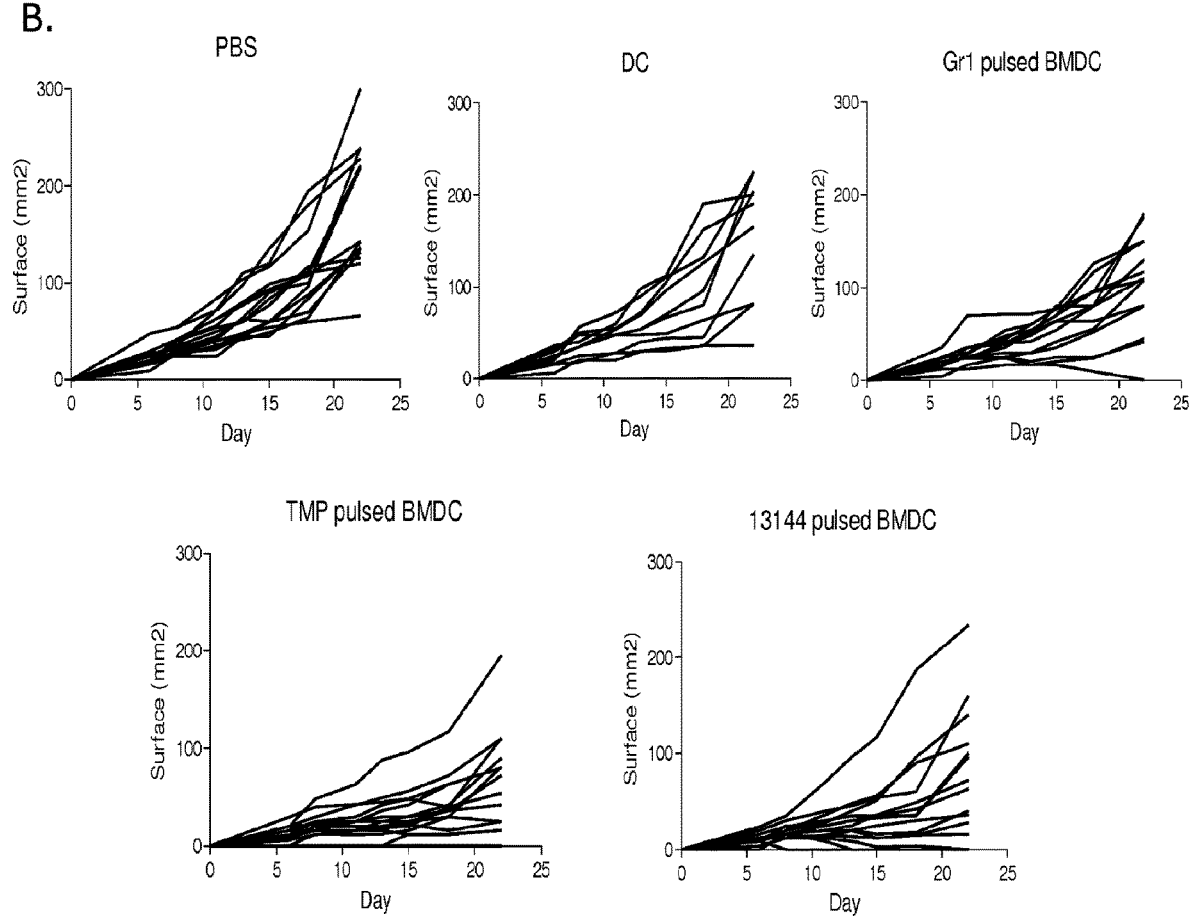
Figure 17A-B

C.
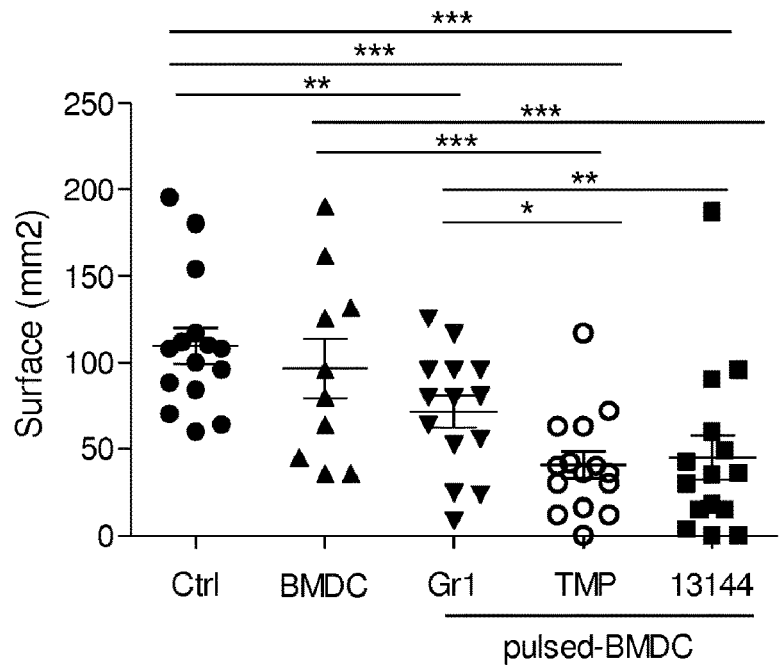
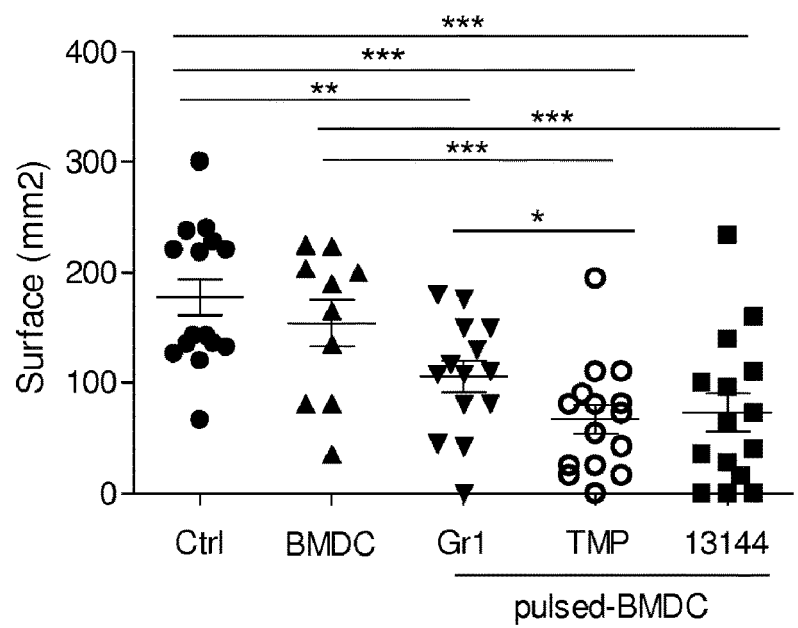
Figure 17C

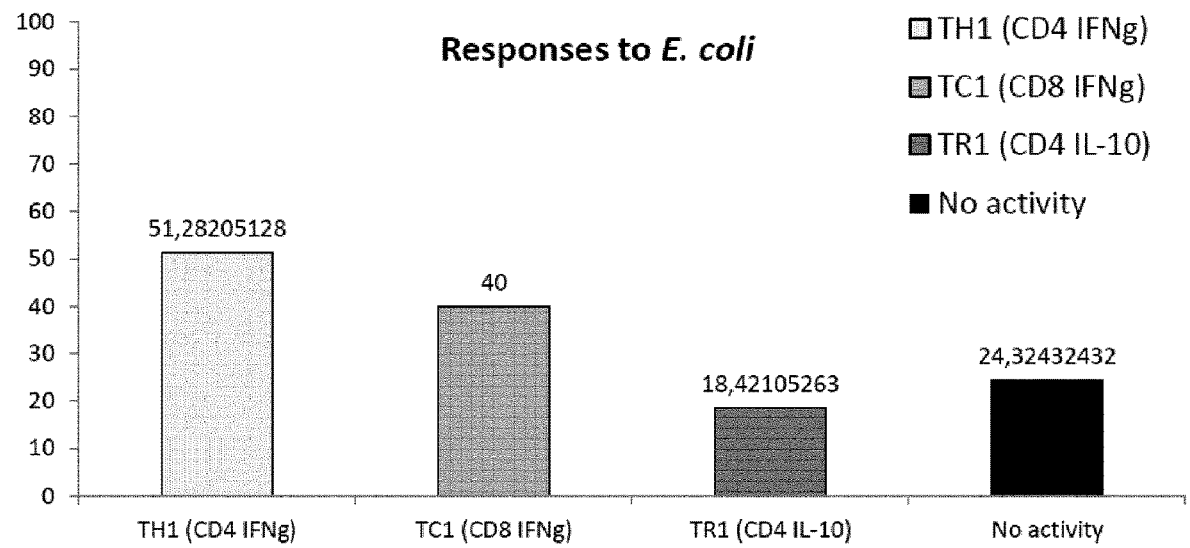
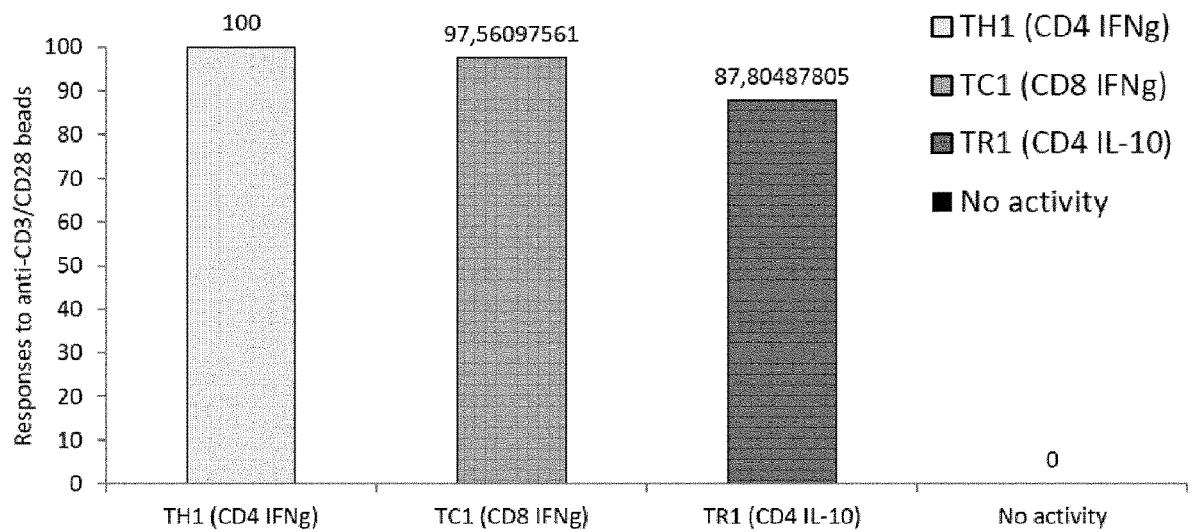
Figure 22B

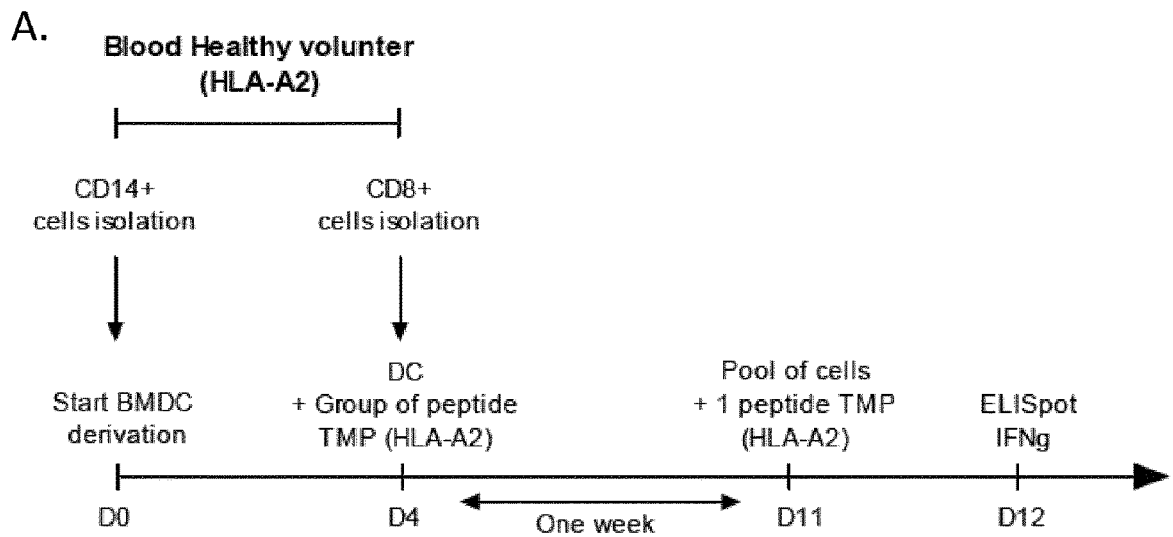
Figure 24A-B

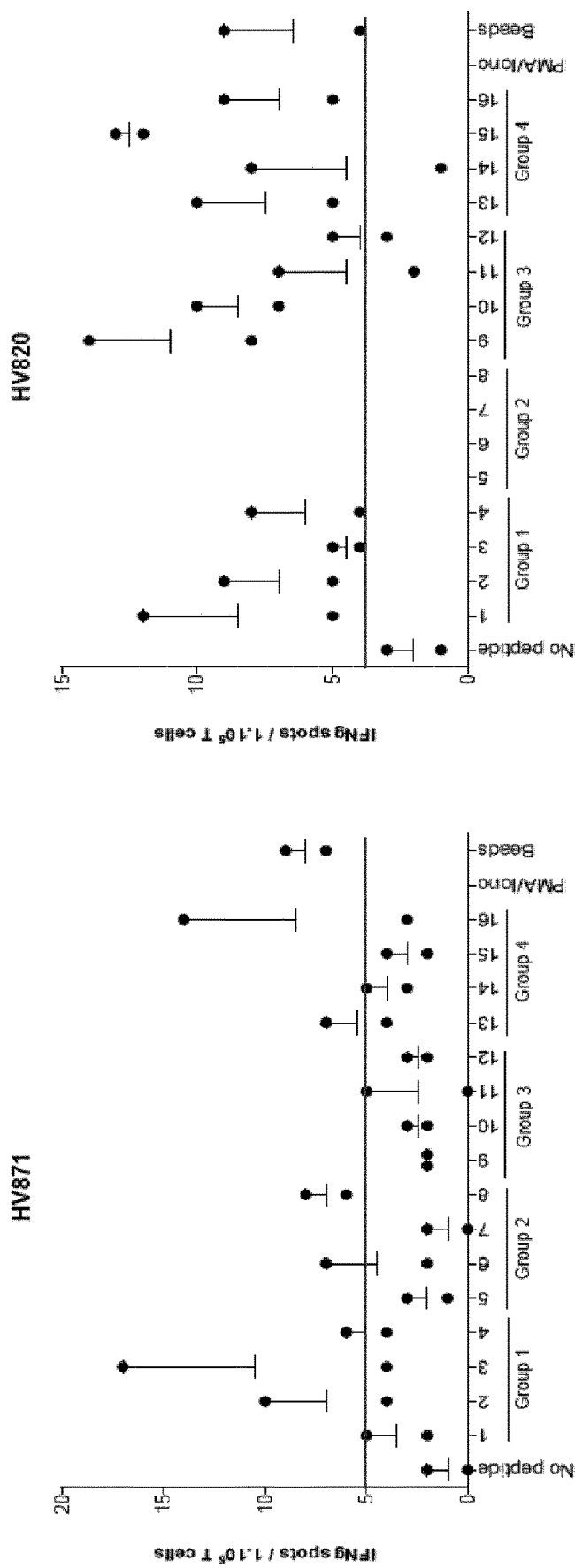
Figure 24D (Following)

E.
| | | Number of positive well | | | | | | | % responders |
|---|---|---|---|---|---|---|---|---|---|
| | | HV4238 | HV7406 | HV9029 | HV9276 | HV871 | HV820 | TOTAL | |
| Peptides TMP (HLA-A2) | 1 | 2 | 0 | 0 | 2 | 0 | 1 | 5 | 50 |
| | 2 | 1 | 2 | 0 | 2 | 1 | 1 | 7 | 83,33 |
| | 3 | 1 | 2 | 0 | 2 | 1 | 0 | 6 | 66,66 |
| | 4 | 0 | 0 | 0 | 2 | 1 | 1 | 4 | 50 |
| | 5 | 0 | 0 | 1 | 2 | 0 | 0 | 3 | 33,33 |
| | 6 | 0 | 1 | 1 | 0 | 1 | 0 | 3 | 50 |
| | 7 | 0 | 0 | 0 | 0 | 0 | 0 | 0 | 16,66 |
| | 8 | 0 | 0 | 2 | 0 | 2 | 0 | 4 | 33,33 |
| | 9 | 2 | 2 | 2 | 0 | 0 | 2 | 8 | 66,66 |
| | 10 | 2 | 0 | 2 | 1 | 0 | 2 | 7 | 66,66 |
| | 11 | 0 | 0 | 2 | 0 | 0 | 1 | 3 | 33,33 |
| | 12 | 0 | 0 | 2 | 1 | 0 | 0 | 3 | 33,33 |
| | 13 | 0 | 2 | 2 | 0 | 1 | 1 | 6 | 66,66 |
| | 14 | 0 | 0 | 0 | 0 | 0 | 1 | 1 | 16,66 |
| | 15 | 0 | 0 | 1 | 0 | 0 | 2 | 3 | 33,33 |
| | 16 | 0 | 0 | 0 | 0 | 1 | 1 | 2 | 33,33 |
F.
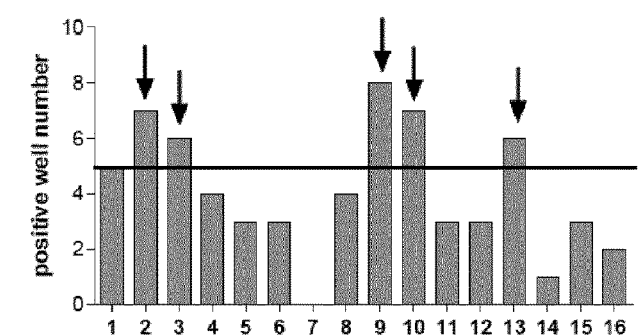
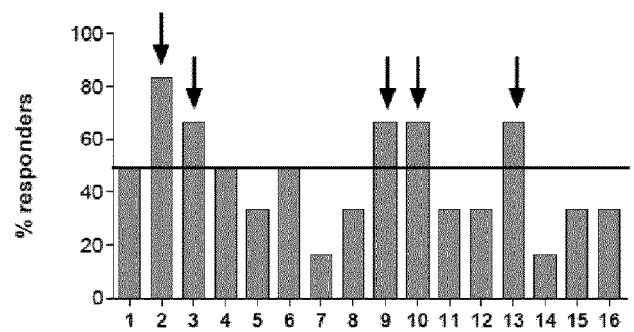
Figure 24E-F

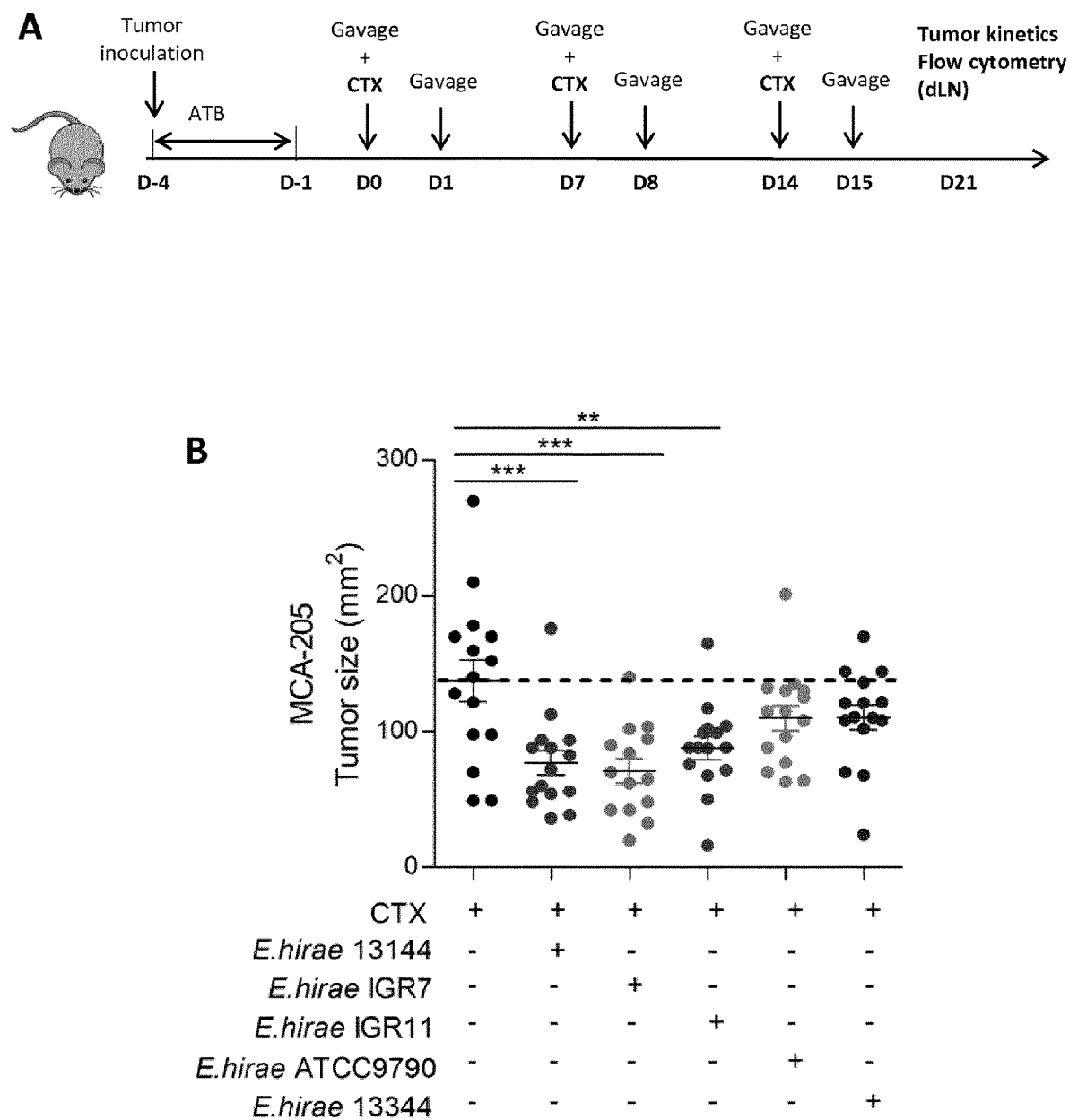
Figure 27A-B

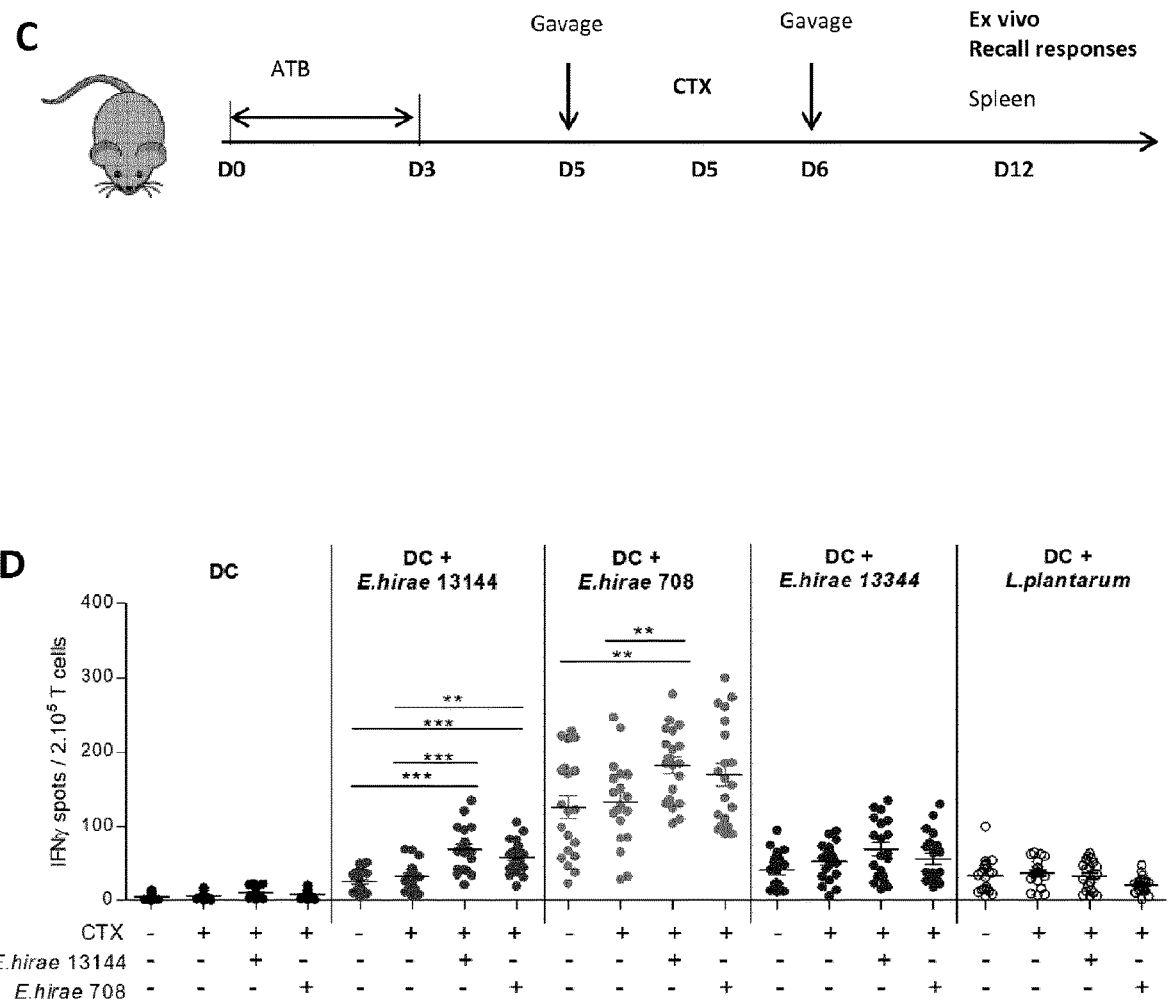
Figure 27C-D

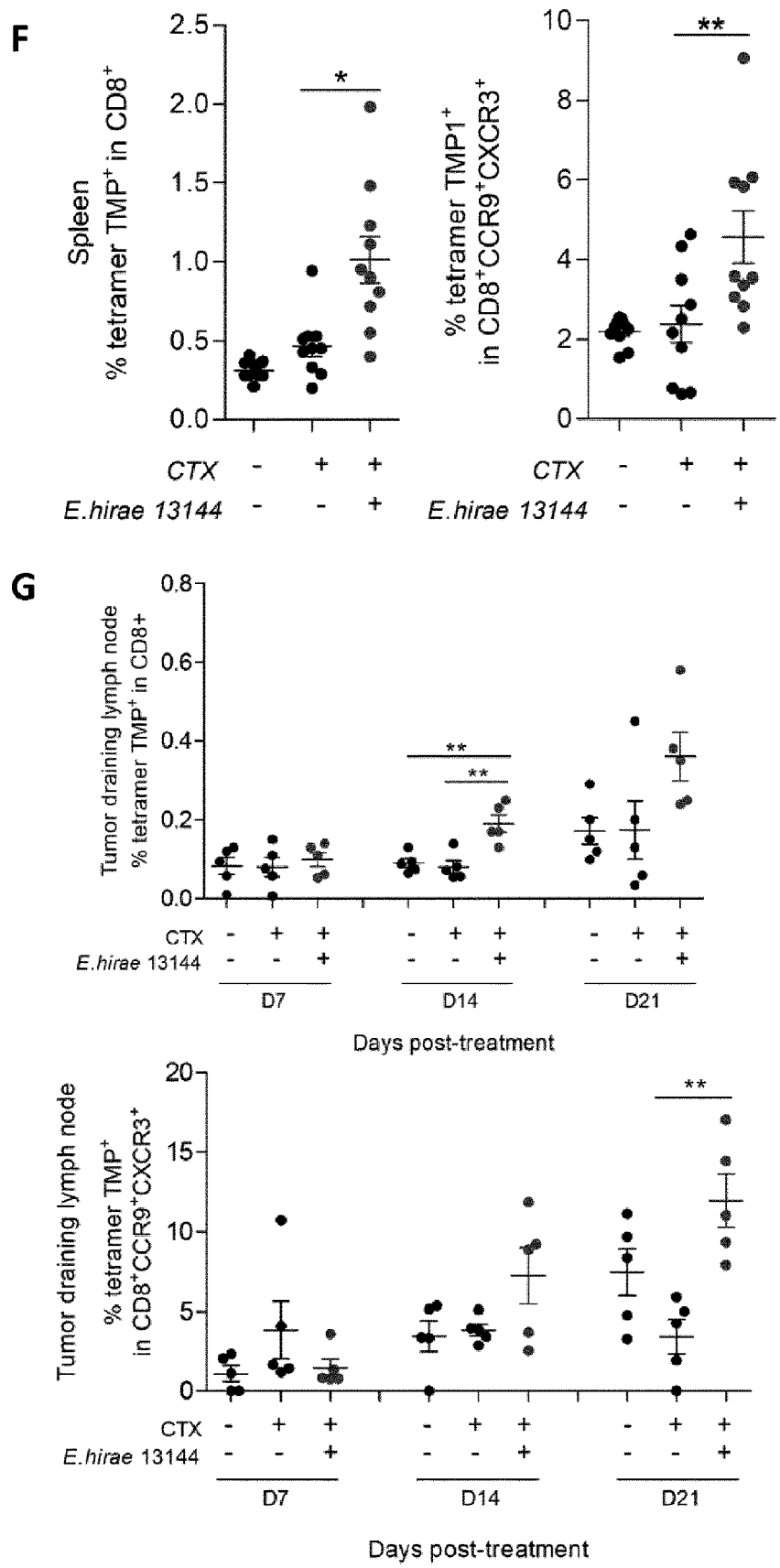
Figure 27F-G

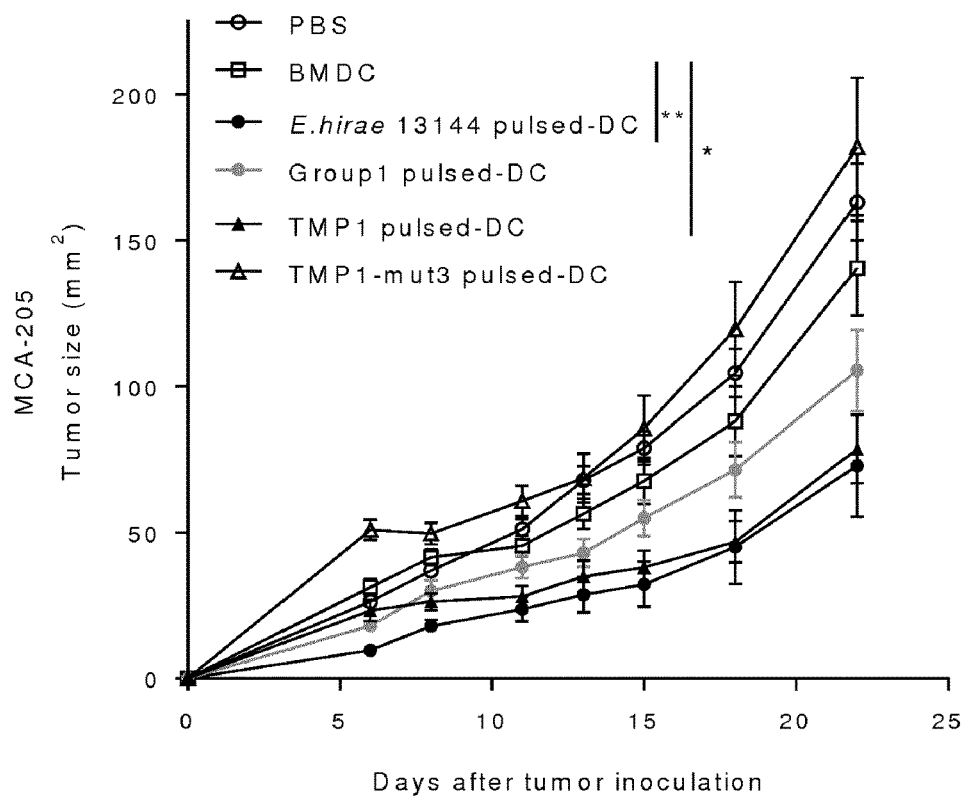
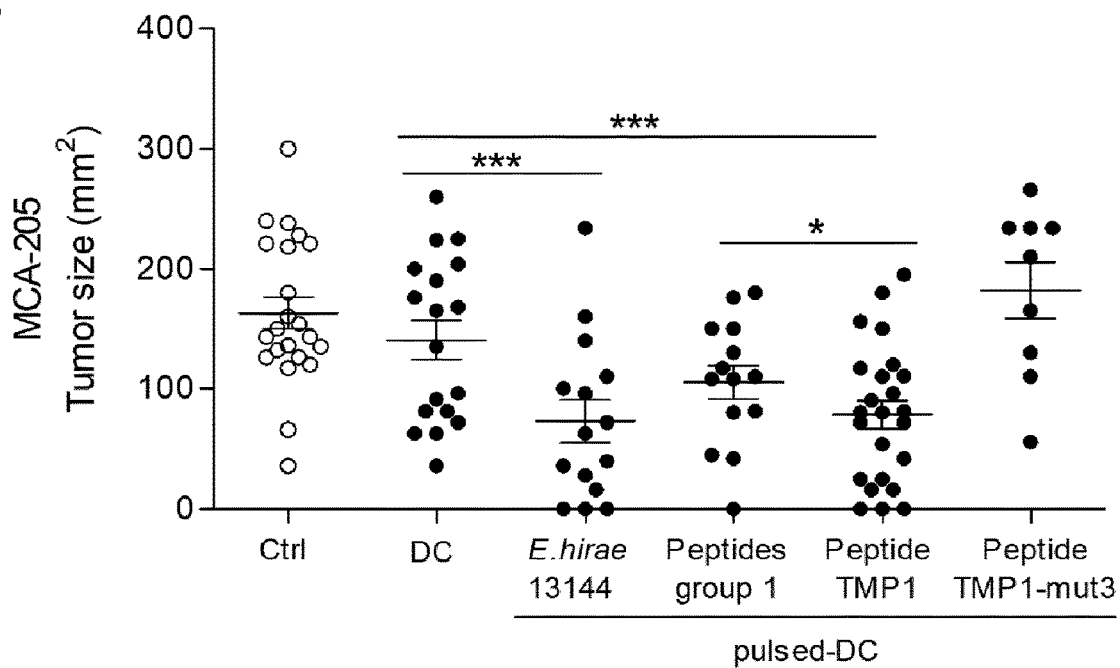
Figure 28A-B

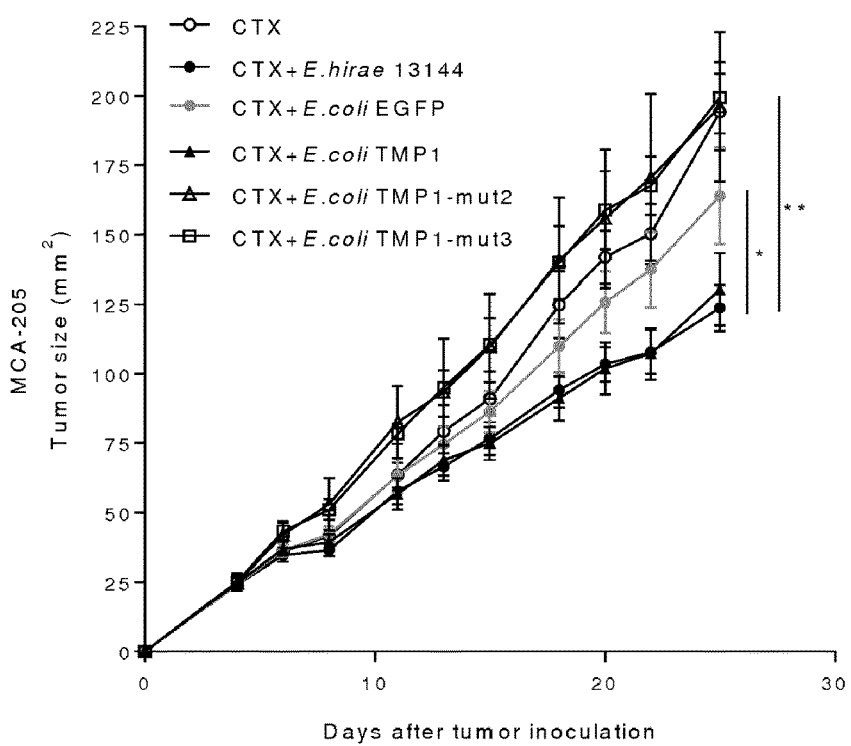
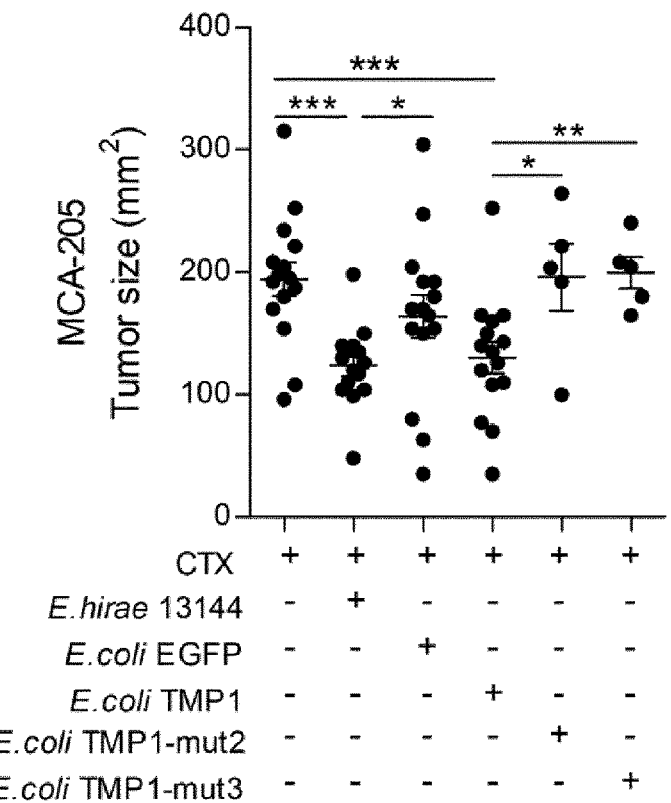
Figure 28C

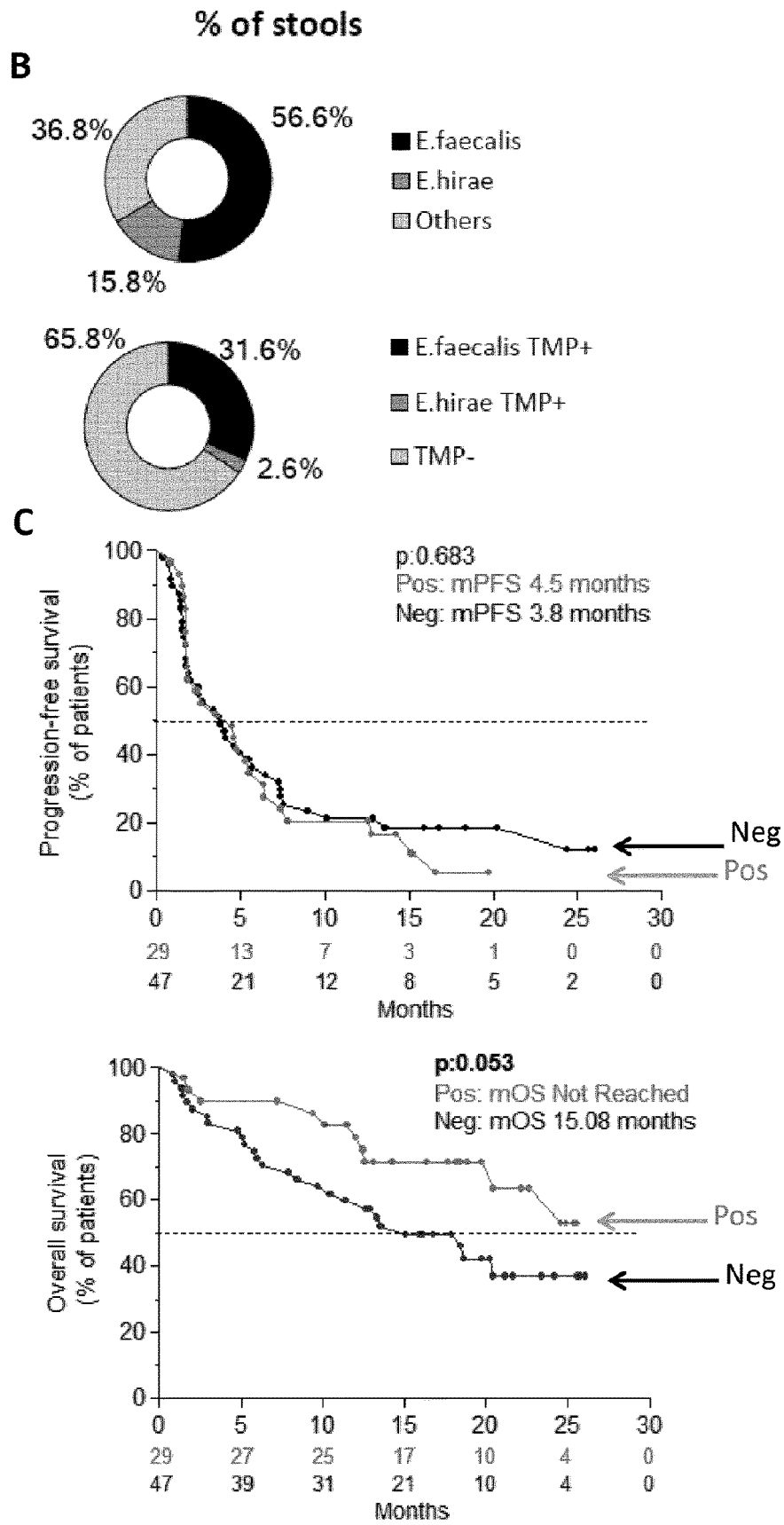
Figure 29B-C

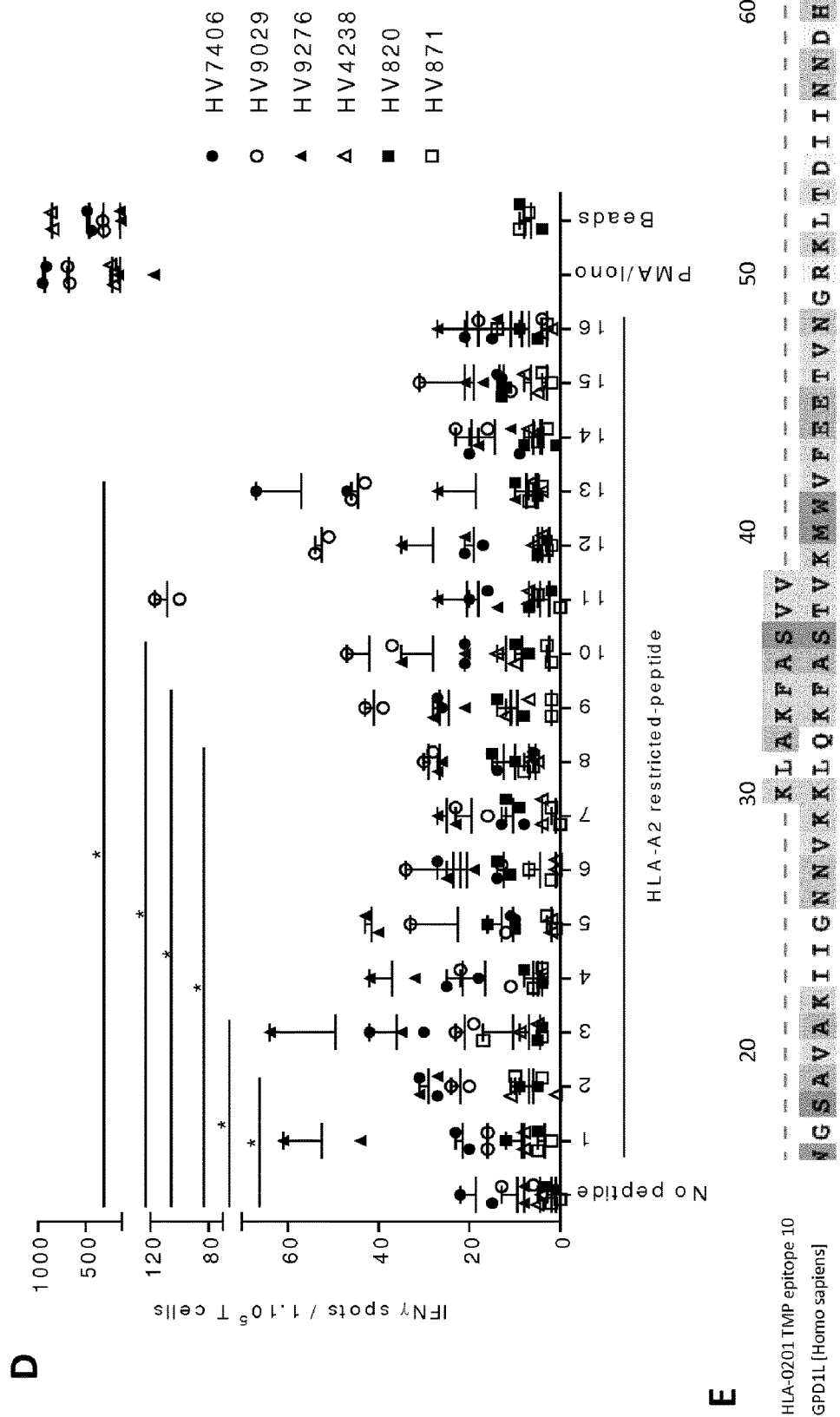
Figure 29D-E

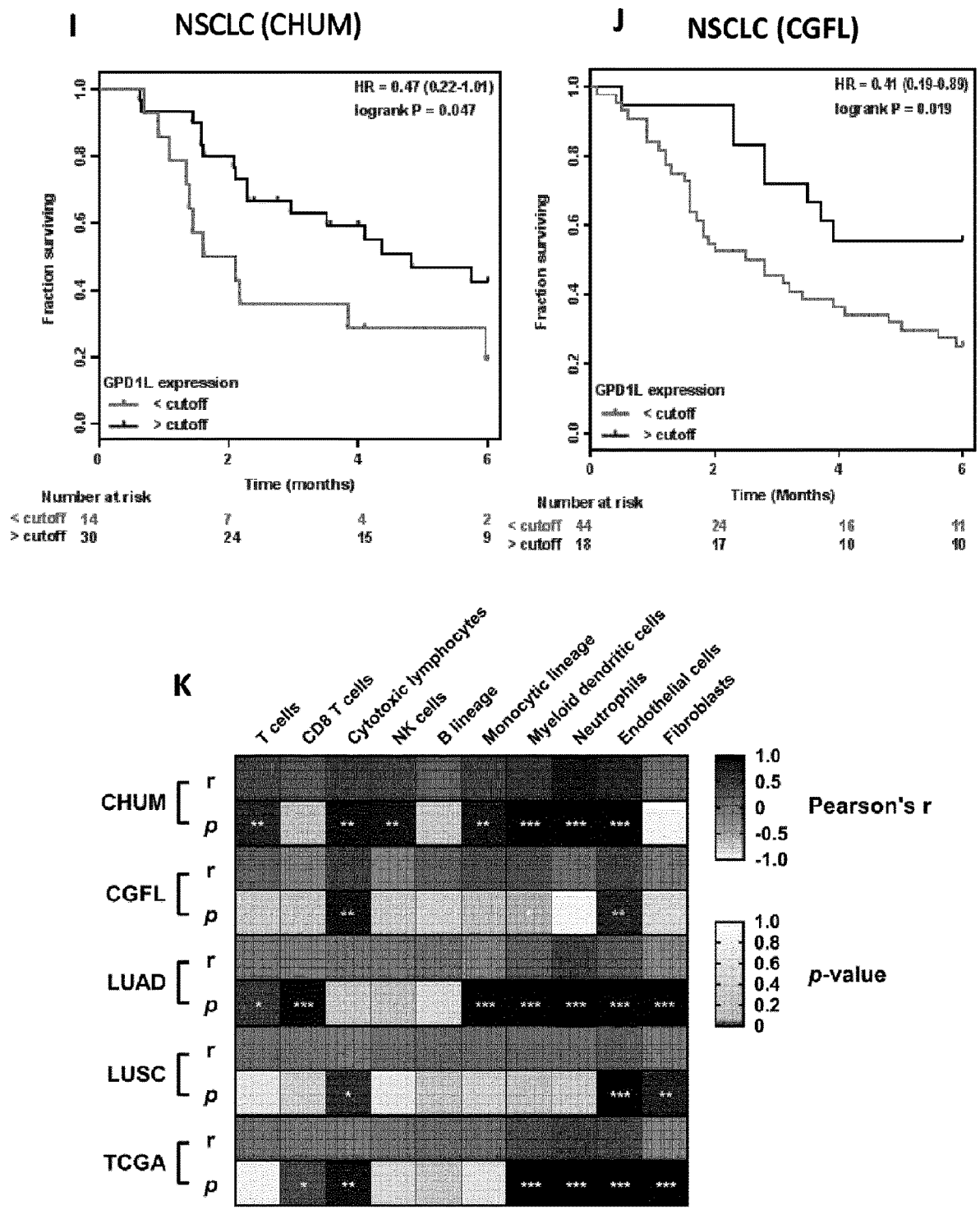
Figure 29I-K

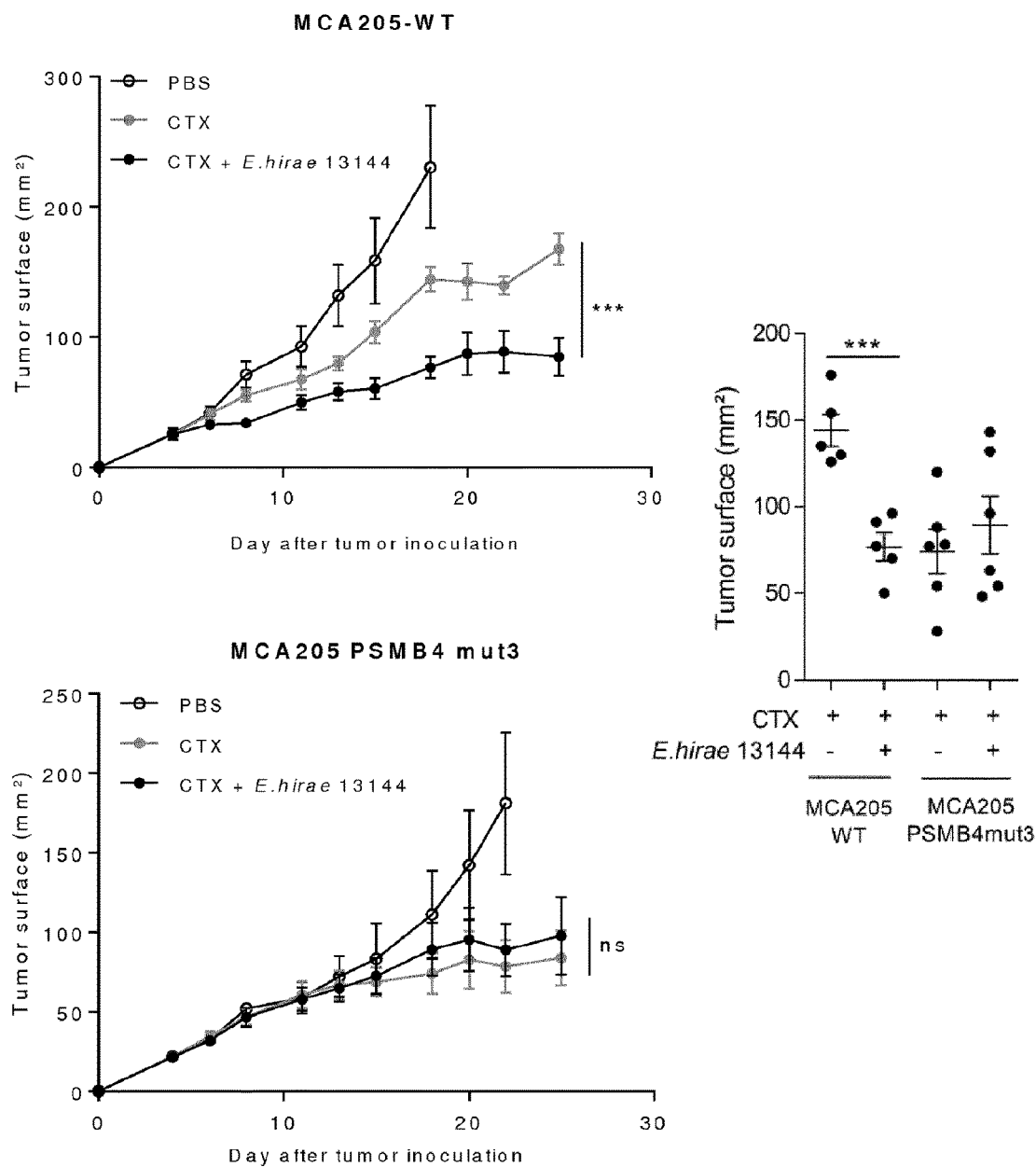
Figure 30A-B

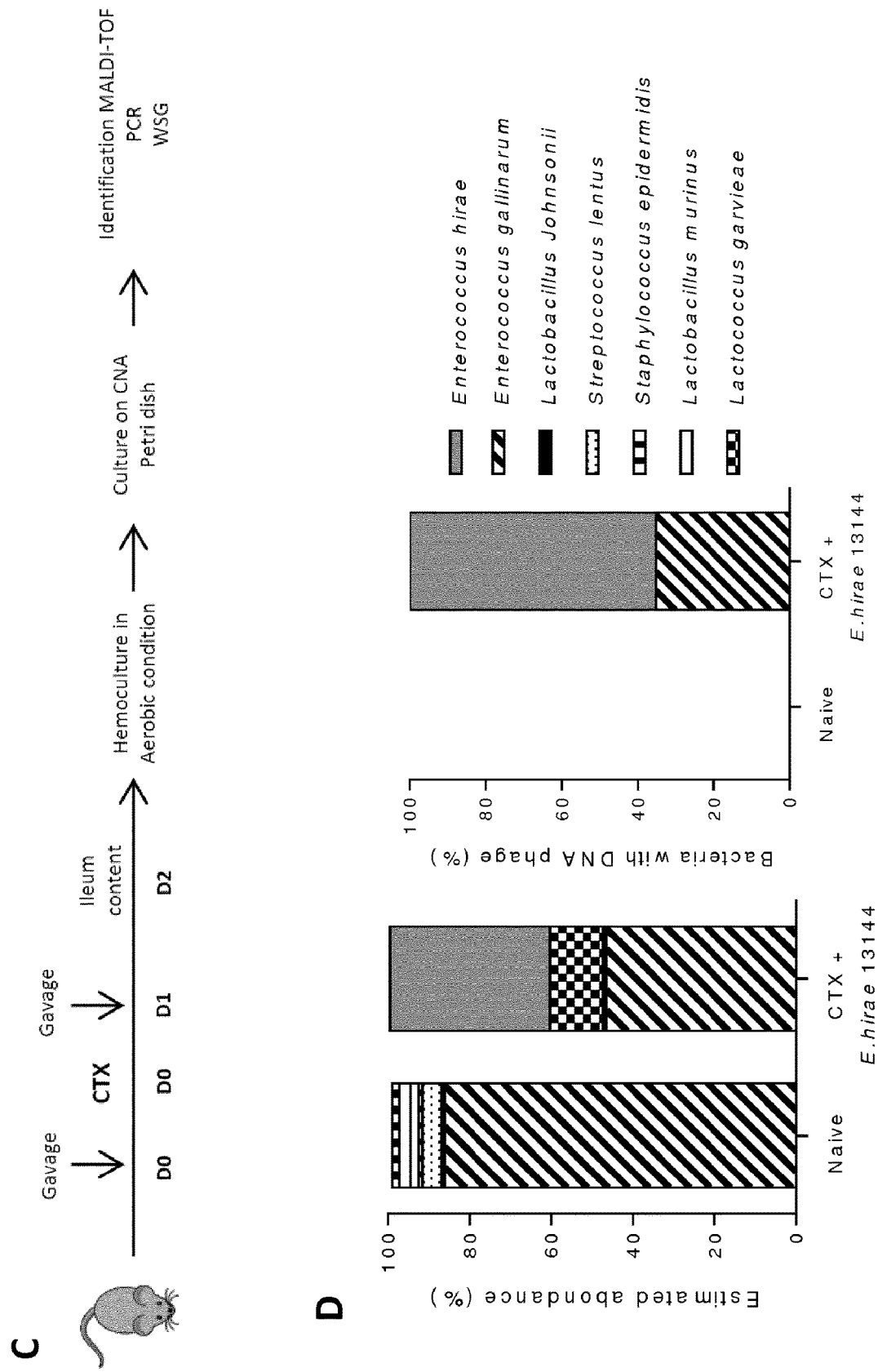
Figure 30C-D

F

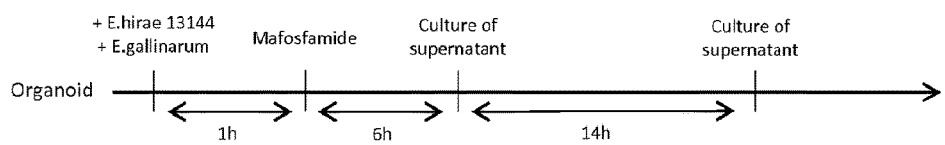

G

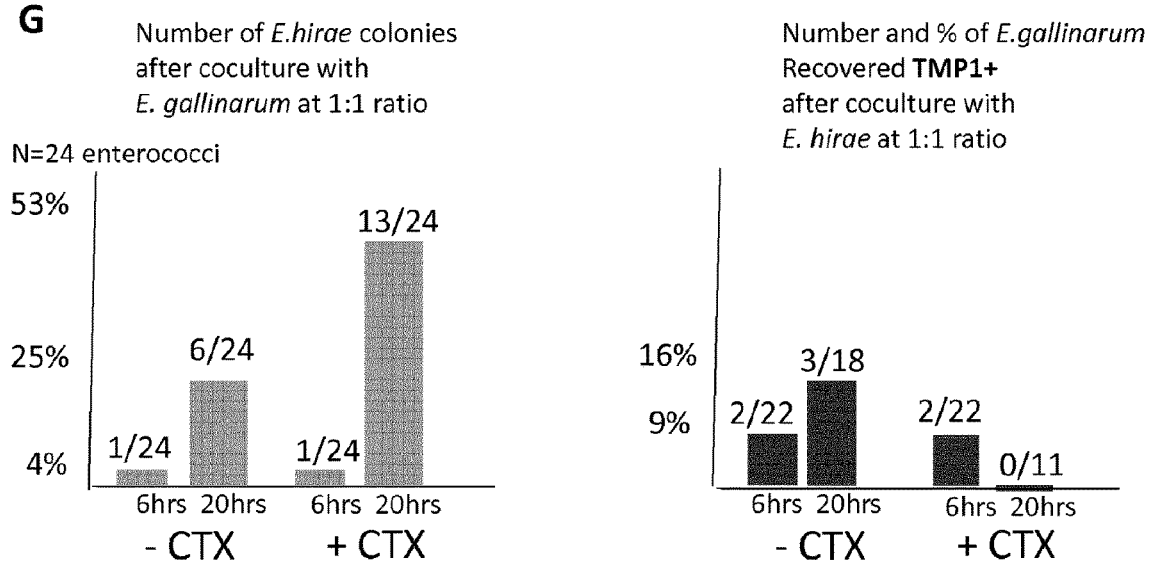

H

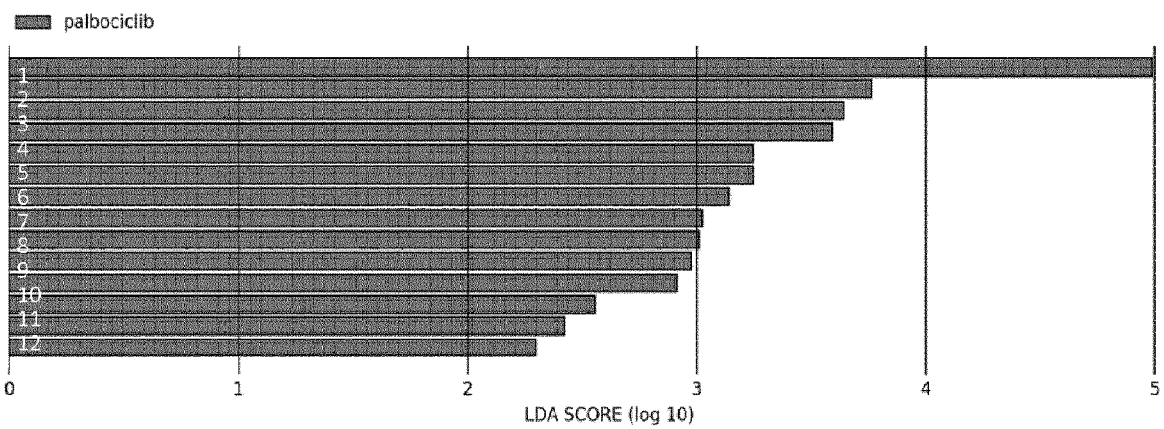

1: s__Sodalis_phage_SO_1; 2: s__Bacteroides_sp_4_3_47FAA; 3: s__Enterobacteria_phage_IL1; 4: s__Lactobacillus_ruminis;
5: s__Escherichia_phage_phAPEC8; 6: s__Collinsella_aerofaciens; 7: s__Lactococcus_phage_ul36;
8: s__Bifidobacterium_bifidum; 9: s__Oscillibacter_sp_KLE_1745; 10: s__Raoultella_ornithinolytica;
11: s__Salmonella_phage_HK620; 12: s__Lachnospiraceae_bacterium_6_1_63FAA; 13: s__Fusobacterium_ulcerans;
14: s__Eubacterium_dolichum

Figure 30F-H

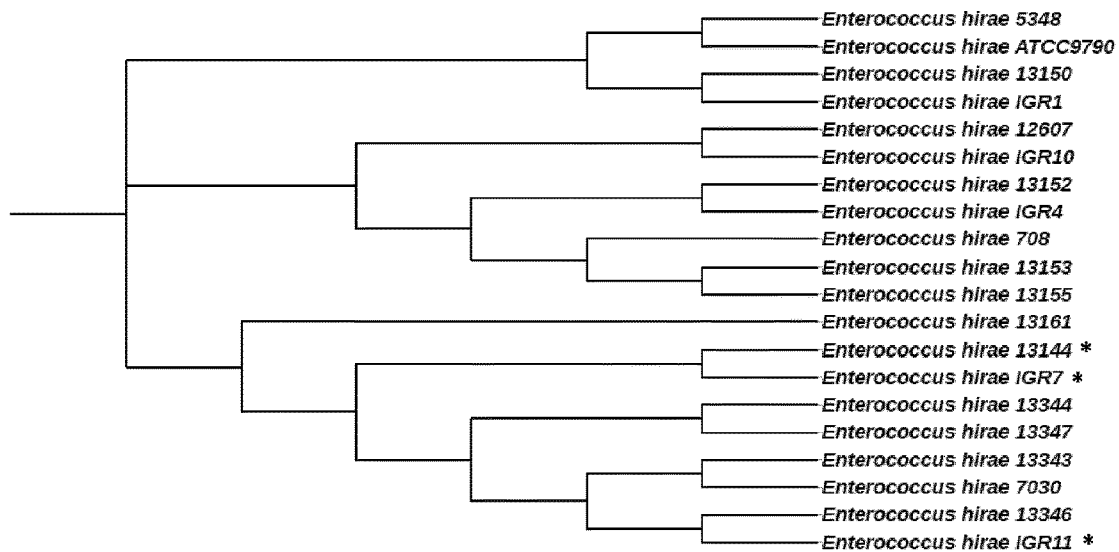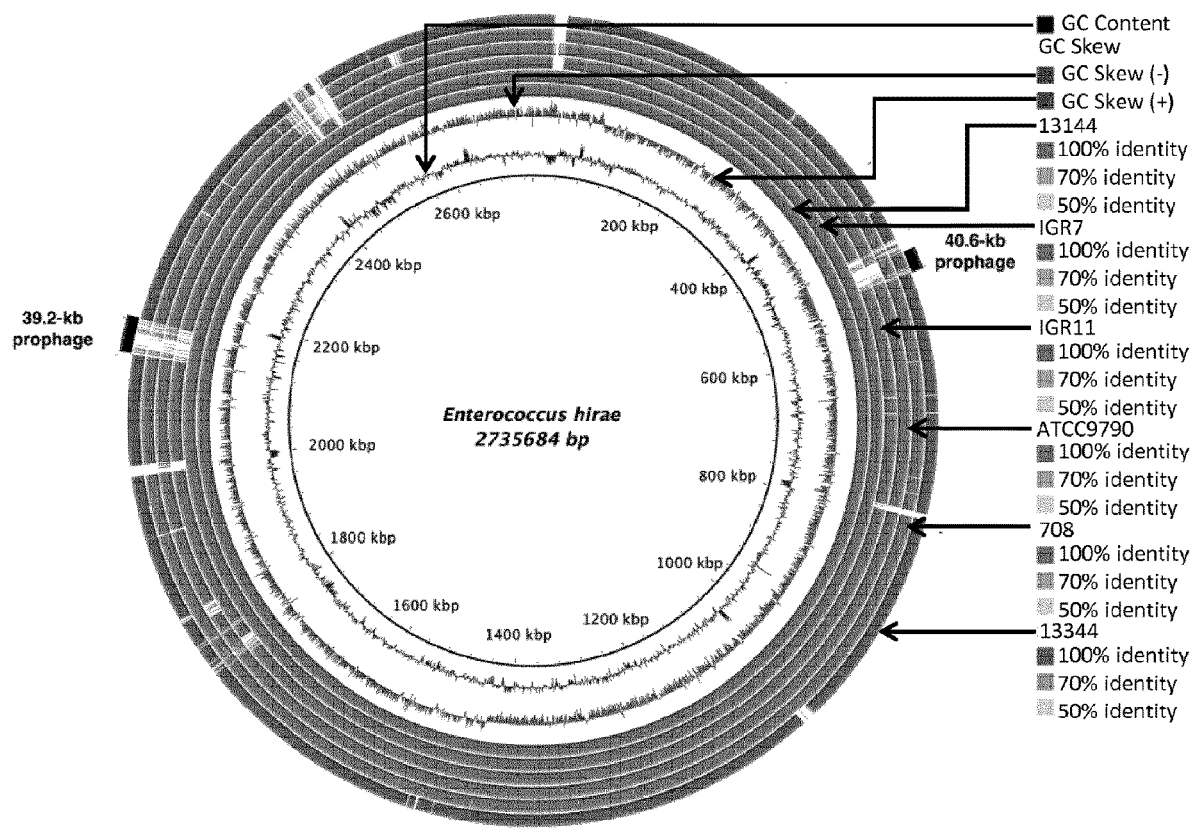
Figure 31B-C

A  TMP 39.2-kb prophage (1506 aa)

>E. hirae_13144_02029

MAQSKTVKAVLTAIDKGFTQTMGSATSSLKKLSSNASDIPSNLNTVSGAMKSFGDKTASIGQSIEKVGGSMTKGITLPIAGAVGAVVTAAVKWESA
FTGVKKTNDEMVDSNGKVIYSYDDLEKGLRDLAKELPTSHEEIAKVAEAAGQLGIKTDKYVGFTKTMIDMGESTNMSADTAATSLARFANITQMS
QDKFSNLGSAIVDLGNNLATTESEITEMGLRLAGAGKQIGMTEGDIVGFAAALSSVGIEAEAGGSAFSRLMVQMQLATETGVKAFEPLKQAVAIQ
GVSWEKFVHAVNWGGKELTAVSKQMGVPASELKKLYKEASKASGSLEDFANVTGRTQEEFAELFKSNPSQAMIEFIQGLKDSEKHGISAIKVLDD
MGITEVRLRDSLLRAANASDVFEGAVKRGNEAFNENTALAEEAGKRYGTTESQLKILRGQLNDVAITFGGPLVAALNSAISAAKPMIEALANMAEA
FASADPKTQEFILKMAALAASAGPVLKVFGKMTSVFGKTISTMFEKAGNIDSKWKQFIVPIKNGSSSALQAVKGFVSKYKSNLAGLESAGINVNLL
TRFTTLKDTIVGLFPTLDTFGANLRASQRQLNMLGEGNKVTNFFRSFSASLQLSNSKLAKFASVVINPIGSLRNLSSAAGKSGTVLSGLGVAASKAGG
GFRTFAATGIRSIASLTGAMLSNPITAILVAITTTIVGVVQAWKSNFMNIQGYVKTAFSGIVKSFKSVLPSSASVTKTIKGLGNIFKWLGTGTLVGVTFA
IAGFVDGLRAIITVGKTAVNAIMAIANGVKGLWQRLKGDSKGADKSFKDVKKSLADIGKDWDTMFSDSALKKAAKSTEELGKKSKDTTKAMSMN
MEEVSNSVENYSSKLDEAKQAMTELFSQQNGSTAGVEAYFNHTLDLVTNLKEQQKKAVETYNKQIEAAEGKSEAEKQKIFANASTEYMKAVQSN
NSDLLKVYTDYSNQLKNNKTVEGQELTDQQRATLQNQTNIIRDQLLDQQKQFVEAGVNKLNNNQALSEQEKEQTLSSLKTFGEIQAQQVQENNA
QIQQLETQKNQAKTESEKAAFQNQITQLQTQNDQIRQSELEQGAQLLAIISQNGANKIAVTADNLAQLKGVTDQQLLGIYQSYVNNGASIDQQM
ALLAGMLRQRGIDGSNGLVQGLQSNDPKLWANMSKADIVNTLQSLPPDLFKNGQDGKNKLIDGLNSGKVEINNVGQELMNQMNSGVKNKKA
EAEKTSGDVASSGAKGAKSKGKEYNSGGNSNAGEYNTGLAKQKSNAKQKGAELGSAPVEGVKTKASAMRSVGEQLGRSFVQGLASQVGSANNA
GRELGNAVKSGAGSVNMTSVGSNMAKGVASGIRASQGEAVSAMQNLVAAVNAEAQKKAKIKSPSRLLKYDVGVFLAQGVAAGIREDTSVAVQS
AKDMISSIHQSITGSRLIKRSNAIEVKHSIDNTPMGKMVEILEEIRHLTVVMDTGQVVGALGSPMNLNLAEQQKQDGRYRS

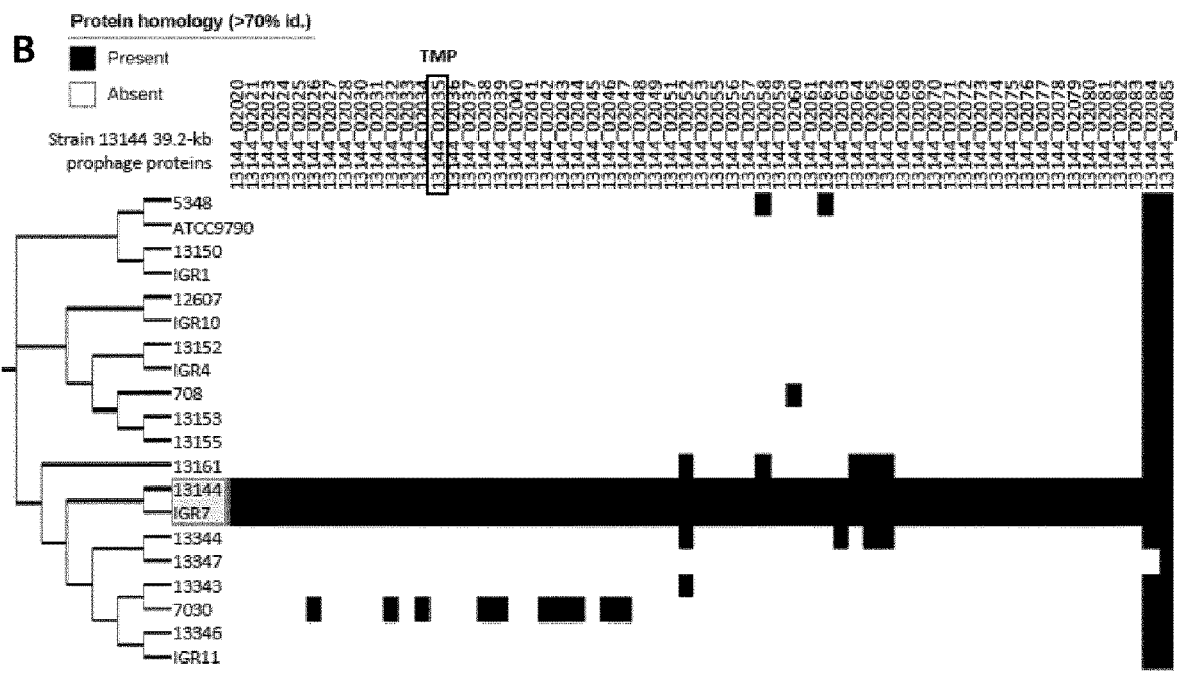

Figure 33A-B

|        | 260        | 270        | 280        | 290        | 300        | 310        |
|--------|------------|------------|------------|------------|------------|------------|
| TMP1   | MIDMGESTNMSADTAATSLARFANIHTQMSQDKFSNLGSAIVDLGNNLATTESEIET |
| 13144  | MIDMGESTNMSADTAATSLARFANIHTQMSQDKFSNLGSAIVDLGNNLATTESEIET |
| IGR7   | MVDMGESTNMSAETAATSLARFANIHTQMSQKDFDKLGSVIVDLGNNLATTESEIET |
| IGR11  | MIDLGESTNMSAETAATSFARFANIHTQMSQKDFERLGAVVVDLGNNLATTESEIET |
| ATCC9790 | LLQYAEINDTDVSQSAIFARQAIEAYNMSYDDLNSVLDVTTKTAQNTGQSVDDIA |
| 13344  | ILGFGGSTD-QVNEAVIQLSQSFSNGKVDAQTWNSMINA---QLGPTLSAIA |
| 708    |            |            |            |            |            |            |

TMP-FLAG => TSLARFANI

MAQSKTVKAVLTAIDKGFTQTMGSATSSLKKLSSNASDIPSNLNTVSGAMKSFGDKTASIGQSIEKVGGSMTKGITLPIAGAVGAVTTAA
VKWESAFTGVKKTNDEMVDSNGKVIYSYDDLEKGLRDLAKELPTSHEEIAKVAEAAGQLGIKTDKVVGFTKTMIDMGESTNMSADTAA
TSLARFANITQMSQDKFSNLGSAIVDLGNNLATTESEITEMGLRLAGAGKQIGMTEGDIVGFAAALSSVGIEAEAGGSAFSRLMVQMQ
LATETGVKAFEPLKQAVAIQGVSWEKFVHAVNWGGKELTAVSKQMGVPASELKKLYKEASKASGSLEDFANVTGRTGEEFAELFKSNP
SQAMIEFIQGLKDSEKHGISAIKVLDMGITEVRLRDSLLR*DYKDDDDK*

TMP-mut2-FLAG (mutation in position 2) => TSLARFANI to TALARFANI

MAQSKTVKAVLTAIDKGFTQTMGSATSSLKKLSSNASDIPSNLNTVSGAMKSFGDKTASIGQSIEKVGGSMTKGITLPIAGAVGAVTTAA
VKWESAFTGVKKTNDEMVDSNGKVIYSYDDLEKGLRDLAKELPTSHEEIAKVAEAAGQLGIKTDKVVGFTKTMIDMGESTNMSADTAA
TALARFANITQMSQDKFSNLGSAIVDLGNNLATTESEITEMGLRLAGAGKQIGMTEGDIVGFAAALSSVGIEAEAGGSAFSRLMVQMQ
LATETGVKAFEPLKQAVAIQGVSWEKFVHAVNWGGKELTAVSKQMGVPASELKKLYKEASKASGSLEDFANVTGRTGEEFAELFKSNP
SQAMIEFIQGLKDSEKHGISAIKVLDMGITEVRLRDSLLR*DYKDDDDK*

TMP-mut3-FLAG (mutation in position 3) => TSLARFANI to TSFARFANI

MAQSKTVKAVLTAIDKGFTQTMGSATSSLKKLSSNASDIPSNLNTVSGAMKSFGDKTASIGQSIEKVGGSMTKGITLPIAGAVGAVTTAA
VKWESAFTGVKKTNDEMVDSNGKVIYSYDDLEKGLRDLAKELPTSHEEIAKVAEAAGQLGIKTDKVVGFTKTMIDMGESTNMSADTAA
TSFARFANITQMSQDKFSNLGSAIVDLGNNLATTESEITEMGLRLAGAGKQIGMTEGDIVGFAAALSSVGIEAEAGGSAFSRLMVQMQ
LATETGVKAFEPLKQAVAIQGVSWEKFVHAVNWGGKELTAVSKQMGVPASELKKLYKEASKASGSLEDFANVTGRTGEEFAELFKSNP
SQAMIEFIQGLKDSEKHGISAIKVLDMGITEVRLRDSLLR*DYKDDDDK*

B

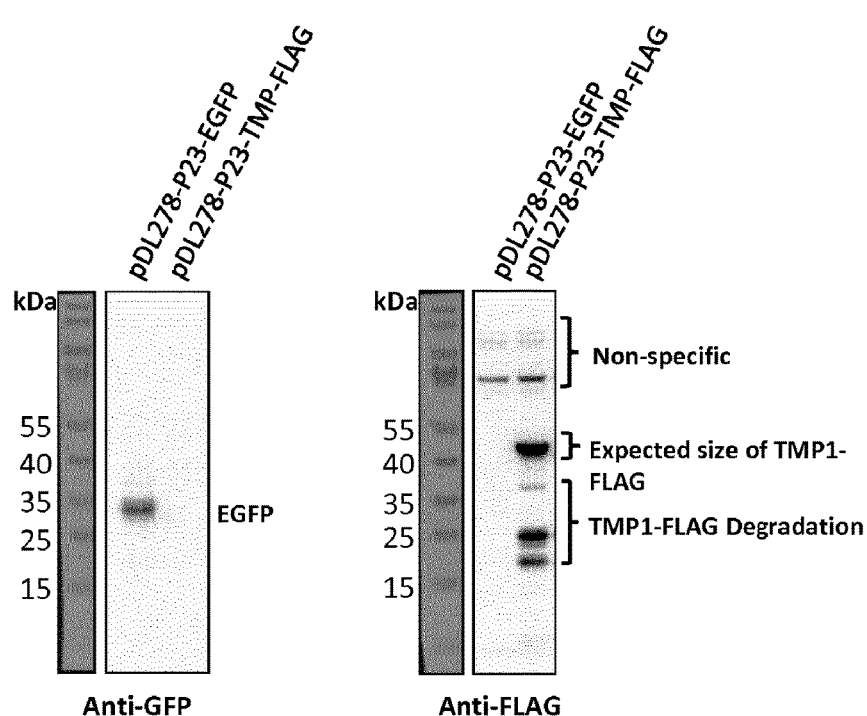

Figure 35A-B

```
TCAACTACGATACCTCCCATCTTGCTTTTGTTGTTCTGCTAAATTAAGATTCATCGGGCTACCTAGTGCTCCCACTACTTGGCCAGTATCC
ATCACAACAGTTAAATGACGTATTTCTTCTAAGATTTCTACCATTTTCCCCATCGGCGTATTATCTATAGAATGTTTTACCTCAATTGCATT
TGATCGTTTTATCAAACGACTGCCTGTAATAGACTGGTGAATGCTTGAAATCATATCTTTTGCACTTTGTACGGCAACTGACGTATCTTC
TCGAATACCTGCTGCCACACCCTGTGCAAGGAAAACACCAACGTCATATTTCAATAGGCGTGATGGAGATTTAATCTTTGCTTTTTTCTG
TGCTTCTGCATTAACTGCAGCTACTAAATTTTGCATAGCAGATACTGCTTCTCCTTGGCTAGCTCTAATACCAGAAGCAACACCTTTAGC
CATATTAGATCCAACGGATGTCATATTGACTGAACCAGCACCACTTTTTACTGCGTTTCCTAATTCTCTACCAGCGTTATTAGCTGAACCA
ACCTGTGATGCCAATCCTTGAACGAAACTACGCCCAAGCTGTTCTCCTACGCTTCGCATAGCAGAAGCTTTCGTTTTTACTCCTTCAACA
GGCGCTGATCCTAATTCTGCACCTTTTTGTTTTGCGTTGCTTTTCTGTTTCGCTAGCCCTGTGTTATACTCTCCAGCATTAGAATTACCGCC
GCTATTGTATTCTTTACCTTTACTTTTTGCGCCCTTTGCACCAGATGAAGCTACATCACCAGAAGTTTTTTCCGCTTCTGCTTTCTTATTTT
TACGCCTGAGTTCATCTGATTCATTAACTCTTGACCGACATTATTGATTTCAACTTTTCCTGAGTTCAACCCGTCGATTAATTTGTTTTTAC
CATCTTGACCGTTTTTAAACAAATCAGGCGGTAATGATTGCAAGGTATTCACAATGTCAGCTTTTGACATATTCGCCCATAATTTAGGAT
CGTTGCTTTGCAATCCTTGAACTAGTCCGTTAGAACCATCAATTCCTCGTTGACGTAACATTCCAGCTAATAAAGCCATTTGTTGGTCAA
TGCTAGCACCGTTGTTTACATACGATTGATAAATTCCTAATAACTGTTGGTCTGTCACTCCTTTTAATTGAGCTAAATTATCAGCCGTCAC
CGCAATTTTATTTGCACCATTTTGTGAAATAATCGCTAGAAGCTGCGCTCCTTGTTCTAATTCACTTTGACGTATCTGATCGTTCTGTGTT
TGTAATTGCGTAATTTGGTTTTGGAAAGCCGCCTTTTCTGATTCAGTTTCGCTTGGTTCTTTTGTGTTTCCAATTGCTGAATTTGTGCATT
ATTCTCCTGCACTTGCTGTGCTTGAATTTCTCCAAAAGTTTTTAAACTTGATAAAGTTTGTTCTTTTCTTGTTCACTTAACGCTTGGTTGT
TATTCAGCTTATTCACACCAGCTTCGACAAACTGTTTCTGTTGATCCAACAATTGATCACGAATAATATTCGTTTGATTTTGCAAAGTTGC
TCTTTGCTGATCGGTTAACTCTTGACCTTCTACCGTTTTATTATTCTTCAACTGATTAGAGTAATCTGTGTATACTTTCAACAGATCGCTAT
TGTTTGATTGAACAGCCTTCATATACTCAGTTGAAGCATTGGCAAAAATCTTTTGTTTTTCAGCTTCCGATTTACCTTCTGCCGCTTCAAT
CTGCTTATTATAGGTTTCAACAGCCTTTTTCTGTTGTTCTTTTAGATTTGTCACTAAATCAAGTGTATGATTGAAATAAGCTTCTACGCCA
GCCGTGCTACCGTTTGCTGTGAGAAAAGTTCAGTCATTGCCTGTTTAGCTTCATCAAGTTTTGATGAGTAATTTTCAACACTATTTGATA
CCTCTTCCATATTCATGGACATGGCTTTCGTAGTGTCTTTCGATTTCTTCCCTAATTCTTCTGTGCTTTTAGCTGCTTTTTTTAGAGCAGAA
TCAGAAAACATGGTATCCCAGTCTTTTCCGATATCAGCTAAACTTTTCTTCACATCTTTAAATGATTTATCGGCTCCTTTTGAATCGCCTTT
TAATCTTTGCCAAAGTCCTTTTACTCCGTTAGCAATGGCCATTATTGCATTTACTGCTGTCTTTCCTACAGTAATAATGGCTCGCAATCCA
TCTACAAAACCTGCAATAGCAAAAGTAACTCCGACAAGAGTTCCTGTTCCTAACCATTTAAAAATATTTCCTAATCCTTTTATTGTTTTAG
TAACACTCGCGGAGCTAGGAAGTACACTTTTAAACGATTTTACTATTCCGCTAAAAGCGGTTTTCACGTAGCCTTGAATGTTCATAAAAT
TGGATTTCCAAGCTTGCACTACACCAACTATTGTAGTGGTTATTGCTACTAAAATTGCAGTTATAGGATTGCTCAACATAGCTCCTGTTA
AACTAGCTATAGATCGTATACCCGTTGCTGCAAATGTTCTAAAACCTCCACCTGCTTTTGAGGCGGCTACACCAAGTCCTGATAAAACC
GTCCCTGATTTACCAGCTGCAGAAGATAAATTCCTTAGCGACCCAATAGGATTAATAACAACGGAGGCGAATTTCGCTAATTTGCTATT
AGATAATTGTAAAGAAGCAGAAAAAGAACGGAAAAAGTTAGTAACTTTATTCCCTTCCCCTAGCATATTTAGCTGTCTTTGGCTTGCTC
GAAGATTTGCTCCAAAAGTGTCCAATGTGGGAAAGAGACCTACAATGGTATCTTTTAGCGTAGTAAAACGGGTAAGCAGATTTACATTT
ATCCCCGCACTTTCAAGCCCTGCAAGATTTGATTTATATTTAGAAACAAACCCTTTTACAGCTTGTAATGCGCTACTAGAACCGTTTTTGA
TAGGAGTAACGATAAATTGTTTCCACTTGCTATCTATGTTTCCAGCTTTCTCAAACATTGTTGAAATTGTTTTGCCAAAAACACTAGTCAT
TTTCCCAAACACTTTTAATACAGGACCAGCAGAAGCAGCTAATGCAGCCATTTTTAAAATAAATTCTTGAGTTTTTGGATCAGCTGATGC
AAAAGCCTCGGCCATATTTGCTAAAGCTTCAATCATAGGCTTAGCAGCACTTATTGCGCTATTTAATGCGGCTACTAATGGACCGCCAA
ACGTAATTGCTACATCGTTTAATTGACCACGTAAAATCTTTAACTGTGATTCTGTAG*TTCCGTATCGTTTGCCAGCTT*CTTCTGCTAGAGC
TGTATTTTCGTTAAACGCTTCGTTACCTCGTTTTACAGCACCTTCAAAGACATCACTCGCATTAGCCGCACGTAGTAAACTATCACGTAAT
CGAACTTCGGTAATCCCCATATCATCAAGTACTTTAATAGCTGAGATTCCATGCTTTTCTGAGTCTTTCAAACCTTGAATAAACTCAATCA
TAGCTTGAGAAGGATTACTCTTGAATAATTCCGCGAACTCTTCGCCAGTTCGACCAGTAACATTTGCAAAATCTTCCAAACTTCCAGACG
CCTTGCTTGCTTCTTTATATAATTTTTTCAATTCTGAAGCTGGTACTCCCATTTGTTTAGAAACAGCTGTTAATTCTTTACCACCCCAATTA
ACAGCATGAACAAATTTTTCCCAAGACACTCCTTGTATAGCTACAGCTTGTTTTAAAGGTTCAAAAGCTTTAACCCCTGTTTCGGTGGCT
AATTGCATTTGTACCATCAACCTAGAAAAAGCTGAACCACCCGCTTCGGCCTCTATACCAACAGATGATAACGCCGCTGCAAAACCGAC
AATGTCTCCTTCAGTCATACCAATTTGTTTTCCTGCACCAGCCAAACGGAGTCCCATTTCTGTGATTTCTGATTCAGTAGTTGCTAAGTTA
TTCCCTAAGTCAACAATAGCTGAGCCAAGATTGCTAAATTTATCTTGAGACATTTGAGTAATATTAGCAAAACGAGCTAAGGAAGTAG
CAGCTGTATCTGCAGACATATTTGTTGATTCGCCCATATCGATCATTGTTTTAGTAAATCCGACAACTTTATCAGTTTTTATTCCTAACTG
TCCAGCTGCTTCTGCTACTTTTGCAATTTCTTCATGACTAGTAGGTAATTCTTTTGCTAAATCTCTAAGGCCTTTTTCTAAATCATCATAAG
AATAAATGACTTTACCGTTAGAATCGACCATCTCATCGTTGGTCTTTTTAACACCAGTAAATGCACTT*TCCCATTTTACGGCTGCAG*TTGT
GACTGCTCCAACAGCACCCGCAATTGGGAGTGTGATACCTTTAGTCATCGAACCGCCGACTTTTCAATGCTTTGGCCGATACTTGCAG
TTTTATCACCAAAACTTTTCATCGCACCACTAACTGTGTTCAAATTACTGGGAATATCAGAAGCATTCGAACTAAGTTTTTTTAGCGAAG
AGGTAGCACTCCCCATTGTCTGAGTAAACCCTTTATCTATTGCTGTAAGTACCGCTTTGACTGTTTTACTTTGTGCCAC
```

Primers

Sequence of TMP1

Figure 36

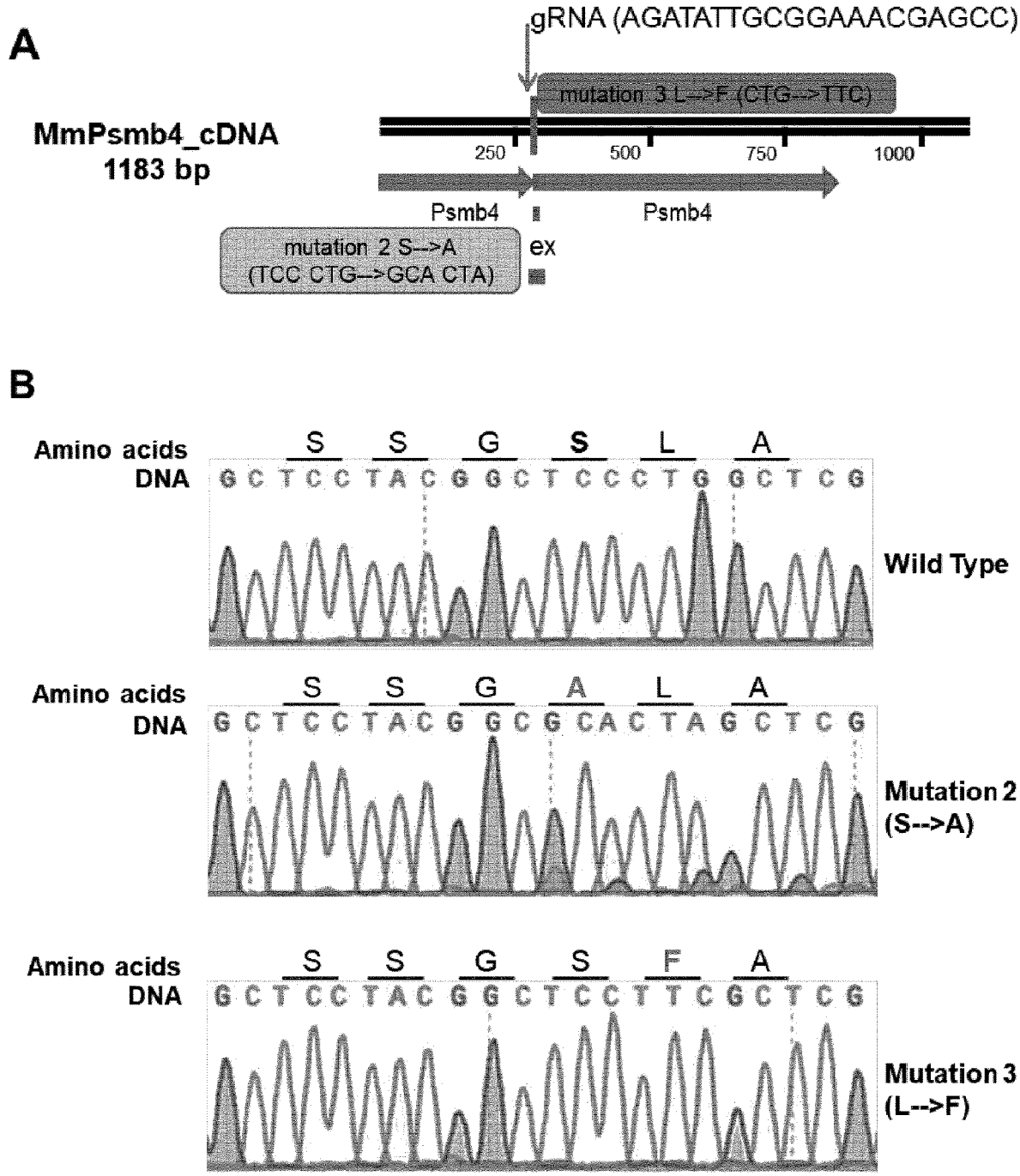
Figure 38A-B

A  Naïve mice
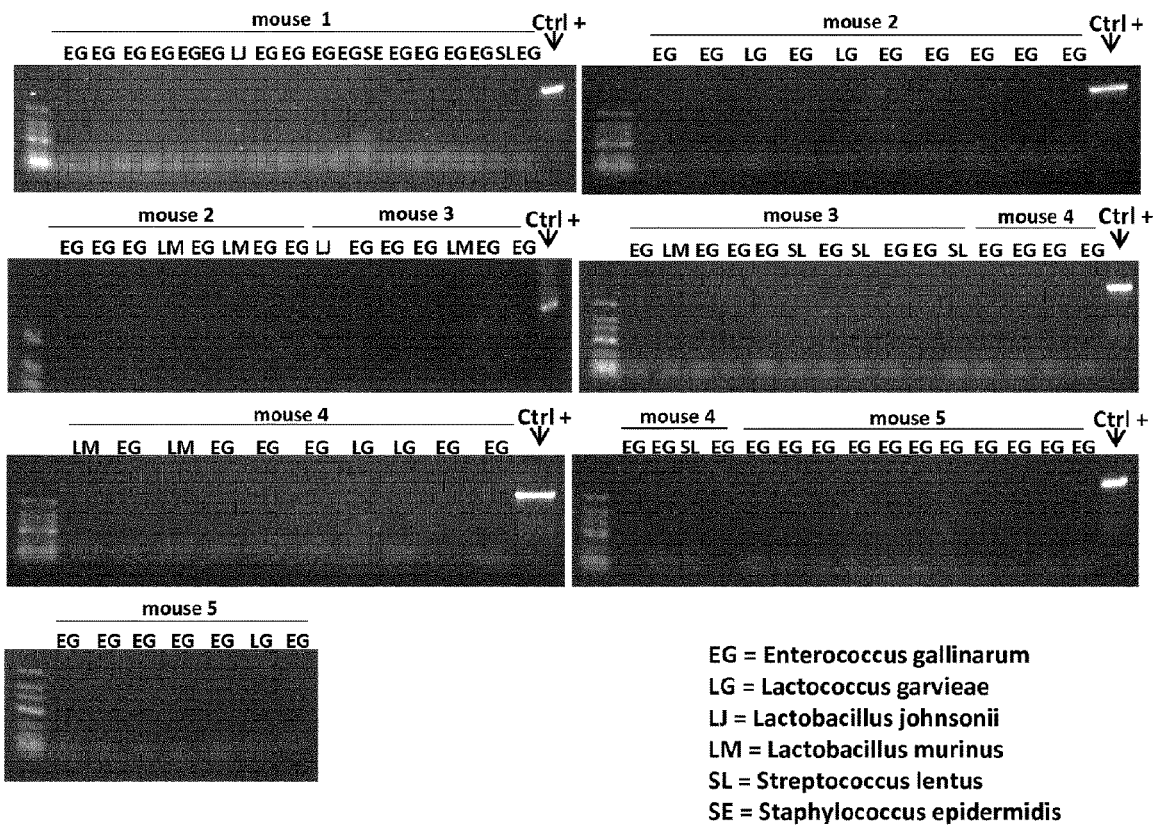
EG = Enterococcus gallinarum
LG = Lactococcus garvieae
LJ = Lactobacillus johnsonii
LM = Lactobacillus murinus
SL = Streptococcus lentus
SE = Staphylococcus epidermidis
B  CTX + *E.hirae* 13144 mice
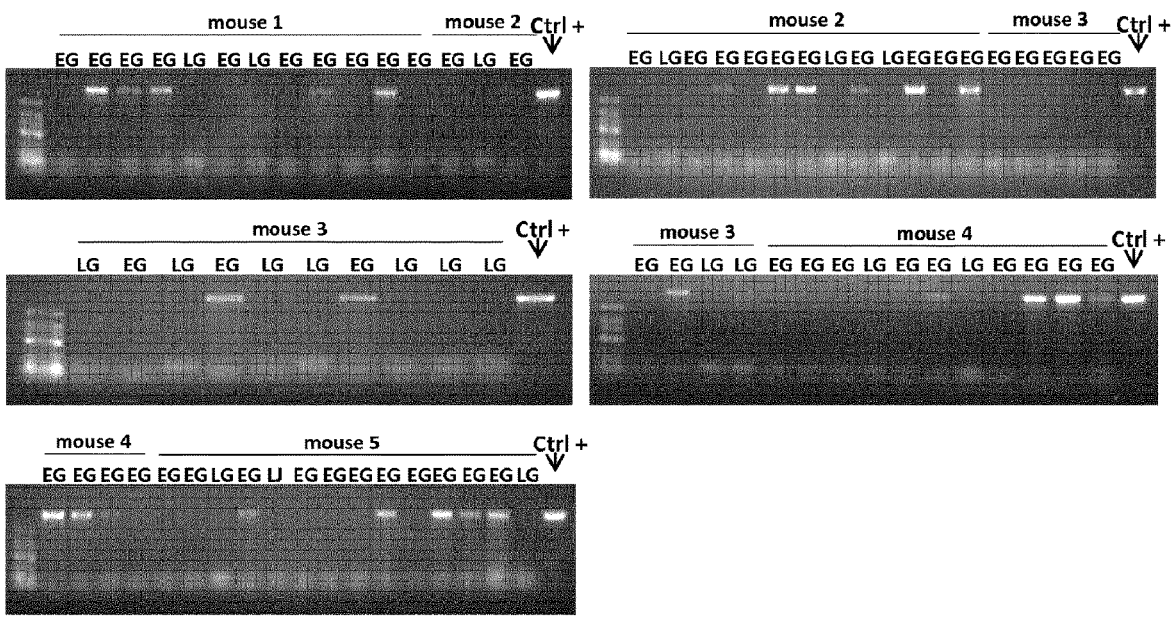
Figure 39A-B

IMMUNOGENIC SEQUENCES FROM A PHAGE TAIL LENGTH TAPE MEASURE PROTEIN, BACTERIA EXPRESSING THE SAME AND THEIR USE IN TREATING A CANCER

SEQUENCE LISTING

The instant application contains a Sequence Listing which has been submitted electronically in ASCII format and is hereby incorporated by reference in its entirety. Said ASCII copy, created on Oct. 6, 2023, is named 16959042_ST25.txt and is 116,270 bytes in size.

FIELD OF THE INVENTION

The present invention relates to the field of probiotic adjuvantization of anticancer treatments. In particular, the present invention concerns immunogenic sequences from a prophage present in bacteria identified as efficient adjuvants of cancer treatments. The invention provides bacterial compositions expressing immunogenic sequences from this prophage and methods using sequences of this prophage, for increasing the anticancer armamentarium.

BACKGROUND OF THE INVENTION

Cancer incidence and progression results from a complex interplay between gene regulation and the environment (Hanahan and Weinberg, 2011). Many epithelial and hematopoietic neoplasias are thought to be under strong immunosurveillance, as indicated by numerous studies revealing that the density, composition, and functional state of immune cells that infiltrate tumors dictate patient prognosis, as well as therapeutic response to adjuvant or neoadjuvant chemotherapy (Ingold Heppner et al., 2016; Palucka and Coussens, 2016) and immune checkpoint blockers (Hodi et al., 2010; Ribas, 2015; Robert et al., 2015). The recognition of cancer cells by immune effectors relies on two parameters, namely, antigenicity (the presence of tumor-associated antigens that are derived from mutations yielding mutated proteins, or the ectopic expression of genes/proteins that are normally only present in embryonic development or in testis) and adjuvanticity (the presence of co-stimulatory signals that activate innate immune effectors) (Zitvogel et al., 2016). Commensal microbial communities inhabiting the intestine, as well as other places in the body, appear to play an unappreciated role in intestinal and extraintestinal carcinogenesis by providing yet to be characterized environmental signals (Zitvogel et al., 2015). Pioneering studies performed in germ-free, gnotobiotic, or antibiotic-treated rodents have revealed an unsuspected role for commensals in tumorigenesis, irrespective of the role of inflammation. In the genesis of colon cancer or hepatocarcinoma, microbes can be direct transforming agents (Abreu and Peek, 2014; Sears and Garrett, 2014), by providing a toxic metabolite, an oncogenic product or by inducing an inflammatory milieu which will culminate in genomic instability and/or DNA damage response and/or immune escape (Garrett, 2015; Gur et al., 2015; Louis et al., 2014). Commensals can also form cooperative biofilms that facilitate cross-feeding or cross-metabolism, redefining the cancer landscape (Bongers et al., 2014; Dejea et al., 2014). Recently, the development of extraintestinal (breast and ovarian) neoplasias were linked to TLR5-mediated IL-6 or IL-17 driven systemic inflammation provoked by intestinal microbes (Rutkowski et al., 2015).

In contrast, other observations support a beneficial role for bacteria in combatting cancer. Prolonged antibiotic treatment with a combination of metronidazole and ciprofloxacine subsequently tripled breast cancer (BC) incidence in protooncogene HER2/neu driven-transgenic mice (Rossini et al., 2006). In humans, epidemiological studies suggest a dose-dependent association between antibiotic use and risk of BC (Blaser, 2011). The beneficial role of intestinal microbiota was first shown via total body irradiation, promoting LPS/TLR4-dependent activation of antigen presenting cells that facilitated the efficacy of adoptive T cell transfer (Paulos et al., 2007). During platinum-based anticancer therapy and immunomodulatory regimens, bacterial-associated TLR4 agonists accounted for the ROS and TNFα-mediated antitumor effects of tumor infiltrating myeloid cells (lida et al., 2013).

Antitumor efficacy of metronomic dosing of the alkylating agent cyclophosphamide (CTX) was also showed to be compromised in germ-free or specific pathogen free animals treated with broad spectrum antibiotics (ATBs) (Daillère et al., 2016; Viaud et al., 2013). Indeed, CTX altered the integrity of the intestinal barrier, promoting the translocation of distinct Gram+ bacteria. Bacterial translocation occurs when commensal gut microbes invade through the gut mucosa to underlying sterile tissues and organs. This phenomenon allowed Gram+ bacteria to mount effector pathogenic $CXCR3^+CCR6^+(IL-17^*IFNg^+)$ Th17 (abbreviated, pathogenic pTh17) and memory Th1 immune responses associated with tumor control. *E. hirae* and *Barnesiella intestinihominis* were identified as the species acting in concert to reshape the tumor microenvironment post-CTX. The small intestine resident Gram+ bacteria *E. hirae* induced tumor antigen-specific, MHC class I-restricted cytotoxic $IFN\gamma^+$ $CD8^+$ T cells (CTL), a decrease in intratumoral regulatory T cells (Treg), and led to an increase in the CTL/Treg ratio commonly associated with tumor control. The colon resident Gram− *B. intestinihominis* boosted systemic polyfunctional Tc1/Th1 responses, reinstated intratumoral IFNγ producing γδT cells, and reduced γδT17 cells in the tumor microenvironment, traits associated with tumor control. These two immunogenic commensals are kept in check by intestinal NOD2 receptors, which limit bacterial accumulation (for *B. intestinihominis*) or translocation (for *E. hirae*) into secondary lymphoid organs. In addition, while CTX plus cancer vaccine (B subunit of Shiga toxin fused with HPV-16 E7 antigen) no longer protected the host against the E7-expressing TC-1 tumor in combination with antibiotic treatment, oral gavages with *E. hirae* (but not *L. johnsonii* nor *E. coli*) restored the accumulation of E7 tetramer-binding $CD8^+$ CTLs leading to tumor rejection. In this model, *E. hirae* mediated anti-tumor effects. Finally, the immunomodulatory role of these two commensals in mice is relevant to cancer-bearing patients. Memory MHC class II-restricted Th1 immune responses against *E. hirae* or *B. intestinihominis* (and not 9 other commensals) were associated with prolonged progression-free survival in end stage lung and ovarian cancer patients who were previously treated with chemotherapy (Daillère et al., 2016). Recently, Zitvogel and others extended these findings to immune checkpoint blockers, demonstrating that distinct intestinal bacterial species belonging to Bacteroidales and Burkholderiales or Bifidobacteriales orders influenced the tumor microenvironment, contributing to the efficacy of anti-CTLA4 or anti-PDL-1 Abs respectively (Sivan et al., 2015; Vétizou et al., 2015). Hence, it is postulated that the intestinal microbiota ecosystem controls not only gut immune homeostasis but also the inflammatory/immune tone of secondary lymphoid organs, thereby shaping the tumor microenvironment throughout the body.

To demonstrate a causal relationship between translocated Gram+ bacteria and CTX-induced tumoricidal activity, Daillère et al. colonized mouse intestines with 109 *E. hirae* (clone 13144 and other isolates), *L. johnsonii* or control bacteria in MCA205 sarcoma-bearing mice rendered dysbiotic by a 14 day-ATBs regimen. ATBs prevented the CTX-mediated control of tumor progression. However, oral gavage with *E. hirae* strain 13144 (EH13144) selectively restored the CTX-mediated antitumor effects while *L. johnsonii, E. coli* or *L. plantarum* isolates failed to do so, despite comparable gut colonization (Daillère et al., 2016). They next selected the best anticancer probiotic capable of boosting the CTX-mediated antitumor effects and tackled the mechanism by which it occurred, and tested various *E. hirae* strains to analyze their differential immunogenicity in vivo and their "oncomicrobiotic" (anticancer probiotic) properties. An investigation of the clonal relationship between these *E. hirae* isolates, performed by rep-PCR, revealed significant genomic diversity among the strains derived from human, mouse or environmental ecosystems (Daillère et al., 2016). Half of the isolates induced pTh17 and Th1 immune responses; only one human isolate (clone 708) induced IFNg producing CD8$^+$ T (Tc1) cells in naïve mice associated with some oncomicrobiotic properties. The only human isolate of *E. hirae* (clone EH17) capable of forming ex vivo biofilms in adherence assays harboured no immunogenic nor oncomicrobiotic properties (Daillère et al., 2016).

Since the publication of Daillère et al. (2016), the inventors isolated 3 novel clones of *E. hirae* (EH) endowed with high immunogenicity and derived from human stools (clone IGR7, clone IGR4 and clone IGR11) that exhibited antitumor effects.

In summary, EH13144, EH clone IGR7 and, to a lesser extent, clone IGR4 and clone IGR11, exerted a significant capacity to induce pTh17 cells in secondary lymphoid organs of CTX-treated animals, which was associated with cancer antigen-specific CTL responses and oncomicrobiotic properties, whereas the EH17 strain did not. The reasons for these differences were however unknown, and the inventors pursued their research to identify the factor(s) responsible for the immunogenic properties of the murine strain EH13144 and the human clones IGR4, IGR7 and IGR11, in order to derive new molecules or microorganisms useful in the treatment of cancer.

The inventors screened several human *E. hirae* isolates cultivated from human patients' feces and compared them with the human EH708 and the mouse EH13144. They cultivated 11 novel isolates of *E. hirae* from feces of non small cell lung cancer patients who responded to anti-PD1 Ab. Among these 11 novel isolates tested in the MCA205 tumor model together with CTX, clone IGR4, clone IGR11 to some extent and clone IGR7 were effective at synergizing with CTX, alone or best, when combined together.

They found that the mouse EH13144 shares a very high sequence homology with the human clone IGR7 (and falls into the same clade in the dendrogramm of >20 EH strains), both being very special isolates with a unique immunogenicity related to the presence of a phage inserted into their genomic sequence. They identified that the immunogenicity relies on the temperate bacteriophage tail tape measure protein (TMP). Additionally, the combination of EH13144+ clone IGR4+clone IGR7 exhibited additive antitumor effects combined with CTX.

SUMMARY OF THE INVENTION

According to a first aspect, the present invention pertains to a bacterial composition comprising bacteria selected from the group consisting of:
  (i) *Enterococcus hirae* strain 13144 (aka EHFS001) deposited on Nov. 7, 2013 at the Collection Nationale de Cultures de Microorganismes (CNCM) 28, rue du Docteur Roux, F-75724 Paris Cedex 15, FRANCE, under the number I-4815,
  (ii) *Enterococcus hirae* strain IGR7 deposited on Aug. 31, 2017 at the CNCM under the number I-5224,
  (iii) *Enterococcus hirae* strain IGR11 deposited on Nov. 27, 2017, at the CNCM under the number 1-5261,
  (iv) any other bacterial strain expressing a protein with at least 65, preferably at least 80 and more preferably at least 95% identity with a fragment of at least 20, preferably at least 30 and more preferably at least 40 nucleotides from the protein of SEQ ID No: 1 (i.e., the TMP of the prophage identified as being responsible for the remarkable immunogenic properties of *Enterococcus hirae* strain 13144, CNCM I-4815), and
  (v) mixtures of at least two of the strains recited in (i) to (iv).

The invention also relates to the use of the above bacterial composition for treating a cancer.

According to one embodiment, the composition according to the present invention is used in combination with an antineoplastic drug, for treating a cancer.

According to another aspect, the invention pertains to a method of increasing the immunogenicity of a bacterial strain of anticancer interest, comprising in vitro introducing, into said strain, a nucleotide sequence encoding the protein of SEQ ID No: 1 of a fragment thereof identified as being immunogenic, such as a fragment comprising at least the peptides of SEQ ID Nos: 13 and 14, or a sequence encoding a peptide of at least 9, preferably at least 20 amino acids comprising at least one of the epitopes likely to be presented by a human HLA molecule, such as epitopes selected from the group consisting of SEQ ID No: 53 to 187

A bacterial strain which has been obtained by the above method is also part of the present invention, as well as its use in treating a cancer.

The present invention also relates to an immunogenic composition comprising a polypeptide comprising a sequence of at least 9 consecutive amino acids from the TMP of SEQ ID No: 1 or a polynucleotide encoding the same, for use as an anticancer vaccine.

According to another aspect, the present invention pertains to a cell composition comprising antigen presenting cells (APC) which have been pulsed ex vivo with a bacterial composition or an immunogenic composition according to the invention.

According to an embodiment, the invention pertains to an MHC multimer for isolating T-cells with high affinity for the protein of SEQ ID No: 1, wherein MHC molecules are bound to an epitope selected from the group consisting of SEQ ID No: 53-187.

The invention also pertains to a bacteriophage composition, wherein said bacteriophage expresses a protein having at least 80, preferably at least 90 and more preferably at least 95% identity with the protein of SEQ ID No: 1, as well as its use for treating a cancer.

According to one embodiment, the invention pertains to a screening method for identifying antineoplastic drugs, comprising using bacteria from the strain CNCM 1-4815 for assessing the ability of drug candidates to trigger the lytic cycle of the phage comprising the protein of SEQ ID No: 1.

The present invention also pertains to a method of determining if a patient is likely to be a good responder to a treatment by chemotherapy or immune checkpoint blockade, comprising assessing the presence, in a biological sample from said patient, of a sequence having at least 80% identity with the protein of SEQ ID No: 1, wherein if such a sequence is present in the sample, the patient is likely to respond to the treatment.

The present invention also pertains to a method of determining if a patient is likely to be a good responder to a treatment by chemotherapy or immune checkpoint blockade, comprising measuring the levels of circulating CCR9+ CXCR3+CD8+ T cells during said treatment, wherein if said level is above a predetermined threshold, the patient is likely to respond to the treatment.

BRIEF DESCRIPTION OF THE DRAWINGS

FIG. 7. Increased accumulation of $CD8^+$ T cells in mLN and spleen post-oral gavages with E. hirae 13144. (A) Experimental setting. Mice are treated with broad spectrum antibiotics for 3 days before performing oral gavage with E. hirae (708 or 13144) and CTX ip injection. One day post-CTX, a second oral gavage with E. hirae is performed. 72 hours post-CTX, CD4+ and CD8+ T cells are isolated from mesenteric lymph node (mLN). Percentage of CD8+ (B) and CD4+(C) T cells in mLN after oral gavage with E. hirae 708 or 13144 and CTX treatment. (D) Experimental setting. Mice are treated with broad spectrum antibiotics for 3 days before performing oral gavage with E. hirae (708 or 13144) every three days for a total of 4 gavages. 5 days after the first oral gavage, mice are treated with CTX. One week post-CTX, CD8+ T cells are isolated from spleen. Percentage of CD8+ T cells (E) and CCR9+CXCR3+CD8 T cells (F) in spleen after oral gavage with E. hirae 708 or 13144 and CTX treatment. Student t'-test statistical analyses: * $p<0.05$,  $p<0.01$, * $p<0.001$.

FIG. 17. 13144 and TMP pulsed-DCs vaccination reduced tumor growth of MCA205. Tumor growth of MCA205 in mice vaccinated with DCs pulsed with gr1 peptides, TMP peptides and E. hirae 13144. (A) Mean±SEM of tumor sizes at different kinetics. (B) Tumor growth kinetics for each individual group of 5-10 mice. (C) Tumor sizes and statistical differences at time of sacrifice. Student t'-test or ANOVA statistical analyses: * p<0.05,  p<0.1, * p<0.001.

Figure 1:
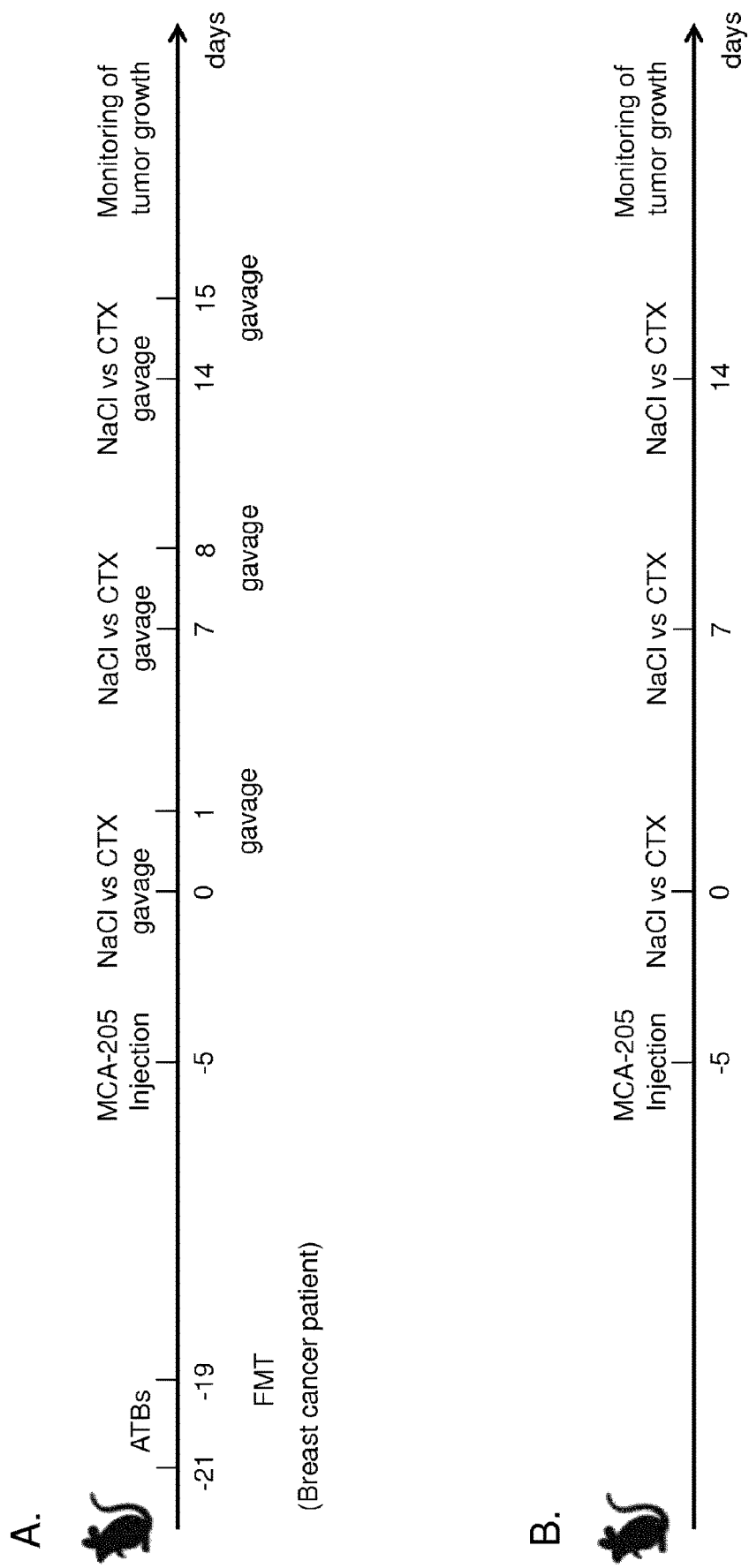
FIG. 1. Experimental setting. (A) Mice are treated with broad spectrum antibiotics (streptomycin, colistin, ampicillin and vancomycine) for 3 days before performing Fecal Microbiota Transplantation (FMT). 14 days post-FMT, MCA-205 sarcoma cell lines are inoculated in the right flank of mice ($8.10^5$ cells per mice). Chemotherapy (Cyclophosphamide, CTX-100 mg/kg) or saline solution (NaCl) is injected weekly ip, starting 5 days post tumor inoculation for a total of 3 injections. Oral gavage with E. hirae strain 13144 ($1.10^9$ bacteria) is performed the day of CTX injection as well as the day after. (B) Non FMT-treated SPF mice are used as control.
Figure 2:
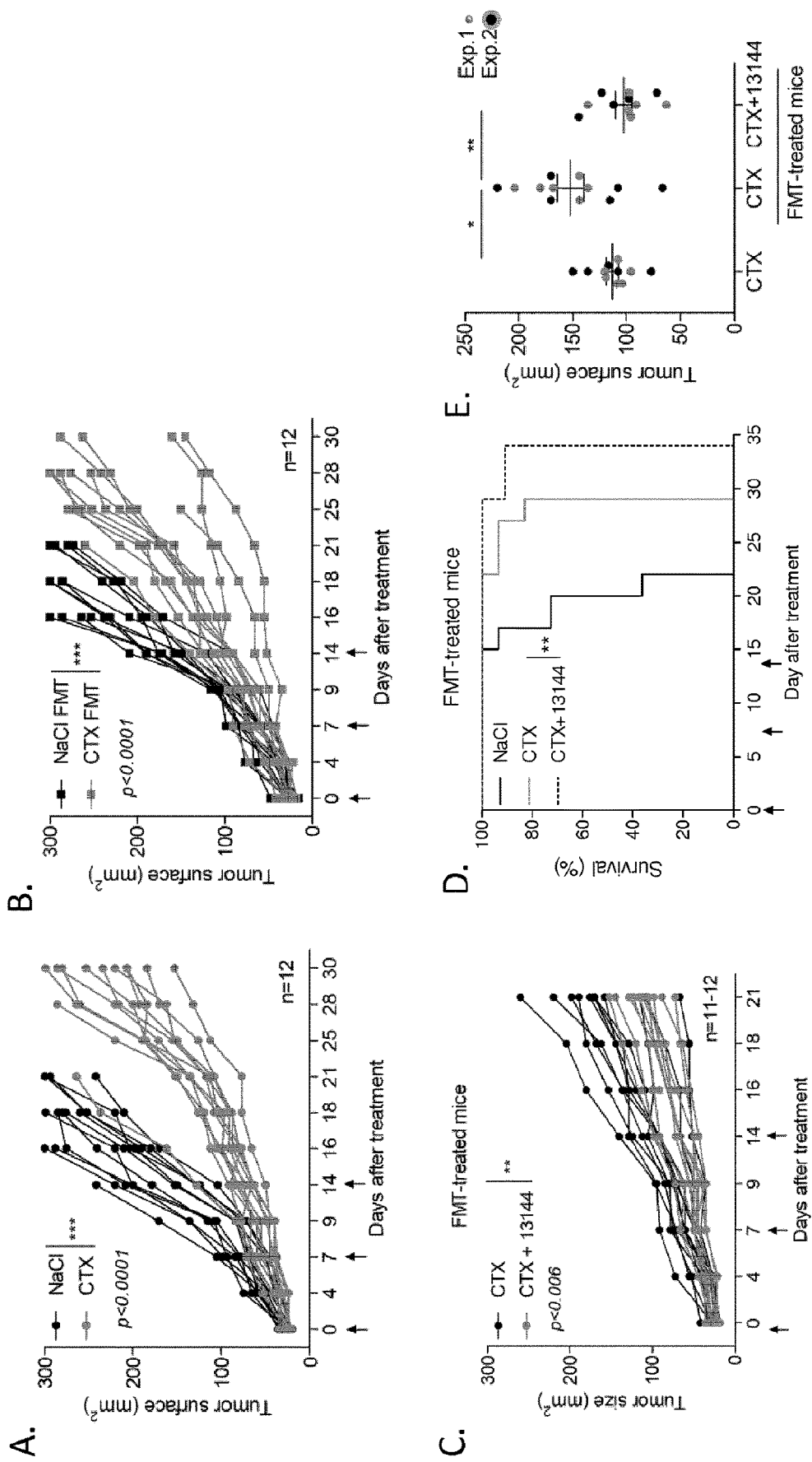
FIG. 2. Dysbiosis by FMT BC patient 1: Effectiveness of E. hirae 13144 to restore CTX-mediated antitumor effects. Tumor growth curves of MCA-205 sarcoma in SPF mice (A) vs FMT-treated mice (B) injected with 3 cycles of CTX vs NaCl. (C) Tumor growth curves of MCA-205 sarcoma in FMT-treated mice after oral gavage with strain E. hirae 13144 or NaCl as control. 2 independent experiments are depicted. (D) Overall survival of FMT-treated, MCA-205 sarcoma bearing mice treated with CTX or NaCl after oral gavage with strain E. hirae 13144. A typical survival curve is depicted for six mice per group. (E) Concatenated data of tumor sizes at day 21 post-CTX from 2 independent experiments are shown. Anova & Student t'-test statistical analyses: * $p<0.05$,  $p<0.01$, * $p<0.001$.
Figure 3:
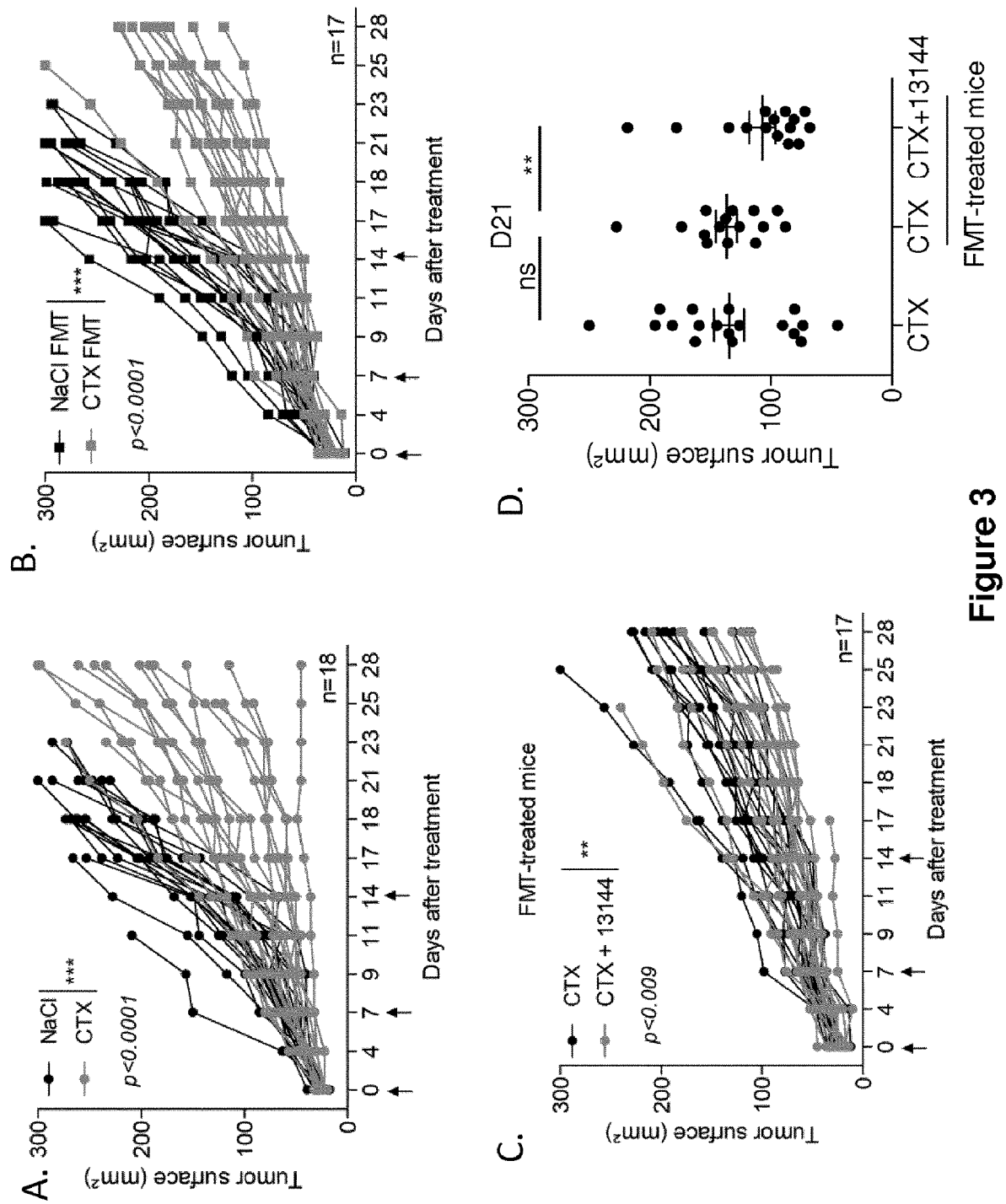
FIG. 3. No dysbiosis by FMT BC patient 2: E. hirae 13144 ameliorates the CTX-mediated antitumor effects. Tumor growth curves of MCA-205 sarcoma in SPF mice (A) vs FMT-treated mice (B) injected with 3 cycles of CTX vs NaCl. (C) Tumor growth curves of MCA-205 sarcoma in FMT-treated mice after oral gavage with strain E. hirae 13144 or NaCl as control. 2 independent experiments are depicted. (D) Concatenated data of tumor sizes at day 21 post-CTX from 2 independent experiments are shown. Anova & Student t'-test statistical analyses: * $p<0.05$,  $p<0.01$, * $p<0.001$.

A and C. Experimental setting. Mice (naive (C), sarcoma bearers (A)) were treated with broad spectrum antibiotics (streptomycin, colistin, ampicilin, vancomycin) for 3 days before performing oral gavage with *E. hirae* strain 13144 ($1.10^9$ bacteria) before and after systemic administration of cyclophosphamide (ip CTX-100 mg/kg) or saline solution (NaCl) at day 5 and 6 respectively, once (C) or three times on a weekly basis (A). One week later (C), purified CD8+ T cells splenocytes were restimulated ex vivo in a recall assay with bone marrow-derived DC loaded with saline or distinct heat killed bacteria strains. B. Tumor sizes at day 25 (sacrifice) of MCA-205 sarcoma in SPF C57BL/6 mice injected with 3 cycles of CTX vs NaCl after weekly oral gavages with various strains of *E. hirae*. D-E. Ex vivo recall assays. After in vivo exposure (C), splenic CD8+ T cells were restimulated with dendritic cells (DCs) pulsed with heat-inactivated bacteria (65° C. during 2 hours) (D) or peptides (E). IFNγ ELIspot was performed at 24 hours to enumerate IFNγ-secreting CD8+ T cells (spots) after co-culture. Each dot represents one mouse. F, G, H. Flow cytometry analyses of $H-2K^b$/TSLARFANI (SEQ ID No: 13) tetramer binding CTL in spleens (F, H) or in tumor draining lymph nodes (G) at 72 hours post-therapy (regimen in A and C), in naive (F, H) or tumor bearers (G). The percentages of TMP1 prophage2-specific CD8+ T cells are depicted among splenic CD8+ T cells (F, left panel, G, H, top panel) or in the gate of CCR9+ CXCR3+ T cells (F, right panel, G, bottom panel) or CCR9+ CTL (H, bottom panel). Each experiment involved one group of 10-15 mice from 2-3 independent experiments (B, D, E, F, H). A representative experiment out of 2 yielding similar results is shown in the kinetics study in G. Anova or Student t'-test statistical analyses: * p<0.05,  p<0.01, * p<0.001.

FIG. 28. Prophylactic and therapeutic immunization using Phage Tail Length Tape Measure Protein against sarcomas.

A-B. Prophylactic vaccinations. TLR3 ligand exposed DC were pulsed with peptides (irrelevant groups, individual TMP1 not mutated (TSLARFANI, SEQ ID No: 13) and TMP1 mutated in position 2 (TALARFANI, SEQ ID No: 216) or in position 3 (TSFARFANI, SEQ ID No: 217)) or heat-inactivated bacteria before inoculation sc in the right flank of naive mice, ten days apart. One month after second injection, sarcoma (MCA205) were implanted subcutaneous in the left flank. C-D. Therapeutic settings. Refer to FIG.

27A for the regimen where MCA205 tumor bearers were treated with CTX and gavaged with *E. hirae* 13144 or *E. coli* genetically modified to express TMP1 (TSLARFANI, SEQ ID No: 13), TMP1 mut2 (TALARFANI, SEQ ID NO: 216), TMP1 mut3 (TSFARFANI, SEQ ID NO: 217) or EGFP sequence (as ctrl). Longitudinal tumor growth kinetics (A, C top panel) or cross-sectional tumor sizes (B, C bottom panel) of MCA205 are depicted as means+SEM of tumor sizes at different time points (A, C top panel) or at sacrifice (B, C bottom panel) for 12-18 animals (A), gathered from 2-3 independent experiments. D. Flow cytometry analyses of H-2K$^b$/TSLARFANI (SEQ ID No: 13) tetramer binding CTL in spleens at sacrifice. The percentages of TMP1 prophage2-specific CD8+ T cells are depicted among splenic CD8+ T cells. Student t'-test or ANOVA statistical analyses: * $p<0.05$,  $p<0.1$, * $p<0.001$.

FIG. 29. Breadth of coverage (BOC) of the enterophage and clinical relevance of its molecular mimic GPD1-L in cancer patients.

A. BOC of the *E. hirae* and prophages genome in the MG reference catalog. 3027 metagenomes from 17 different datasets (referenced at the bottom, individual samples in columns) were screened for the presence of *E. hirae* strains and enterococcal phages genomes (featuring in rows). B-C. Percentages of stools with detectable *E. hirae* and/or *E. faecalis* colonies (B, top panel) and TMP in *E. hirae* and/or *E. faecalis* (B, bottom panel) colonies assessed by culturomics followed by PCR in 76 NSCLC and RCC bearing patients (cohort described in Routy et al. Science 2018) and corresponding Kaplan Meier curves indicating time to progression (C, top panel) or overall survival (C, bottom panel). Log-rank (Mantel-Cox) analysis with indicated p-value. D. Priming of naive CD8+ T cells from six HLA-A02*01 healthy volunteers with autologous monocyte-derived DC pulsed (or not) with 16 HLA-A02*01 binding TMP epitopes (Table 9, FIG. 24B and FIG. 37). Restimulation at day 7 with each of the 16 TMP peptides for IFNγ ELIspot assays and enumeration of positive spots. ANOVA statistical analyses: * $p<0.05$. E. Blast sequence alignment of immunogenic epitopes selected in D with the publicly available NCBI BLASTP suite and TCGA data set seaking >75% homology. Only epitope 10 (KLAKFASVV, SEQ ID No: 63) obtained a significant match and was identified in the sequence of GPD1-L protein. The match corresponds to sequence KLOKFASTV, having SEQ ID No: 188. The figure shows a fragment of GPD1-L sequence, having SEQ ID No: 212. F-H. Expression levels of GPD1-L gene product among bladder (F), lung adenocarcinoma (G), 530 renal cell cancer (H, according to HLA-A02*01 typing, bottom panel) patients from the TCGA data sets segregated according to the mean and Kaplan Meier curves of survival in univariate analysis. I-J. Time to progression following PD-1 blockade in second line therapy in 44 stage IIIC/IV NSCLC patients (CHUM validation cohort, I) validated with a second cohort of 62 stage IIIC/IV NSCLC patients (CGFL test cohort, J). Kaplan Meier curves for time to progression; patients were stratified according to the value value of the GPD1L expression. The cutoff was defined with an optimal cutoff strategy. K. Pearson correlations between GPD1-L expression and tumor immune infiltrates in all lung cancer type of TCGA assays (TCGA), lung adenocarcinoma (LUAD), lung squamous cells carcinoma (LUSC), CHUM and CGFL cohorts.

Figure 30E:
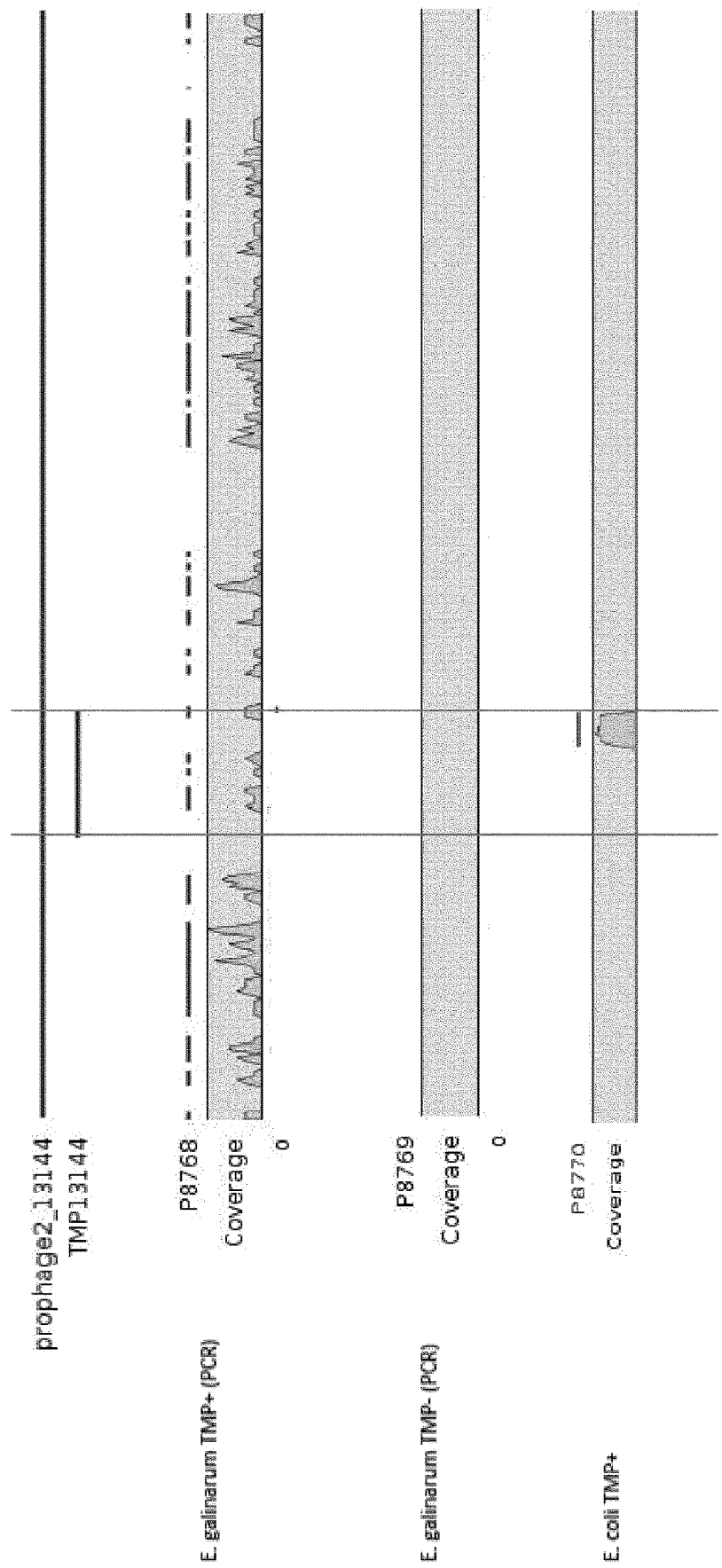

FIG. 30. Molecular mimicry between enterophage TMP and the oncogenic driver PSMB4 in mouse cancers.

A. Blast sequence alignment of the only one immunogenic epitope TSLARFANI (SEQ ID No: 13) selected in 27E with the publicly available TCGA data set seaking >70% homology. Only one hit (GSLARFRNI, SEQ ID No: 189) obtained a significant match and was identified in the sequence of PSMB4 protein (amino acids 65-107 of SEQ ID No: 225). B. Therapeutic settings comparing wild type versus knock in tumoral clones of MCA205. Id. as in FIG. 27A but mice were either inoculated with the WT MCA205 cell line or with distinct clones harboring a knock in mutation in position 3 of TSLARFANI (SEQ ID No: 13), and then, were treated with CTX+/−gavaged with *E. hirae* 13144 (or saline). Longitudinal tumor growth kinetics (B) or cross-sectional tumor sizes (B, right) of MCA205 are depicted as means±SEM of tumor sizes at different time points (top and bottom) or at sacrifice (right) for 6 animals/group, in a representative experiment out of 2 yielding similar conclusions. ANOVA statistical analyses: * $p<0.05$,  $p<0.1$, * $p<0.001$. C-D. In vivo excision-infection cycle of the *E. hirae* siphoviridae phage. Gavage with *E. hirae* before and after CTX followed by harvesting of ileal content, for cultivation and isolation of bacterial colonies, MALDI-TOF identification and PCR using TMP specific probe sets (C). Graph depicting the proportions of colonies for each species in naive and gavaged animals, with colonies harboring the TMP sequence in PCR (D). Results of 5 mice/group and >70 colonies identified and scrutinized in PCR. Also refer to FIG. 39. E. Alignment of phage genome with *E. gallinarum* harboring TMP sequence in PCR after sequencing of this strain. F-G. Culture of organoid with *E. hirae* (10$^8$) and *E. gallinarum* (10$^8$) during 1 hour followed by mafosfamide treatment (25 µg/ml). Six hours and 20 hours after mafosfamide treatment, supernatant were harvested for cultivation and isolation of bacterial colonies (F), MALDI-TOF identification and PCR using TMP specific probe sets (G). H. LEfSe analysis was performed on bacterial and viral species after MetaPhlAn2 analysis on localized breast cancer shotgun data, reporting the most discriminant ones (LDA score >2) in decreasing order for neoadjuvant palbociclib treatment on 10 patients from 83 included, the 73 others did not receive neoadjuvant CDK4/6 inhibitorss. Student t'-test or ANOVA statistical analyses: * $p<0.05$,  $p<0.1$, * $p<0.001$.

FIG. 31. Clading and genomic analysis of *E. hirae* strains.

A. Dendrogramm of the various strains based on 16S sequence similarities. B. Phylogenomic tree of 20 *E. hirae* isolates based on SNPs alignment. C. Comparative genomic analysis of 13144 strain against five complete *E. hirae* genomes. From the center to the outside: GC skew, GC content, 13144, IGR7, IGR11, ATCC 9790, 708, 13344 strains. Prophages positions appear in black.

Figure 32:
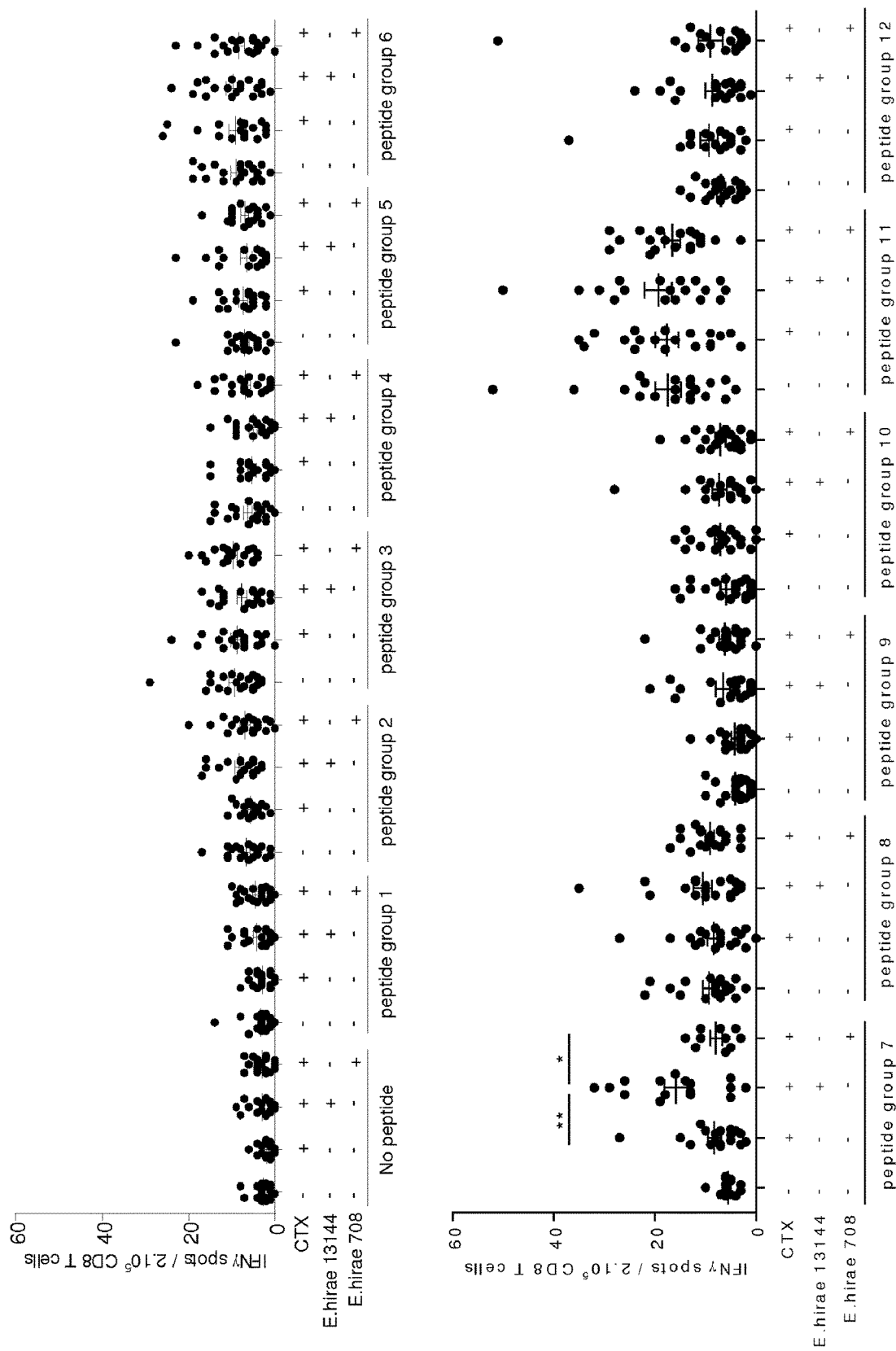

FIG. 32. Pre-identification of group 7 as the only immunogenic peptide group.

Naive mice were treated with broad spectrum antibiotics (streptomycin, colistin, ampicillin, vancomycin) for 3 days before performing oral gavage with *E. hirae* strain 13144 or 708 (1.10$^9$ bacteria) before and after systemic administration of cyclophosphamide (ip CTX-100 mg/kg) or saline solution (NaCl) at day 5 and 6 respectively. One week later, purified CD8+ T cells splenocytes were restimulated ex vivo in a recall assay with bone marrow-derived DC loaded with saline or distinct groups of peptides (refer to the list in Table 6). IFNγ ELIspot was performed at 24 hrs to enumerate IFNγ-secreting CD8+ T cells (spots) after co-culture. Each dot represents one mouse. Statistical analyses revealed that only group 7 reached significant response: Anova test: * $p<0.05$, ** $p<0.1$.

FIG. 33. Sequence of the TMP protein and comparative analysis of *E. hirae* 13144 prophage 2 protein sequence.

A. Whole TMP protein sequence of the 13144 prophage 2 (SEQ ID No: 1). B. Comparative analysis through a "heatmap" clustering based on a matrix of presence (black) and absence (white) of the 13144 prophages 2 protein sequences.

FIG. 34. Sequence alignment of the immunogenic epitope region within prophage 2 of *E. hirae* 13144.

The immunogenic peptide TSLARFANI (SEQ ID No: 13) from *E. hirae* 13144 was identified in experiments depicted and detailed in FIG. 27. The y axis presents the sequences of 6 other *E. hirae* strains in the same region tested in our models. 13144 and IGR7 lines corresponds to an amino acids 163-217 of SEQ ID No: 1. IGR11 line corresponds to SEQ ID No: 226. ATCC9790 line corresponds to SEQ ID No: 228. 13344 line corresponds to SEQ ID No: 230. 708 line corresponds to SEQ ID No: 231.

FIG. 35. Sub-cloning expression of part of the TMP gene in *E. coli*.

A. Amino acid sequences of TMP-FLAG (SEQ ID No: 213), TMP-mut2-FLAG (SEQ ID No: 214) and TMP-mut3-FLAG (SEQ ID No: 215) expressed in *E. coli* DH5a. Note that only the N-terminal part of the TMP protein, including the indicated variants of the epitope (underlined), was expressed as fusion protein with a C-terminal FLAG tag (italics). The underlined epitopes of TMP-FLAG (TSLARFANI), TMP-mut2-FLAG (TALARFANI) and TMP-mut3-FLAG (TSFARFANI) have SEQ ID Nos: 13, 216 and 217, respectively. B. Western blot analysis demonstrating expression of EGFP and TMP-FLAG in *E. coli* strains transformed with pDL28-P23-EGFP or pDL28-P23-TMP-FLAG, respectively.

FIG. 36. Sequence of the Phage Tail Length Tape Measure Protein in *E. hirae*. Genetic sequence of the whole TMP protein with binding areas for PCR primers indicated in italics. The displayed genetic sequence corresponds to nucleotides 9983 to 14503 of SEQ ID No: 2.

Figure 37:
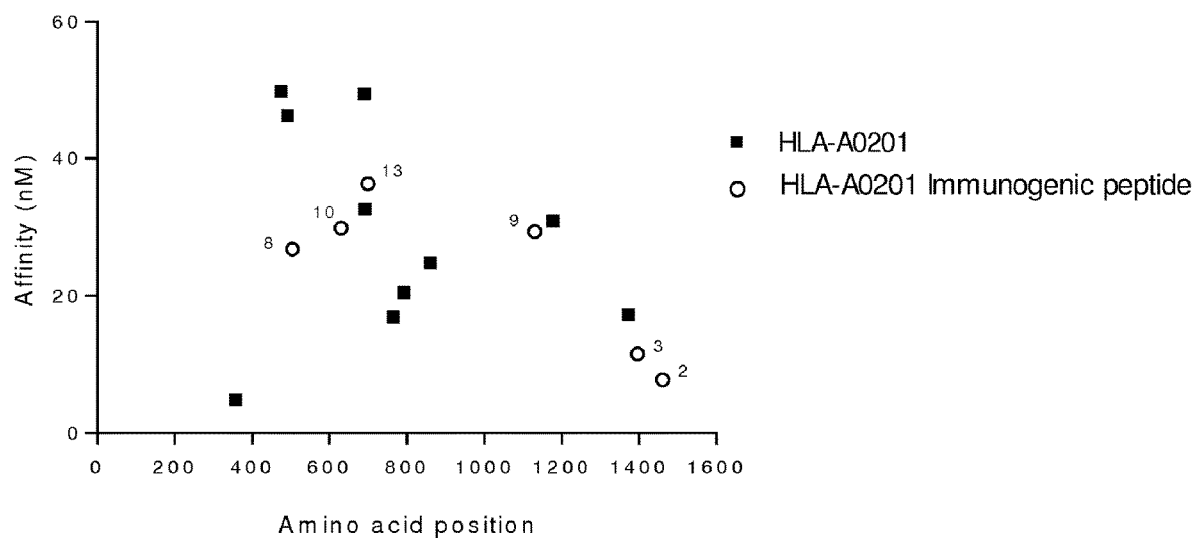

FIG. 37. Localization of the HLA-A02*01 binding and immunogenic epitopes in the GPD1-L protein and their affinity (refer to FIG. 30A).

All the HLA-A02*01 binding and/or immunogenic epitopes found in Table 9 and depicted in FIG. 29D are located in a precise region of the whole TMP protein, as indicated by the color code and the amino acid sequence position, as a function of its binding affinity to the MHC class I allele.

FIG. 38. Generation of pmsb4-mutated MCA205 cell lines by means of the CRISPR/Cas9 technology.

A. Schematic diagrams of Psmb4 cDNA, and the designed mutation sites. The target site of sgRNA and point mutations are indicated. The gRNA sequence corresponds to SEQ ID No: 205. B. Representative sequence electropherograms for the validation of Psmb4 mutation 2 and mutation 3 introduced by CRISPR/Cas9. Mutated amino acids are highlighted in grey. FIG. 38B provides an extract of wild type Pmsb4 amino acid sequence (SEQ ID No: 219), and its corresponding coding DNA sequence (SEQ ID No: 220); an extract of Psmb4 mutation 2 amino acid sequence (SEQ ID No: 221), and its corresponding coding DNA sequence (SEQ ID No: 222); and an extract of Psmb4 mutation 3 amino acid sequence (SEQ ID No: 223), and its corresponding coding DNA sequence (SEQ ID No: 224).

FIG. 39. Identification of ileal bacterial colonies with or without treatment composed of CTX+oral gavage with $10^9$ cfu *E. hirae* 13144.

PCR amplification of the TMP sequence (refer to FIG. 36) in each colony growing after seeding of ileal content in aerobic conditions to isolate Gram+ bacteria. A photograph of each agarose electrophoresis gel is shown for each animal. A depicts the results in 5 naive mice and B depicts the findings after CTX+oral gavage with the phage encoding bacterium. Each vertical lane corresponds to one bacterium identified in MALDI-TOF. Initials are detailed in the lower part of panel A. The positive control (Ctl+) represents the DNA of *E. hirae* 13144.

DETAILED DESCRIPTION OF THE PREFERRED EMBODIMENTS

In the present text, the following general definitions are used:

Gut Microbiota

The "gut microbiota" (formerly called gut flora or microflora) designates the population of microorganisms living in the intestine of any organism belonging to the animal kingdom (human, animal, insect, etc.). While each individual has a unique microbiota composition (60 to 80 bacterial species are shared by more than 50% of a sampled population on a total of 400-500 different bacterial species/individual), it always fulfils similar main physiological functions and has a direct impact on the individual's health:
- it contributes to the digestion of certain foods that the stomach and small intestine are not able to digest (mainly non-digestible fibers);
- it contributes to the production of some vitamins (B and K);
- it protects against aggressions from other microorganisms, maintaining the integrity of the intestinal mucosa;
- it plays an important role in the development of a proper immune system;
- a healthy, diverse and balanced gut microbiota is key to ensuring proper intestinal functioning.

Taking into account the major role gut microbiota plays in the normal functioning of the body and the different functions it accomplishes, it is nowadays considered as an "organ". However, it is an "acquired" organ, as babies are born sterile; that is, intestine colonisation starts right after birth and evolves afterwards.

The development of gut microbiota starts at birth. Sterile inside the uterus, the newborn's digestive tract is quickly colonized by microorganisms from the mother (vaginal, skin, breast, etc.), the environment in which the delivery takes place, the air, etc. From the third day, the composition of the intestinal microbiota is directly dependent on how the infant is fed: breastfed babies' gut microbiota, for example, is mainly dominated by Bifidobacteria, compared to babies nourished with infant formulas.

The composition of the gut microbiota evolves throughout the entire life, from birth to old age, and is the result of different environmental influences. Gut microbiota's balance can be affected during the ageing process and, consequently, the elderly have substantially different microbiota than younger adults.

While the general composition of the dominant intestinal microbiota is similar in most healthy people (4 main phyla, i.e., Firmicutes, Bacteroidetes, Actinobacteria and Proteobacteria), composition at a species level is highly personalised and largely determined by the individuals' genetic, environment and diet. The composition of gut microbiota may become accustomed to dietary components, either temporarily or permanently.

Dysbiosis

Although it can adapt to change and has a high resilience capacity, a loss of balance in gut microbiota composition may arise in some specific situations. This is called "dysbiosis", a disequilibrium between potentially "detrimental" and "beneficial" bacteria in the gut or any deviation to what is considered a "healthy" microbiota in terms of main bacterial groups composition and diversity. Dysbiosis may be linked to health problems such as functional bowel disorders, inflammatory bowel diseases, allergies, obesity, diabetes and also cancer. It can also be the consequence of a treatment, such as a cytotoxic treatment or an antibiotic treatment.

Antineoplastic Treatments

"Antineoplastic treatments" herein designate any treatment for cancer except surgery. They include chemotherapy, hormonal and biological therapies, radiotherapy and targeted therapies (such as c-KIT, EGFR or HER2/HER3 or MET or ALK inhibitors . . . ).

Chemotherapy

"Chemotherapy" is defined herein as the treatment of cancer with one or more chemotherapeutic agents. Chemotherapeutic agents are chemical molecules which act by killing cells that divide rapidly, one of the main properties of most cancer cells. Several categories of chemical agents exist:

- alkylating agents;
- spindle poisons such as mebendazole, colchicine;
- mitotic inhibitors (including taxanes (paclitaxel (Taxol®), docetaxel (Taxotère®)) and *vinca* alkaloids (e.g.: vincristine, vinblastine, vinorelbine, vindesine)),
- cytotoxic/antitumor antibiotics: such as anthracyclines (e.g.: doxorubicin, daunorubicin, adriamycine, idarubicin, epirubicin and mitoxantrone, valrubicin), *streptomyces* (e.g.: actinomycin, bleomycin, mitomycin, plicamycin)
- anti-metabolites (such as pyrimidine analogues (e.g.: fluoropyrimidines analogs, 5-fluorouracil (5-FU), floxuridine (FUDR), Cytosine arabinoside (Cytarabine), Gemcitabine (Gemzar®), capecitabine; purine analogues (e.g.: azathioprine, mercaptopurine, thioguanine, fludarabine, pentostatin, cladribine, capecitabine, clofarabine); folic acid analogues (e.g.: methotrexate, folic acid, pemetrexed, aminopterin, raltitrexed, trimethoprim, pyrimethamine),
- topoisomerase inhibitors (e.g.: camptothecins: irinotecan, topotecan, amsacrine, etoposide, etoposide phosphate, teniposide);
- DNA methyltransferase inhibitors: 2'-deoxy-5-azacytidine (DAC), 5-azacytidine, 5-aza-2'-deoxycytidine, 1-[beta]-D-arabinofuranosyl-5-azacytosine, dihydro-5-azacytidine;
- vascular disrupting agents, such as flavone acetic acid derivatives, 5,6-dimethylxanthenone-4-acetic acid (DMXAA) and flavone acetic acid (FAA);
- also other chemotherapeutic drugs such as aprepitant, bortezomib (Velcade®, Millenium Pharmaceuticals), imatinib mesylate (Gleevec®), carmustine (BCNU), lomustine (CCNU), tamoxifen, gefitinib, erlotinib, carboxyamidotriazole, efaproxiral, tirapazamine, xcytrin, thymalfasin, vinflunine.

Immune Checkpoint Blockers

In the present text, a "drug blocking an immune checkpoint", or "immune checkpoint blocker (ICB)" or "immune checkpoint blockade drug" designates any drug, molecule or composition which blocks an immune checkpoint of T lymphocytes. Such a drug reactivates the host immune system, and kills tumor cells indirectly by effector T lymphocytes. In particular, these terms encompass anti-CTLA-4 antibodies, anti-PD1 antibodies, anti-PD-L1 antibodies (such as Atezolizumab or Durvalumab) and anti-PD-L2 antibodies. More particularly, an ICB can be an anti-PD1 monoclonal antibody such as Nivolumab or Pembrolizumab. Other ICB include anti-Tim3, anti-BTLA, anti-VISTA, anti-CD38, anti-TIGIT, anti-GITR, anti-LAG3, anti-KIR antibodies, anti-OX40 antibodies, which also inhibit immune checkpoints.

Although the currently used drugs antagonizing CTLA-4, PD1, PD-L1, PD-L2, etc. are monoclonal antibodies, other molecules specifically binding to these could be used for the development of future ICB such as, for example, antibody fragments or specifically designed aptamers. Of course, the phrases "drug blocking an immune checkpoint", or "immune checkpoint blocker (ICB)" or "immune checkpoint blockade drug" encompass any therapy with active molecules that antagonize and immune checkpoint such as CTLA-4, PD1, PD-L1, PD-L2, etc., such as oncolytic viruses recombinant for anti-CTLA4, anti-PD1 or PDL1 Abs.

Immune-Targeting Antibodies for Activating Receptors

In the present text, a "drug activating an immunostimulatory receptor", designates any drug, molecule or composition which activates a T or NK cell receptor reactivating the host immune system, and killing tumor cells indirectly by effector T lymphocytes. In particular, it encompasses anti-ICOS antibodies, anti-OX40 antibodies, anti-CD137, anti-CD28 antibodies . . .

CDK4/6 Inhibitors

In the present text, a "CDK4/6 inhibitor" designates a cyclin-dependent kinase 4 and 6 (CDK4/6) inhibitor, such as palbociclib, ribociclib, and abemaciclib. These drugs are currently used to treat patients with hormone receptor (HR)-positive, human epidermal growth factor receptor 2 (HER2)-negative (HR+/HER2−) advanced breast cancer, but could also be used to treat other cancers, such as ovarian cancer and acute myeloid leukaemia.

Probiotics

"Probiotics" are micro-organisms that have claimed health benefits when consumed. Probiotics are commonly consumed as part of fermented foods with specially added active live cultures, such as in yogurt, soy yogurt, or as dietary supplements. Generally, probiotics help gut microbiota keep (or re-find) its balance, integrity and diversity. The effects of probiotics can be strain-dependent. Here we will use the phrase "anticancer probiotics" or the neologisms "oncobax" and "oncomicrobiotics" to designate any commensal composition that restores responsiveness to chemotherapy, PD1/PD-L1 blockade or combination of anti-CTLA4+anti-PD1 or PD-L1 Ab. In the context of the present invention, a "probiotic composition" is thus not limited to food or food supplements, but it generally designates any bacterial composition comprising microorganisms which are beneficial to the patients. Such probiotic compositions can hence be medicaments or drugs.

Cancer, Treatment, Etc.

As used herein, "cancer" means all types of cancers. In particular, the cancers can be solid or non solid cancers. Non limitative examples of cancers are carcinomas or adenocarcinomas such as breast, prostate, ovary, lung, pancreas or colon cancer, sarcomas, lymphomas, melanomas, leukemias, germ cell cancers and blastomas.

The immune system plays a dual role against cancer: it prevents tumor cell outgrowth and also sculpts the immunogenicity of the tumor cells. Drugs blocking an immune checkpoint can hence be used to treat virtually any type of cancer. Thus, the methods according to the invention are potentially useful for patients having a cancer selected amongst adrenal cortical cancer, anal cancer, bile duct cancer (e.g. periphilar cancer, distal bile duct cancer, intrahepatic bile duct cancer), bladder cancer, bone cancers (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancers (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancers (e.g. endometrial adenocarcinoma, adenocanthoma, papillary serous adenocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancers (e.g. hemangioma, hepatic-adenoma, focal nodular hyperplasia, hepatocellular carcinoma), lung cancers (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancers (e.g. seminoma, nonseminoma germ cell cancer), thymus cancer, thyroid cancers (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma). More particularly, the method according to the invention can be used for predicting and optimizing a patient's response to a medicament targeting an immune checkpoint, wherein the patient has a cancer selected from the group consisting of metastatic melanoma, non-small cell lung carcinoma (NSCLC), small cell lung cancer (SCLC), mesothelioma, bladder cancer, renal cell carcinoma, head and neck cancers, oesophageal and gastric cancers, rectal cancers, hepatocarcinoma, sarcoma, Wilm's tumor, Hodgkin lymphoma, ALK-neuroblastoma, (hormone refractory) prostate cancers and GIST.

Other definitions will be specified below, when necessary.

According to a first aspect, the present invention pertains to the use of a bacterial composition in a combined treatment for treating a cancer, wherein the bacterial composition comprises at least one bacterial strain which expresses the protein of SEQ ID No: 1 or a fragment thereof of at least 9, preferably at least 20 amino acids comprising at least one epitope selected from the group consisting of SEQ ID Nos: 13, 14, 53 to 188 and 209.

In the frame of this invention, the at least one bacterial strain present in the composition can be either a naturally occurring strain or an artificial, engineered strain obtained by gene technology or any other technique. Strains different from the *Enterococcus hirae* strain 13144 deposited on Nov. 7, 2013 at the CNCM under the number 1-4815 can be used according to the invention.

In the present text, a "bacterial composition" designates any composition comprising bacteria, especially live bacteria. The composition can comprise a pure culture of one single strain, a mix of several cultured strains and/or a complex material such as fecal material for performing Fecal Microbiota Transplantation (FMT). The composition can be a liquid composition. Alternatively, the composition can comprise freeze dried or lyophilized materials, which can be formulated or manufactured into or as an edible or friable product, e.g., a biscuit-like product, which can be e.g., crushed into a powder to dissolve in a drink or to insert into a tablet or a capsule. Alternatively, the bacterial composition can be in the form of a dry lozenge or a chewing gum or equivalent. Compositions according to the present invention can also be prepared and/or formulated in a powdered form, or equivalent; these formulations can be useful for storage in e.g., a tablet or capsule, or in an ampoule to e.g; crack open and dissolve in a liquid for, e.g., insertion, mixing or injection into a channel of a colonoscope or a naso-enteric tube and the like; or as a powder in a bag ready to add, for example as a solution which can be infused into a nasogastric tube (or equivalent), or a colonoscope, or a gastroscope etc. Components possibly present in a bacterial composition according to the invention (apart from the bacteria) include salts, buffers, nutrients, water, pharmaceutically acceptable excipients, cryoprotectants, etc.

Using the bacterial composition in a combined treatment for treating a cancer means that the bacterial composition is used in combination with an antineoplastic drug in order to potentiate or increase the effects of this antineoplastic drug. Non-limiting example of drugs that can advantageously be administered in combination with the bacterial compositions according to the invention include chemotherapy, especially alkylating agents (e.g. cyclophosphamide), immune checkpoint blockers (e.g., drugs antagonizing CTLA-4, PD1, PD-L1 or PD-L2 etc., used alone or in combination), immune-targeting antibodies for activating receptors (e.g., anti-ICOS, anti-OX40, anti-CD137, anti-CD28 antibodies), CDK4/6 inhibitors, etc. The physician will chose, depending on the context, what drug is to be administered to the patient in combination with the bacterial composition, as well as the therapeutic protocol (i.e., the sequence of administration of the antineoplastic drug(s) and the bacterial composition).

According to a preferred embodiment of the composition according to the invention, the at least one bacterial strain comprises a prophage genome encoding a protein with at least 80, preferably at least 90 and more preferably at least 95% identity with the protein of SEQ ID No: 1.

In a particular embodiment of the invention, at least one strain in the bacterial composition harbours a prophage genome with at least 80 and preferably at least 90 or 95% identity with the prophage of SEQ ID No: 2 (prophage of *E. hirae* 13144 identified as "prophage 2" in the experimental part below), so that the phage encoded by this prophage can in vivo infect the other strains of the composition and/or commensal bacteria of the gut microbiota of the patient to which the composition is administered.

The present invention also pertains to a bacterial composition comprising bacteria selected from the group consisting of:

(i) *Enterococcus hirae* strain 13144 deposited on Nov. 7, 2013 at the Collection Nationale de Cultures de Microorganismes (CNCM) under the number 1-4815, (ii) *Enterococcus hirae* strain IGR7 deposited on Aug. 31, 2017 at the CNCM under the number 1-5224, (iii) *Enterococcus hirae* strain IGR11 deposited on Nov. 27, 2017, at the CNCM under the number 1-5261, (iv) any other bacterial strain expressing a protein with at least 65, preferably at least 80 and more preferably at least 95% identity with a fragment of at least 20, preferably at least 30 and more preferably at least 40 nucleotides from the tail tape measure protein (TMP) of SEQ ID No: 1 (called "the TMP of prophage 2" in the experimental part below), and (v) mixtures of at least two of the strains recited in (i) to (iv).

According to one embodiment, this bacterial composition is used for treating a cancer.

The bacterial strains present in the composition according to the invention can belong to any bacterial family. Of course, since the bacteria are administered to a patient suffering from cancer, non pathogenic bacteria will be preferentially used. Hence, bacteria other than *Enterococcus hirae* strains can also be used according to the present invention.

As already mentioned, the bacterial composition is typically administered to a patient in need thereof in combination with an antineoplastic drug.

According to one embodiment, the bacterial composition of the invention further comprises *Enterococcus hirae* strain IGR4, deposited on Nov. 27, 2017, at the CNCM under the number 1-5260.

According to one embodiment, illustrated in the experimental part below, the composition comprises *Enterococcus hirae* strain 13144 (CNCM I-4815), *Enterococcus hirae* strain IGR7 (CNCM I-5224) and *Enterococcus hirae* strain IGR4 (CNCM I-5260).

According to a particular embodiment of the invention, the bacterial composition is used in combination with an antineoplastic drug capable of triggering the lytic cycle of a phage encoded by the prophage. Non-limitative examples of such a drug are mitomycin C, as illustrated in Example 8 below, as well as CDK4/6 inhibitors, as illustrated in Example 16.

According to one embodiment, the bacterial composition comprises at least one strain harbouring a prophage genome with at least 80 and preferably at least 95% identity with the prophage of SEQ ID No: 2, so that the phage encoded by this prophage can in vivo infect other strains of the composition and/or, possibly, other bacteria already present in the patient's gut microbiota.

Another aspect of the present invention is a method of increasing the immunogenicity of a bacterial strain of anti-cancer probiotic interest, by in vitro introducing into said bacterial strain a nucleotide sequence encoding the TMP of SEQ ID No: 1 of a fragment thereof comprising at least the peptides of SEQ ID Nos: 13 and 14, or a sequence encoding a peptide of at least 9, preferably at least 20 amino acids comprising at least one epitope selected from the group consisting of SEQ ID No: 53 to 187 or a sequence encoding a peptide of at least 9, preferably at least 20 amino acids comprising at least one epitope of SEQ ID No: 209. The peptides of SEQ ID Nos: 13 and 14 correspond to immunogenic epitopes binding to mouse H-2Kb, but they might also be immunogenic in humans harbouring appropriate HLA class I haplotypes capable of binding some of these sequences or broader sequences, shared across species. The sequences of SEQ ID No: 53 to 187 have been identified in silico as being epitopes from the TMP of SEQ ID No: 1 which are bound by human HLA molecules (see Table 9 below). SEQ ID No: 209 (KLX1KFASX2V with X1=A or Q and X2=V or T) corresponds to the TMP1 HLA-A*0201-restricted immunogenic epitope of sequence KLAKFASVV (SEQ ID No: 63), the human HLA-A*0201-restricted epitope from GPD1L of sequence KLQKFASIV (SEQ ID No: 188), as well as two hybrids of these two epitopes: KLAKFASTV (SEQ ID No: 210) and KLQKFASVV (SEQ ID No: 211). Advantageously, the bacterial strain of anti-cancer probiotic interest is transduced with a sequence comprising several epitopes, which can be presented by different HLA haplotypes, to that the resulting bacterial strain is immunogenic in patients of different HLA haplotypes.

According to one embodiment, the nucleotide sequence encodes at least KMVEILEEI (SEQ ID No: 55), RLL-KYDVGV (SEQ ID No: 56), LLGIYQSYV (SEQ ID No: 62), KLAKFASVV (SEQ ID No: 63) or ILVAITTTI (SEQ ID No: 66), which are HLA-A0201-restricted epitopes, the immunogenicity of which has been experimentally confirmed in humans (see Example 7 and FIG. 24B below). In a particular embodiment, the nucleotide sequence encodes at least KLAKFASVV (SEQ ID No: 63), KLQKFASTV (SEQ ID No: 188) or any other epitope of sequence KLX1KFASX2V with X1=A or Q and X2=V or T (SEQ ID No: 209).

According to one embodiment, the bacterial strain is transduced with a nucleic acid (for example, a plasmid) encoding a protein having 80%, 90% or 95%, preferably 97.5% and more preferably 98,7% identity with the TMP of SEQ ID No: 1, or encoding a fragment of said protein including at least one epitope as above-described. The skilled artisan will chose appropriate sequences (promoter etc.) so that the resulting bacterial strain expresses the TMP or fragment thereof.

According to one embodiment, bacteria of the strain are infected with a bacteriophage encoding a TMP with at least 80%, preferably at least 90% and more preferably at least 95% identity with the TMP of SEQ ID No: 1.

Again, any bacterial strain of interest can be used in this method, provided it is not highly pathogenic. In particular, bacterial strains already known for their probiotic interest can be engineered by in vitro infection with a bacteriophage or by transduction with a plasmid encoding the TMP or fragment thereof. Non-limitative examples of such bacteria include *Akkermansia muciniphila, Ruminococcacae, Faecalibacterium, Clostridium ramosum, Clostridium XVIII, Alistipes* species (*A. onderdonkii, A. finegoldii, A. shahii*), *Eubacterium* species, *Bacteroidales* species, *Methanobrevibacter smithii, Lactobacillus johnsonii, Bacteroides fragilis, Bacteroides thetaiotaomicron, Bacteroides salyersiae, Burkholderia cepacia, Burkholderia cenocepacia, Barnesiella intestinihominis,* Erysipeloclostridia and *Erysipelotrichaceae, Colinsella intestinalis, Collinsella takakaei, Eggerthella lenta/Coriobacteriaceae , Bifidobacteria (longum, breve, termophilus, adolescentis . . . )* and *E. coli*. More particularly, *Escherichia coli, Enterococcus gallinarum, Enterococcus faecalis* and *Enterococcus hirae* can advantageously be used as starting material to obtain a bacterial strain with increased immunogenicity through a method as above-described.

According to a particular embodiment of the above method, the bacteriophage has a genome comprising a nucleotide sequence of the SEQ ID Nos:2 or a sequence having at least 90% or at least 95% identity thereto. According to a preferred embodiment, the bacteriophage has a genome identical to the prophage of 39.2 kb present in *Enterococcus hirae* 13144 (CNCM I-4815).

According to a particular embodiment, the present invention pertains to a bacterial strain which has been obtained by a method as above-described. In particular, the invention pertains to a non-naturally occurring bacterial strain, obtained by in vitro infection of a probiotic strain with a phage encoding the TMP protein defined above, wherein the probiotic strain is not known to be infected by this bacteriophage in nature. According to another embodiment, the invention pertains to a non-naturally occurring bacterial strain obtained by transduction with a nucleic acid encoding the TMP protein defined above or a fragment thereof, by gene editing or by any other technology.

The bacterial strains according to the invention, engineered to have increased immunogenicity and improved anticancer properties, are advantageously used in the treatment of cancer.

These engineered bacterial strains, in particular those that express a protein, polypeptide or peptide comprising an epitope selected amongst SEQ ID Nos: 63, 188 and 209, can efficiently be used to treat cancer in a HLA-A*0201 patient.

As already mentioned, the bacterial compositions of the invention, including those comprising an engineered bacterial strain as above-described, are advantageously used in combination with an antineoplastic drug capable of triggering the lytic cycle of a phage encoded by a prophage present in bacteria and/or with an immune checkpoint blocker.

The present invention also relates to an immunogenic composition comprising a polypeptide comprising a sequence of at least 9 consecutive amino acids from the TMP of SEQ ID No: 1 or a sequence of SEQ ID No: 209 or a polynucleotide encoding the same. Such a composition can advantageously be used as an anticancer vaccine, either as a nucleotide sequence (mRNA or cDNA) or as a peptide stretch of at least 9 amino acids, for example between 9 aa (short peptides directly binding to the proper MHC class I grove) and 20 to 30 amino acids (long peptides cross presented by DC in their MHC class I and II molecules). Dendritic cells or artificial antigen presenting cells presenting this polypeptide or recombinant for this cDNA could serve as a plateform to prime and amplifiy naïve or effector memory T lymphocytes from a tumor or blood from a patient or a healthy volunteer.

According to a particular embodiment of the immunogenic composition according to the invention, the sequence of at least 9 consecutive amino acids from the TMP is a peptide which has been identified as likely to be presented by a MHC I human molecule, such as the peptides of SEQ ID No: 53-187. Specific immunogenic compositions according to the invention comprise the peptidic sequences of SEQ ID Nos: 55, 56, 62, 63 or 66, which have been demonstrated to be immunogenic in HLA-A2 individuals (example 7). According to another specific embodiment, the immunogenic composition comprises a peptide comprising a sequence of SEQ ID No: 63, SEQ ID No: 188 or SEQ ID No: 209 or a polynucleotide encoding the same. Such an immunogenic composition is particularly useful as an anticancer vaccine in a HLA-A*0201 patient, especially if this patient has a tumor exhibiting a high GPD1L expression level (measured at the mRNA or protein level).

According to a particular immunogenic composition according to the invention, the polypeptide is a short polypeptide (9-, 10-or 11-mer). When such short peptides are subcutaneously injected, they bind directly to MHC molecules of every cells present at the site of injection. According to this embodiment of the invention, a cocktail of peptides, comprising several TMP epitopes, can advantageously be used. It is to be noted that when several epitopes specific for the same HLA molecule are used together, the epitopes are in competition for the binding to the corresponding HLA molecule. Contrarily, by using a mix of different HLA-restricted epitopes (such as HLA-A*0201, HLA-A*2402, HLA-B*0702 or others), there will be no competition for HLA binding. Another advantage of such a cocktail of peptides is that it will be efficacious in a broader range of patients i.e., in individuals expressing any of the HLA molecules corresponding to the epitopes present in the cocktail.

According to another particular immunogenic composition according to the invention, the polypeptide is a long polypeptide of 20 to 50 amino acids, preferably 25 to 40 amino acids encompassing at least one 9-10 TMP immunogenic stretch selected amongst SEQ ID No: 53 to 187, flanked by 10-20 amino acids, which will be in vivo internalized and processed by antigen presenting cells. These cells will then present fragments thereof, thereby triggering an immunogenic response against TMP epitopes. Such long polypeptides are advantageously able to be cross-presented by local DC into not only MHC class I but also MHC class II molecules of the host. For example, chimeric polyepitope polypeptides, i.e., polypeptides comprising a concatenation of epitopes of the TMP, possibly separated by peptidic linkers, can be used. Of course, for the same reasons as mentioned in the above paragraph, a long polypeptide advantageously comprises different HLA-restricted epitopes. Such chimeric polyepitope polypeptides can also comprise epitopes from antigens different from the TMP, for example epitopes from tumor antigens.

The immunogenic compositions according to the invention also advantageously comprise appropriate adjuvants. The skilled artisan will chose, depending on the type of peptide and the type of application, the most appropriate adjuvant. Non-limitative adjuvant which can be used according to the present invention include Montanide, Flt3L, cyclophosphamide, DC and TLR or STING agonists.

According to one embodiment, the immunogenic composition comprises a polynucleotide encoding a polypeptide comprising a sequence of at least 9 consecutive amino acids from the TMP of SEQ ID No: 1. Such a composition can advantageously be used as an anticancer vaccine. Examples of polynucleotide compositions according to the invention include naked DNA, mRNAs encoding TMP, RNA loaded nanoparticles and recombinant viruses (such as lentiviruses, oncolytic viruses adenoviruses, poxviruses etc.). Of course, the considerations mentioned above regarding the advantages of mixing epitopes specific for different HLA molecules in polypeptide compositions apply when designing the polynucleotides to be included in the compositions according to the invention. Alternatively, the epitopes can be selected and personalized according to the HLA haplotype of the patient (Table 9).

According to another aspect, the present invention pertains to a cell composition comprising antigen presenting cells (APC) which have been pulsed ex vivo with a bacterial composition as above described or with an immunogenic composition according to the invention. Such a cell composition can advantageously be used for cell therapy of cancer patients.

According to another of its aspects, the present invention relates to a MHC multimer, for isolating T-cells with high affinity for the TMP of SEQ ID No: 1. In such a MHC multimer, MHC molecules are preferably bound to a peptide selected from the group consisting of SEQ ID No: 53 to 187, for example to at least one peptide selected amongst those of SEQ ID Nos: 55, 56, 62, 63 and 66, or to at least one peptide of SEQ ID No: 188 or 209. MHC multimers according to the invention range in size from dimers to octamers (e.g.: tetra, penta, hexamers) or use even higher quantities of MHC per multimer (e.g., dextramers). Particular MHC multimers according to the invention are HLA-A*0201/KLAKFASVV (SEQ ID No: 63) multimers, HLA-A*0201/KLOKFASTV (SEQ ID No: 188) multimers, HLA-A*0201/KLQKFASVV (SEQ ID No: 211) multimers and HLA-A*0201/KLAK-FASTV (SEQ ID No: 210) multimers (e.g., tertramers or dextramers).

Another cell composition according to the present invention comprises CD4+ or CD8+ T cells specific for the TMP of SEQ ID No: 1. Cells comprised in such a composition can be obtained either by cell sorting (using, for example, a MHC multimer as above-described) followed by ex vivo expansion, or by transduction of T lymphocytes with a cDNA encoding a TCR with a high avidity for TMP. Examples of protocols that can be used to obtain such compositions are disclosed in examples 10 and 11 below.

As already mentioned, the immunogenic compositions and the cell compositions described above can be used for treating a cancer. In such a treatment, they can be used alone or combined with peptidic or nucleotide vaccines as described above and/or combined with antineoplastic treatments such as chemotherapy, for example an alkylating agent such as cyclophosphamide, or immune checkpoint blockers, especially anti-PD1/PD-L1/PD-L2 antibodies.

The present invention also pertains to the use of a bacteriophage expressing a protein having at least 90, preferably at least 95-98.7% identity with the TMP of SEQ ID No: 1 for treating a cancer. Such a bacteriophage is preferably formulated in a pharmaceutically acceptable composition, which can be administered per os or intratumorally.

According to a particular embodiment of the bacteriophage composition of the invention, the bacteriophage has a genome comprising a nucleotide sequence of SEQ ID NOs: 2 or a sequence having at least 90% or 95% identity thereto.

When treating a cancer patient, a bacteriophage composition according to the invention can advantageously be administered in combination with a drug blocking an immune checkpoint, for example in combination with anti-PD1/PD-L1/PD-L2 antibodies.

As explained in the experimental part below, the inventors found that the HLA-0201-restricted epitope KLAKFASVV (SEQ ID No: 63), shares a 78% sequence homology with an epitope (KLQKFASTV, SEQ ID No: 188) of the glycerol-3 phosphate dehydrogenase 1 like protein (GPD1L, gene encoded on 3p22.3), and it is conceivable that cross-reactivities between TMP phage specific TCR and self tissues or tumor tissues overexpressing GPD1L account for the anticancer effectiveness of the phage delivered in the context of the invention. The bacterial compositions, the immunogenic compositions, the cell compositions and the bacteriophage compositions of the invention are thus particularly useful for treating a tumor overexpressing GPD1L, i.e., having mRNA levels of GPD1L superior to levels expressed in paired normal tissues (for example lung cancer versus surrounding "healthy" lung parenchyma). Tumors overexpressing GPD1L would indeed be considered as electively eligible for an oral therapy with E. hirae 13144 or EH IGR7 or EH IGR11 or a combination of all the 3 strains, or with any other bacterium recombinant for the TMP of SEQ ID No: 1 or a fragment thereof comprising SEQ ID No: 63, with or without intradermal boosts with TMP phage-related HLA restricted-peptides or nucleic acid or other vaccine modality. This applies to lung cancers, melanoma, tumors of the digestive tract, bladder cancer, RCC and breast cancer or any tumor expressing foetal antigens.

Another aspect of the present invention is a screening method for identifying antineoplastic drugs, comprising assessing the ability of drug candidates to trigger the lytic cycle of the phage comprising the TMP of SEQ ID No: 1 when they are incubated with bacteria from the strain CNCM 1-4815 (or any other bacterial strain harbouring a prophage genome with at least 80 and preferably at least 90% or 95% identity with the prophage of SEQ ID No: 2). When performing this method, the skilled artisan can use different concentrations of the drug candidates and measure the phage excision at several time points of incubation.

The present invention also pertains to theranostic methods for determining if a patient is likely to be a good responder to a treatment by chemotherapy or immune checkpoint blockade, all based on the results disclosed below showing the importance of the phage TMP protein expressed by the strain CNCM I-4815 in the patient's response to the treatment. These methods are particularly useful to determine if a patient having a cancer such as NSCLC, RCC, bladder cancer, pancreas cancer, colorectal cancer and breast cancer is likely to be a good responder to a treatment by chemotherapy or immune checkpoint blockade. More particularly, such a method can advantageously be used for a patient at diagnosis of a NSCLC or RCC prior to immunotherapy with an ICB.

According to one embodiment of this aspect of the invention, the theranostic method of the invention comprises assessing the presence, in a biological sample from said patient, of a sequence having at least 80%, 90% or 95% identity with the TMP of SEQ ID No: 1. According to this method, the patient is considered as likely to respond to the treatment if such a sequence is present in the sample. Non-limitative examples of biological samples which can be used for performing this method are the tumor genome, intratumoral bacterial load, fecal phages, fecal bacteria containing the phages, feces samples, bronchoalveolar samples, buccal samples and sputum.

More specifically, this method can be performed by PCR amplification of specific sequences and comprise the following steps:
(i) cultivating a stool sample from the patient in aerobic conditions in a permissive medium to allow isolation of enterococci colonies,
(ii) performing a PCR on several cultivable isolated colonies with a pair of primers specific for a fragment of SEQ ID No: 1, and
(iii) detecting the amplified fragment.

More precisely, in step (ii), the PCR can be done within each E. gallinarum, E. hirae and E. faecalis isolated stool colony, or at least in 3 to 5 of them. For example, the PCR can be performed with the primers of SEQ ID Nos: 191 and 192, generating an amplicon of 1026 bp.

The present invention also pertains to a method of determining if a patient is likely to be a good responder to a treatment by chemotherapy or immune checkpoint blockade, comprising measuring, for example by flow cytometry or TMP tetramer-binding T lymphocytes, the levels of circulating $CCR9^+CXCR3^+CD8^+$ T cells during said treatment, wherein if said level is above a predetermined threshold, the patient is likely to respond to the treatment.

According to a particular embodiment, a MHC multimer as above-described is used to assess the presence of T cells specific to the protein of SEQ ID No: 1, in a biological sample from a cancer patient. The presence of such T cells in the sample indicates that the patient is likely to respond to the treatment. More particularly, when this method is performed for assessing whether a HLA-A*0201 patient is likely to be a good responder to a treatment by chemotherapy or immune checkpoint blockade, a HLA-A*0201/SEQ ID No: 209 multimer can be used.

According to another embodiment, the theranostic method of the invention comprises assessing the level of GPD1L mRNA or the level of GPD1L protein in the tumor, wherein if said level is above a predetermined threshold, the patient is likely to respond to the treatment.

Of course, the physician or skilled technician can combine the above methods to refine the prognosis that a patient will respond to the treatment, for example by assessing both the GPD1L expression level in the tumor and the presence of T cells specific for KLAKFASVV (SEQ ID No: 63), or the GPD1L expression level and the presence of a sequence having a high percentage of identity with the TMP of SEQ ID No: 1.

If, when performing a theranostic method as above-described, the patient is not identified as likely to respond to a treatment by chemotherapy or immune checkpoint blockade, a probiotic treatment with a bacterial composition according to the present invention can advantageously be administered to the patient to increase his/her chances to respond to the treatment. Another preconditioning treatment to increase the patient's response is a vaccination with an immunogenic composition as above-described.

Other characteristics of the invention will also become apparent in the course of the description which follows of the biological assays which have been performed in the framework of the invention and which provide it with the required experimental support, without limiting its scope.

EXAMPLES

Some of the experiments illustrating the present invention are described two times in the following examples, showing the continued research effort made by the inventors in the past years, which led to a more precise knowledge of the mechanism explaining the effects of *E. hirae* strains 13144, IGR7 and IGR11 and to the design of newly engineered strains with anti-tumor properties.

Materials and Methods

For each experiment illustrated in FIGS. 1 to 26, the materials and methods used to perform the experiment are detailed in the figure legend.

The following table summarizes the *E. hirae* strains referred to in examples 1 to 11 below.

TABLE 1

| Example | Strain | Origin | Deposit number |
|---|---|---|---|
| 1-9 | 13144 | Murine-CTX-treated stools of lung cancer patients | CNCM I-4815 |
| 1, 5, 9 | IGR 1 | | CNCM I-5260 |
| 1, 9 | IGR 4 | | CNCM I-5224 |
| 1, 3, 5, 9 | IGR 7 | | CNCM I-5261 |
| 1, 9 | IGR 10 | | |
| 1, 5, 9 | IGR 11 | | |
| 2, 3, 5, 6 | 708 | Human-Unknown | |
| 2, 3, 5 | EH17 (13344) | Human-Blood | |
| 1, 3, 5 | 10815 (ATCC 9790) | Type strain CIP 53.48$^T$ | ATCC 9790 |
| 9 | 5348 | Human-Unknown | |
| | 7030 | Human-Liver abscess | |
| | 12607 | Environmental-RiskManche project | |
| | 13150 | Environmental-Water | |
| | 13152 | Environmental-Water | |

TABLE 1-continued

| Example | Strain | Origin | Deposit number |
|---|---|---|---|
| | 13153 | Environmental-Water | |
| | 13155 | Environmental-RiskManche project | |
| | 13161 | Environmental-Cockle | |
| | 13343 | Conservation liquid of kidney | |
| | 13346 | Human-Urine | |
| | 13347 | Blood culture | |

Strains used in this study. Strains called "IGR" were isolated by U1015 INSERM at Gustave Roussy, Villejuif, in 2017, anonymously from non small cell lung cancer patients at diagnosis about to be treated with nivolumab as a second line therapy. 708 comes from INRA but was originally sent by a spanish collaborator more than 10 years ago. All the other strains come from Dr Vincent Cattoir, director of the reference center for commensal and pathogenic enterocci, CHU de Rennes—Hôpital Ponchaillou-Service de Bact ériologie-Hygiène hospitalière-2 rue Henri Le Guilloux —35033 RENNES Cedex.

The following materials and methods were also used for performing the experiments reported in Examples 12 to 16 below.

Cell Culture, Reagents and Tumor Cell Lines

MCA-205 WT were cultured at 37° C. with 5% $CO_2$ in RPMI 1640 containing 10% FCS, 2 mM L-glutamine, 100 UI/ml penicillin/streptomycin, 1 mM sodium pyruvate and MEM non-essential amino acids (henceforth referred to as complete RPMI1640). All reagents were purchased from Gibco-Invitrogen (Carlsbad, CA, USA).

Mice

All animal experiments were carried out in compliance with French and European laws and regulations. The local institutional board approved all mouse experiments (permission numbers: 2016-109-7450). Experiments were performed in accordance with Government and institutional guidelines and regulations. Female C57BL/6 were purchased from Harlan (France). Mice were used at an age between 7 and 12 weeks of age. All mouse experiments were performed at the animal facility in Gustave Roussy Cancer Campus where animals were housed in specific pathogen-free conditions.

Antibiotic Treatments

Mice were treated during 3 days with an antibiotic solution (ATB) containing ampicillin (1 mg/ml), streptomycin (5 mg/ml), colistin (1 mg/ml) (Sigma-Aldrich) and vancomycin (0.25 mg/ml) added in the sterile drinking water of mice. Antibiotic activity was confirmed by cultivating fecal pellets resuspended in BHI+15% glycerol at 0.1 g/ml on COS (BD Columbia Agar with 5% Sheep Blood) plates for 48 h at 37° C. in aerobic and anaerobic conditions. In the context of bacterial transplantation experiments, mice received 3 days of ATB before undergoing bacterial transplantation the next day by oral gavage using animal feeding needles.

Tumor Challenge and Treatment

Syngeneic C57BL/6 mice were implanted with $0.8 \times 10^6$ MCA-205 WT sarcoma cells subcutaneously and treated intraperitoneally (i.p.) when tumors reached 20 to 35 $mm^2$ in size with CTX (100 mg/kg). Depending on the experimental setting, mice were injected once or 3 times at 1-week interval. Tumor size was routinely monitored every 3 days by means of a caliper.

Gut Colonization with Dedicated Commensal Species

*Enterococcus hirae* 13144 were originally isolated from spleens of SPF mice treated with CTX in our laboratory. *E. hirae* 708 was provided by INRA (P. Langella), while *E. hirae* 13344, ATCC9790 were provided by Prof. Cattoir, CHU de Caen, France. *L. plantarum* was provided by Prof. Ivo Gomperts Boneca, Institut Pasteur strain repository, France. All *E. hirae* IGR strains were isolated from NSCLC patient stools in our laboratory, according to patient informed consent and local IRB approval (study Oncobiotics). All bacteria were grown on COS plates for 24 h-48 h at 37° C. in aerobic conditions. Colonization of ATBs pre-treated mice was performed by oral gavage with 100 µl of suspension containing $1\times10^9$ bacteria. For bacterial gavage: suspensions of $10^8$ CFU/mL were obtained using a fluorescence spectrophotometer (Eppendorf) at an optical density of 600 nm in PBS. Depending on the experimental setting, 2 or 6 bacterial gavages were performed for each mouse: the first, the same day as CTX injection, and then 24 h after the injection of CTX. The efficacy of colonization was confirmed by culturing the feces 48 h post-gavage. Fecal pellets were harvested and resuspended in BHI+15% glycerol at 0.1 g/ml. Serial dilutions of feces were plated onto COS plates and incubated for 48 h at 37° C. in aerobic and anaerobic conditions. After 48 h, the identification of specific bacteria was accomplished using a Matrix-Assisted Laser Desorption/Ionisation Time of Flight (MALDI-TOF) mass spectrometer (Andromas, Beckman Coulter, France).

Culture and Propagation of Bone Marrow-Derived Dendritic Cells

Bone marrow-derived dendritic cells (BM-DCs) were generated by flushing bone marrow precursors from the femurs and tibia of female C57Bl/6 WT mice aged of 8 to 12 weeks. Bones were collected in sterile PBS, washed in alcohol and Iscove's medium (IMDM, Sigma-Aldrich) baths, extremities of bones were cut and flushed using a 26 G needle. After red blood cell lysis, cells were cultured in IMDM supplemented with 10% of FCS+2 mM L-glutamine+100 UI/ml penicillin/streptomycin+50 µM 2-mercaptoethanol (Sigma-Aldrich) (referred herein as complete IMDM medium) at $0.5\times10^6$/ml and treated with 40 ng/ml of GM-CSF (supernatant of GM-CSF transfected-cells J558) and 10 ng/ml of recombinant interleukin-4 (IL-4) for BM-DCs (from Peprotech). Cells were split at day 3 and used in experiments on day 7 or 8.

Test of Memory TC1 Immune Response and H2-$K^b$ Restricted-Peptides on Splenic CD8+ T Cells by ELISpot IFNγ

IFN-γ ELISPOT assay was performed in 96-well PVDF bottomed sterile plates (Millipore MSIP S4510) by using a IFN-γ ELISPOT kit (Cell sciences, Newburyport, Etats-Unis) according to the manufacturer's instructions. After PVDF membrane activation with ethanol 35%, plates were coated overnight with capture antibody to IFN-γ and washed before incubation of blocking buffer during 2 h. BM-DC cells ($1\times10^5$/well) were infected with heat-inactivated (2 h at 65° C.) bacterial strains (*E. hirae* 13144, *E. hirae* 708, *E. hirae* 13344 and *L. plantarum*) at a multiplicity of infection 1:10 (MOI) or pulsed with peptides (20 µg/ml) and were added together with CD8+ T cells ($2\times10^5$/well) and incubated for 20 h at 37° C. Cells were then removed and plates were developed with a detection antibody to IFN-γ (biotinylated) during 1 h30 and streptavidin-alkaline phosphatase during 1 h. Finally, substrate of streptavidin (BCIP/NBT buffer) were incubated 5-20 min. Spots were counted by using CTL Immunospot Analyzer (Germany).

Mice Vaccination

After DCs differentiation, these DCs were activated with poly I:C (10 µg/ml, Invivogen) overnight before infection with heat-inactivated (2 h at 65° C.) bacterial strains (MOI 10) or pulsed with peptides (20 µg/ml, peptide 2.0). After 6 hours of incubation with bacteria or 1 hour of incubation with peptides, BM-DCs were washed 3 times with PBS before subcutaneous injection in the right flank of mice ($1.5\times10^5$ cells per mice). Mice were vaccinated twice at 10 days apart and challenged 4 weeks after the second vaccination with the minimal tumorigenic dose of MCA-205 tumor cells in left flank.

Flow Cytometry Analyses

In experiments without tumor, spleens were harvested 7 days after the injection of CTX. In tumor growth experiments, spleens, tumors and tumor draining lymph node were harvested at different time points, 7, 14 and 21 days after the first injection of CTX into mice bearing MCA-205 tumors. Excised tumors were cut into small pieces and digested in RPMI medium containing Liberase TM at 25 µg/mL and DNase1 at 150 UI/ml (Roche) for 30 minutes at 37° C. and then crushed and filtered twice using 100 and 40 µm cell strainers (BD). Lymph nodes and spleen were crushed in RPMI medium and subsequently filtered through a 70 µm cell strainer. Two million splenocytes, tumor cells or lymph node cells were pre-incubated with purified antimouse CD16/CD32 (clone 93; eBioscience) for 15 minutes at 4° C., before membrane staining. Dead cells were excluded using the Live/Dead Fixable Yellow dead cell stain kit (Life Technologies). Antimouse antibodies for CD3 (145-2C11), CD4 (GK1.5), CD8 (eBioH35-17.2), CXCR3 (CXCR3-173), CCR9 (CW-1.2), and TMP specific tetramer (BD, BioLegend, eBioscience and Cliniscience) were used. Stained samples were acquired on Canto II 7 colors cytometer (BD) and analyses were performed with FlowJo software (Tree Star, Ashland, OR, USA).

Human T Cell Responses to HLA-A02*01 Restricted-TMP Epitopes

Cytapheresis cones were collected from healthy volunteers (EFS, Etablissement français du sang) and peripheral blood mononuclear cells (PBMC) were separated using a Ficoll Hypaque gradient. We selected only donors with HLA-A02*01 haplotype determined by flow cytometry with anti-HLA-A2 antibodies. PBMC were washed and resuspended in the separation medium (PBS, 1 mM EDTA, 2% human AB+ serum) for magnetic bead separation. CD14+ monocytic cells (human CD14 MicroBeads, Miltenyi) were enriched from $75\times10^6$ PBMC and cultured at $0.5\times10^6$/ml in IMDM supplemented with 10% human AB+ serum, 1% of 2 mmol/L glutamine (GIBCO Invitrogen), 1000 IU/ml GM-CSF and 1000 IU/ml IL-4 (Miltenyi). Cells were split at day 3 and used in experiments on day 6 or 7. Monocytes were seeded in 96-well plates at $1\times10^5$ cells/well either alone or in the presence of peptides (20 µg/ml), and incubated for 2 hour at 37° C., 5% $CO_2$. The remaining autologous PBMC fractions were enriched for CD8+ T cells (CD8+ T Cell Isolation Kit, human, Miltenyi). The enriched CD8+ T cells were washed, counted and resuspended at $1\times10^5$ cells/well in RPMI-1640 supplemented with 10% human AB+ serum, 1%2 mMol/L glutamine, 1% penicillin/streptomycin (GIBCO Invitrogen) and 50 U/mL IL-2 (Proleukin). Monocyte-peptide/T cell co-cultures were incubated for one week at 37° C., 5% $CO_2$ (medium was changed every 2 days). Then, the pools of cells were seeded in 96-well ELIspot plates at $2\times10^5$ cells/well and restimulated with or without peptides (20 µg/ml) or anti-CD3/anti-CD28 coated beads (1 µL/mL, Dynabeads T-Activator, Invitrogen) as a positive control for 20 h at 37° C. IFN-γ ELISPOT assay were performed in 96-well PVDF bottomed sterile plates (Millipore MSIP S4510) by using a IFN-γ ELISPOT kit (Cell sciences, Newburyport, Etats-Unis) according to the manufacturer's instructions.

Stool Detection of Phage TMP Sequence by PCR

We cultivated the stools (of patients) or ileal material (mice) after several dilutions in aerobic conditions and permissive medium to allow isolation of enterococci colonies (according to a procedure described in (Samb-Ba et al., 2014)). We performed a PCR of the TMP sequence in each single cultivable *Enterococcus* colony. One colony was put in 100 µl of nuclease-free water to release the bacterial DNA and PCR was performed with 5 µl of DNA, 12.5 µl of PCR master mix (Thermoscientific), 5 µl of nuclease-free water and 1.25 µl of each TMP primers (20 UM). PCR products were separated on 1.5% agarose gel containing ethidium bromide and revealed by UV exposition. The sequence of primers are: forward 5'-ACTGCAGCCGTAAAATGGGA-3' ID No: reverse 5'-(SEQ 191) and TCCGTATCGTTTGCCAGCTT-3' (SEQ ID No: 192) (amplicon 1026 bp).

Generation of TMP-Expressing *E. coli*

A DNA fragment containing the P23 promoter sequence was generated by two complementary primers (5'-CAATAAAAAATCAGACCTAAGACT-GATGACAAAAAGAGCAAATTTTGATAAAATAGTATT AGAATTAAATTAAAAAGGGAGGCCAAATATAG-3' (SEQ ID No: 193) and 5'-GATCCTATAT-TTGGCCTCCCTTTTTAATTTAATTCTAATACTATTT-TATCAAAATTTGCTCT TTTTGTCATCAGTCT-TAGGTCTGATTTTTTATTGCATG-3' (SEQ ID No: 194)). The sequence was then inserted into SphI/BamHI-digested vector pDL278 (Addgene 46882, gift from Gary Dunny (LeBlanc et al., 1992) to generate vector pDL278-P23. A part of the TMP gene (N-terminal 1185 nucleotides of TMP, including the epitope TSLARFANI (SEQ ID No: 13), fused to a C-terminal FLAG-tag) was amplified from *E. hirae* 13144 genomic DNA (5'-TCCGGATC-CATGGCACAAAGTAAAACAGTCAAAGCG-3', (SEQ ID No: 195) 5'-CAGGAATTCTTACTTGTCGT-CATCGTCTTTGTAGTCACGTAGTAAACTAT-CACGTAATCG AACTTC-3' (SEQ ID No: 196)) and inserted into BamHI/EcoRI-digested vector pDL278-P23 to generate vector pDL278-P23-TMP-FLAG. Mutations in the epitope were introduced using the QuikChange Lightning Kit (Agilent). Primers 5'-AACGAGCTAAGGCAGTAGCAGCTGTATCTGCA-GAC-3' (SEQ ID No: 197) and 5'-GTCTGCAGATA-CAGCTGCTACTGCCTTAGCTCGTT-3' (SEQ ID No: 198) were used to mutate position 2 (S to A, pDL278-P23-TMP-mut2-FLAG), primers 5'-ATT-AGCAAAACGAGCGAAGGAAGTAGCAGCTGTATC TG-3' (SEQ ID No: 199) and 5'-CAGATACAGCTGC-TACTTCCTTCGCTCGTTTTGCTAAT-3' (SEQ ID No: 200) were used to mutate position 3 (L to F, pDL278-P23-TMP-mut3-FLAG). To generate the control plasmid pDL278-P23-EGFP, EGFP was amplified from pCIB1(delt-aNLS)-pmGFP (Addgene 28240, gift from Chandra Tucker (Kennedy et al., 2010)) using primers 5'-CTTGGATC-CATGGTGAGCAAGGGCGAG-3' (SEQ ID No: 201) and 5'-CAGGAATTCCTACATAATTACACACTTTGTC-3' (SEQ ID No: 202) and inserted into BamHI/EcoRI-digested vector pDL278-P23. Plasmids were transformed into chemically competent *E. coli* DH5a (NEB) and the presence of plasmids with the correct insert was verified by sequence analysis (5'-CCCAGTCACGACGTTGTAAAACG-3' (SEQ ID No: 203) and 5'-GAGCGGATAACAATTT-CACACAGG-3' (SEQ ID No: 204)). Expression of EGFP and TMP-FLAG in *E. coli* was verified by western blot analysis using antibodies targeting GFP (Cell Signaling, 2956) or FLAG (Sigma-Aldrich, F7425), respectively.

CRISPR/Cas9-Mediated Mutations of Mouse Psmb4 in MCA205 Cells

Wild type MCA205 cell line was purchased from the American Type Culture Collection (ATCC, Manassas, VA, USA) and was maintained in RPMI-1640 medium (Thermo Fisher Scientifc, Inc., Waltham, MA, USA) supplemented with 10% FBS (hermo Fisher Scientifc, Inc), 100 U/ml penicillin and 100 µg/ml streptomycin (Thermo Fisher Scientifc, Inc.) at 37° C. For the CRISPR knock in mutations, we designed the gRNA (sequence AGATATTGCG-GAAACGAGCC (SEQ ID No: 205)) by using the CRISPR design tool developed by the Zhang lab (http://crispr.mit-.edu/). Oligonucleotides containing the designed sequence were synthesized (Sigma) and ligated into the pX458 backbone (Addgene #48138, (Ran et al., 2013)) containing the Cas9 gene (human codon-optimised and fused with 2A-GFP allowing for selection) under a CBh promoter and the cloned sgRNA under a U6 promoter. Homology templates (sequence attached) containing the mutation sites were synthesized by Invitrogen GeneArt Gene Synthesis (Thermo Fisher Scientifc, Inc.). The cloned pX458 plasmid and synthesized homology arms were cotransfected into MCA205 cells by means of lipofectamine 3000 (Thermo Fisher Scientifc, Inc.) following the manufacture's protocol. Forty-eight hours after transfection, GFP-positive cells were sorted to 96-well plates as single cells before surviving clones were expanded in duplicated conditions, one for frozen storage at-80 and the other for genomic DNA extraction. The targeted region in genomic DNA from clones was further amplified by PCR using the Phusion® High-Fidelity PCR Master Mix (New England BioLabs; pswich, MA, USA) and primers 5'CTCAGGGACCCTTTTCACGA 3' (SEQ ID No: 206) and 5'CCCACTCCCTGTTCTACACA 3' (SEQ ID No: 207), and purified with the Monarch® DNA Gel Extraction Kit (New England BioLabs) before being sent to Eurofins Genomics GmbH (BERSBERG GERMANY) for sequencing with the primer 5'GGACCCTTTTCACGATTCAGG 3' (SEQ ID No: 208). According to sequence results, positive clones were expanded and subjected to DNA extraction for validating sequences. Transfected single cell clones that did not harbor the designed mutations were used as "WT" clones.

Genome Sequencing and Analysis

The whole genome sequence of 5 *E. hirae* (13144, 708, 13152, 13344 and EH-17) strains was determined with PacBio technology (GATC Biotech, Konstanz, Germany). Genomic DNA was isolated from 15 other *E. hirae* isolates using the using the Quick-DNA fungal/bacterial miniprep kit (Zymo Research, Irvine, CA) according to the manufacturer's recommendations. After DNA shearing, the DNA libraries were prepared using the NEBNext Ultra DNA library prep kit for Illumina (New England Biolabs, Ipswich, MA) and sequenced as paired-end reads (2×300 bp) using an Illumina MiSeq platform and the MiSeq reagent kit version 3. The Illumina reads were trimmed using Trimmomatic (Bolger et al., 2014), quality filtered with the Fastx-toolkit (http://hannonlab.cshl.edu/fastx_toolkit/) and assembled using SPAdes (Bankevich et al., 2012). Protein sequences were predicted using prokka v1.11 software (Seemann, 2014). Prophage regions were detected using PHAST software. Predicted proteins were annotated using BLASTp against the National Center for Biotechnology Information (NCBI) non-redundant (NR) database.

Phylogenomic and Comparative Genomics

Single nucleotide polymorphism between 20 *E. hirae* genomes was investigated using the parsnp program (Treangen et al., 2014) and strain 13144 genome sequence as a reference. Phylogenetic analysis was performed by considering the 47,303 polymorphic sites retained in the core genome of the 20 genomes. Maximum likelihood phylogeny was constructed using Fastree (Guindon et al., 2010). Phylogenetic tree was visualized using figtree (http://tree.bio.ed.ac.uk/software/figtree/). Complete Proteome sequences of 20 E. hirae strains were compared using by BlastP and pairwise alignments using ClustalW. We clustered the E. hirae homologous genes using orthoMCL (Li et al., 2003) on the translated protein sequences of all predicted genes with a conservative parameter value of 70% amino acid sequence identity and 50% sequence coverage. The determination of the different unique core genomes was based on the homology clusters found by orthoMCL.

Statistical Analyses

Data analyses and representations were performed either with Prism 6 (GraphPad, San Diego, CA, USA). Tumor size differences were calculated either using Anova or dedicated software (https://kroemerlab.shinyapps.io/TumGrowth/). Briefly, tumor growth was subjected to a linear mixed effect modeling applied to log pre-processed tumor surfaces. P-values were calculated by testing jointly whether both tumor growth slopes and intercepts (on a log scale) were different between treatment groups of interests. Survival probabilities were estimated using the Kaplan-Meier method, best cutoffs for continuous variables were chosen using the median value or an optimal cutoff approach. Survival curves were evaluated using the log-rank test. All reported tests are two-tailed and were considered significant at P-values <0.05. The normalized gene expression values (FPKM-UQ) and the corresponding clinical data were downloaded from the TCGA data portal. For the survival analysis patients were grouped by the median expression of GPD1L across per cancer type datasets and by predicted HLA-alleles (Charoentong et al., 2017). Hazard ratio (HR) and 95% confidence interval (CI) for overall survival (OS) and progression-free survival (PFS) were calculated with Cox regression analysis. The tumor-infiltrating immune cell compositions were determined using CIBERTSORT (absolute mode) (Newman et al., 2015) and were compared with gene expression using Pearson correlation.

Example 1: Different Strains of E. hirae Exhibit Distinct Immunogenic Potential and Antitumor Effects We first tested our E. hirae isolates in a more physiological setting of dysbiosis than the one caused by the 14 day-administration of a broad spectrum antibiotics. We indeed transferred feces (FMT) from two breast cancer patients exhibiting or not a deviated repertoire of the gut microbiome (and a distinct prognosis) into ATB-treated recipients and compensated their dysbiosis with different strains of adjunctive E. hirae (FIG. 1) attempting to restore full blown efficacy of CTX (as shown in eubiotic mice). While the FMT from a dysbiotic BC patient confered resistance to CTX compared with eubiotic littermates (FIGS. 2A-B), live EH13144 was very effective at restoring the efficacy (FIGS. 2C-E). In a second example of FMT from a different BC patient (exhibiting no overt dysbiosis (FIGS. 3A-B), the effects mediated by live EH13144 were also significant (FIG. 3C-D). However, in a similar setting, other strains of E. hirae (IGR1 and IGR11), cultivated from stools of lung cancer patients were not immunogenic (FIG. 4A-C), although as effective as EH13144 to induce IL-1B and IL-12 production by BM-DC (not shown).

Figure 4:
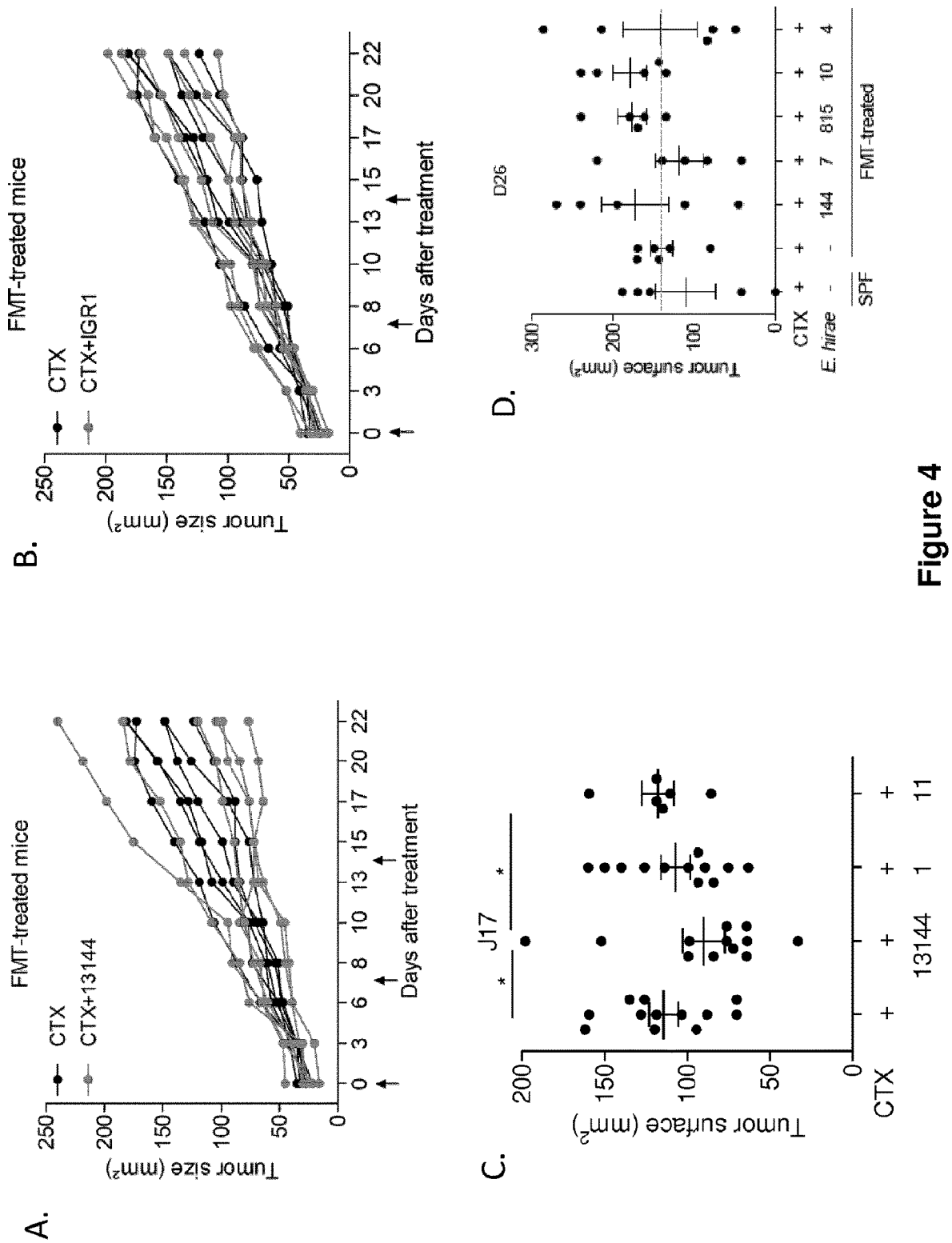
FIG. 4. E. hirae IGR1, IGR10 and 10815 failed to efficiently boost CTX tumoricidal activity in a dysbiotic FMT setting. Tumor growth curves of MCA-205 sarcoma in FMT-treated mice after oral gavage with strain E. hirae 13144 (A), IGR1 (B) or NaCl as control. A typical curve is depicted for six mice per group. (C) Concatenated data of tumor sizes at day 17 post-CTX from 1-2 independent experiments are shown. (D). Comparaison of various strains of E. hirae for their capacity to control tumor growth. Identification and discovery of two novel strains EH IGR 4 and 7 which display efficacy comparable to EH 13144. EH10815 fails to work and that may be related to a mutation residing in TMP2 (see below FIG. 13B). Student t'-test statistical analyses: * $p<0.05$,  $p<0.01$, * $p<0.001$.
Figure 5:
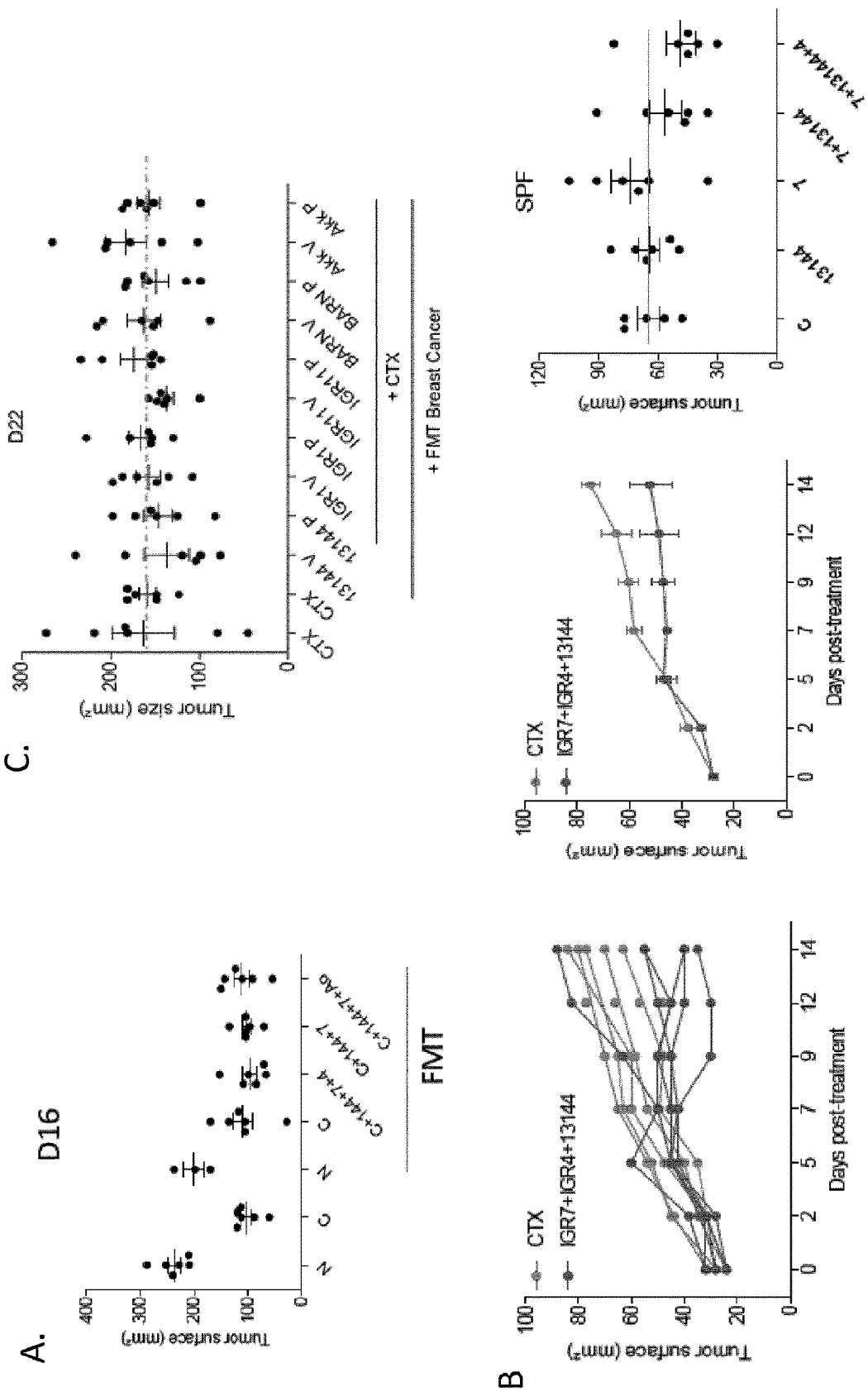
FIG. 5. The combination of EH13144+ IGR4+ IGR7 is superior to EH13144 leading compound. (A) Tumor surface of MCA-205 sarcoma in FMT-treated mice after oral gavage with strain E. hirae 13144, IGR4, IGR7, Actinomycetes spp (Ao) and injected with 3 cycles of CTX (C) vs NaCl (N). Each dot is one mouse/tumor. (B) Tumor growth curves of MCA-205 sarcoma in SPF mice of the best group, means+ SEM of tumor sizes at each time point and tumor sizes at sacrifice (C: CTX). Each dot is one mouse/tumor. Anova statistics indicating significant differences between CTX and the triple combination. (C) Tumor surface of MCA-205 sarcoma in FMT-treated mice after oral gavage with strains EH13144, IGR1, IGR11, Barnesiella or Akkermansia and injected with 3 cycles of CTX. Bacterial strains are used alive (V) or pasteurized (P). For pasteurization, bacteria are incubated 30 min at 70° C. and frozen at −80° C. at least 6 hours.

In addition, EH10815 did not mediate antitumor effects while E. hirae (IGR4 and IGR7), cultivated from stools of lung cancer patients were also immunogenic, as observed with 13144 (FIG. 4 D). Moreover, the combination of EH13144, IGR4 and IGR7 is superior to EH13144 leading compound (FIG. 5).

Figure 6:
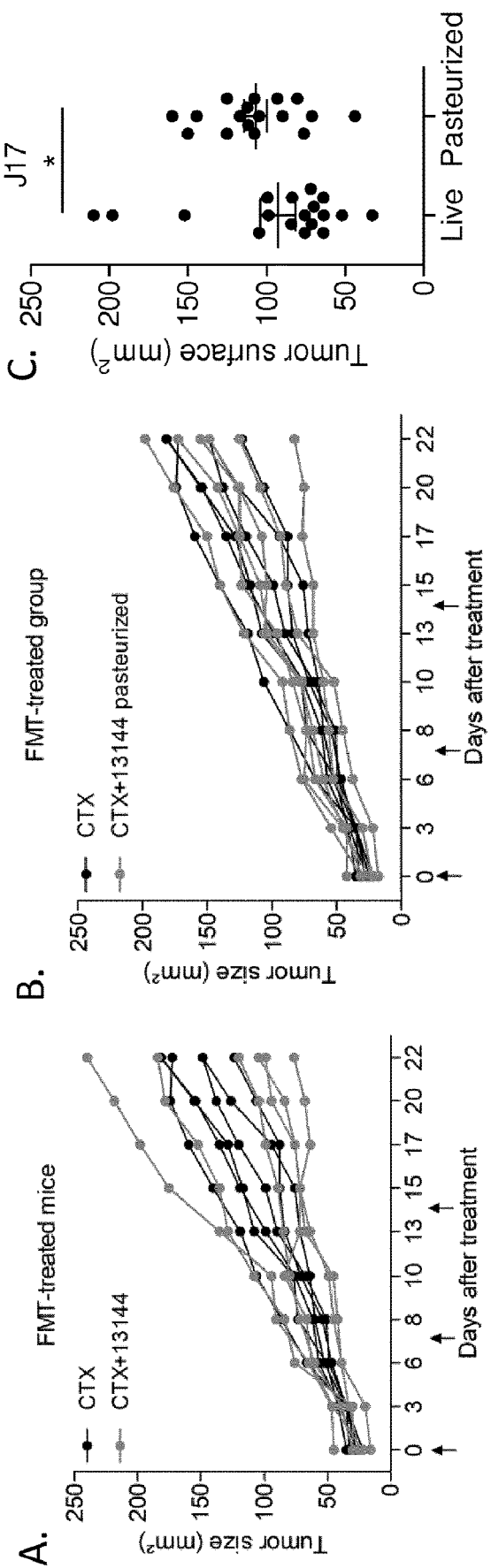
FIG. 6. Mouse E. hirae 13144 mediates its efficacy only when used alive. Tumor growth curves of MCA-205 sarcoma in FMT-treated mice after oral gavage with strain E. hirae 13144 alive (A), pasteurized (B) or NaCl as control. A typical curve is depicted for six mice per group. (C) Concatenated data of tumor sizes at day 17 post-CTX from 3 independent experiments are shown. Student t'-test statistical analyses: * $p<0.05$,  $p<0.01$, * $p<0.001$.

Interestingly, pasteurized EH13144 was far less effective than its live counterpart and failed to restore CTX tumoricidal activity in a dysbiotic FMT (FIG. 6).

We conclude that EH13144 have unique properties to boost CTX immune and tumoricidal activity against MCA205 sarcoma in not only ATB-but also FMT-induced patients' dysbiosis.

Example 2: E. hirae 13144 Amplifies CD8+Tc1 Cells in the Mesenteric Lymph Nodes and Spleens Cross-Reactive with EH708

Figure 8:
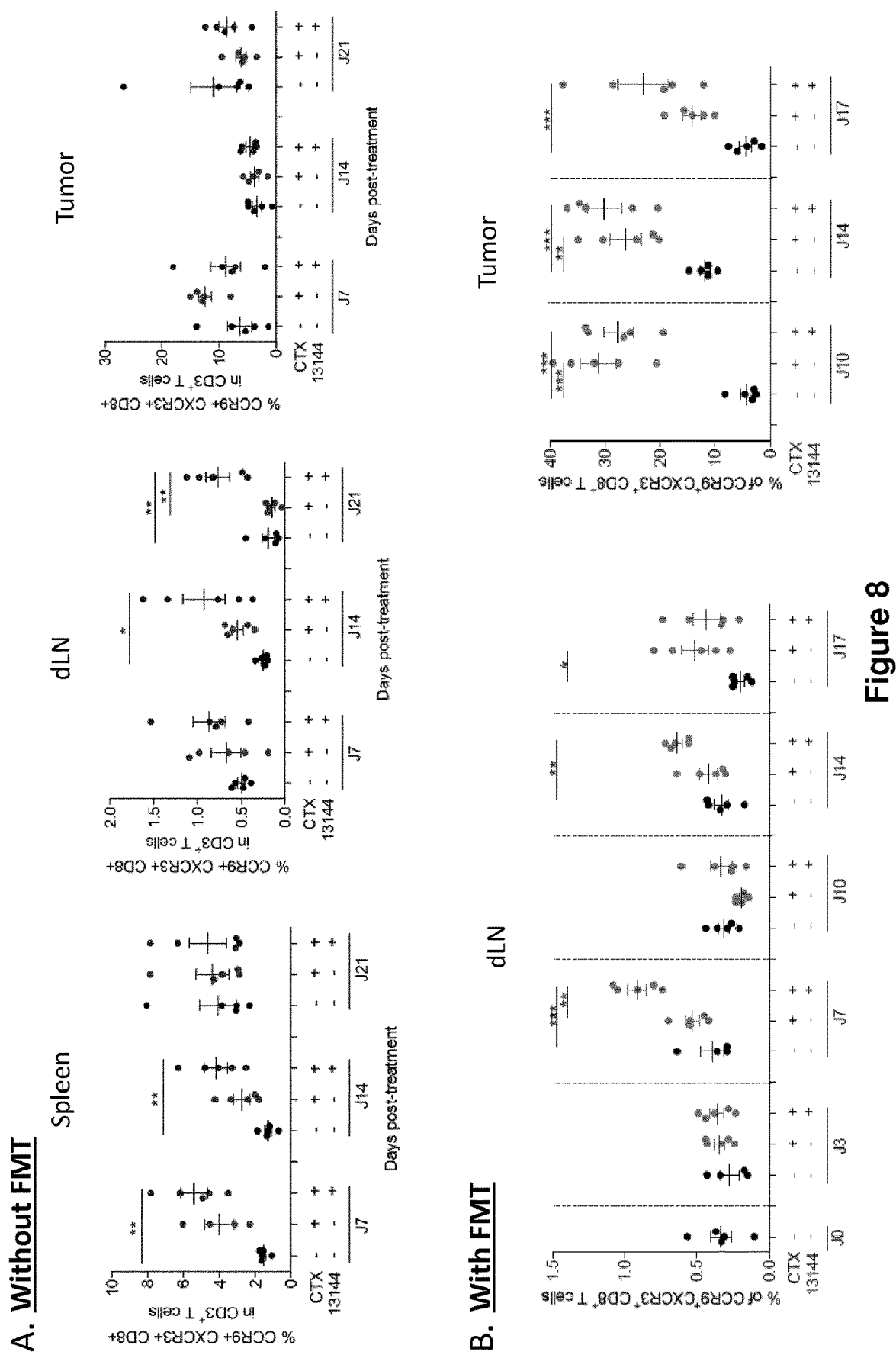
FIG. 8. Sustained accumulation of CD8+CCD9+ CXCR3+ T cells in tumor beds post oral gavage with EH13144: considering CD8+CXCR3+CCR9+ as a tumor associated-biomarker of sustained anticancer responses with OncoBax. (A) SPF mice were treated with ATB for 3 days and then oral gavages with EH13144 before and after CTX systemic administration, every other week for 3 weeks. Mice were sacrificed 7, 14 and 21 day after the first CTX treatment to harvest spleen, tumor draining lymph node (dLN) and tumor (MCA205 (B) FMT-treated mice were subjected to oral gavages with EH13144 before and after CTX systemic administration, every other week for 3 weeks. Mice were sacrificed the day of CTX treatment and 72 hrs post-CTX 1, 2, 3 (day J0, J3, J7, J10, J14, J17) to harvest dLN and tumor (MCA205). Flow cytometry analyses of CD45+ cells gating on CD8+CD3+ analyzing the percentages of CCR9+ CXCR3+ double positive cells are presented. A representative experiment of 3 groups comprising 5 mice/group. Anova statistical analyses: *p<0.05,  p<0.01, * p<0.001.
Figure 9:
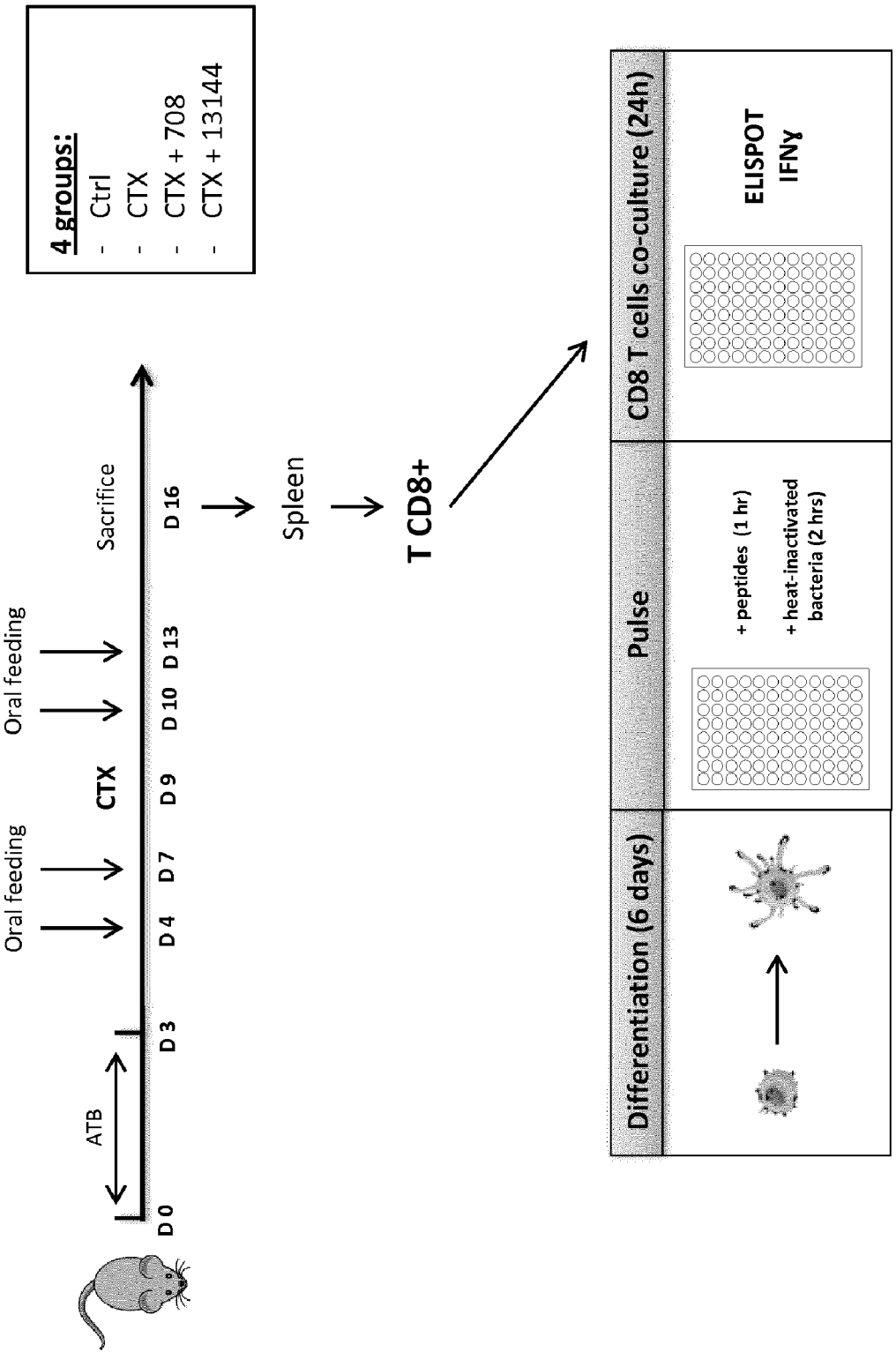
FIG. 9. Experimental immunization protocols to elucidate the immunogenicity of EH peptides. Mice are treated with broad spectrum antibiotics for 3 days before performing oral gavage with E. hirae (708 or 13144) every three days for a total of 4 gavages. 5 days after the first oral gavage, mice are treated with CTX. One week post-CTX, CD8+ T cells are isolated from spleen. These CD8+ T cells are incubated with dendritic cells (DCs) pulsed with 20 µg/ml of peptides (during 1 hour) or with heat-inactivated bacteria (during 6 hours). Inactivation of bacteria consists in incubation at 65° C. during 2 hours. After 24 hours of culture, ELIspot of IFNγ is performed.
Figure 10:
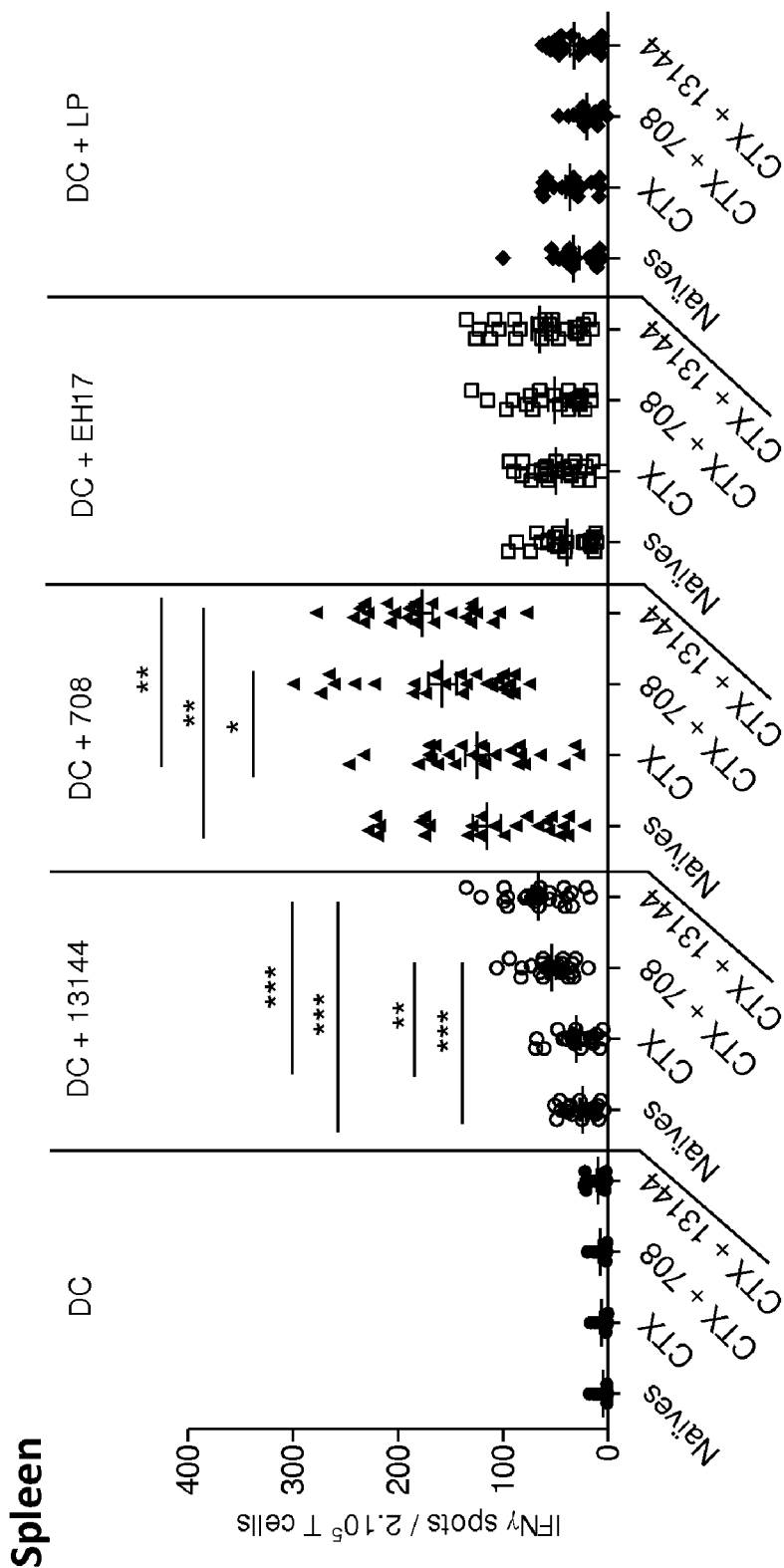
FIG. 10. Cross-reactivity between the two E. hirae 708 and 13144 species for CTL splenic reactivity. Number of IFNγ spot representing IFNγ-secreting CD8+ T cells after co-culture with DCs pre-incubated with or without heat-inactivated bacteria (708, 13144, EH17 and L. plantarum). The corresponding experimental setting is indicated in FIG. 9. Student t'-test statistical analyses: * p<0.05,  p<0.01, * p<0.001.
Figure 11:
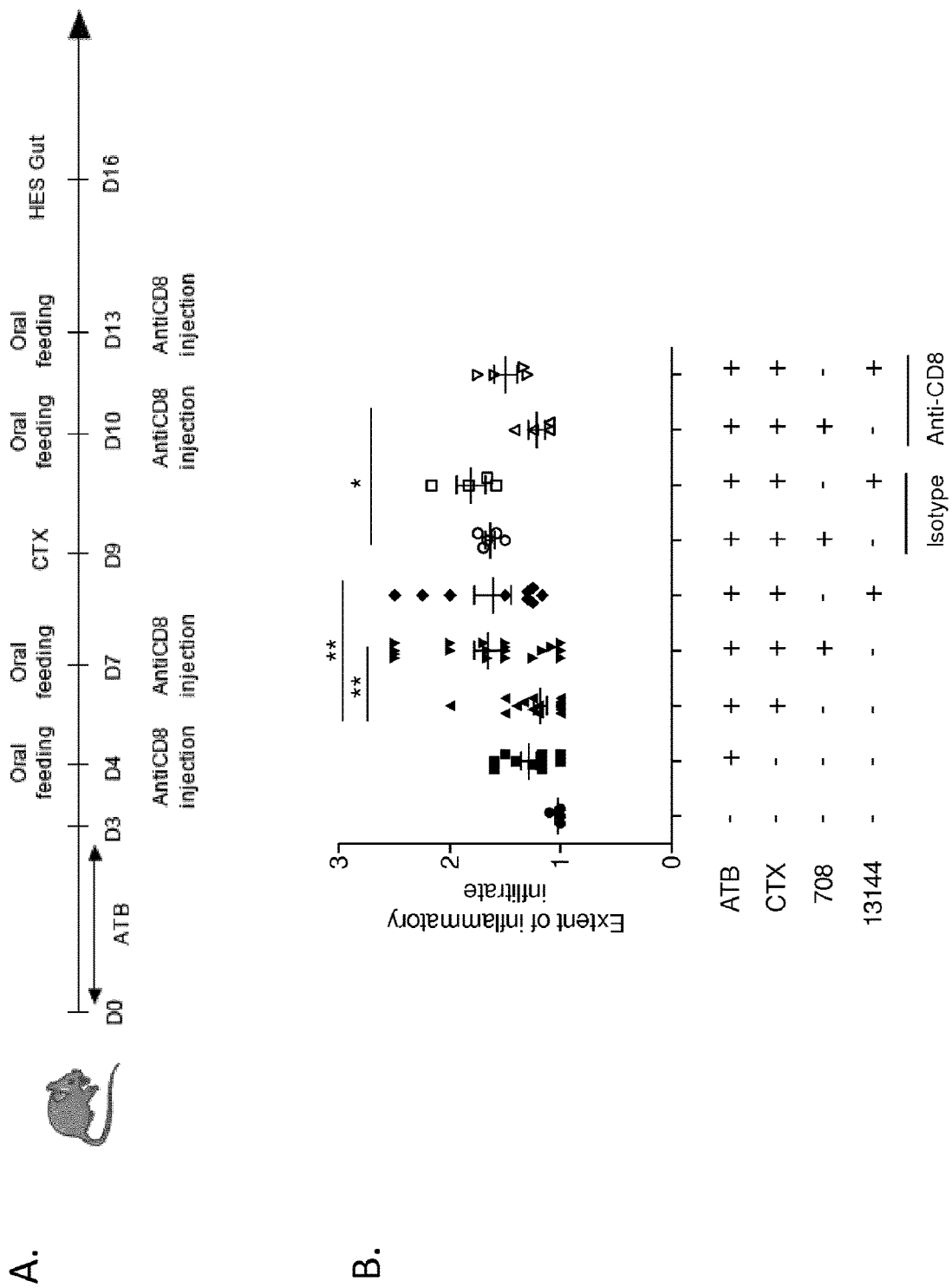
FIG. 11. Effects of EH on gut inflammation and role of CD8+ T cells in this inflammation: EH-specific CTL amplified in the mLN may return into the lamina propria. (A) Experimental setting. Mice are treated with broad spectrum antibiotics for 3 days. Then, we performed oral gavage with E. hirae (708 or 13144) and anti-CD8 injection (200 µg per mice) every three days for a total of 4 gavages/injections. 5 days after the first oral gavage, mice are treated with CTX. One week post-CTX, colon is removed for Hematoxylin Eosin Staining (HES). (B) Extent of inflammatory infiltrates in colon of mice colonized with E. hirae and treated with anti-CD8 ablating Abs and CTX. Student t'-test statistical analyses: * p<0.05, ** p<0.01.

EH13144 plays an adjuvant role with cyclophosphamide to boost antitumor immune responses and anticancer effects in a T cell- and IFNγ-dependent manner (Daillère et al., 2016). We dissected the mechanisms of the immunogenicity of EH13144 by analyzing the dynamics of the T cell immune responses in secondary lymphoid organs from the mesenteric lymph node (mLN) and the spleen (FIGS. 7A and 7D). EH13144 as well as E. hirae 708 were both capable of inducing the accumulation of CD8+ T cells in both, mLN after 1 week and spleen after 2 weeks (FIGS. 7B and 7E). However, while EH13144 induces an efficient anti-tumor immune response, E. hirae 708 fails to do so (FIG. 1D of Daillère et al., 2016). EH13144 also amplified the CD4+ T cell pool in the mLN (FIG. 7C). Moreover, EH13144 induce accumulation of CD8+CCR9+CXCR3+ in spleen (FIG. 7F) and in the tumor beds (FIG. 8).

To analyze the specificity of this CD8+ T cell expansion, we challenged splenic CD8+ T cells with bone marrow-derived dendritic cells (BM-DC) infected with various EH isolates (13144, EH708 and EH17 or L. plantarum). A commensal-specific memory CD8+ T cell response was monitored by an ELISPOT assay at 24 hrs by the enumeration of IFNγ positive spots (FIG. 9), pathognomonic of a Tc1 immune response. Interestingly, only EH708 and EH13144 could induce memory Tc1 immune responses with a cross-protection inbetween themselves (FIG. 10) while EH17 failed to do so, corroborating the poor protective antitumor effects of EH17 reported by Daillère et al. (Daillère et al., 2016).

Figure 18:
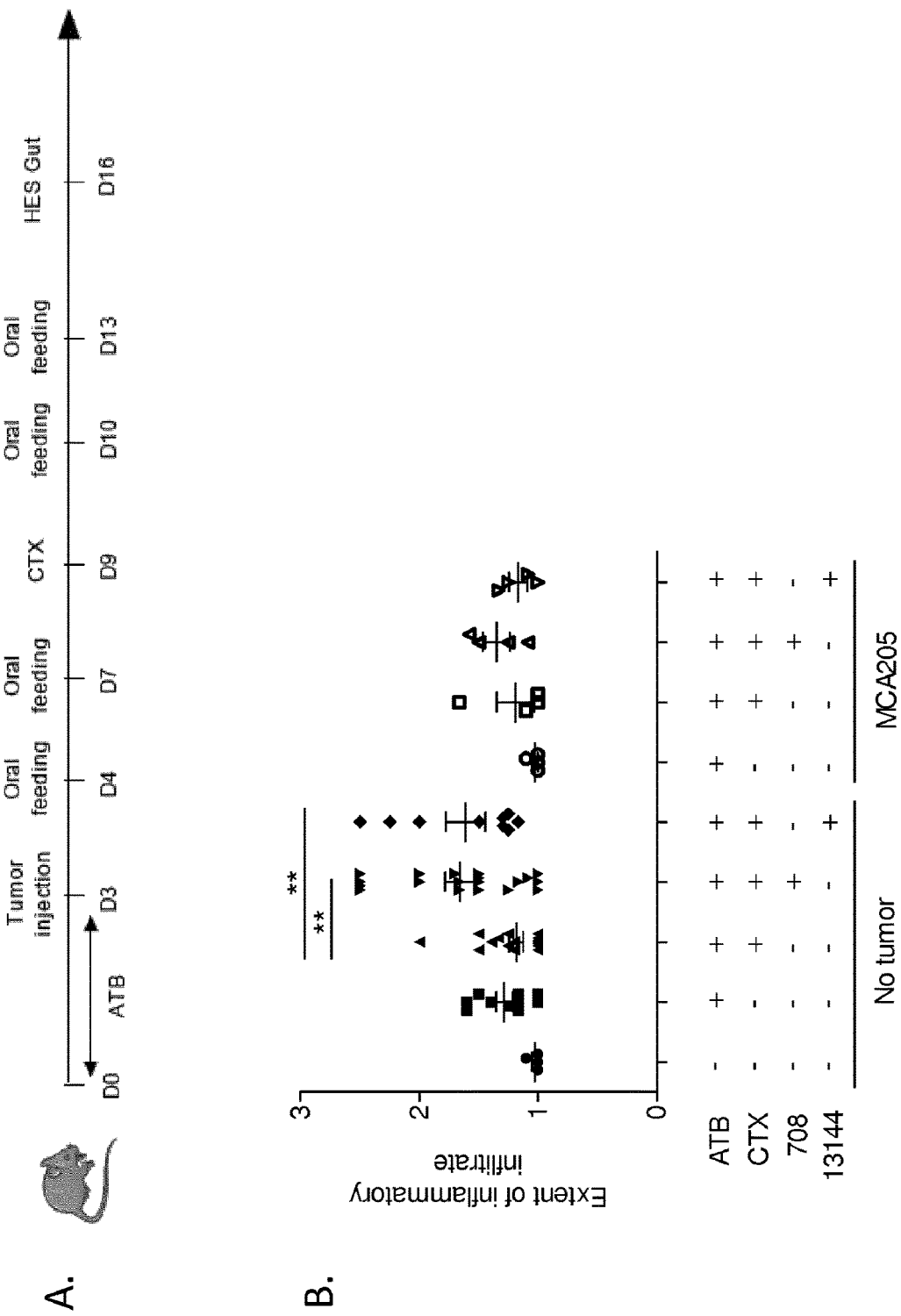
FIG. 18. The presence of a sarcoma at a distant site prevents the gut inflammatory lesions induced by oral gavages with E. hirae 13144. (A) Experimental setting. Mice are treated with broad spectrum antibiotics for 3 days before subcutaneous injection of MCA205 tumor cells in right flank. Then we performed oral gavage with E. hirae (708 or 13144) every three days for a total of 4 gavages. 5 days after the first oral gavage, mice were treated with CTX. One week post-CTX, colons are removed to be embedded in PPFE for Hematoxylin, Eosin and Safran staining (HES). (B) Extent of inflammatory infiltrates in colons of mice bearing MCA205 tumors or not and colonized with *E. hirae* and treated with CTX. Student t'-test statistical analyses: ** p<0.01.
Figure 19:
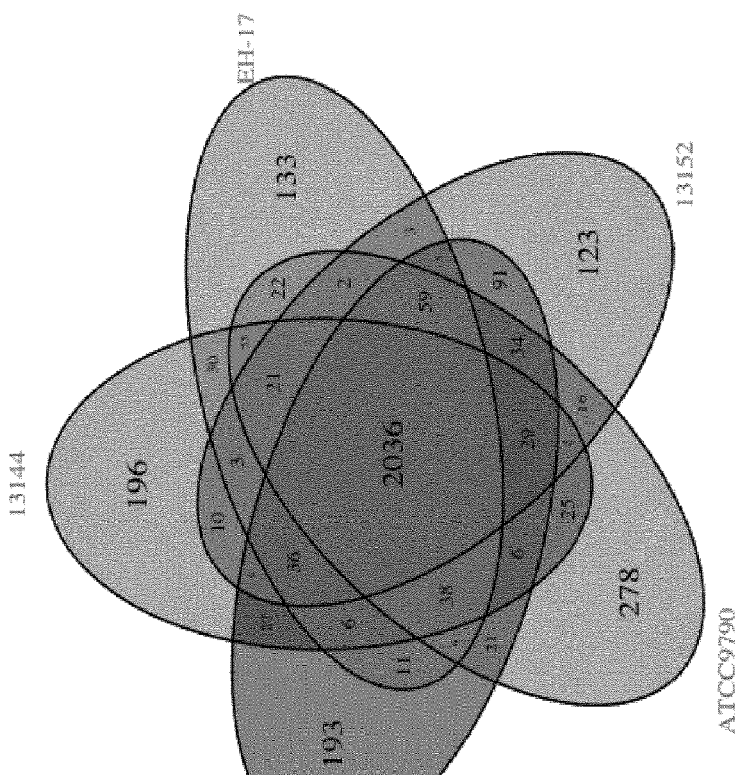
FIG. 19. Comparative genomic analysis of *E. hirae* 13144 with four other *E. hirae* strains. (A) Pangenomic analysis of the five *E. hirae* genomes. (B) List of prophages regions in 13144 genome and homology to other phage—from the web server PHASTER (PHAge Search Tool Enhanced Release), dedicated to the identification and annotation of prophage sequences within bacterial genomes and plasmids.

We scrutinized colon mucosae for CD8+ T cell infiltrates by monitoring intestinal inflammatory lesions in the presence or absence of neutralizing anti-CD8 antibodies in immunohistochemistry (FIG. 11A). Hematoxylin eosin stained colon mucosae were more infiltrated after oral gavages with EH13144 or EH708 than without commensals post-CTX but these infiltrates were drastically reduced when animals were pretreated by ip administrations of neutralizing anti-CD8 Abs (FIG. 11B). Of note, these CD8+ T cells primed in mLN or spleen have a tendency to home to the lamina propria in the absence of a distant tumor but not if a sarcoma deposit is introduced subcutaneously (FIG. 18).

Altogether, these findings suggest that oral gavages with EH13144 or EH708 in the context of cyclophosphamide trigger not only a splenic Th1 (Daillère et al., 2016) but also a systemic Tc1 immune response recognizing both EH708 and EH13144 (but not EH17) sequences with the potential to traffic back to the colon if no tumor deposit exist or to tumor beds when they develop.

Figure 12:
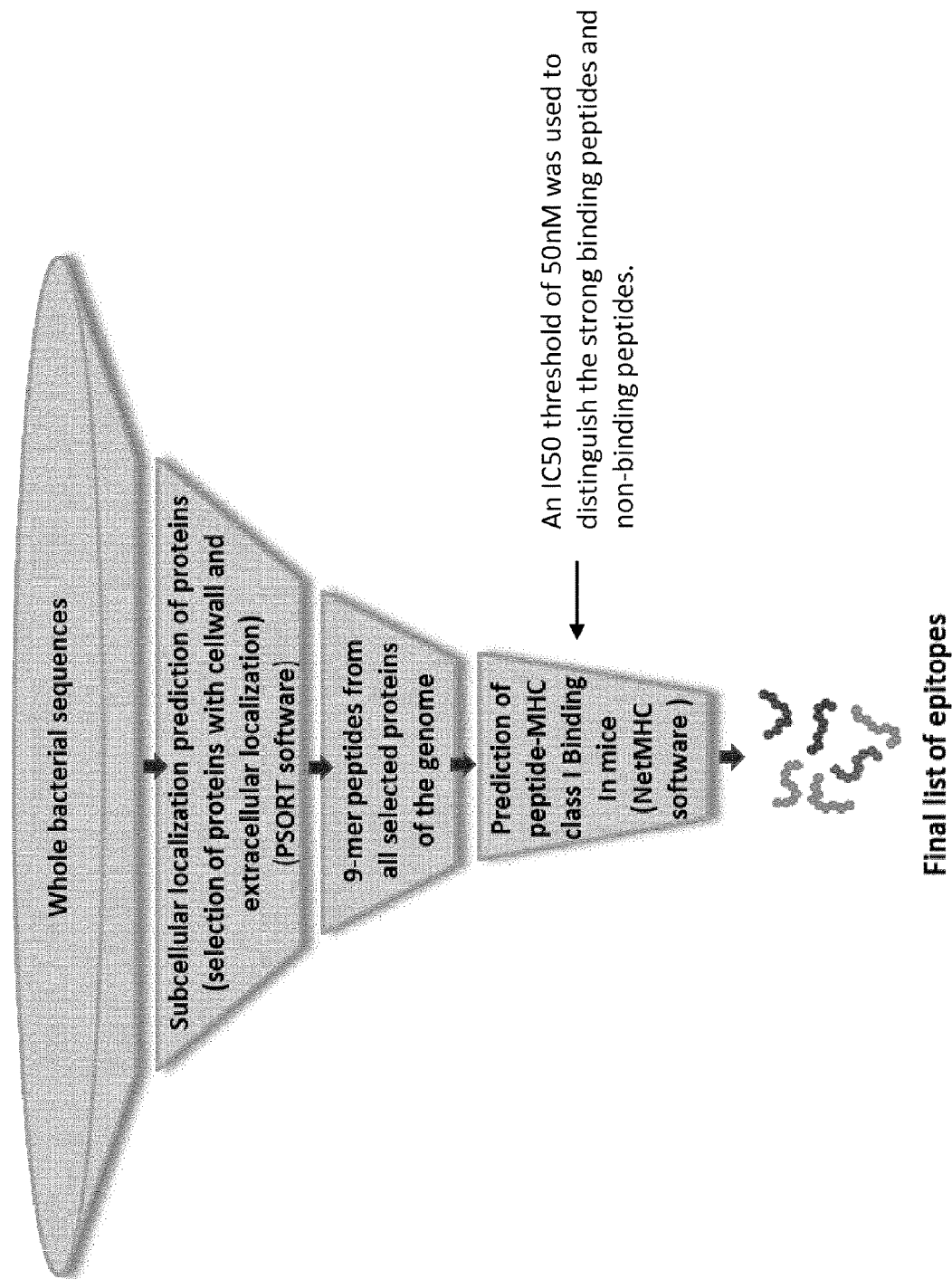
FIG. 12. Schematic overview of the filters used to select the MHC class I binding peptides from EH. From whole bacterial sequences of E. hirae (708, 13144 and EH17), we selected proteins with cell wall and extracellular localization with PSORT software. Then, proteins were divided in peptides of nine amino acids. These peptides were tested for their ability to bind MHC class I H-2K$^b$ with NetMHC software and only strong-binders were retained (IC50<50 nM).

Example 3: Screening EH Specific H-2$K^b$ Restricted Peptides: E. hirae 13144 Genome Contains Immunogenic Peptide Sequences in the TMP Phage Protein Whole genome differential analyses were performed on three E. hirae strains (13144, 708 and EH17) to identify potential 9-mer MHC class 1-binding epitopes. The search focused on subcellular localization (enrichment for cell wall and extracellular proteins, via PSORT software), and on binding affinity to H2-$K^b$ (<50 nM binding affinity, NetMHC software) (FIG. 12, Tables 2-5).

TABLE 2

H-2b restricted-EH13144 peptides not present in the other strains

| Hirae | sequence | names of the proteins | SEQ ID No: |
|---|---|---|---|
| 13144 | SAFPYEQEL | C3 family ADP-ribosyltransferase | 3 |
| 13144 | YNYSKSYPV | hypothetical protein | 4 |
| 13144 | VSFSHYRPG | hypothetical protein | 5 |
| 13144 | VTFLGYNAF | cell surface protein | 6 |
| 13144 | TVYTFHVNI | cell surface protein | 7 |
| 13144 | TSYSPLFLL | cell surface protein (putative) | 8 |
| 13144 | TNYIYPNIL | 2',3'-cyclic-nucleotide 2'-phosphodiesterase | 9 |
| 13144 | VVPILFLGL | FmtB protein | 10 |
| 13144 | KNYKAYVEL | hypothetical protein | 11 |
| 13144 | SAMKYGIPL | hypothetical protein | 12 |
| 13144 | TSLARFANI | Phage tail length tape-measure protein | 13 |
| 13144 | AMIEFIQGL | Phage tail length tape-measure protein | 14 |
| 13144 | VAITFGGPL | Phage tail length tape-measure protein | 15 |
| 13144 | VSTNHYGLL | hypothetical protein | 16 |
| 13144 | VMFGLFITI | cell surface protein precursor | 17 |
| 13144 | TVFSLVSLL | Chitinase | 18 |
| 13144 | SIYNLEKPL | IgA1 protease | 19 |
| 13144 | YTIIRYGNL | IgA1 protease | 20 |
| 13144 | SNGLLYTPM | IgA1 protease | 21 |
| 13144 | NNYHYVGGL | IgA1 protease | 22 |
| 13144 | SMFLNCNNL | hypothetical protein | 23 |
| 13144 | IAFQGYSSL | hypothetical protein | 24 |
| 13144 | QVTNFFNMF | hypothetical protein | 25 |
| 13144 | IMLGLFMTM | cell surface protein precursor | 26 |

TABLE 3

H-2b restricted-EH708 peptides not present in the other strains

| Hirae | sequence | names of the proteins | SEQ ID No: |
|---|---|---|---|
| 708 | INAKFSSQL | Membrane proteins related to metalloendopeptidases | 27 |
| 708 | YIYNHYKDM | Membrane proteins related to metalloendopeptidases | 28 |
| 708 | YVYGKSRTM | Membrane proteins related to metalloendopeptidases | 29 |
| 708 | IAFLSYKLF | cell surface protein precursor | 30 |
| 708 | IMYEYMYPV | hypothetical protein | 31 |
| 708 | SSMEYFLKV | Phage tail length tape-measure protein | 32 |
| 708 | ISFFQENQL | Collagen adhesin | 33 |

TABLE 3-continued

H-2b restricted-EH708 peptides not present in the other strains

| Hirae | sequence | names of the proteins | SEQ ID No: |
|---|---|---|---|
| 708 | TNLLFMTSL | extracellular protein | 34 |
| 708 | KIFSIFMLL | Phosphatidylinositol-specific phospholipase C | 35 |
| 708 | LNIFKFNRF | Chitinase | 36 |
| 708 | MTYDYRGGF | Chitinase | 37 |
| 708 | PSYMFRTSF | Chitinase | 38 |
| 708 | QSYTYYMTA | cell wall surface anchor family protein | 39 |
| 708 | ITFSHYEPT | cell wall surface anchor family protein | 40 |

TABLE 4

H-2b restricted-EH17 peptides not present in the other strains

| Hirae | sequence | names of the proteins | SEQ ID No: |
|---|---|---|---|
| EH17 | MSFTFFSST | hypothetical protein | 41 |
| EH17 | IAFQNFVNL | Chitinase | 42 |
| EH17 | SMFIAFQNF | Chitinase | 43 |
| EH17 | LNYDYGNRI | Chitinase | 44 |
| EH17 | AGICFFTGV | Peptidoglycan N-acetylglucosamine deacetylase | 45 |
| EH17 | VEYTYFPTL | Membrane proteins related to metalloendopeptidases | 46 |
| EH17 | AAYVFEMNF | Membrane proteins related to metalloendopeptidases | 47 |
| EH17 | EMYRKLSTL | Membrane proteins related to metalloendopeptidases | 48 |
| EH17 | YNYGYKSVL | enhancin family protein | 49 |
| EH17 | VIHELYNSL | bacteriocin immunity protein | 50 |

TABLE 5

H-2b restricted-EH13144/EH708 common peptides

| Hirae | sequence | names of the proteins | SEQ ID No: |
|---|---|---|---|
| 708-13144 | TNYVKLRPL | hypothetical protein | 51 |
| 708-13144 | QAVNHFTGI | Portal protein phage associated | 52 |

Figure 13C:
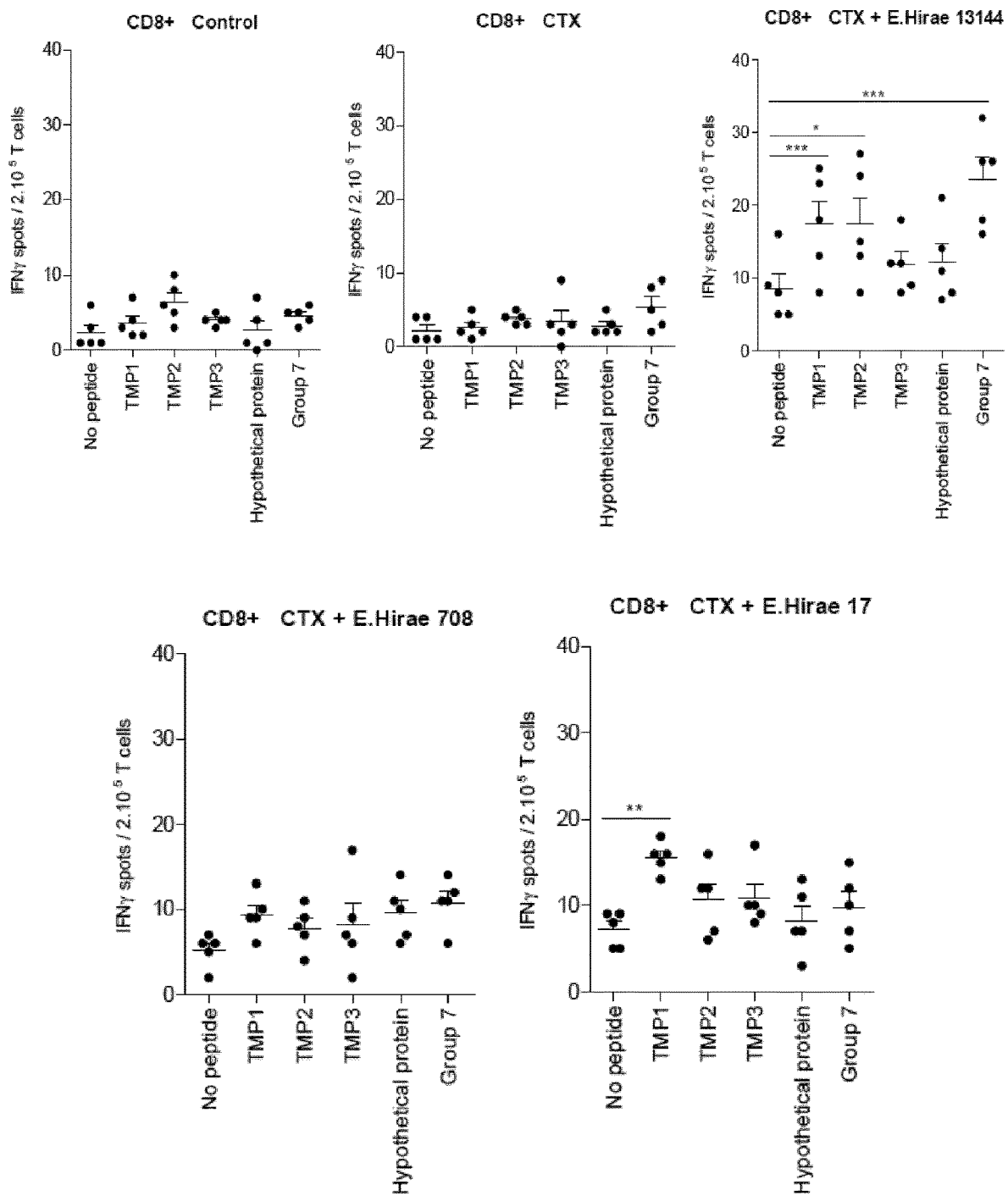
FIG. 13. Peptides from group 7 containing the TMP1 and TMP2 epitopes activate CD8+ T cells from spleen of mice immunized against E. hirae 13144. Number of IFNγ spot, representing IFNγ-secreting CD8+ T cells, after incubation with DCs pulsed with 13 different group of peptide (Table 6). Just group n° 1 (A) and group n° 7 (B) are shown. (C, E) Number of IFNγ spot, representing IFNγ-secreting CD8+ T cells, after incubation with DCs pulsed with 4 peptides belong to group n° 7 (in table 7). The corresponding experimental setting is indicated in FIG. 9. (D) Sequence alignment of TMP1 and TMP2 of EH10815 (SEQ ID Nos: 228 and 229 respectively) compared to EH13144 (fragments of SEQ ID NO: 1) at the level of immunogenic peptides. Amino acid sequence TSLARFANI corresponds to SEQ ID No: 13. Amino acid sequence TSFARFANI corresponds to SEQ ID No: 217. Amino acid sequence AMIEFIQGL corresponds to SEQ ID Nos: 14. Amino acid sequence AIIEFIKGL corresponds to SEQ ID No: 218. (E) In vitro reactivity of splenic CTL in a recall response to TMP1 and TMP2 as well as Group7 after in vivo immunization with other strains of EH. Anova statistical analyses: * p<0.05,  p<0.01, * p<0.001.
Figure 13E:
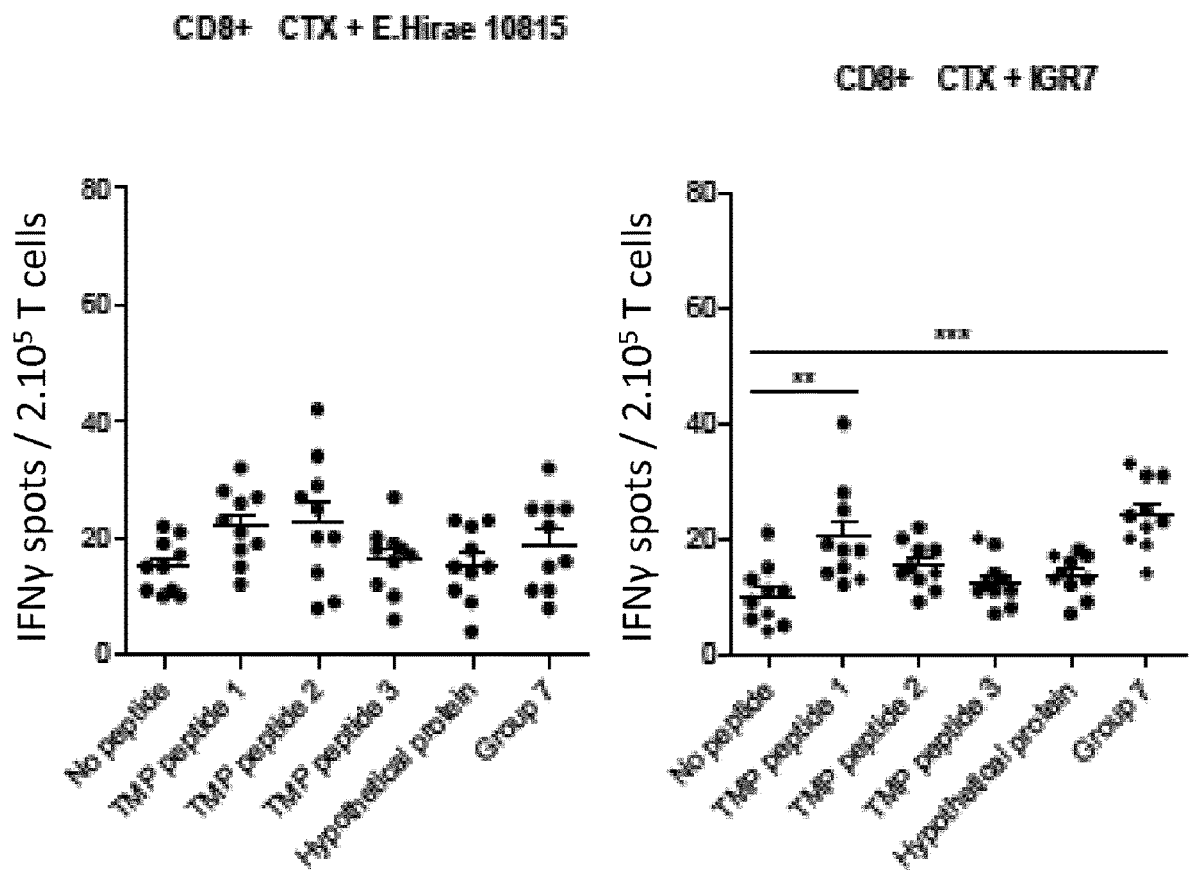

CD8+ T cell splenocytes isolated from CTX-treated mice were restimulated with pooled 9-mer peptides (group1-13, Table 6) to identify potentially immunogenic epitopes in vivo. Using the same protocol as the one outlined in FIG. 9, we found that the immunogenicity of 13144 relied upon group 7 associated peptides (FIG. 13B) contrary to other group of peptides (data not shown) such as group 1 (FIG. 13A). Next, we split the group 7 into the four H-2K$^b$ peptides (Table 7). Immunogenicity of E. hirae 13144 could reside within the Phage Tail Length Tape Measure Protein (Tmp) (Table 7). Indeed, we unveiled that only TMP1 and TMP2 peptides were highly recognized by memory EH13144 (but not 708 and EH17)-induced Tc1 cells (FIG. 13C). Of note, the strain EH10815, which harbored the two same prophages as EH13144 but mutations in position 3 in TMP1 and in positions 2 and 7 of TMP2 (FIG. 13D), does not induce recall responses (FIG. 13E) and might explain why this bacterium failed to mediate significant antitumor effects. In contrast, results obtained with EH clone IGR7 which shares a very high sequence homology with EH13144, induce recall responses (FIG. 13E).

TABLE 6

H-2b restricted *E. hirae* peptides by groups used in in vivo experiments

| Group | n° | Hirae | sequence | names of the proteins | SEQ ID No: |
|---|---|---|---|---|---|
| 1 | 1 | 708 | INAKFSSQL | Membrane proteins related to metalloendopeptidases | 27 |
| | 2 | 708 | YIYNHYKDM | Membrane proteins related to metalloendopeptidases | 28 |
| | 3 | 708 | YVYGKSRTM | Membrane proteins related to metalloendopeptidases | 29 |
| | 4 | 708 | IAFLSYKLF | cell surface protein precursor | 30 |
| 2 | 5 | 708 | IMYEYMYPV | hypothetical protein | 31 |
| | 6 | 708 | SSMEYFLKV | Phage tail length tape-measure protein | 32 |
| | 7 | 708 | ISFFQENQL | Collagen adhesin | 33 |
| | 8 | 708 | TNLLFMTSL | extracellular protein | 34 |
| 3 | 9 | 708 | KIFSIFMLL | Phosphatidylinositol-specific phospholipase C | 35 |
| | 10 | 708 | LNIFKFNRF | Chitinase | 36 |
| | 11 | 708 | MTYDYRGGF | Chitinase | 37 |
| | 12 | 708 | PSYMFRTSF | Chitinase | 38 |
| 4 | 13 | 708 | QSYTYYMTA | cell wall surface anchor family protein | 39 |
| | 14 | 708 | ITFSHYEPT | cell wall surface anchor family protein | 40 |
| | 15 | 13144 | SAFPYEQEL | C3 family ADP-ribosyltransferase | 3 |
| | 16 | 13144 | YNYSKSYPV | hypothetical protein | 4 |
| 5 | 17 | 13144 | VSFSHYRPG | hypothetical protein | 5 |
| | 18 | 13144 | VTFLGYNAF | cell surface protein | 6 |
| | 19 | 13144 | TVYTFHVNI | cell surface protein | 7 |
| | 20 | 13144 | TSYSPLFLL | cell surface protein (putative) | 8 |
| 6 | 21 | 13144 | TNYIYPNIL | 2',3'-cyclic-nucleotide 2'-phosphodiesterase | 9 |
| | 22 | 13144 | VVPILFLGL | protein | 10 |
| | 23 | 13144 | KNYKAYVEL | hypothetical protein | 11 |
| | 24 | 13144 | SAMKYGIPL | hypothetical protein | 12 |
| 7 | 25 | 13144 | TSLARFANI | Phage tail length tape-measure protein | 13 |
| | 26 | 13144 | AMIEFIQGL | Phage tail length tape-measure protein | 14 |
| | 27 | 13144 | VAITFGGPL | Phage tail length tape-measure protein | 15 |
| | 28 | 13144 | VSTNHYGLL | hypothetical protein | 16 |
| 8 | 29 | 13144 | VMFGLFITI | cell surface protein precursor | 17 |
| | 30 | 13144 | TVFSLVSLL | Chitinase | 18 |
| | 31 | 13144 | SIYNLEKPL | IgA1 protease | 19 |
| | 32 | 13144 | YTIIRYGNL | IgA1 protease | 20 |
| 9 | 33 | 13144 | SNGLLYTPM | IgA1 protease | 21 |
| | 34 | 13144 | NNYHYVGGL | IgA1 protease | 22 |
| | 35 | 13144 | SMFLNCNNL | hypothetical protein | 23 |
| | 36 | 13144 | IAFQGYSSL | hypothetical protein | 24 |
| 10 | 37 | 13144 | QVTNFFNMF | hypothetical protein | 25 |
| | 38 | 13144 | IMLGLFMTM | cell surface protein precursor | 26 |
| | 39 | EH17 | MSFTFFSST | hypothetical protein | 41 |
| | 40 | EH17 | IAFQNFVNL | Chitinase | 42 |
| 11 | 41 | EH17 | SMFIAFQNF | Chitinase | 43 |
| | 42 | EH17 | LNYDYGNRI | Chitinase | 44 |
| | 43 | EH17 | AGICFFTGV | Peptidoglycan N-acetylglucosamine deacetylase | 45 |
| | 44 | EH17 | VEYTYFPTL | Membrane proteins related to metalloendopeptidases | 46 |
| 12 | 45 | EH17 | AAYVFEMNF | Membrane proteins related to metalloendopeptidases | 47 |
| | 46 | EH17 | EMYRKLSTL | Membrane proteins related to metalloendopeptidases | 48 |
| | 47 | EH17 | YNYGYKSVL | enhancin family protein | 49 |
| | 48 | EH17 | VIHELYNSL | bacteriocin immunity protein | 50 |
| 13 | 49 | 708-13144 | TNYVKLRPL | hypothetical protein | 51 |
| | 50 | 708-13144 | QAVNHFTGI | Portal protein phage associated | 52 |

TABLE 7

Proteins corresponding to the immunogenic EH peptide sequences

| Group | n° | Hirae | sequence | names of the proteins | SEQ ID No: |
|---|---|---|---|---|---|
| 7 | 1 | 13144 | TSLARFANI | Phage tail length tape-measure protein | 13 |
|   | 2 | 13144 | AMIEFIQGL | Phage tail length tape-measure protein | 14 |
|   | 3 | 13144 | VAITFGGPL | Phage tail length tape-measure protein | 15 |
|   | 4 | 13144 | VSTNHYGLL | hypothetical protein | 16 |

Figure 14:
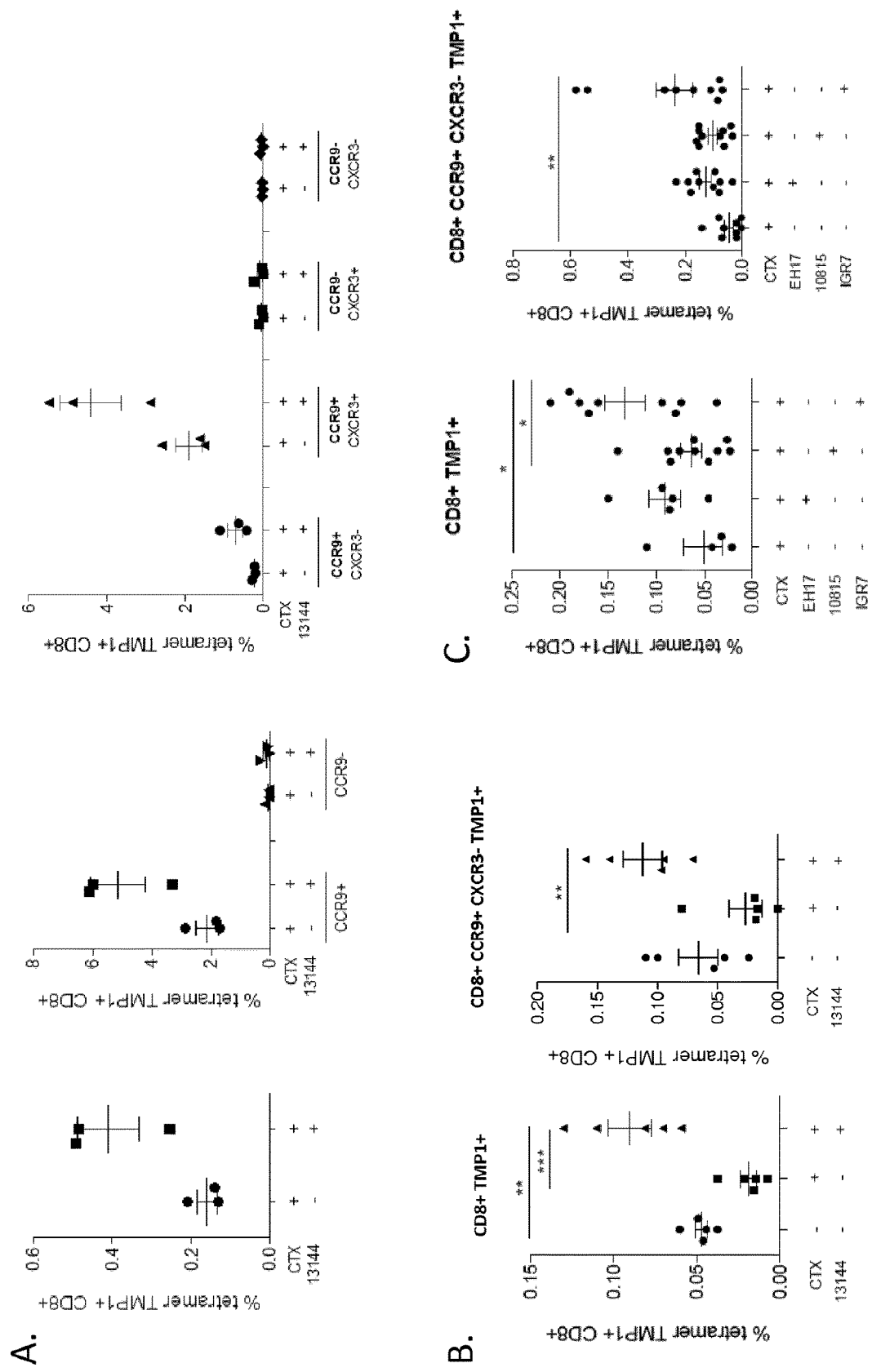
FIG. 14. TMP epitope 1 prophage 2 specific CD8+ T cells accumulate in dLN and spleen post oral gavage with EH13144 and IGR7. Mice are treated with broad spectrum antibiotics for 3 days before performing oral gavage with E. hirae 13144 (A,B) or 10815 or EH17 or IGR7 (C) and CTX ip injection. The corresponding experimental setting is indicated in FIG. 7A for mLN and FIG. 7D for spleen. TMP1 specific CD8+ T cells are isolated with tetramer from mesenteric lymph node (A) and spleen (B,C). Flow cytometry analysis of TMP1 prophage 2 specific CD8+ T cells and TMP1-specific CD8+ T among CCR9+ or CCR9-T cells in mLN and spleen. Each dot represents one mLN or spleen. 5-6 mice/group. Anova statistical analyses: * p<0.05,  p<0.01, * p<0.001.
Figure 15:
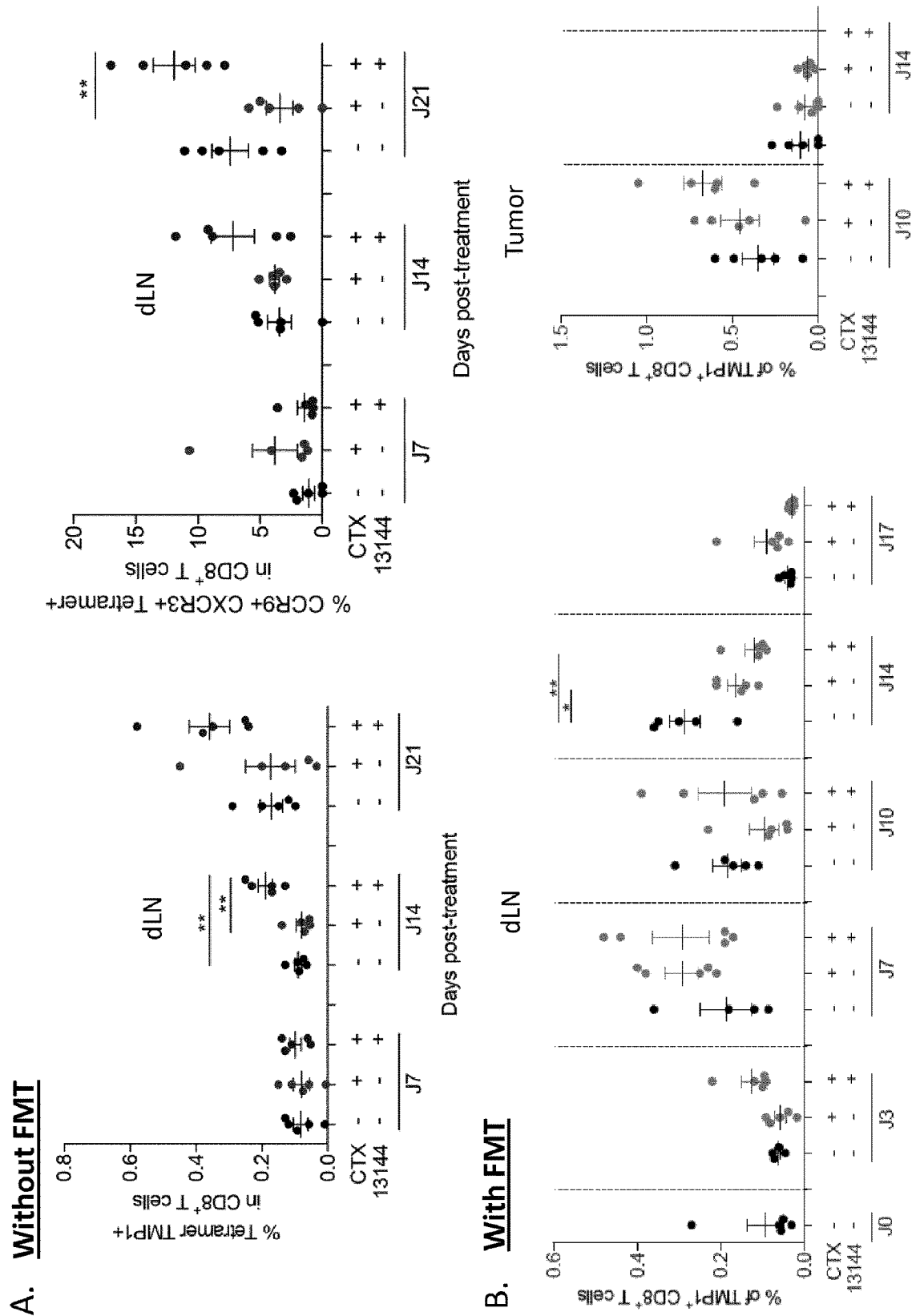
FIG. 15. TMP epitope 1 prophage 2 specific CD8+ T cells accumulate in tumor beds. (A) SPF mice were treated with ATB for 3 days and then oral gavages with EH13144 before and after CTX systemic administration, every other week for 3 weeks. Mice were sacrificed 7, 14 and 21 day after the first CTX treatment to harvest tumor draining lymph node (dLN) and tumor (MCA205). (B) FMT-treated mice were treated with ATB for 3 days and then oral gavages with EH13144 before and after CTX systemic administration, every other week for 3 weeks. Mice were sacrificed the day of CTX treatment and 72 hrs post-CTX 1, 2, 3 (day J0, J3, J7, J10, J14, J17) to harvest dLN and tumor (MCA205). Flow cytometry analyses of TMP1-specific CD8 T cells and TMP1-specific CD8 T cells among CCR9+CXCR3+ double positive cells are presented. A representative experiment of 3 groups comprising 5 mice/group. Anova statistical analyses: * p<0.05,  p<0.01, * p<0.001.

The manufacturing of TMP1 specific tetramers allowed us to monitor TMP1-specific T cells in the mLN (FIG. 14A) and the spleen (FIG. 14B-C) in mice without tumor and post-oral gavages with EH13144, EH17, 10815 or IGR7 and CTX treatment. We observed that only T cells from the gut (CCR9+ T cells) are TMP1-specific T cells for EH13144 and IGR7 (FIG. 14). Moreover, in tumor bearing mice, TMP-specific tetramer stainings in tumor draining lymph node and tumor show that TMP epitope 1 prophage 2 specific CD8+ T cells accumulate in tumor beds and are contained in the CCR9+CXCR3+CTLs (FIG. 15).

Temperate bacteriophages are bacterial viruses that transfer virulence, antimicrobial resistance genes, and immunogenic sequences to new bacterial hosts via transduction (Weinbauer, 2004). The Phage Tail Length Tape Measure Protein (Tmp) is highly conserved in a large number of phages and prophages, most importantly in Siphoviridae family of phages, containing a variable number of tandem repeats with highly conserved tryptophan and phenylalanine aminoacids at fixed positions. Phages belonging to the Siphoviridae family contain several motifs in their Tmp (Belcaid et al., 2011; Piuri and Hatfull, 2006), among which peptidoglycan hydrolases facilitating their infectivity of surrounding bacteria and containing rescuscitation-promoting factors (Rpfs). Rpfs have not only been implicated in the reactivation of dormant bacteria but also modulate innate responses to *Mycobacterium tuberculosis* (Russell-Goldman et al., 2008) as well as cognate long-term immune responses (Commandeur et al., 2011). In fact, *M. tuberculosis* Rpfs T cell epitopes were reported to be key immunogens in the human immune responses to *M. tuberculosis* (Commandeur et al., 2011).

Figure 16:
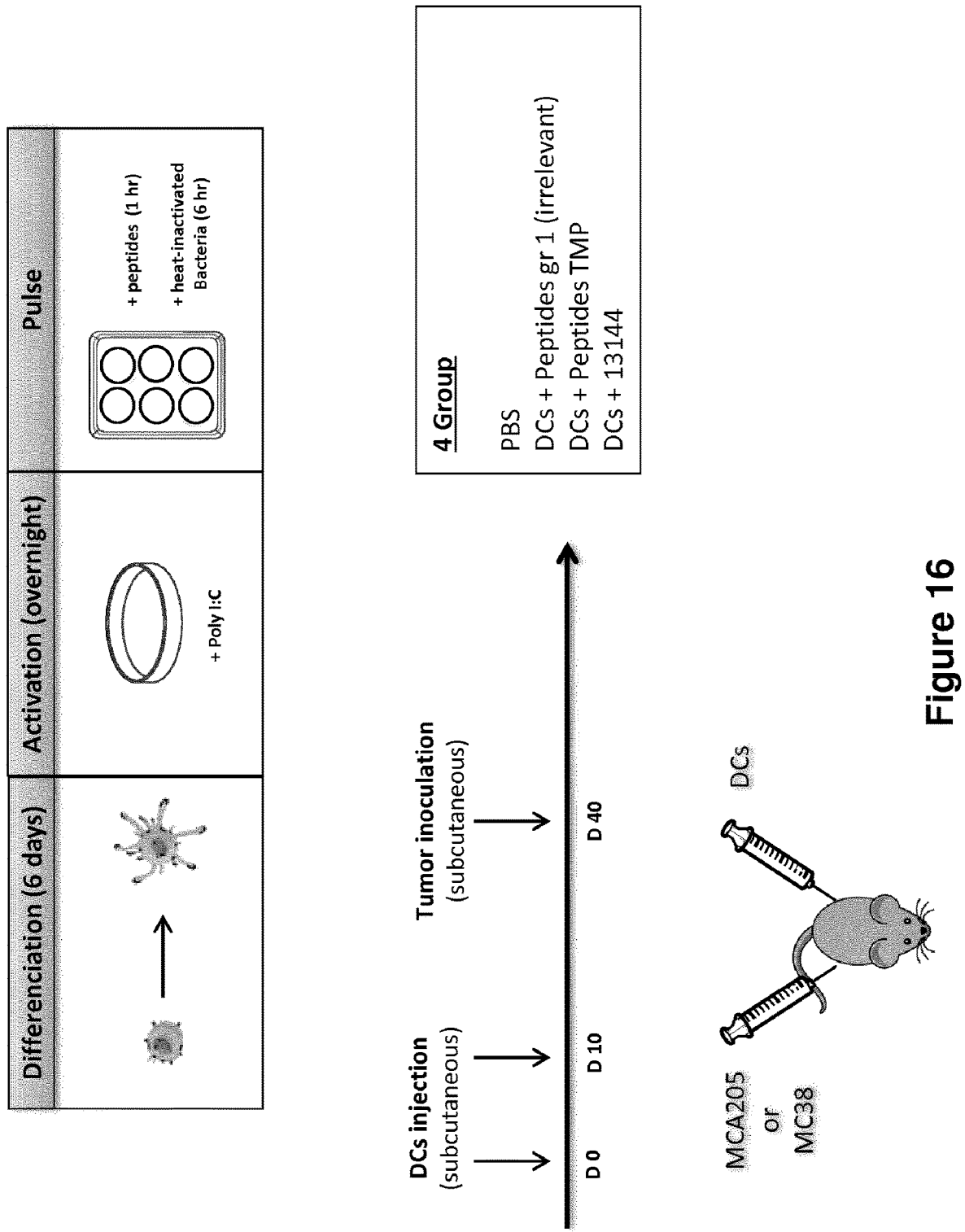
FIG. 16. Protocol of immunization with DC pulsed with TMP peptides. After DCs differentiation (with GM-CSF and IL-4 during 6 days), we incubated them with poly I:C (10 µg/ml) overnight before the addition of peptide (1 hour) or heat-inactivated bacteria (6 hours). These DCs are injected subcutaneous on right flank at day 0 and 10. One month after second injection, sarcoma (MCA205) or colon (MC38) tumor cells lines are injected subcutaneous on left flank (8.10$^5$ and 1.10$^6$ cells per mice respectively). We constitute 4 groups, one group without DCs, one group with DCs pulsed with 20 µg/ml of irrelevant peptides (gr1) or TMP peptides or 13144 heat-inactivated bacteria. Mean tumor sizes over time (A), each mouse tumor kinetics for each group (B), and the detailed comparison in between groups at the two last time points before sacrifice for MCA205 are shown (C), each dot representing one mouse. MC38 related data are not shown.

Example 4: Immunization with *E. hirae* 13144 Tmp Peptides or Live Bacteria Confer Protection Against Tumor Challenge We performed a subcutaneous vaccination using $1.5.10^5$ BM-DC activated with poly I:C followed by exposition to TMP peptides or live *E. hirae* 13144 to immunize twice, 10 days apart, naïve C57BL/6 animals against MCA205 sarcomas or syngeneic MC38 colon cancers (FIG. 16). While unpulsed BM-DC or BM-DC exposed to Group 1 peptides were not efficient at mediating protection against a lethal challenge with MCA205, BM-DC exposed to TMP1-TMP2 markedly conveyed protective effects against MCA205 (FIG. 17) as efficiently as live bacteria.

We hypothesized that oral gavages with *E. hirae* 13144 trigger an immune response in the mLN and spleen that can either traffick back to intestinal mucosae or in the tumor microenvironment. To link gut and tumor immunosurveillance, we compared the relative immune infiltrates induced by sequential oral gavages with *E. hirae* 13144 in naive versus tumor bearing mice. Indeed, we found that *E. hirae* 13144-induced CD8+ T cell-dependent colon inflammatory lesions (FIG. 11) were markedly reduced in tumor bearers, supporting the competition between the gut and tumor microenvironment during oral administration of the bacteria (FIG. 18).

Example 5: *E. hirae* 13144 Genome Encodes Two 40.6-Kb and 39.2-Kb Prophage Sequences of the Siphoviridae Family Strain EH13144 and four other *E. hirae* genomes (708, 10815, 13152 and EH17) were annotated using Prokka program. The homology relationships between genes of each different strain were assessed using BLASTP program and Roary software with >80% amino acid identity cutoff. Core genome alignment of the five *E. hirae* genomes was performed using PRANK program. Prophage regions were predicted using PHASTER online program.

Comparative analysis of *E. hirae* strains yielded a pangenome of 12,748 genes. The core genome (the set of genes shared by all strains) was composed of 2,036 orthologous genes (59%) and the accessory genome (the set of genes present in some but not all the species) was composed of 570 orthologous genes and 923 unique genes (unique genes to individual species). Strain EH13144 encoded 196 unique genes while strains 13144 and 708 shared 27 orthologous proteins (FIG. 19A).

Figure 20A:
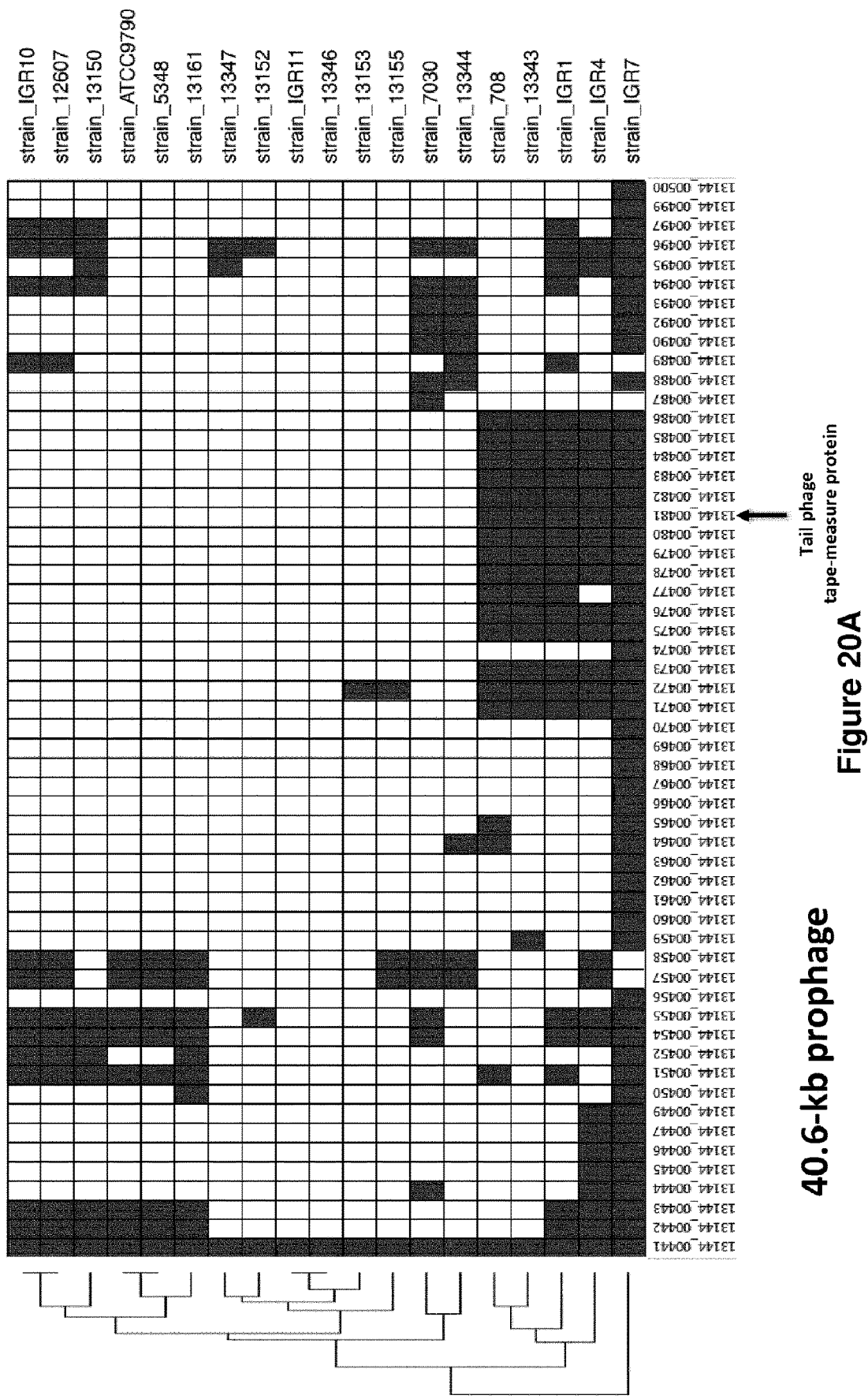
FIG. 20. *Enterococcus hirae* prophages comparative analysis. (A) Alignment of the sequences of several EH strains and location of the TMP sequences. A comparative analysis through a "heatmap" cluster based on a matrix of presence (black) and absence (white) of the 40.6-kb prophage (A) and 39.2-kb prophage (B) genes sequences and blast alignment parameter=80% identity and >=70% coverage.
Figure 20B:
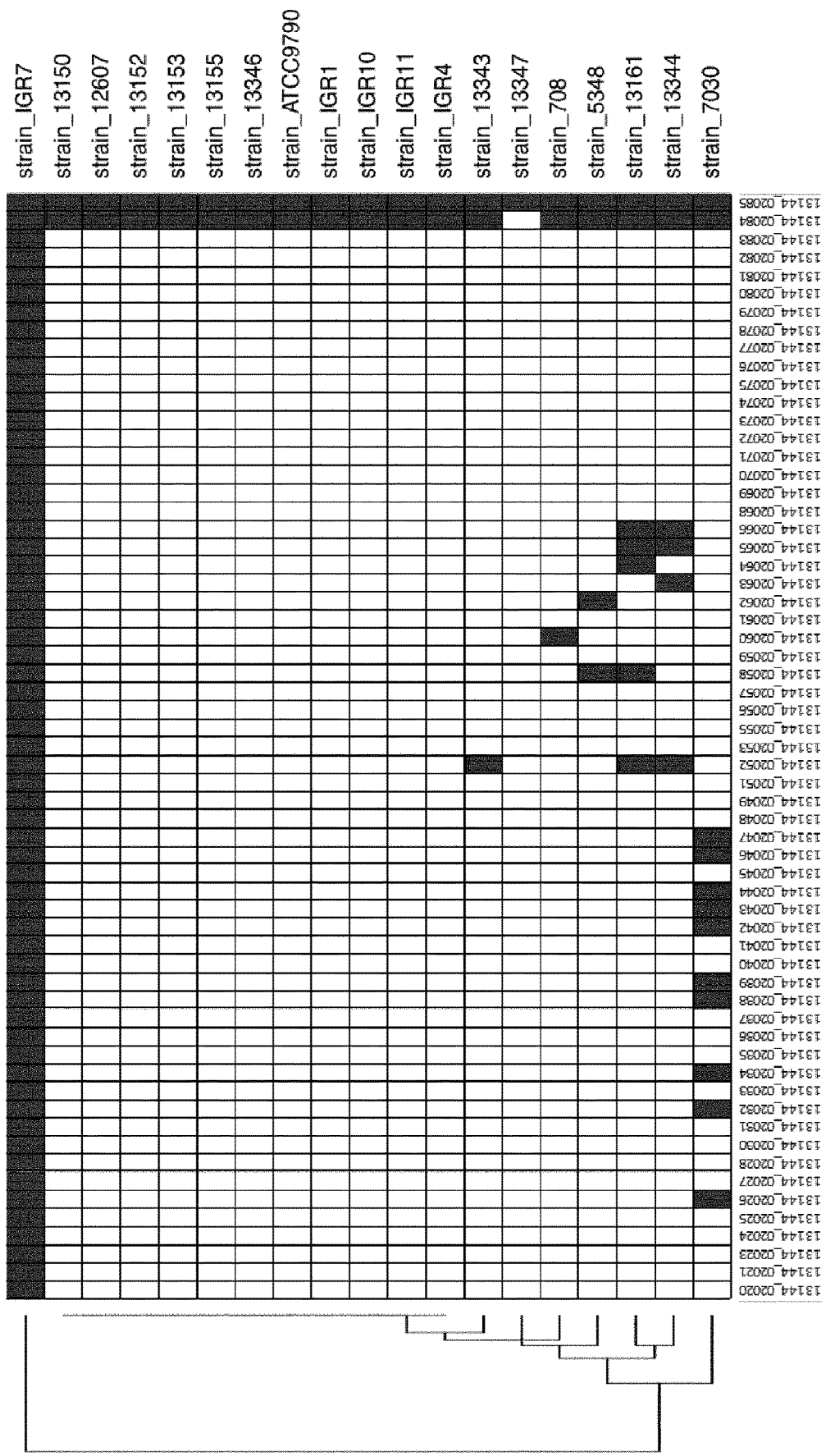
Figure 21:
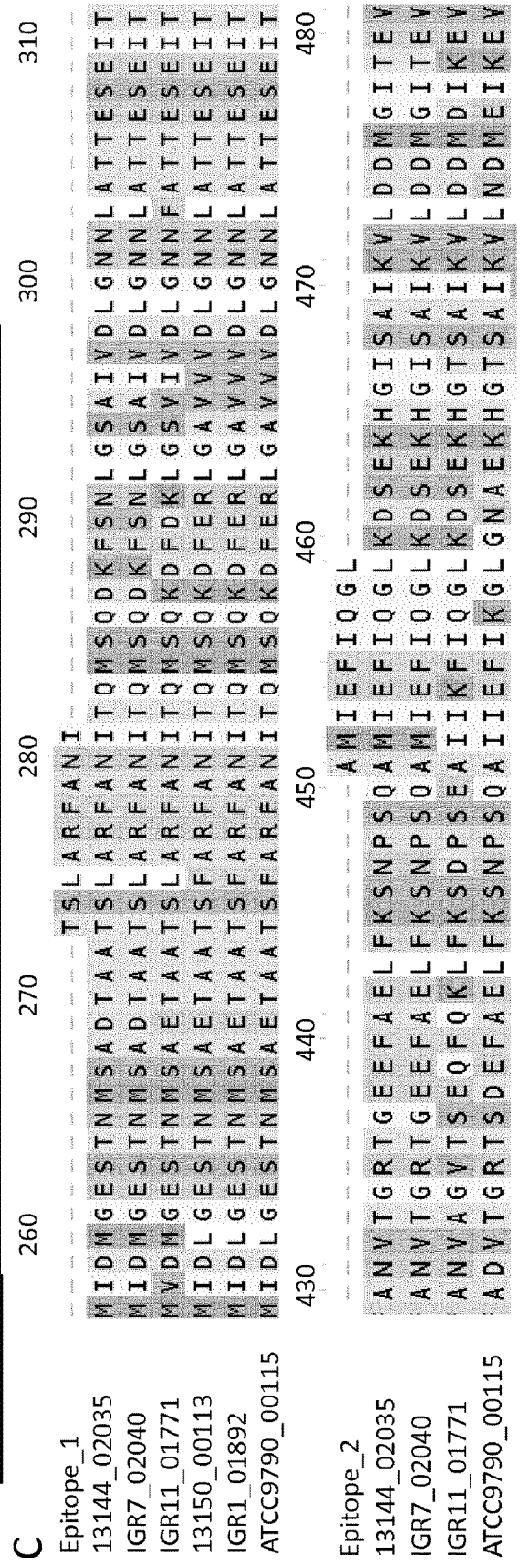
FIG. 21. Homology between epitopes TMP of EH13144 and other *E. hirae* strains. (A) TMP from prophage 2 EH13144 is homologous to TMP from IGR7 (because both EH13144 and EH IGR7 sequences are identical). (B) Epitope TMP1 of EH13144 presents some homology with other *E. hirae* strains: 100% in IGR11 and 88.89% in IGR1 and 10815 (with 1 mutation indicated in (C). Epitope TMP2 of EH13144 presents 77% homology in IGR11 and 10815 (with 2 mutations indicated in (C). Epitope_1 corresponds to SEQ ID No: 13. Epitope_2 corresponds to SEQ ID No: 14. 13144_02035 lines correspond to extracts from SEQ ID No: 1. IGR7_02040 lines are identical to 13144_02035 lines. IGR11_01771 lines correspond to SEQ ID Nos: 226 and 227. 13150_00113, IGR1_01892 and ATCC9790_00115 lines correspond to SEQ ID Nos: 228 and 229.

A particularity in the genome of *E. hirae* 13144 is that it encodes two intact prophages regions (40.6-kb and a 39.2-kb) showing sequence homology to *Enterococcus* phage phiEf11 and *Staphylococcus* phage CNPx, respectively (FIG. 19B). The 40.6-kb prophage encoded 57 genes, including 12 shared between the five genomes, 16 shared between strains 13144 and 708 and 8 unique to *E. hirae* 13144 (FIG. 20A). The 39.2-kb prophage encoded 65 genes, including 7 shared between the five genomes, 3 shared between strains 13144 and 708 and 22 unique to *E. hirae* 13144 (FIG. 20B). Genomic structures of both prophages suggested that they belonged to the Siphoviridae family. Indeed, the two prophages harbor genes encoding capsid, portal and tail structure, a characteristic of Siphoviridae phages. The two prophages encoded a tail tape measure protein (TMP) with a 38% amino acid homology. The TMP of the 40.6-kb prophage presented sequence homology with *E. hirae*, *Enterococcus villorum* and *Enterococcus faecium* prophage TMPs with 98.8%, 96.7%, and 97.7% amino acid identity, respectively. The TMP of the 39.2-kb prophage showed sequence homology with only EH clone IGR7 (CNCM I-5224) with 100% homology (FIG. 21, Table 8) and to a lesser extent with *E. faecalis* prophage TMP with 89.2% amino acid identity. Despite sequence homologies with other phage genes, the whole two prophages were uniquely encoded in the strain 13144. Finally, both TMP1 and TMP2 peptides are part of the same phage tail tape measure protein (TMP) gene of the second prophage (SEQ ID No: 2). TMP1 of 13144 presented 100% homology with IGR7 and IGR11 but 88.89% homology with 10815 and IGR1 (1 mutation in position 3). TMP2 of 13144 presented 100% homology only with IGR7 and 77.78% homology with 10815 and IGR11 (2 mutations in position 2 and 7 or 2 and 4 respectively) (FIG. 21, Table 8).

TABLE 8 summary of the characteristics of the strains

| Strains | Anti-tumor effect | Epitope TMP1 (Prophage no 2) | Epitope TMP2 (Prophage no 2) | TMP Protein (prophage no 1) | TMP Protein (prophage no 2) |
|---|---|---|---|---|---|
| 13144 | Yes | — | — | — | — |
| 708 | No | No homology | No homology | 98.72% | No homology |
| EH17 (13344) | No | No homology | No homology | 25.52% | No homology |
| 10815 (ATCC9790) | No | 88.8889% (1 mutation) | 77.778% (2 mutations) | 24.03% | 66.38% |
| IGR 1 | No | 88.8889% (1 mutation) | No homology | 99.04% | 74.77% |
| IGR 4 | Yes | No homology | No homology | 99.15% | No homology |
| IGR 7 | Yes | 100% | 100% | 100% | 100% |
| IGR 10 | No | No homology | No homology | No homology | No homology |
| IGR 11 | Yes | 100% | 77.778% (2 mutations) | No homology | 66.52% |

Figure 29A:
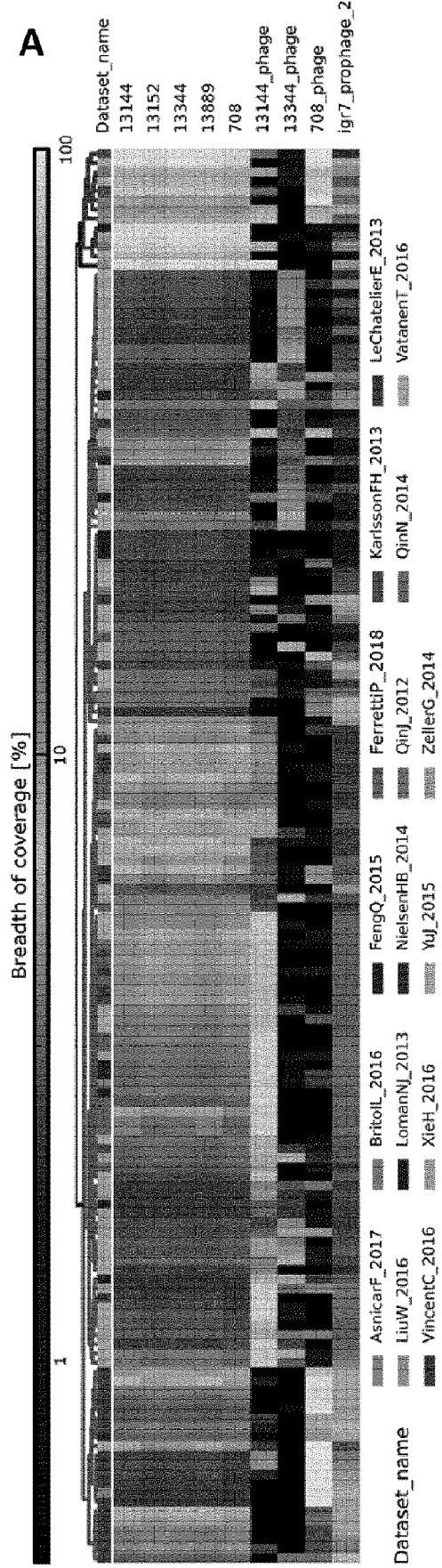

Example 6: *E. hirae* 13144 Bacterial and Phage Sequences have been Occasionally Found in the MG Reference Catalog Containing >3,000 Metagenomes in Humans A total of 3027 metagenomes from 17 different datasets were screened (FIG. 29A). They were—for the large majority—gut microbiomes (stools) but also oral cavity, skin, vagina, and sputum. Most of the datasets are publicly available covering all continents, including several non-westernized populations. We also included some of Nicola Segata's unpublished data (most notably of 25 paired mother/infant subjects followed longitudinally). We assessed the breadth of coverage (BOC) of the *E. hirae* genome and its phages in each of the sample. The BOC measures the fraction of the genome that is covered by the reads in the metagenomes. A BOC of 1.0 means that the whole genome of the reference strain is found in the metagenome. Based on this score, we could confidently conclude that *E. hirae* is present for sure in two samples. One is from a mongolian subject, the other from a Swedish one (BOC of 0.9 and 0.75 respectively). There are other 5 samples with a BOC between 0.1 and 0.37 that are probably indicative of *E. hirae* presence. Below a BOC of 0.1, we fail to characterize the presence of a *E. hirae* strain. As for the phages sequences, it seems that the mongolian subject positive for *E. hirae* also has prophage 2 from 13144 of SEQ ID No: 2, whereas the Swedish one has prophage 2 from 708. The phages seem to be present in more samples than the bacterium genome. One interesting case is the presence at 0.66 BOC of the Phage 13144 in three samples from an infant at 1, 3, and 7 days of life (samples CA_C10006IS2084FE_t1M15, CA_C10006IS2087FE_t2M15,CA_C10006IS2091FE_t3M15). These three samples do not have *E. hirae*, but seem to have another strain from another *Enterococcus* species. This might suggest that this phage is not specific of *E. hirae* only.

Figure 22A:
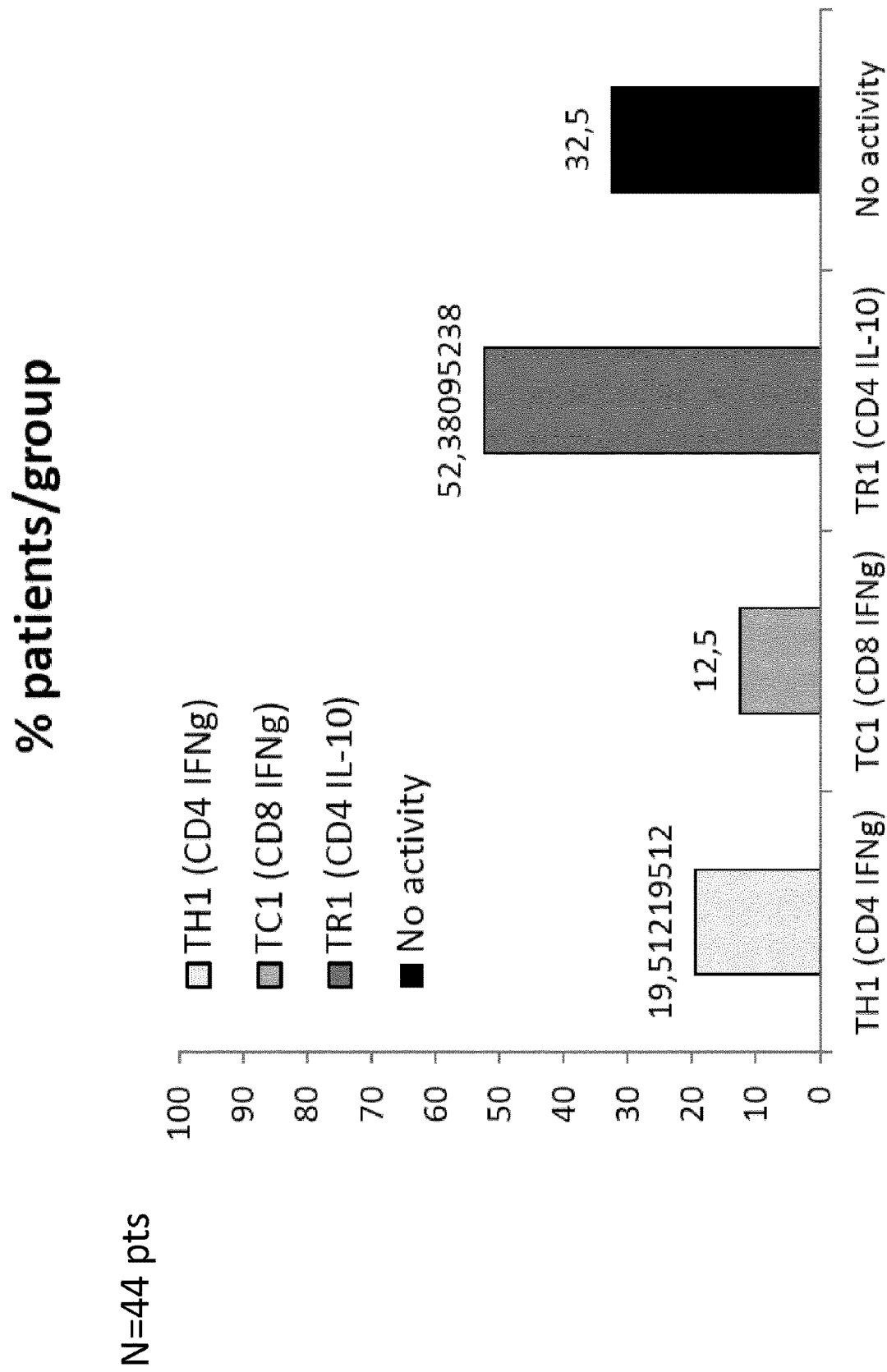
FIG. 22. T cell responses against commensals in blood from breast cancer patients at diagnosis priori to chemotherapy. Autologous monocytes harvested from breast cancer patients were stimulated with distinct bacterial spp. and then incubated with autologous CD4+ T cells or CD8+ T cells to monitor IFN-γ and IL-10 release. (A) TH1/Tc1/Tr1 immune responses to *E. hirae* 13144. Less than 20% breast cancer (BC) patients at diagnosis exhibit a blood TH1/Tc1 immune response to *E. hirae* 13144 prior to chemotherapy. (B) TH1/Tc1/Tr1 immune responses to *E. coli* or TCR cross-linking. BC women display memory T cell responses against *E. coli* and respond to TCR cross-linking.
Figure 23:
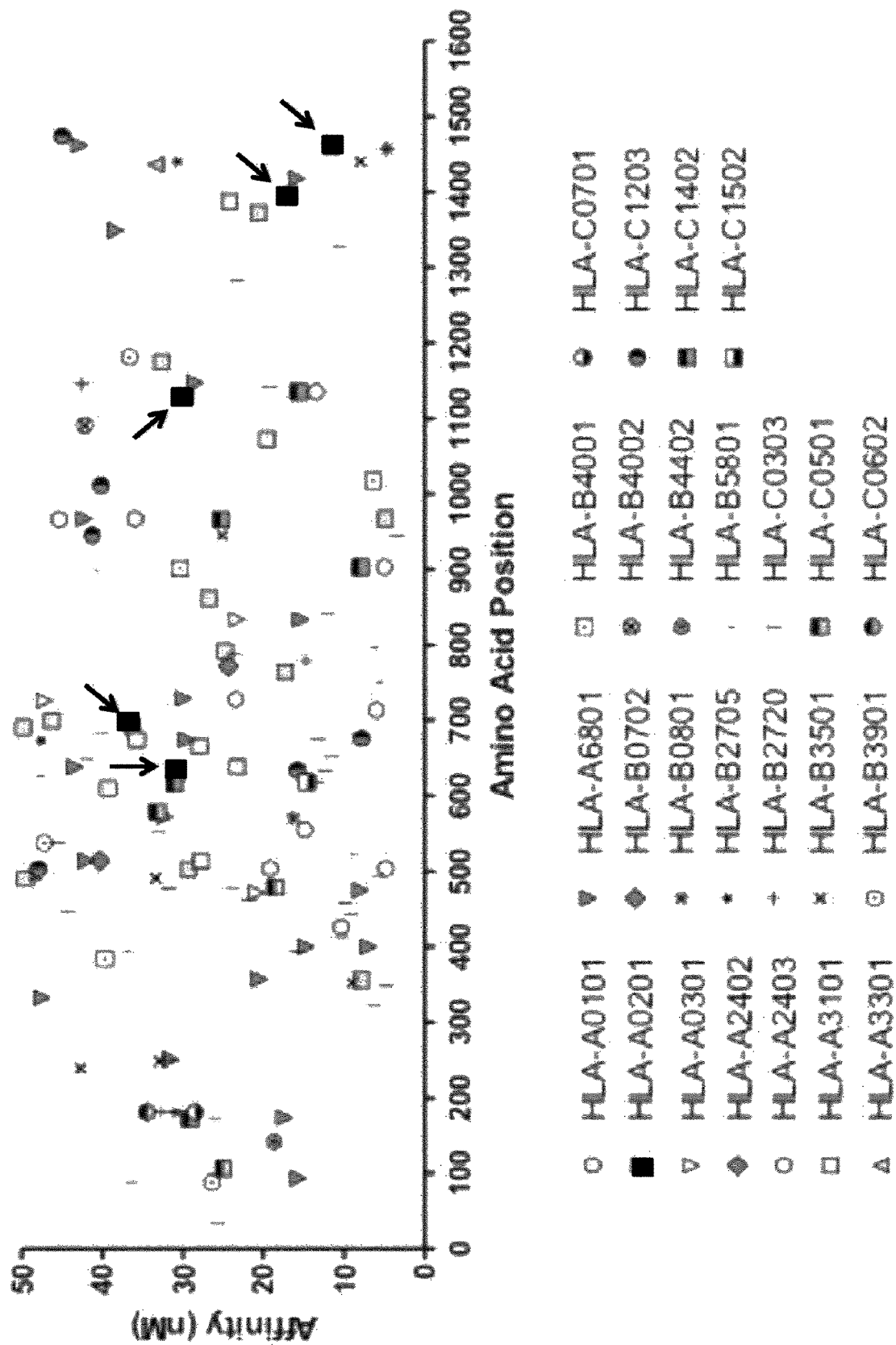
FIG. 23. Localization of the predicted peptides of TMP for each HLA haplotype to be tested in humans. Localization of predicted peptides of Tmp with significant binding potential for MHC Class I alleles (threshold of 50 nM) that was assessed using NetMHC software. For each peptide and allele, symbols represent the first amino acid of the identified sequence corresponding to 9 amino acid long peptides with their binding affinity to MHC Class I allele. Sequences of predicted peptides were resumed in table 9.
Figure 24C:
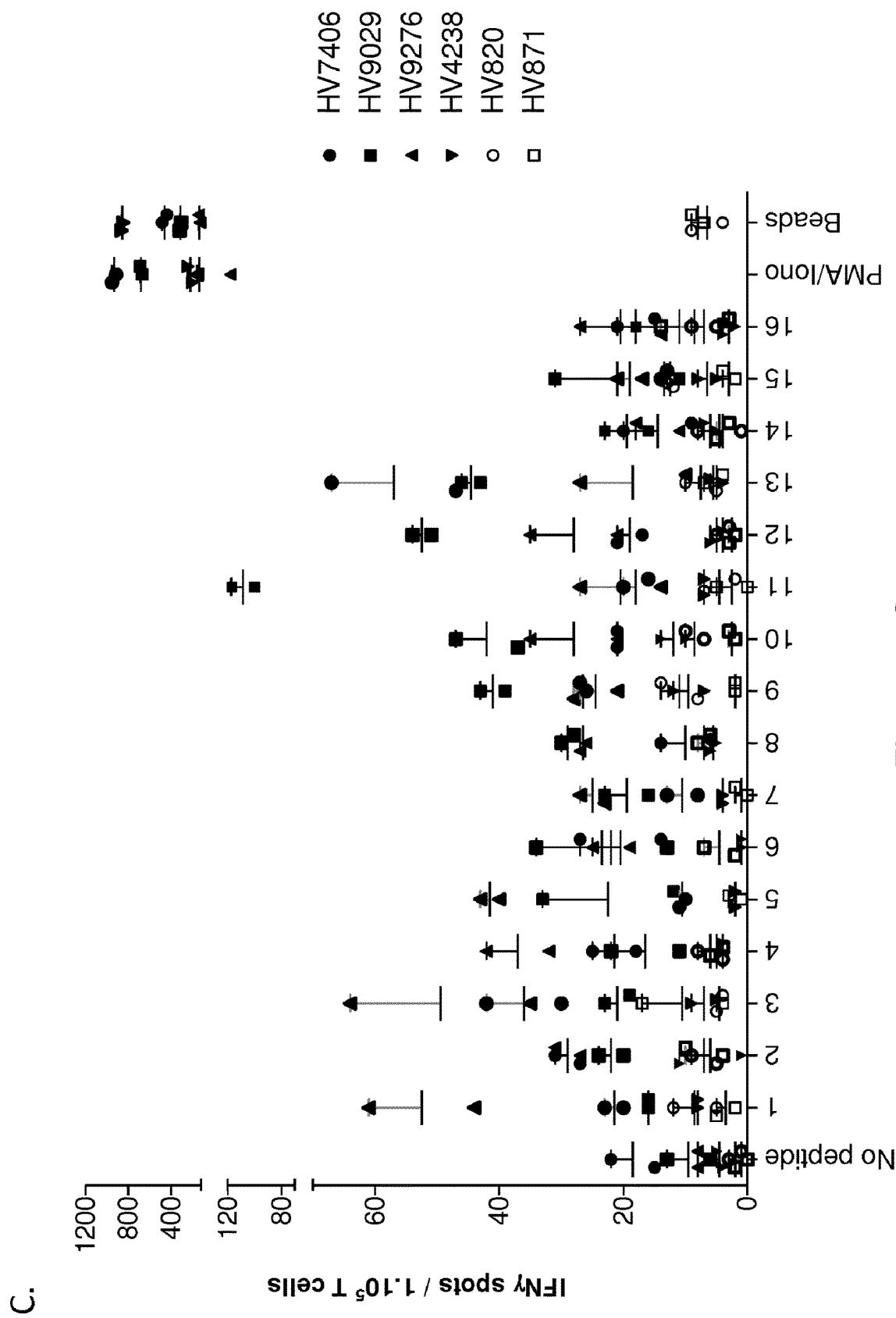
FIG. 24. Antigenicity of TMP peptides in human PBMCs from healthy volunteers. In vitro stimulation assays of recall responses either indirectly, after 2 rounds of stimulations by DCs pulsed with peptides (groups or individual peptides) to educate central memory CD8+ T cells from PBMCs using ELISPOT to reveal IFNγ release after 24 hr restimulation (A). Each peptide is HLA-A2 restricted (B) and 6 healthy volunteers "HV" (individualized with a 6 digit number) were selected on their HLA-A2.1 genotype (C). In (B), we underlined the peptides which are endowed with immunogenicity in the following graphs. We determined the threshold for each HV (D) and calculated the number of "positive" wells (above the threshold) and the pourcentages of responders for each peptide Isited in table B (E). When we represent these results in bar graphs, we observe that 5 peptides may be significantly associated with the immunogenicity of TMP in humans because they have been found to trigger Tc1 immune recall responses in at least 50% of HV (F). Arrows indicate the most significant epitopes (G). The list of peptides for each group and the most significant epitopes (2, 3, 9, 10, 13) are indicated in B and correspond to SEQ ID Nos: 54 to 69.
Figure 24D:
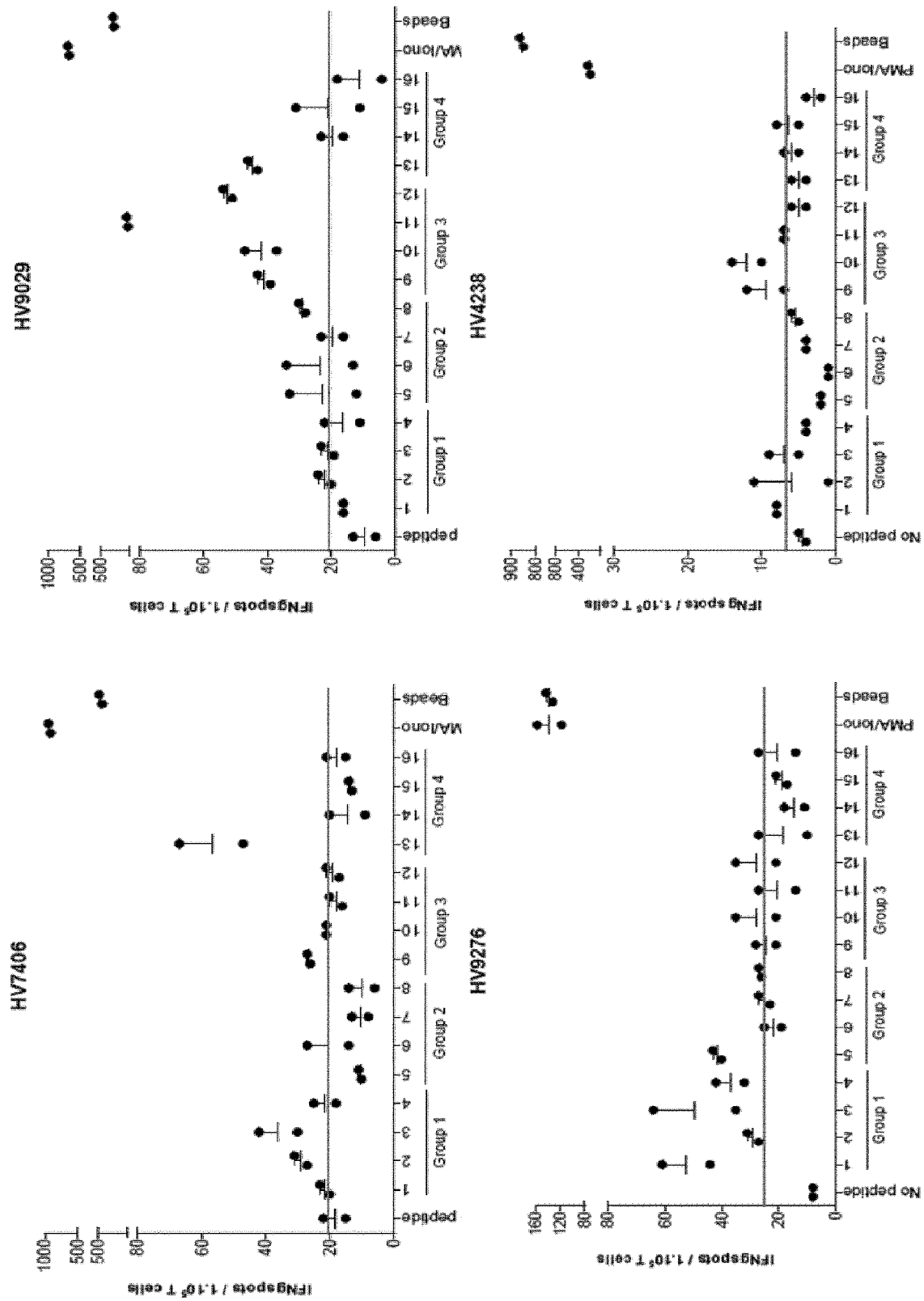
Figure 24G:
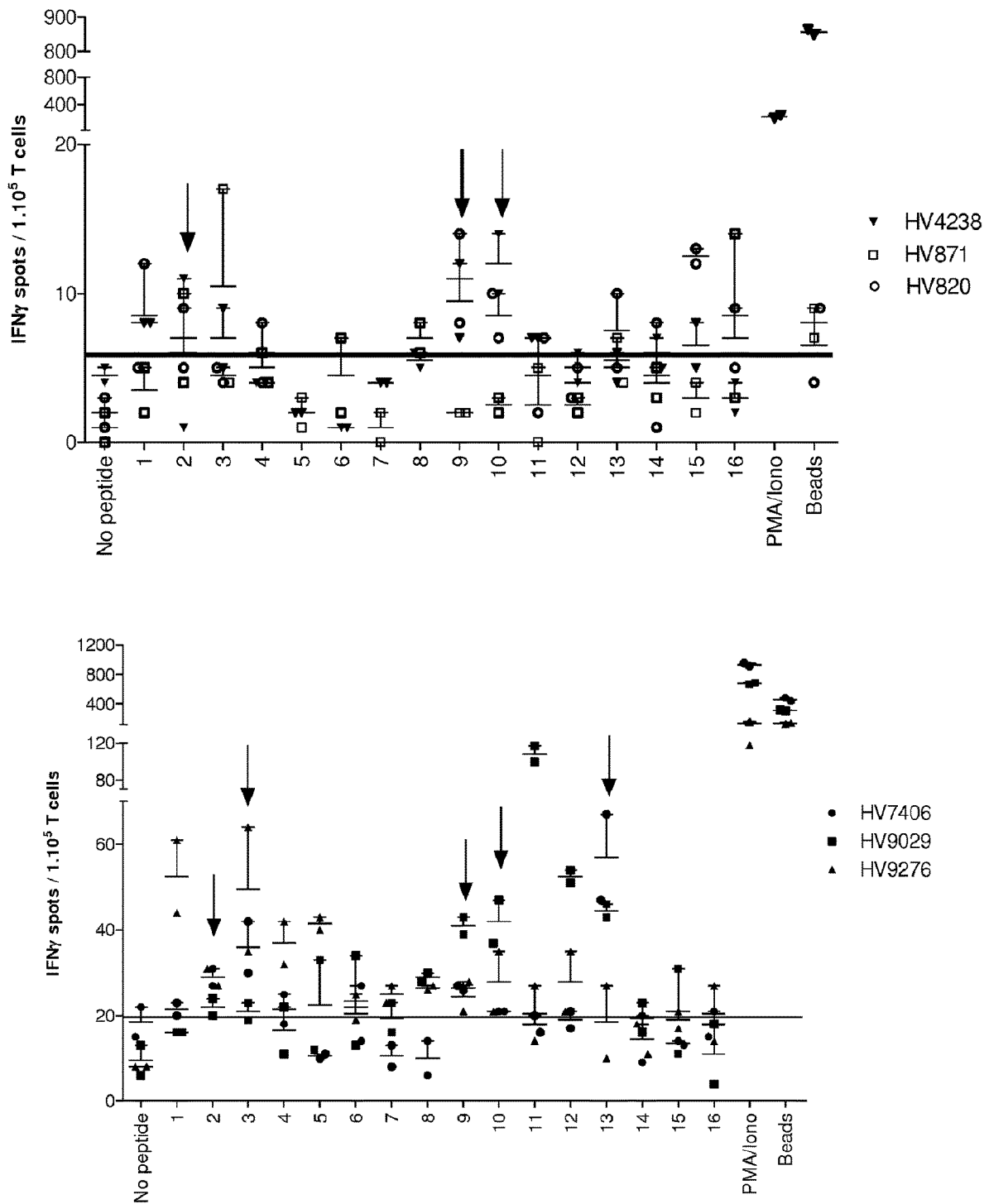
Figure 25:
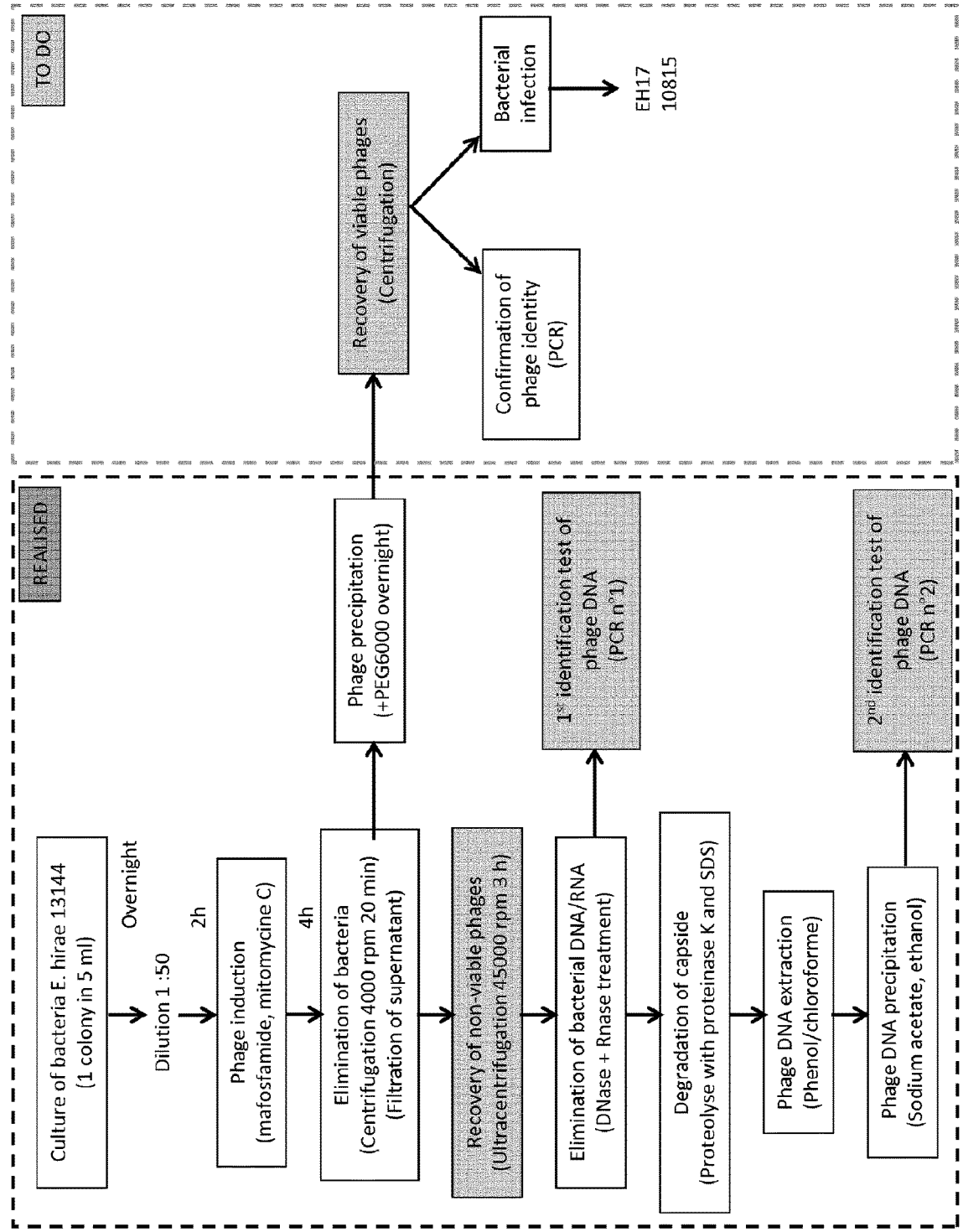
FIG. 25. Protocol for phage excision by mitomycin C. Each step of the technical procedure is indicated.

Example 7: *E. hirae* 13144 is Immunogenic not Only in Mice but Also in Humans (Normal Volunteers and Breast Cancer Patients): Defining TMP-Specific Peptides of High Immunogenicity in Humans Since *E. hirae* 13144 is a mouse strain but its sequence has been recovered in study alignment with human stool metagenomics, we postulated that humans (normal volunteers or breast cancer patients) could develop immune responses against some of the epitopes presented by this strain, as reported in (Daillère et al., 2016). FIG. 22A shows that 12 to 19% of CD4 and CD8+ T cells can display memory IFNγ-geared T cell responses to *E. hirae* 13144, suggesting that indeed, this EH strain can be recognized by human cells. FIG. 22A also highlights that 32% of BC patients have CD4+ T cells exhibiting no reactivity to monocytes pulsed with EH13144 while 52% developed IL-10 producing memory CD4+ T cell responses. This is in sharp contrast with the reactivity of the memory CD4+TH1 cells to *E. coli* and TCR cross-linking (FIG. 22B). The predicted peptides of Tmp to be tested in human PBMC or TILs are listed in Table 9 below, and their localization has been described in FIG. 23. Are indicated their binding potential for MHC class I alleles (threshold set at <50 nM, Y axis) assessed using NetMHC software. For each peptide and allele, symbols represent the first amino acid of the identified sequence corresponding to 9 amino acid long (mer) peptides. Next, we tested all HLA-A2-restricted Tmp epitopes on PBMC by in vitro stimulation assays of recall responses (FIG. 24A) from six HLA-A2+ healthy volunteers (HV) (FIG. 24C) and found that 5 peptides (indicated in FIG. 24B) exhibited significant reactivities at least in 50% of HV (FIG. 24 D-E). Arrows indicate the most significant epitopes (FIG. 24F-G).

TABLE 9

Predicted peptides of Tmp for each HLA haplotype

| Start | Stop | HLA | Peptide | Affinity(nM) | SEQ ID No: |
|---|---|---|---|---|---|
| 968 | 976 | HLA-A0101 | YTDYSNQLK | 35.98 | 53 |
| 357 | 365 | HLA-A0201 | AMIEFIQGL | 4.88 | 54 |
| 1462 | 1470 | HLA-A0201 | KMVEILEEI | 7.8 | 55 |
| 1397 | 1405 | HLA-A0201 | RLLKYDVGV | 11.55 | 56 |
| 765 | 773 | HLA-A0201 | TLVGVTFAI | 16.94 | 57 |
| 1374 | 1382 | HLA-A0201 | AMQNLVAAV | 17.32 | 58 |
| 793 | 801 | HLA-A0201 | AIMAIANGV | 20.56 | 59 |

TABLE 9-continued

Predicted peptides of Tmp for each HLA haplotype

| Start | Stop | HLA | Peptide | Affinity(nM) | SEQ ID No: |
|---|---|---|---|---|---|
| 862 | 870 | HLA-A0201 | AMSMNMEEV | 24.83 | 60 |
| 504 | 512 | HLA-A0201 | KVFGKMTSV | 26.84 | 61 |
| 1130 | 1138 | HLA-A0201 | LLGIYQSYV | 29.4 | 62 |
| 631 | 639 | HLA-A0201 | KLAKFASVV | 29.89 | 63 |
| 1176 | 1184 | HLA-A0201 | KLWANMSKA | 30.99 | 64 |
| 692 | 700 | HLA-A0201 | MLSNPITAI | 32.68 | 65 |
| 700 | 708 | HLA-A0201 | ILVAITTTI | 36.32 | 66 |
| 491 | 499 | HLA-A0201 | KMAALAASA | 46.27 | 67 |
| 691 | 699 | HLA-A0201 | AMLSNPITA | 49.58 | 68 |
| 473 | 481 | HLA-A0201 | NMAEAFASA | 49.85 | 69 |
| 835 | 843 | HLA-A0301 | TMFSDSALK | 20.82 | 70 |
| 573 | 581 | HLA-A0301 | LLTRFTTLK | 23.32 | 71 |
| 727 | 735 | HLA-A0301 | KTAFSGIVK | 32.3 | 72 |
| 515 | 523 | HLA-A0301 | KTISTMFEK | 47.18 | 73 |
| 505 | 513 | HLA-A2402 | VFGKMTSVF | 40.33 | 74 |
| 904 | 912 | HLA-A2403 | AYFNHTLDL | 4.83 | 75 |
| 714 | 722 | HLA-A2403 | AWKSNFMNI | 5.04 | 76 |
| 427 | 435 | HLA-A2403 | RYGTTESQL | 5.97 | 77 |
| 1136 | 1144 | HLA-A2403 | SYVNNGASI | 10.38 | 78 |
| 556 | 564 | HLA-A2403 | KYKSNLAGL | 13.47 | 79 |
| 505 | 513 | HLA-A2403 | VFGKMTSVF | 14.88 | 80 |
| 729 | 737 | HLA-A2403 | AFSGIVKSF | 19.19 | 81 |
| 967 | 975 | HLA-A2403 | VYTDYSNQL | 23.45 | 82 |
| 1074 | 1082 | HLA-A2403 | AFQNQITQL | 45.36 | 83 |
| 639 | 647 | HLA-A3101 | VINPIGSLR | 19.59 | 84 |
| 1389 | 1397 | HLA-A3101 | KAKIKSPSR | 23.3 | 85 |
| 515 | 523 | HLA-A3101 | KTISTMFEK | 24.29 | 86 |
| 667 | 675 | HLA-A3101 | ASKAGGGFR | 27.79 | 87 |
| 675 | 683 | HLA-A3101 | RTFAATGIR | 28.02 | 88 |
| 611 | 619 | HLA-A3101 | GNKVTNFFR | 35.72 | 89 |
| 1437 | 1445 | HLA-A3101 | ITGSRLIKR | 39.31 | 90 |
| 401 | 409 | HLA-A3301 | DVFEGAVKR | 33.42 | 91 |
| 476 | 484 | HLA-A6801 | EAFASADPK | 6.97 | 92 |
| 401 | 409 | HLA-A6801 | DVFEGAVKR | 7.96 | 93 |
| 835 | 843 | HLA-A6801 | TMFSDSALK | 14.72 | 94 |
| 94 | 102 | HLA-A6801 | ESAFTGVKK | 15.34 | 95 |
| 1419 | 1427 | HLA-A6801 | TSVAVQSAK | 15.68 | 96 |
| 175 | 183 | HLA-A6801 | DTAATSLAR | 15.91 | 97 |
| 358 | 366 | HLA-A6801 | MIEFIQGLK | 17.45 | 98 |
| 1148 | 1156 | HLA-A6801 | MALLAGMLR | 20.5 | 99 |
| 675 | 683 | HLA-A6801 | RTFAATGIR | 28.54 | 100 |
| 730 | 738 | HLA-A6801 | FSGIVKSFK | 29.62 | 101 |
| 252 | 260 | HLA-A6801 | EAGGSAFSR | 29.95 | 102 |
| 1350 | 1358 | HLA-A6801 | TSVGSNMAK | 31.53 | 103 |
| 515 | 523 | HLA-A6801 | KTISTMFEK | 38.32 | 104 |
| 968 | 976 | HLA-A6801 | YTDYSNQLK | 42.02 | 105 |
| 1463 | 1471 | HLA-A6801 | MVEILEEIR | 42.29 | 106 |
| 639 | 647 | HLA-A6801 | VINPIGSLR | 42.9 | 107 |
| 333 | 341 | HLA-A6801 | EDFANVTGR | 43.39 | 108 |
| 773 | 781 | HLA-A6801 | IAGFVDGLR | 47.53 | 109 |
| 1458 | 1466 | HLA-B0702 | TPMGKMVEI | 24.41 | 110 |
| 572 | 580 | HLA-B0801 | NLLTRFTTL | 4.7 | 111 |
| 1441 | 1449 | HLA-B0801 | RLIKRSNAI | 16.31 | 112 |
| 182 | 190 | HLA-B2705 | ARFANITQM | 30.73 | 113 |
| 674 | 682 | HLA-B2705 | FRTFAATGI | 30.97 | 114 |
| 780 | 788 | HLA-B2705 | LRAIITVGK | 47.66 | 115 |
| 182 | 190 | HLA-B2720 | ARFANITQM | 14.78 | 116 |
| 1146 | 1154 | HLA-B2720 | QQMALLAGM | 32.65 | 117 |
| 1441 | 1449 | HLA-B2720 | RLIKRSNAI | 42.54 | 118 |
| 353 | 361 | HLA-B3501 | NPSQAMIEF | 7.99 | 119 |
| 946 | 954 | HLA-B3501 | FANASTEYM | 9.08 | 120 |
| 250 | 258 | HLA-B3501 | EAEAGGSAF | 25.17 | 121 |
| 492 | 500 | HLA-B3501 | MAALAASAG | 32.95 | 122 |
| 240 | 248 | HLA-B3501 | FAAALSSVG | 33.38 | 123 |
| 495 | 503 | HLA-B3501 | LAASAGPVL | 42.72 | 124 |
| 89 | 97 | HLA-B3501 | AAVKWESAF | 48.3 | 125 |
| 1182 | 1190 | HLA-B3901 | SKADIVNTL | 26.44 | 126 |
| 539 | 547 | HLA-B3901 | IKNGSSSAL | 36.65 | 127 |
| 1018 | 1026 | HLA-B3901 | NKLNNNQAL | 47.23 | 128 |
| 902 | 910 | HLA-B4001 | VEAYFNHTL | 6.41 | 129 |
| 385 | 393 | HLA-B4001 | TEVRLRDSL | 30.39 | 130 |
| 1092 | 1100 | HLA-B4001 | SELEQGAQL | 39.74 | 131 |
| 385 | 393 | HLA-B4002 | TEVRLRDSL | 42.24 | 132 |
| 143 | 151 | HLA-B4402 | AEAAGQLGI | 18.68 | 133 |

TABLE 9-continued

Predicted peptides of Tmp for each HLA haplotype

| Start | Stop | HLA | Peptide | Affinity(nM) | SEQ ID No: |
|---|---|---|---|---|---|
| 752 | 760 | HLA-B5801 | KGLGNIFKW | 6.09 | 134 |
| 797 | 805 | HLA-B5801 | IANGVKGLW | 6.74 | 135 |
| 523 | 531 | HLA-B5801 | KAGNIDSKW | 9.31 | 136 |
| 351 | 359 | HLA-B5801 | KSNPSQAMI | 12.06 | 137 |
| 619 | 627 | HLA-B5801 | RSFSASLQL | 13.45 | 138 |
| 395 | 403 | HLA-B5801 | RAANASDVF | 37.43 | 139 |
| 898 | 906 | HLA-B5801 | STAGVEAYF | 41.32 | 140 |
| 693 | 701 | HLA-B5801 | LSNPITAIL | 42.57 | 141 |
| 627 | 635 | HLA-B5801 | LSNSKLAKF | 48.23 | 142 |
| 946 | 954 | HLA-00303 | FANASTEYM | 3.56 | 143 |
| 350 | 358 | HLA-00303 | FKSNPSQAM | 4.75 | 144 |
| 495 | 503 | HLA-00303 | LAASAGPVL | 5.93 | 145 |
| 324 | 332 | HLA-00303 | EASKASGSL | 6.31 | 146 |
| 445 | 453 | HLA-00303 | VAITFGGPL | 9.21 | 147 |
| 459 | 467 | HLA-00303 | SAISAAKPM | 9.9 | 148 |
| 412 | 420 | HLA-00303 | EAFNENTAL | 10.33 | 149 |
| 1328 | 1336 | HLA-00303 | SANNAGREL | 10.61 | 150 |
| 652 | 660 | HLA-00303 | AAGKSGTVL | 11.56 | 151 |
| 844 | 852 | HLA-00303 | KAAKSTEEL | 12.11 | 152 |
| 635 | 643 | HLA-00303 | FASVVINPI | 12.38 | 153 |
| 677 | 685 | HLA-00303 | FAATGIRSI | 13.26 | 154 |
| 395 | 403 | HLA-00303 | RAANASDVF | 15.87 | 155 |
| 1142 | 1150 | HLA-00303 | ASIDQQMAL | 19.24 | 156 |
| 463 | 471 | HLA-00303 | AAKPMIEAL | 21.86 | 157 |
| 1284 | 1292 | HLA-00303 | NAKQKGAEL | 23.31 | 158 |
| 789 | 797 | HLA-00303 | TAVNAIMAI | 23.51 | 159 |
| 480 | 488 | HLA-00303 | SADPKTQEF | 23.9 | 160 |
| 35 | 43 | HLA-00303 | NASDIPSNL | 25.71 | 161 |
| 173 | 181 | HLA-00303 | SADTAATSL | 26.05 | 162 |
| 478 | 486 | HLA-00303 | FASADPKTQ | 31.85 | 163 |
| 250 | 258 | HLA-00303 | EAEAGGSAF | 31.9 | 164 |
| 553 | 561 | HLA-00303 | FVSKYKSNL | 33.06 | 165 |
| 89 | 97 | HLA-00303 | AAVKWESAF | 36.44 | 166 |
| 685 | 693 | HLA-00303 | IASLTGAML | 40.14 | 167 |
| 651 | 659 | HLA-00303 | SAAGKSGTV | 41.97 | 168 |
| 449 | 457 | HLA-00303 | FGGPLVAAL | 44.33 | 169 |
| 539 | 547 | HLA-00303 | IKNGSSSAL | 45.59 | 170 |
| 480 | 488 | HLA-00501 | SADPKTQEF | 18.54 | 171 |
| 107 | 115 | HLA-00501 | MVDSNGKVI | 25.04 | 172 |
| 173 | 181 | HLA-00501 | SADTAATSL | 29.14 | 173 |
| 580 | 588 | HLA-00501 | LKDTIVGLF | 33.18 | 174 |
| 182 | 190 | HLA-00602 | ARFANITQM | 34.48 | 175 |
| 182 | 190 | HLA-00701 | ARFANITQM | 28.58 | 176 |
| 677 | 685 | HLA-C1203 | FAATGIRSI | 7.86 | 177 |
| 635 | 643 | HLA-C1203 | FASVVINPI | 15.83 | 178 |
| 1012 | 1020 | HLA-C1203 | FVEAGVNKL | 40.2 | 179 |
| 946 | 954 | HLA-C1203 | FANASTEYM | 41.29 | 180 |
| 1475 | 1483 | HLA-C1203 | VVMDTGQVV | 45.03 | 181 |
| 504 | 512 | HLA-C1203 | KVFGKMTSV | 47.93 | 182 |
| 904 | 912 | HLA-C1402 | AYFNHTLDL | 7.99 | 183 |
| 1136 | 1144 | HLA-C1402 | SYVNNGASI | 15.64 | 184 |
| 967 | 975 | HLA-C1402 | VYTDYSNQL | 25.25 | 185 |
| 617 | 625 | HLA-C1402 | FFRSFSASL | 31.08 | 186 |
| 619 | 627 | HLA-C1502 | RSFSASLQL | 14.65 | 187 |

Example 8: Phage Excision in EH13144 In Vitro

Figure 26A:
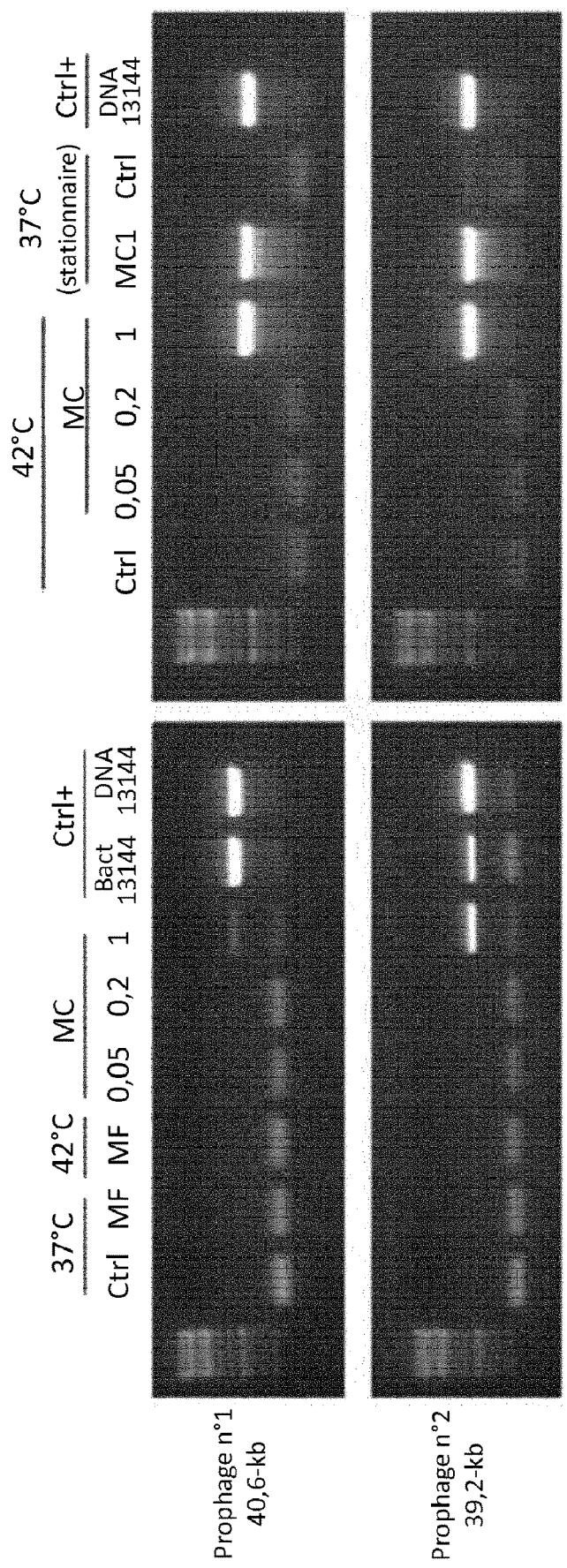
FIG. 26. PCR detection of phage nucleic acids in the supernatants of *E. hirae*13144. Supernatants of EH13144 cultivated at various temperatures (37 or 42° C.), at various concentrations of mitomycine C (0, 0.2 and 1 μM), or active metabolite of CTX (mafosfamide-25 μg/ml) were treated to harvest the phage proteins encoding DNA with (B) or without (A) capside disruption. PCR was run to detect specific sequences of the prophage 1 or 2.
Figure 26B:
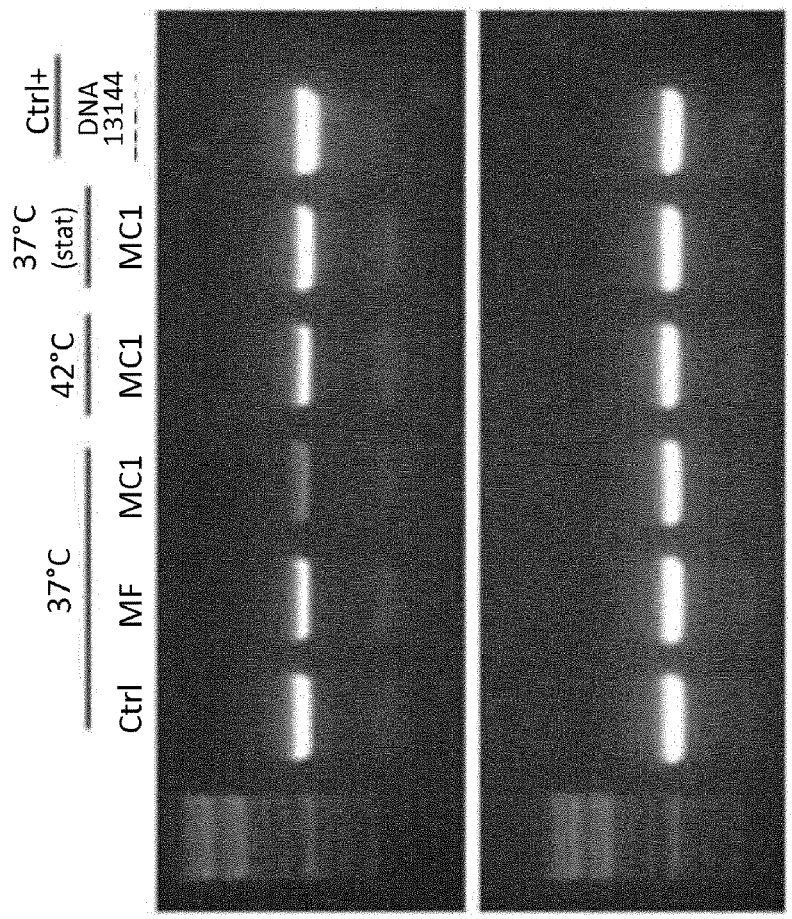

Using a classical procedure to excise a phage and harvest it in the supernatants of the *E. hirae* (FIG. 25) (Duerkop et al., 2014), we could observe prophage 1 and 2 excision after incubation of EH13144 with mitomycin C (1 µg/ml) but not CTX (FIG. 26A), at different temperatures (37° C. and 42° C.) regardless of expansion phase of the bacterium. After capside lysis of the supernatants (augmenting the sensitivity of phage DNA detection), prophages DNA were visualized in spontaneous conditions, suggesting that phages can also be released without excision stresses (FIG. 26B).

Example 9: Identification of Novel Strains Harboring the Gene Encoding the TMP of SEQ ID No: 1

The genomes of twenty different *E. hirae* strains (Table 10 below) were sequenced and aligned. Remarkably, 3 prophage regions, of which 2 regions are intact, were identified in the genome of the strain IGR7, which proved immunogenic (see example 1 above), and it was found that this genome encode the same TMP as the TMP of SEQ ID No: 1 encoded by *E. hirae* 13144 (Table 9). This strain was deposited at the CNCM on 12 Oct. 2017, under the number 1-5224. Moreover, IGR11 which proved efficient to mediate some tumoricidal activity with CTX have also the same TMP1 epitope encoded by 13144 (Table 9). This strain was deposited at the CNCM on Nov. 27, 2017, at the CNCM under the number 1-5261.

TABLE 10

| Strain | No of scaffolds | Length | GC % | No of CDS |
|---|---|---|---|---|
| 5348 | 4 | 2773687 | 36.84 | 2541 |
| 7030 | 2 | 2839464 | 36.72 | 2665 |
| 12607 | 3 | 2981483 | 36.62 | 2662 |
| 13150 | 3 | 2881518 | 36.76 | 2692 |
| 13153 | 1 | 2732232 | 36.84 | 2479 |
| 13155 | 9 | 2956728 | 36.56 | 2688 |
| 13161 | 2 | 2814115 | 36.90 | 2696 |
| 13343 | 2 | 2748768 | 37.01 | 2555 |
| 13346 | 3 | 2758418 | 36.98 | 2511 |
| 13347 | 3 | 2876247 | 36.71 | 2668 |
| IGR1 | 2 | 2874823 | 36.73 | 2681 |
| IGR4 | 3 | 2958768 | 36.71 | 2649 |
| IGR7 | 2 | 2705237 | 36.84 | 2543 |
| IGR10 | 2 | 2921736 | 36.70 | 2589 |
| IGR11 | 3 | 2836600 | 36.91 | 2600 |
| 13144 | 1 | 2735684 | 36.96 | 2542 |
| 13152 | 1 | 2835470 | 36.92 | 2486 |
| 13344 | 1 | 2711996 | 37.12 | 2472 |
| ATCC9790 | 1 | 2827741 | 36.94 | 2670 |
| 708 | 1 | 2951512 | 36.89 | 2613 |

Example 10: Cell Sorting and Expansion of TIL or Blood T Cells Specific for the TMP Several protocols can be used to obtain TILs or T cells specific for the TMP of SEQ ID No: 1.
Protocol 1: Immunomagnetic Cell Sorting and Expansion of T Cell Sorted Populations HLA-A*0201/TMP monomers (20 µg/ml) are incubated for 1 h at room temperature with $6.7.10^6$ streptavidin-coated beads (Dynabeads M-280 streptavidin, DYNAL, Compiegne, France) and washed in PBS/0.1% BSA. $5·10^6$ PBMC are rotated for 4 h at 4° C. with monomer-coated beads (Bodinier et al., 2000). After ten washes, bead coated cells are expanded using a polyclonal T cell stimulation protocol (Jotereau et al., 1991). Subsequently, cells are incubated with sheep anti-mouse IgG coated Dynabeads (Dynal Biotec, Compiegne, France) at a 1:1 ratio for 4 h at 4° C. with gentle rotation. The cell/bead suspension are incubated in culture medium in 6-well plates overnight at 37° C. to allow beads to detach. After overnight incubation, beads are extracted by the magnet, and sorted lymphocytes are transferred on feeder cells, as previously described (Jotereau et al., 1991). Briefly, 2000 bead-coated T cells/well are distributed in 96-well plates mixed with irradiated feeder cells [LAZ EBV-B cells ($2·10^4$/well) and allogeneic PBMC ($10^5$/well)], in 150 µl of culture medium supplemented with IL-2 (150 U/ml) and PHA (15 µg/ml).
Protocol 2

Tumor samples from cancer specimens are cultured with cytokines (IL-2, IL-15, and IL-21) to expand TILs. After 10 days of culture, TILs are stimulated with an anti-CD3 antibody (OKT3) and irradiated allogeneic peripheral blood mononuclear cells (as described in Meng et al., 2016).

Example 11: Obtention of T Cells Specific for the TMP by Transduction of T Lymphocytes Autologous or allogeneic T cells are placed in an expanding phase using anti-CD3/CD28 coated beads or low dose IL-2 (and IL-7, IL-15, IL-21) before being exposed to retroviral vectors or lentiviral vectors engineered to express the beta chain of the high avidity TCR encoding cDNA (for the TMP prophage 2 epitope corresponding to HLA-A2 or other haplotypes) and/or the alpha chain of the high avidity TCR encoding cDNA (for the TMP prophage 2 epitope corresponding to HLA-A2 or other haplotypes) and the CDR3 region of this TCR encoding cDNA (for the TMP prophage 2 epitope corresponding to HLA-A2 or other haplotypes). Polyclonal T cells are then cloned and tested for their specificity (IFNg or TNFa release upon exposure to TMP epitopes) in 96 well plates. Cytokine-producing T cells are then selected and reexpanded with T cell growth factors (IL-2; IL-7, IL-15, IL-21) on a weekly basis for two to three weeks until expansion to $10^{10}$ to $10^{12}$ cells in GMP cell factories.

DISCUSSION

Our findings revealed that the antigenicity of mouse EH 13144 and the newly cloned human EH IGR7 (CNCM I-5224) or EH IGR11 (both 100% homologous in their sequence) relies on the Phage Tail Length Tape Measure Protein (Tmp) of the Siphoviridae phages (lactococcal bacteriophage tail tape measure protein TP901 family) mainly in the 39.2-kb prophage encoded 65 genes, including 7 shared between the five genomes, 3 shared between strains 13144 and 708 and 22 unique to E. hirae 13144. Transfer of genetic materials inbetween enterococci species have been reported (Mazaheri Nezhad Fard et al., 2010, 2011). Of note, phages that infect Gram positive bacteria often contain peptidoglycan-hydrolysing motifs corresponding to peptidase and transglycosylase activities localized within tape measure proteins of Siphoviridae phages (Piuri and Hatfull, 2006). We will now attempt to restore immunogenicity of non-immunogenic E. hirae strains (EH17, 10815) by transducing these strains with bacteriophages belonging to the family of Siphoviridae, or with genetically modified plasmids encoding the whole Phage Tail Length Tape Measure Protein (Tmp) or epitopes selected from TMP prophage 2, and with negative controls (proteins or epitopes mutated in the MHC binding groove). Of note, M. tuberculosis Rpfs T cell antigens were reported to be important targets in the human immune responses to M. tuberculosis (Commandeur et al., 2011).

These mouse data have a clinical relevance. Based on in silico prediction (sequence alignment of the several strains of E. hirae, protein subcellular localization and algorithms of prediction of MHC binding affinities), a list of candidate epitopes harbouring a putative immunogenicity has been established in the first step of the selection (FIG. 23). In a second step, in vitro stimulation assays using peripheral blood mononuclear cells from HLA-A0201+ normal volunteers with 4 groups of 4 nine mer-TMP specific epitopes followed by a recall response using single 9 mer epitopes performed in 6 healthy volunteers revealed that 5 epitopes could be considered immunogenic (FIG. 24). Third step, a bioinformatic screening of the normal human proteome and gene expression in >350 tumors cell lines investigating sequence homologies between these 5 human immunogenic TMP epitopes and such proteomes concluded that one of this HLA-0201 epitope KLAKFASVV (SEQ ID No: 63), shares a 78% sequence homology with the glycerol-3 phosphate dehydrogenase 1 like protein (GPD1L, gene encoded on 3p22.3). GPD1L is a cytosolic protein, associated at the plasma membrane with a sodium channel, voltage-gated, type V alpha subunit (SCN5A). GPD1L is a hypoxia-associated protein negatively regulated by miR-210, overexpressed in many tissues (brain, during embryo- and foetogenesis), and contributes to the proteosomal degradation of hypoxia inducible factor 1-alpha (HIF-1a). Indeed, MiR-210 represses levels of the glycerol-3-phosphate dehydrogenase 1-like (GPD1L) enzyme, contributing to suppression of prolyl hydroxylase (PHD) activity. Under normal physiological conditions, PHD hydroxylates prolines in hypoxia inducible factor 1-alpha (HIF-1a), leading to its degradation by the proteasome. When PHD activity is suppressed due to downregulation of GPD1L by miR-210, HIF-1a is not degraded by the proteasome and translocates to the nucleus where it forms a heterodimer with hypoxia-inducible factor 1-beta (HIF-1B); dimerization of HIF-1a and HIF-1B activates transcriptional responses that contribute to cancer metastasis (Costales et al., 2017). Hence, higher mRNA levels and/or protein expressions of GPD1L in head and neck squamous cell carcinoma compared with healthy surrounding tissues was an independent prognostic parameter and a favorable predictor of longer time to local recurrence and distant metastases in multivariate Cox regression analyses (Feng et al., 2014).

Since the binding affinity for HLA-A0201 of this phage peptide is similar to the one of normal tissue peptide, the phage peptide could be viewed as an immunogenic molecular mimick of the normal peptide. It is therefore conceivable that cross-reactivities between TMP phage specific TCR and self tissues or tumor tissues (overexpressing GPD1L), mainly foetal tissues or stem cells, could account for the anticancer effectiveness of the phage delivered in the context of this EH bacterium. Of note, tumor cell lines can express variable levels of GPD1L protein, as appears from gene expression atlas available on the web.

HLA-A0201 restricted-epitope TMP 2 (KMVEILEEI, SEQ ID No: 55), epitope 3 (RLLKYDVGV, SEQ ID No: 56), epitope 9 (LLGIYQSYV, SEQ ID No: 62), epitope 10 (KLAKFASVV, SEQ ID No: 63, homologous to sequences from GPD1L) and epitope TMP 13 (ILVAITTTI, SEQ ID No: 66) have been found so far (FIG. 24), enabling tetramer manufacturing, T cell capture in tumor bearers (human patients or mice) and structural and functional characterization. Reactivity of E. hirae-specific CTL clones from tumor infiltrating lymphocytes can be tested against a variety of syngeneic tumor cell lines to bring up the proof of principle of molecular mimicry between microbial and tumor antigens.

This asset accounts for the quasi-unique antigenicity of E. hirae 13144 exploitable for cancer vaccines and T cell transfer and prompts to the use of this phage to infect other bacterial strains for use as anticancer probiotics or OncoBax in combination with any drug identical or different from cyclophosphamide capable of enabling the niching of the dedicated species and/or stressing the excision of this phage. For instance, cyclophosphamide could allow the overrepresentation of E. hirae over its competitor E. gallinarum while the competition between these two strains promoted phage excision per se.

Example 12: Phage Tail Length Tape Measure Protein as the Unique Antigenic Sequence in E. hirae 13144

Unleashing immune responses against tumor-associated antigens through chemotherapy, radiotherapy, targeted therapies or immune checkpoint inhibitors has become the mainstay of successful cancer treatments (Galluzzi et al., 2015; Sharma and Allison, 2015). The recent discovery that the gut microbiota determines the cancer-immune set point, thus influencing the clinical outcome of anticancer therapies, has rekindled the concept that microbes or their products modulate not only intestinal but also systemic immunity (Zitvogel et al., 2018). Indeed, memory IFNγ producing CD4+(TH1) and CD8+(TC1) T cell responses directed against Enterococcus hirae, Bacteroides fragilis, and Akkermansia muciniphila are associated with favorable clinical outcome in cancer patients (Daillère et al., 2016; Rong et al., 2017; Routy et al., 2018; Vétizou et al., 2015), suggesting that pre-existing microbe-specific T cells may contribute to anticancer immune responses. However, the question how microbes may affect the development of systemic autoimmune disease or local intestinal chronic inflammation has not been resolved (Rose, 2017). The theory of molecular mimicry posits that T cells elicited by bacteria or viruses may accidentally recognize autoantigens as they 'escaped' from self-tolerance inducing mechanisms (such as clonal deletion or inactivation). While MHC class I and class II binding epitopes from bacterial genomes have been identified to mediate immunogenicity in vitro or in vivo (Chai et al., 2017; Perez-Muñoz et al., 2015; Rubio-Godoy et al., 2002; Vujanovic et al., 2007; Yang et al., 2014), very few reports have unarguably demonstrated the functional relevance of microbe-specific CD4+ or CD8+ T lymphocytes for immune responses against normal or neoplastic tissues (Balachandran et al., 2017; Bradley et al., 2017; Ji et al., 2010).

Figure 31A:
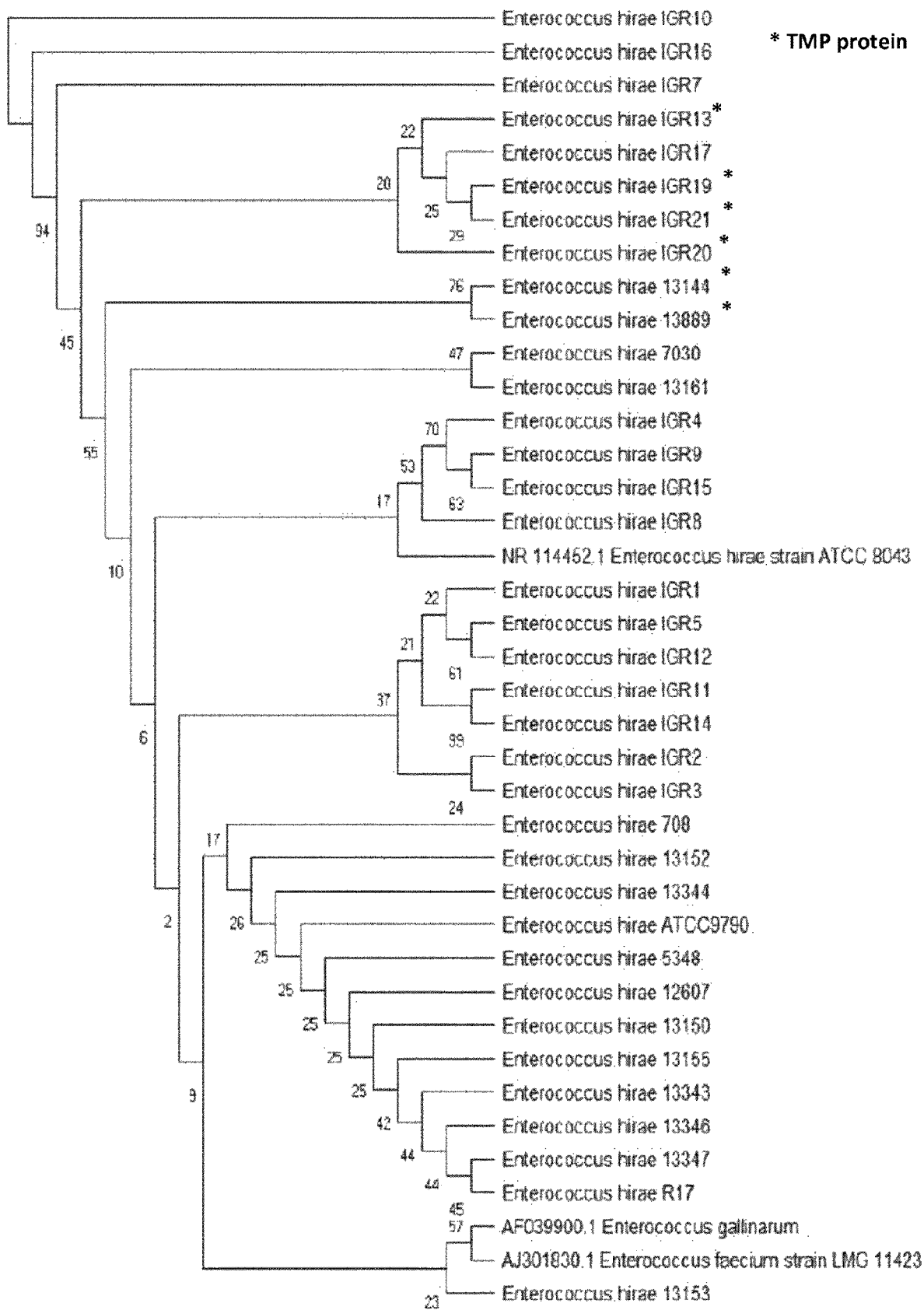

Cyclophosphamide (CTX) induces the translocation of E. hirae from the gut lumen to the mesenteric and splenic immune tissues, thereby eliciting specific CD4+ and CD8+T lymphocytes producing IL-17 and IFNγ, correlating with therapeutically effective anticancer immune responses (Daillère et al., 2016; Viaud et al., 2013). Broad-spectrum antibiotics abolished the therapeutic efficacy of CTX unless E. hirae was supplied by oral gavage (Daillère et al., 2016). When comparing a panel of E. hirae strains (Table 11, FIG. 31A) for their capacity to restore the antibiotic-perturbed anticancer effects of CTX, we found that only a few E. hirae isolates (such as 13144, IGR7, and IGR11) were efficient (FIG. 27A-B, (Daillère et al., 2016)). Given that the therapeutic efficacy of the combination of CTX and E. hirae 13144 is abrogated by the depletion of CD8+ T cells or the neutralization of IFNγ (Daillère et al., 2016), we screened the differential capacity of E. hirae strains to elicit memory TC1 immune responses after a prime-boost exposure of the host (FIG. 27C), and ex vivo restimulation of splenic CD8+ T cells with various E. hirae strains loaded onto dendritic cells (DC). While E. hirae 13144 triggered specific TC1 immune responses (that were not cross-reactive against irrelevant Enterococci), E. hirae 708 (a prototypic inefficient strain) failed to do so (FIG. 27D). Pan genomic analysis of twenty E. hirae strains yielded a core genome of 1,677 orthologous genes (59%) and the accessory genome was composed of 946 and 477 orthologous and unique genes respectively (FIG. 31B). This phylogenomic analysis showed that the strain 13144 is 100% homologous to strain IGR7 with 86 orthologous unique genes (FIG. 31B).

TABLE 11

Description of E. hirae strains

| Species | Samples | Origin | Cancer | Patient outcome |
|---|---|---|---|---|
| Enterococcus hirae 13144 | | Murine—CTX-treated | | |
| Enterococcus hirae 708 | | Human-Unknown | | |
| Enterococcus hirae 13344 | | Human-Blood | | |
| Enterococcus hirae ATCC9790 | | Type strain CIP 53.48T | | |
| Enterococcus hirae IGR1 | MAT-HE | Human (stool) | Lung | Responder |
| Enterococcus hirae IGR2 | AND-CL | Human (stool) | Lung | Responder |
| Enterococcus hirae IGR3 | BLO-VA | Human (stool) | Lung | Responder |
| Enterococcus hirae IGR4 | SAI-GE | Human (stool) | Lung | Complete Responder (HR selon RECIST) |
| Enterococcus hirae IGR5 | CAR-RO | Human (stool) | Lung | Responder |
| Enterococcus hirae IGR6 | BOU-MO | Human (stool) | Lung | Responder |
| Enterococcus hirae IGR7 | BOU-MO | Human (stool) | Lung | Responder |
| Enterococcus hirae IGR8 | AND-CL | Human (stool) | Lung | Responder |
| Enterococcus hirae IGR9 | AND-CL | Human (stool) | Lung | Responder |
| Enterococcus hirae IGR10 | ADO-EL | Human (stool) | Lung | Responder |
| Enterococcus hirae IGR11 | ADO-EL | Human (stool) | Lung | Responder |
| Enterococcus hirae IGR12 | TROJA | Human (stool) | Kidney | Responder |
| Enterococcus hirae IGR13 | LOUNO | Human (stool) | Kidney | Responder |
| Enterococcus hirae IGR14 | BOIAR | Human (stool) | CRC | Responder |
| Enterococcus hirae IGR15 | NAIFE | Human (stool) | CRC | Responder |
| Enterococcus hirae IGR16 | GIRAL | Human (stool) | CRC | Responder |
| Enterococcus hirae IGR17 | LEZPH | Human (Tumor juice) | Melanoma | Responder |
| Enterococcus hirae IGR18 | PRIMI | Human (Tumor juice) | Melanoma | Responder |
| Enterococcus hirae IGR19 | NONRO | Human (Tumor juice) | Melanoma | NA |
| Enterococcus hirae IGR20 | Lyon No 1 (CAR) | Human (Tumor juice) | Melanoma | NA |
| Enterococcus hirae IGR21 | PRUPA | Human (Skin swab) | | |

Figure 27E:
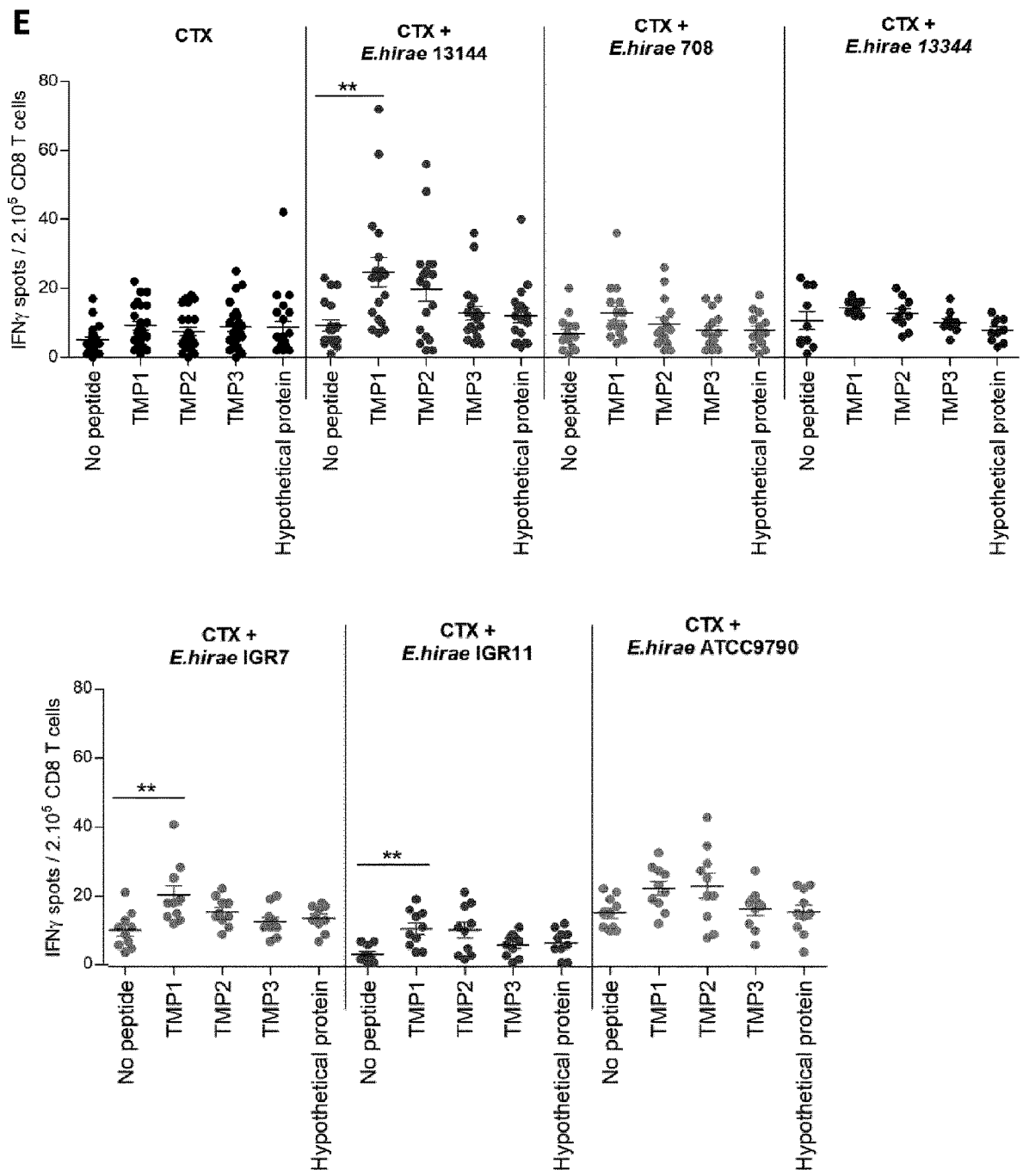
FIG. 27. Phage Tail Length Tape Measure Protein as the unique antigenic sequence in *E. hirae* 13144.
Figure 27H:
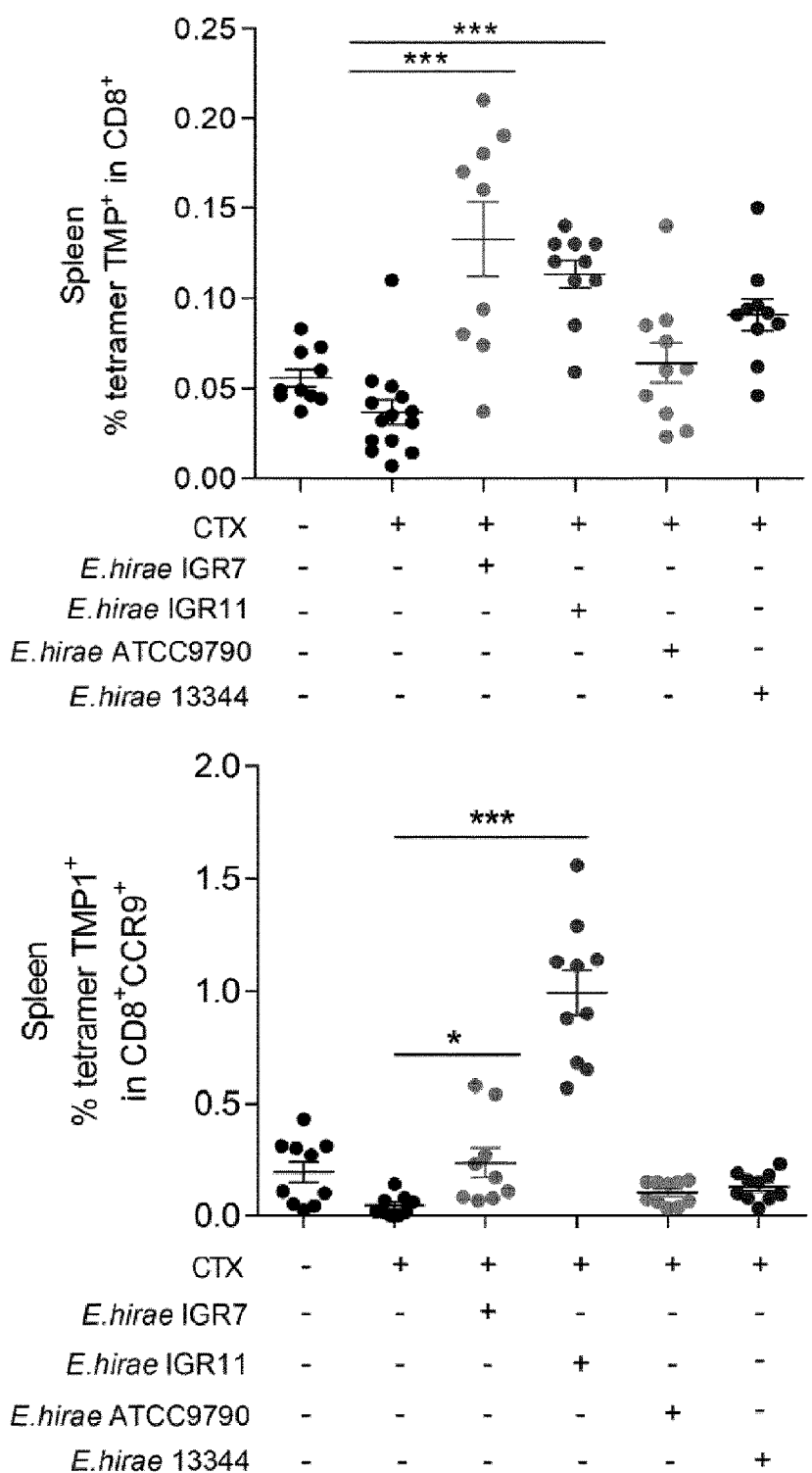

Next, we performed sequence alignment of bacterial genes encoding cell wall and secreted proteins (PSORT software) for immunogenic (13144) versus non-immunogenic (708 and 13344) bacterial strains followed by the identification of nonapeptides with strong binding affinities for the MHC class I H-2K$^b$ protein (<50 nM binding affinity, NetMHC software) (Table 6 in Example 3). Subsequently, we recovered splenic CD8+ T cells from mice that had been repeatedly exposed to E. hirae 13144 and CTX (FIG. 27C). These T cells were restimulated in vitro with pools of potentially immunogenic nonapeptides from E. hirae 13144 (Table 6) to measure IFNγ production (FIG. 32), then splitting the most efficient group 7 into individual peptides (FIG. 27E). This approach led to the identification of one dominant epitope (one-letter amino acid code: TSLARFANI (SEQ ID No: 13), abbreviation TMP1) in position 179 to 187 of the amino acid sequence of the phage tail length tape measure protein (TMP) from a prophage of 39.2 kb (1506 aa) of E. hirae 13144 (FIG. 33A). Indeed, a particular genomic trait of E. hirae 13144 is that it encodes two intact prophages regions (40.6-kb and a 39.2-kb) showing weak sequence homologies with the most common Enterococcus phages phiEf11 vB_EfaS_IME197 (14% and 11% of shared genes respectively) (FIG. 31C, Table 12). Comparative analysis of the 39.2-kb prophage of E. hirae 13144 with 19 other sequenced E. hirae genomes showed 100% protein identity with IGR7 prophage proteins. The 39.2-kb prophage encodes 65 genes, including 1 shared between all genomes and 38 unique to E. hirae 13144 and IGR7 (FIG. 33B), encoding capsid, portal and tail structure, a characteristic of Siphoviridae phages. Importantly, the TMP1 epitope of the 39.2-kb prophage from E. hirae 13144, E. hirae IGR7 and E. hirae IGR11 showed 100% sequence homology (FIG. 34). As a matter of fact, E. hirae IGR7 and E. hirae IGR11 were as efficient as E. hirae 13144 in reducing the growth of MCA205 fibrosarcomas treated with CTX (FIG. 27B). In contrast, no homologies (observed in E. hirae 708 and 13344) and a mutation in position 3 of the TSLARFANI peptide (SEQ ID No: 13) (L→F observed in E. hirae ATCC9790, FIG. 34) correlated with a reduced anticancer effect of these E. hirae strains (FIG. 27B and (Daillère et al., 2016). Elispot assays designed to detect peptide-specific IFNγ-producing T cells revealed that mice gavaged with E. hirae 13144 (or strain E. hirae IGR7 and IGR11) mounted a TC1 response against TMP1 (but not the control peptides TMP2 and TMP3), while E. hirae strains devoid of anticancer activity and lacking TMP1 (strains 708, 13344, ATCC9790) were unable to do so (FIG. 27E). We used a fluorescent H-2K$^b$/TSLARFANI (SEQ ID No: 13) tetrameric complex to detect the frequency and distribution of TMP1-specific cytotoxic T lymphocytes (CTLs) in naive and MCA205 fibrosarcoma bearing C57BL/6 mice. Up to 1% of splenic CD8+ T recognized the TMP1 peptide at day 12 following a CTX/*E. hirae* 13144 regimen (FIG. 27F, left panel) with a 3-5 fold enrichment of TMP1-specific CTLs in the TC1 subset harboring the ileal chemokine receptor CCR9 in spleens from naive (FIG. 27F, right panel) and tumor bearers, as well as in tumor draining lymph nodes (FIG. 27G). Of note, H-2K$^b$/TSLARFANI (SEQ ID No: 13) tetramers also revealed a high proportion of splenic TMP1-specific CTLs after immunization with *E. hirae* strains/GR7 or IGR11 but not with ATCC9790 nor *E. hirae* 13344 (FIG. 27H).

closely related to *E. hirae* were detectable. In 90% of the samples in which *E. hirae* was found, one of the three phages (from *E. hirae* 13144, 708 or 13344) sequence were inserted in the genome in a mutually exclusive fashion (FIG. 29A). However, the *E. hirae* 13144 phage was detectable in many samples lacking the presence of the *E. hirae* core genome, suggesting that other bacteria than *E. hirae* can host this phage as well. We could detect the presence of the phage 13144 at 0.66 BOC in three mother-infant paired stool specimens and in the infant at 1, 3, and 7 days after birth. Contrasting with metagenomics analyses that are unable to

TABLE 12

Seeking prophage sequences in *E. hirae* 13144 genomes

| Region | Region Length | Completeness | Score | # Total Proteins | Region Position | Most Common Phage | GC % |
|---|---|---|---|---|---|---|---|
| 1 | 40.6 Kb | intact | 150 | 58 | 481066-521729 | PHAGE_Entero_phiEf11_NC_013696(9) | 33.79% |
| 2 | 39.2 Kb | intact | 140 | 59 | 2123983-2163272 | PHAGE_Entero_vB_IME197_NC_028671(6) | 34.95% |

Figure 28D:
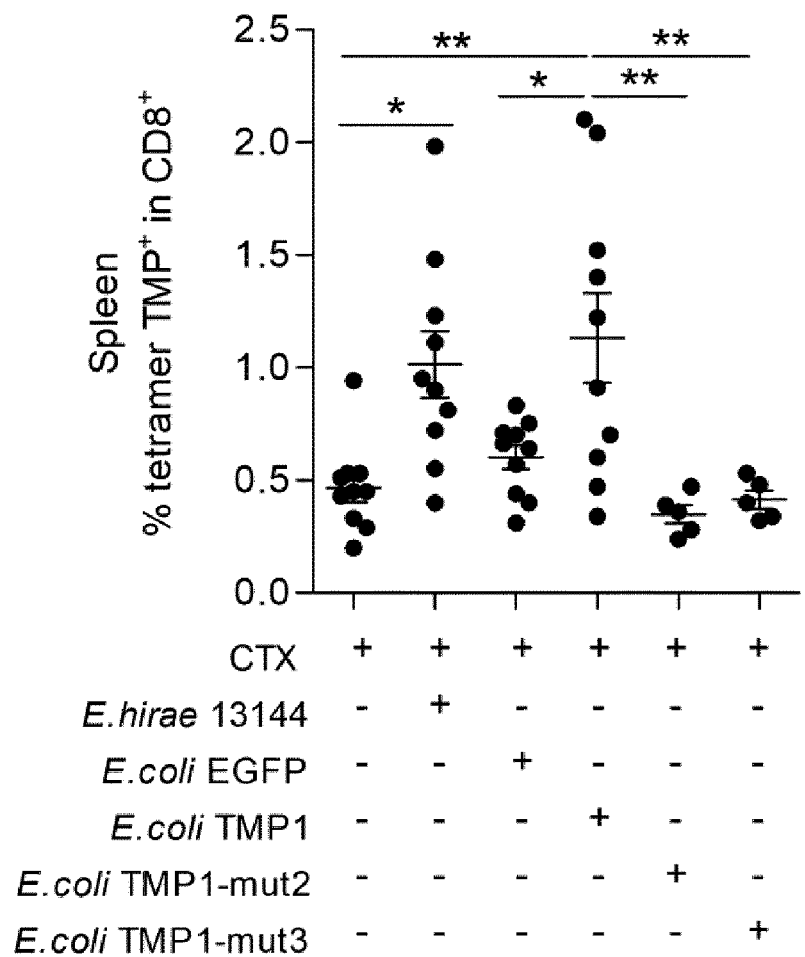

Example 13: Prophylactic and Therapeutic Immunization Using Phage Tail Length Tape Measure Protein in a Mouse Model To explore the capacity of TMP1-specific H-2K$^b$ restricted TC1 cells to control the growth of MCA205 cancers, we subcutaneously (s.c.) immunized naive C57BL/6 mice with dendritic cells (DC) loaded with heat-inactivated *E. hirae* (positive control), the naturally occurring TSLARFANI peptide (SEQ ID No: 13) from 13144, IGR7 or IGR11, its L→F mutant from *E. hirae* ATCC9790 ('mut3', FIG. 34) or other non-immunogenic bacterial peptides (group 1, FIG. 32). In this prophylactic setting, DC pulsed with TSLARFANI (SEQ ID No: 13) (but not mut3 TSFARFANI, SEQ ID No: 217) were as efficient as the whole *E. hirae* extract in preventing or restraining tumor outgrowth (FIG. 28A-B). Next, we explored whether the TMP1 peptide would be able to confer immunogenicity to the usually inefficient bacterium *Escherichia coli* strain DH5a in the therapeutic setting, in which antibiotic treatment is followed by gavage with different bacterial strains and CTX-based chemotherapy (FIG. 27A, (Daillère et al., 2016)). *E. coli* engineered to express the TSLARFANI (SEQ ID No: 13) peptide (FIG. 35) was as efficient as *E. hirae* 13144 in restraining MCA205 tumor growth (FIG. 28C) and eliciting the generation of tetramer binding CTL in the spleen (FIG. 28D). In contrast, *E. coli* expressing an irrelevant sequence (encoding mouse EGFP protein) or a mutant peptide bearing a S→A exchange in the anchor position 2 ('mut2', TALARFANI, SEQ ID No: 216) or the 'mut3' TMP1 peptide failed to induce such a cancer-protective immune response (FIG. 28C-D).

Example 14: Clinical Relevance of the Enterophage's Effects in Cancer Patients

Figure 29F:
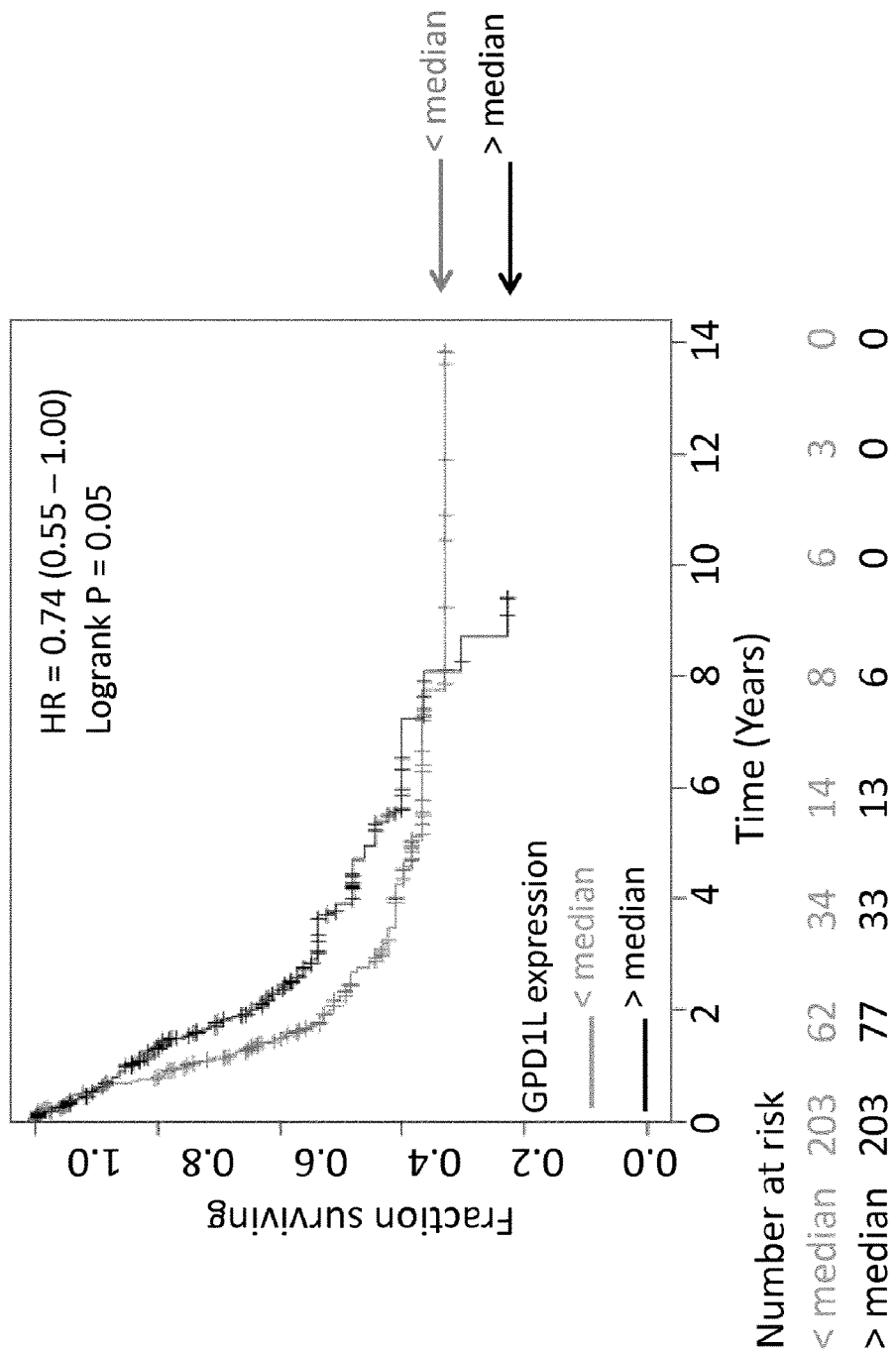
Figure 29G:
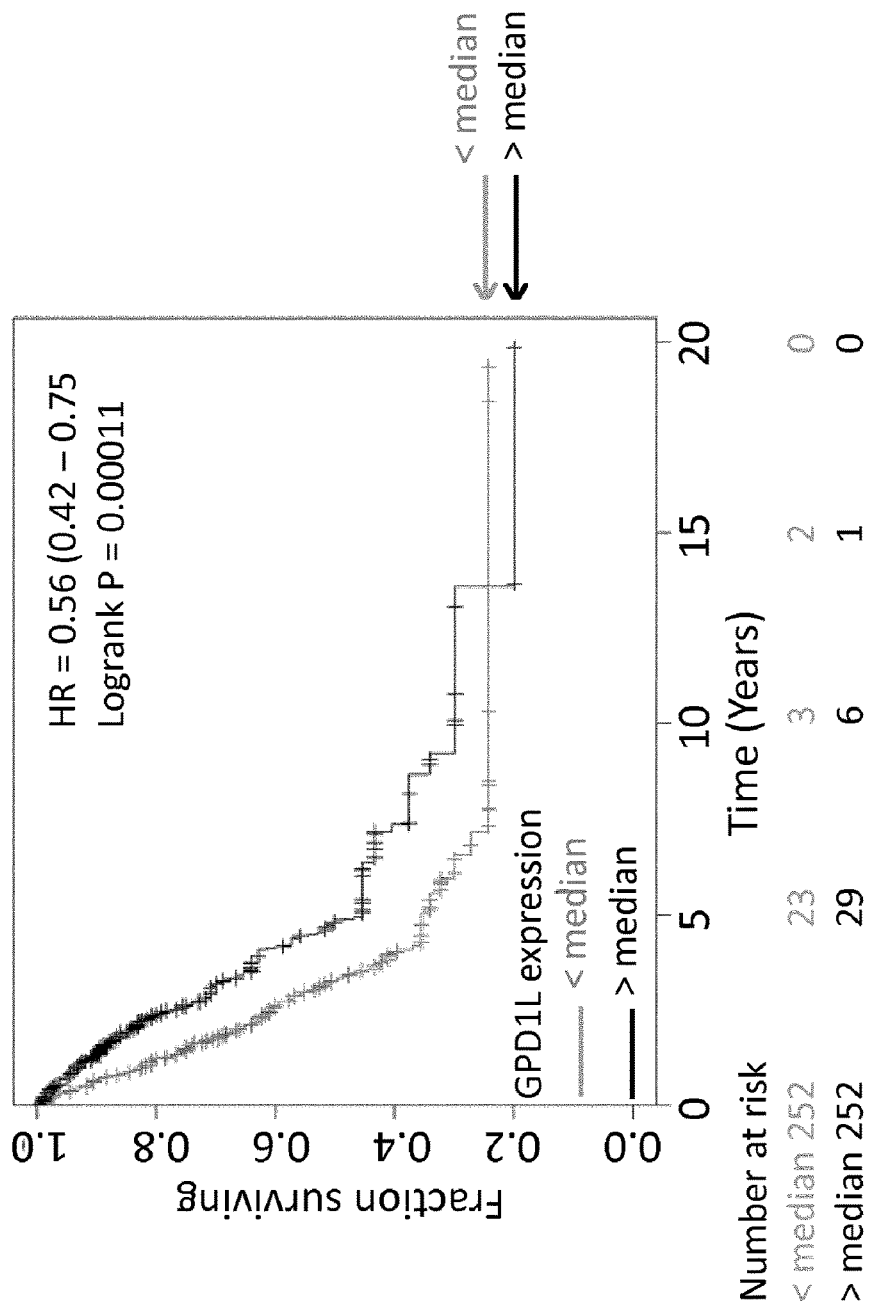
Figure 29H:
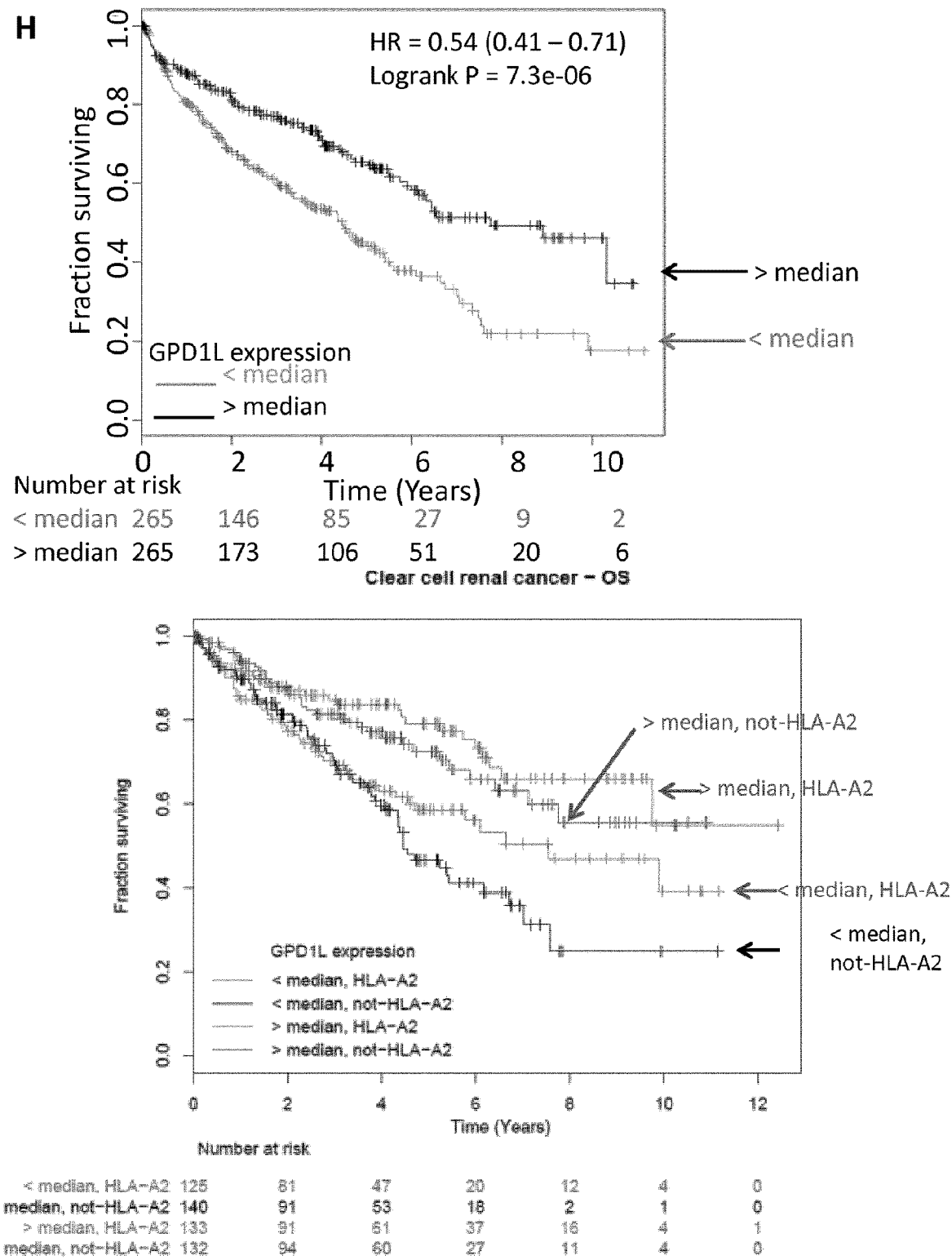

We next explored the possible pathophysiological relevance of these findings. We screened a total of 3027 adult and mother-infant metagenomes (mostly from human stools but also from various mucosae) from 17 publicly available datasets to assess the breadth of coverage (BOC) of the *E. hirae* genome and its phages (FIG. 29A). *E. hirae* was present with 100% confidence in 13 samples from disparate geography, age and datasets. In other ~40 cases, strains detect low-abundant species, culturomics followed by matrix-assisted laser desorption ionization time-of-flight mass spectrometry (MALDI-TOF) provides a technology for detecting even rare *E. hirae* colonies in the stool of healthy individuals (Samb-Ba et al., 2014) or cancer patients (Routy et al., 2018). PCR analyses of each single cultivatable enterococcal colony (up to 5 per species and individual, representing colonies from *E. hirae*, *E. gallinarum*, *E. durans*, *E. faecium*, *E. faecalis*, *E. casseliflavus* or *E. avium*) from 76 cancer patients led to the detection of the TMP sequence encompassing the TMP1 peptide (FIG. 36) in 34% of the patients, mostly inside *E. faecalis* (FIG. 29B). Renal and lung cancer patients with detectable fecal TMP at diagnosis exhibited a prolonged overall survival after therapy with immune checkpoint inhibitors (FIG. 29C). Therefore, we screened sixteen TMP-derived nonapeptides predicted to bind the human MHC class I HLA-A02*01 with high affinity (SEQ ID Nos: 54-69) for their ability to prime naive CD8$^+$ T cells from six healthy volunteers in vitro. We found 6 out of 16 epitopes capable of triggering significant peptide-specific IFNγ release that were located in two distinct regions of the TMP protein (504-708 and 1397-1462, FIG. 29D, FIG. 37, FIG. 24B, Table 9). Using the NCBI BLASTP suite, we searched the human peptidome associated with significant expression levels in human cancer biopsies (TCGA database) for a high degree of homology with these 6 HLA-A02*01-restricted immunogenic nonapeptides. We found that only peptide KLAKFASVV (631-639, SEQ ID No: 63) shared an 78% homology (7 out of nine 9 positions, with identical amino acids at the MHC anchoring positions 2 and 9) with a peptide contained in the protein glycerol-3-phosphate dehydrogenase 1-like GPD1-L (FIG. 29E). GPD1-L reportedly counteracts the oncogenic HIF1a-dependent adaptation to hypoxia and is associated with favorable prognosis in head and neck squamous cell carcinomas (Feng et al., 2014; Kelly et al., 2011; Liu et al., 2014). To our knowledge, no mutation in the GPD-1L gene has been reported in cancers. The TCGA transcriptomics database unveiled that high expression of GPD1-L is associated with improved overall survival in bladder, lung adenocarcinoma and in a large cohort of >500 kidney cancers (with a trend towards a worse prognosis in tumors with low GPD-1L that do not express HLA-02*01) (FIG. 29F-H).

Moreover, high expression of GPD1-L mRNA by tumors at diagnosis was associated with improved progression-free survival in two independent cohorts of non-small cell lung cancer (NSCLC) patients treated with anti-PD1/PDL-1 Abs (FIG. 29I, J). Interestingly, expression levels of GPD-1L correlated with the cytotoxic lymphocytes, myeloid dendritic cells, neutrophils and endothelial cells gene signature in TCGA dataset of lung cancer (LUAD, LUSC and TCGA) and in the two cohorts of NSCLC patients (CHUM and CGFL) (FIG. 29K).

Example 15: Molecular Mimicry Between Enterophage TMP and the Oncogenic Driver PSMB4 in Mouse Cancers In order to identify the mechanism by which TMP1 exerted its anticancer activity in the mouse model (MCA205 tumors in C57/B6 mice, FIG. 27-28), we investigated whether there exist any H-2K$^b$-restricted mouse tumor antigens with high homology to the TMP1 peptide (TSLARFANI, SEQ ID No: 13). Using the NCBI BLASTP suite we found that the peptide (GSLARFRNI, SEQ ID No: 189) belonging to the proteasome subunit beta type-4 (PSMB4) between amino acid positions 76-84 shared an 78% homology (7 out of 9 amino acid, with identical amino acids at the MHC anchoring positions 2 and 9) (FIG. 30A). We queried the potential neoepitopes of MCA205 but found no significant homology that would explain our results, hence our focus on the non-mutated PSMB4 peptide. PSMB4 is an oncogenic driver involved in proliferation and invasion (Lee et al., 2014) in a variety of malignancies such as glioblastoma (Cheng et al., 2018), melanoma (Zhang et al., 2017) and breast cancers (Wang et al., 2018), associated with dismal prognosis (Cheng et al., 2018; Lee et al., 2014; Wang et al., 2018). CRISPR/Cas9-mediated genomic knock-in of the PSMB4 sequence replacing GSLARFRNI (SEQ ID No: 189) by GSFARFRNI (SEQ ID No: 190) (with an L→F exchange in position 3 equivalent to mut 3 of TSLARFANI, SEQ ID NO: 13) in MCA205 cells (FIG. 38) slowed down spontaneous tumor growth kinetics but drastically blunted the anticancer effects of E. hirae 13144 while not interfering with the CTX treatment alone (FIG. 30B). These results support the idea that the TSLARFANI TMP1 peptide (SEQ ID No: 13) encoded by E. hirae 13144 indeed induces a therapy-relevant response against the PSMB4-derived GSLARFRNI peptide (SEQ ID No: 189).

Example 16: Capacity of E. hirae 13144 to Contagiously Disseminate the Phage TMP Sequence Temperate bacteriophages are bacterial viruses that transfer virulence, antimicrobial resistance genes, and immunogenic sequences to new bacterial hosts (Weinbauer, 2004). The TMP protein, which contains a variable number of tandem repeats with highly conserved tryptophan and phenylalanine residues at fixed positions is encoded by the genome of Siphoviridae phages (Belcaid et al., 2011; Piuri and Hatfull, 2006). To analyze the capacity of E. hirae 13144 to contagiously disseminate the phage TMP sequence, we performed culturomic analyses of the ileal content from C57BL/6 mice subjected to oral gavage with E. hirae 13144 and systemic CTX therapy (FIG. 30C). We tested 7 to 18 bacterial colonies from each animal to discover that, out of 76 colonies, E. gallinarum was the only by-stander Enterococci transduced by the E. hirae-born phage in vivo, as confirmed by sequencing of the phage genome (FIG. 30D, E and FIG. 39). Of note, none of the 90 colonies (mostly of E. gallinarum) isolated from naive mice harbored the TMP sequence (FIG. 39). Moreover, CTX plays a role in eliminating the E. gallinarum, allowing the niching and/or colonization of E. hirae in the small intestine, as shown in vitro in enteroid systems or in PCR of the ileal content (FIG. 30G and not shown). Importantly, incubation of small intestine enteroids with a balanced 1:1 ratio of E. hirae or E. gallinarum harbouring or not the phage respectively, lead to the transmission of the infectious/lytic phage to E. gallinarum by E. hirae in 9% of colonies at 6 hrs and 26% at 20 hrs (FIG. 30G).

In contrast to cyclophosphamide, CDK4/6 inhibitors (such as palbociclib) appear to trigger phage excision in breast cancer patients. Indeed, shot gun metagenomics analyses of patients stools harvested prior to surgery in 10 patients treated by 3 week-palbociclib, versus 73 non treated patients revealed a drastic enrichment and over-representation of phages sequences (from Lactococcus, Salmonella, Sodalis, Escherichia, enterobacteria) as shown in the LefSe diagramm (FIG. 30H).

This observation suggests that the peptide encoding phage exhibiting this molecular mimicry with cancer antigens is infectious, in line with its detection in E. faecalis in humans.

To the best of our knowledge, these results represent the first demonstration that an enterococcal phage codes for an MHC class I-restricted antigen, TMP1, that induces a memory TC1 immune response, which then cross-reacts with cancer antigens, following three major lines of evidence. First, naturally occurring ('mut3') or artificial mutations ('mut2' or 'mut3') introduced into the MHC class I-binding TMP1 epitope suppressed the tumor-prophylactic and therapeutic potential of the phage-bearing E. hirae strains. Second, transfer of the TMP1-encoding gene into E. coli conferred immunogenic capacity to this proteobacterium, which acquired the same antitumor properties as TMP1-expressing E. hirae. Third, when cancer cells were genetically modified to remove the TMP1-crossreactive peptide within the PSMB4 protein, they formed tumors that could no longer be controlled upon oral gavage with TMP1-expressing E. hirae.

Discussion 2

Phages are among the most abundant biological entities on earth. Their numbers have been estimated to reach as high as 1031 particles with the potential of 1025 phage infections occurring every second (Pedulla et al., 2003; Wommack and Colwell, 2000). The antigenicity of the 'enterophage' studied here resides in hot spots of the TMP protein. Beyond their structural role in determining the length of the phage tail, TMP encoded by phages from the Siphoviridae family contains several functional domains, one of which has peptidoglycan hydrolase activity, facilitating efficient infection of bacteria, and another one with lysozyme activity, acting as resuscitation-promoting factor, Rpf (Duerkop et al., 2014). Rpfs have not only been implicated in the reactivation of dormant bacteria but also modulate innate responses to Mycobacterium tuberculosis (Russell-Goldman et al., 2008) and cognate long-term immune responses (Commandeur et al., 2011). In fact, T cell epitopes contained in M. tuberculosis Rpfs are key for the human immune response against this pathogen (Commandeur et al., 2011). Beyond their specific antigenic properties, phages convey broad adjuvanticity to DNA vaccines through filamentous bacteriophage coat protein III domain I (Cuesta et al., 2006; Larsen et al., 2008). Thus, the perspective opens that bacteriophages may enrich the therapeutic armamentarium for stimulating anticancer immune responses.

Abbreviations Used in this Text

ATB: Antibiotic
BHI: Brain heart infusion
BM-DC: Bone marrow dendritic cell
cDNA: complementary deoxyribonucleic acid
CGFL: Centre Georges François Leclerc
CHUM: Centre Hospitalier Universitaire de Montréal
CTL: Cytotoxic Tcell
Ctrl: Control
CTX: Cyclophosphomide
DC: Dendritic cell
DNA: Deoxyribonucleic acid
GM-CSF: Granulocyte-macrophage colony-stimulating factor
GPD1-L: Glycerol-3-phosphate dehydrogenase 1-like
IFNγ: Interferon gamma
IMDM: Iscove's Modified Dulbecco's Medium
Ip: Intraperitoneal
MALDI-TOF: Matrix-assisted laser desorption ionization time-of-flight
MHC: Major histocompatibility complex
NaCl: Sodium chloride
NSCLC: Non-small cell lung cancer
PBMC: Peripheral blood mononuclear cell
PCR: Polymerase chain reaction
PSMB4: Proteasome subunit beta type-4
PVDF: Polyvinylidene difluoride
RCC: Renal cell carcinoma
Rpf: Resuscitation-promoting factor
RPMI: Roswell Park Memorial Institute
Sc: Subcutaneous
SEM: Standard error of mean
Tc1: T cytotoxic cell type 1
Th1: T helper cell type 1
TLR3: Toll-like receptor 3
TMP: Tape-measure protein

REFERENCES

Abreu, M. T., and Peek, R. M. (2014). Gastrointestinal malignancy and the microbiome. Gastroenterology 146, 1534-1546.e3.

Balachandran, V. P., Łuksza, M., Zhao, J. N., Makarov, V., Moral, J. A., Remark, R., Herbst, B., Askan, G., Bhanot, U., Senbabaoglu, Y., et al. (2017). Identification of unique neoantigen qualities in long-term survivors of pancreatic cancer. Nature 551, 512-516.

Bankevich, A., Nurk, S., Antipov, D., Gurevich, A. A., Dvorkin, M., Kulikov, A. S., Lesin, V. M., Nikolenko, S. I., Pham, S., Prjibelski, A. D., et al. (2012). SPAdes: a new genome assembly algorithm and its applications to single-cell sequencing. J. Comput. Biol. J. Comput. Mol. Cell Biol. 19, 455-477.

Belcaid, M., Bergeron, A., and Poisson, G. (2011). The evolution of the tape measure protein: units, duplications and losses. BMC Bioinformatics 12 Suppl 9, S10.

Blaser, M. (2011). Antibiotic overuse: Stop the killing of beneficial bacteria. Nature 476, 393-394.

Bolger, A. M., Lohse, M., and Usadel, B. (2014). Trimmomatic: a flexible trimmer for Illumina sequence data. Bioinforma. Oxf. Engl. 30, 2114-2120.

Bongers, G., Pacer, M. E., Geraldino, T. H., Chen, L., He, Z., Hashimoto, D., Furtado, G. C., Ochando, J., Kelley, K. A., Clemente, J. C., et al. (2014). Interplay of host microbiota, genetic perturbations, and inflammation promotes local development of intestinal neoplasms in mice. J. Exp. Med. 211, 457-472.

Bradley, C. P., Teng, F., Felix, K. M., Sano, T., Naskar, D., Block, K. E., Huang, H., Knox, K. S., Littman, D. R., and Wu, H.-J. J. (2017). Segmented Filamentous Bacteria Provoke Lung Autoimmunity by Inducing Gut-Lung Axis Th17 Cells Expressing Dual TCRs. Cell Host Microbe 22, 697-704.e4.

Chai, J. N., Peng, Y., Rengarajan, S., Solomon, B. D., Ai, T. L., Shen, Z., Perry, J. S. A., Knoop, K. A., Tanoue, T., Narushima, S., et al. (2017). *Helicobacter* species are potent drivers of colonic T cell responses in homeostasis and inflammation. Sci. Immunol. 2.

Charoentong, P., Finotello, F., Angelova, M., Mayer, C., Efremova, M., Rieder, D., Hackl, H., and Trajanoski, Z. (2017). Pan-cancer Immunogenomic Analyses Reveal Genotype-Immunophenotype Relationships and Predictors of Response to Checkpoint Blockade. Cell Rep. 18, 248-262.

Cheng, Y.-C., Tsai, W.-C., Sung, Y.-C., Chang, H.-H., and Chen, Y. (2018). Interference with PSMB4 Expression Exerts an Anti-Tumor Effect by Decreasing the Invasion and Proliferation of Human Glioblastoma Cells. Cell. Physiol. Biochem. Int. J. Exp. Cell. Physiol. Biochem. Pharmacol. 45, 819-831.

Commandeur, S., van Meijgaarden, K. E., Lin, M. Y., Franken, K. L. M. C., Friggen, A. H., Drijfhout, J. W., Oftung, F., Korsvold, G. E., Geluk, A., and Ottenhoff, T. H. M. (2011). Identification of human T-cell responses to *Mycobacterium tuberculosis* resuscitation-promoting factors in long-term latently infected individuals. Clin. Vaccine Immunol. CVI 18, 676-683.

Costales, M. G., Haga, C. L., Velagapudi, S. P., Childs-Disney, J. L., Phinney, D. G., and Disney, M. D. (2017). Small Molecule Inhibition of microRNA-210 Reprograms an Oncogenic Hypoxic Circuit. J. Am. Chem. Soc. 139, 3446-3455.

Cuesta, A., Angeles Esteban, M., and Meseguer, J. (2006). Cloning, distribution and up-regulation of the teleost fish MHC class I I alpha suggests a role for granulocytes as antigen-presenting cells. Mol. Immunol. 43, 1275-1285.

Daillère, R., Vétizou, M., Waldschmitt, N., Yamazaki, T., Isnard, C., Poirier-Colame, V., Duong, C. P. M., Flament, C., Lepage, P., *Roberti*, M. P., et al. (2016). *Enterococcus hirae* and Cyclophosphamide-Induced *Barnesiella intestinihominis* Facilitate Therapeutic Immunomodulatory Effects. Immunity 45, 931-943.

Dejea, C. M., Wick, E. C., Hechenbleikner, E. M., White, J. R., Mark Welch, J. L., Rossetti, B. J., Peterson, S. N., Snesrud, E. C., Borisy, G. G., Lazarev, M., et al. (2014). Microbiota organization is a distinct feature of proximal colorectal cancers. Proc. Natl. Acad. Sci. U.S.A 111, 18321-18326.

Denkert, C., Loibl, S., Noske, A., Roller, M., Müller, B. M., Komor, M., Budczies, J., Darb-Esfahani, S., Kronenwett, R., Hanusch, C., et al. (2010). Tumor-associated lymphocytes as an independent predictor of response to neoadjuvant chemotherapy in breast cancer. J. Clin. Oncol. Off. J. Am. Soc. Clin. Oncol. 28, 105-113.

Denkert, C., von Minckwitz, G., Brase, J. C., Sinn, B. V., Gade, S., Kronenwett, R., Pfitzner, B. M., Salat, C., Loi, S., Schmitt, W. D., et al. (2015). Tumor-infiltrating lymphocytes and response to neoadjuvant chemotherapy with or without carboplatin in human epidermal growth factor receptor 2-positive and triple-negative primary breast cancers. J. Clin. Oncol. Off. J. Am. Soc. Clin. Oncol. 33, 983-991.

Dieci, M. V., Mathieu, M. C., Guarneri, V., Conte, P., Delaloge, S., Andre, F., and Goubar, A. (2015b). Prognostic and predictive value of tumor-infiltrating lymphocytes in two phase III randomized adjuvant breast cancer trials. Ann. Oncol. Off. J. Eur. Soc. Med. Oncol. 26, 1698-1704.

Dieci, M. V., Criscitiello, C., Goubar, A., Viale, G., Conte, P., Guarneri, V., Ficarra, G., Mathieu, M. C., Delaloge, S., Curigliano, G., et al. (2015a). Prognostic value of tumor-infiltrating lymphocytes on residual disease after primary chemotherapy for triple-negative breast cancer: a retrospective multicenter study. Ann. Oncol. Off. J. Eur. Soc. Med. Oncol. 26, 1518.

Duerkop, B. A., Palmer, K. L., and Horsburgh, M. J. (2014). Enterococcal Bacteriophages and Genome Defense. In Enterococci: From Commensals to Leading Causes of Drug Resistant Infection, M. S. Gilmore, D. B. Clewell, Y. Ike, and N. Shankar, eds. (Boston: Massachusetts Eye and Ear Infirmary), p.

Feng, Z., Li, J. N., Wang, L., Pu, Y. F., Wang, Y., and Guo, C. B. (2014). The prognostic value of glycerol-3-phosphate dehydrogenase 1-like expression in head and neck squamous cell carcinoma. Histopathology 64, 348-355.

Galluzzi, L., Buqué, A., Kepp, O., Zitvogel, L., and Kroemer, G. (2015). Immunological Effects of Conventional Chemotherapy and Targeted Anticancer Agents. Cancer Cell 28, 690-714.

Garrett, W. S. (2015). Cancer and the microbiota. Science 348, 80-86.

Guindon, S., Dufayard, J.-F., Lefort, V., Anisimova, M., Hordijk, W., and Gascuel, O. (2010). New algorithms and methods to estimate maximum-likelihood phylogenies: assessing the performance of PhyML 3.0. Syst. Biol. 59, 307-321.

Gur, C., Ibrahim, Y., Isaacson, B., Yamin, R., Abed, J., Gamliel, M., Enk, J., Bar-On, Y., Stanietsky-Kaynan, N., Coppenhagen-Glazer, S., et al. (2015). Binding of the Fap2 protein of *Fusobacterium nucleatum* to human inhibitory receptor TIGIT protects tumors from immune cell attack. Immunity 42, 344-355.

Hanahan, D., and Weinberg, R. A. (2011). Hallmarks of cancer: the next generation. Cell 144, 646-674.

Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. N. Engl. J. Med. 363, 711-723.

Ji, Q., Perchellet, A., and Goverman, J. M. (2010). Viral infection triggers central nervous system autoimmunity via activation of CD8+ T cells expressing dual TCRs. Nat. Immunol. 11, 628-634.

Kelly, T. J., Souza, A. L., Clish, C. B., and Puigserver, P. (2011). A hypoxia-induced positive feedback loop promotes hypoxia-inducible factor 1alpha stability through miR-210 suppression of glycerol-3-phosphate dehydrogenase 1-like. Mol. Cell. Biol. 31, 2696-2706.

Kennedy, M. J., Hughes, R. M., Peteya, L. A., Schwartz, J. W., Ehlers, M. D., and Tucker, C. L. (2010). Rapid blue-light-mediated induction of protein interactions in living cells. Nat. Methods 7, 973-975.

Iida, N., Dzutsev, A., Stewart, C. A., Smith, L., Bouladoux, N., Weingarten, R. A., Molina, D. A., Salcedo, R., Back, T., Cramer, S., et al. (2013). Commensal bacteria control cancer response to therapy by modulating the tumor microenvironment. Science 342, 967-970.

Ingold Heppner, B., Untch, M., Denkert, C., Pfitzner, B. M., Lederer, B., Schmitt, W., Eidtmann, H., Fasching, P. A., Tesch, H., Solbach, C., et al. (2016b). Tumor-Infiltrating Lymphocytes: A Predictive and Prognostic Biomarker in Neoadjuvant-Treated HER2-Positive Breast Cancer. Clin. Cancer Res. Off. J. Am. Assoc. Cancer Res. 22, 5747-5754.

Ingold Heppner, B., Loibl, S., and Denkert, C. (2016a). Tumor-Infiltrating Lymphocytes: A Promising Biomarker in Breast Cancer. Breast Care Basel Switz. 11, 96-100.

Kroemer, G., Senovilla, L., Galluzzi, L., André, F., and Zitvogel, L. (2015). Natural and therapy-induced immunosurveillance in breast cancer. Nat. Med. 21, 1128-1138.

Ladoire, S., Enot, D., Senovilla, L., Ghiringhelli, F., Poirier-Colame, V., Chaba, K., Semeraro, M., Chaix, M., Penault-Llorca, F., Arnould, L., et al. (2016). The presence of LC3B puncta and HMGB1 expression in malignant cells correlate with the immune infiltrate in breast cancer. Autophagy 12, 864-875.

Larsen, M., Jensen, K. B., Christensen, P. A., Suarez, E., Paris, D., Sanz, L., Ravn, P., Sauce, D., Saas, P., Goletz, S., et al. (2008). Functionally fused antibodies—a novel adjuvant fusion system. J. Immunol. Methods 339, 220-227.

LeBlanc, D. J., Lee, L. N., and Abu-Al-Jaibat, A. (1992). Molecular, genetic, and functional analysis of the basic replicon of pVA380-1, a plasmid of oral streptococcal origin. Plasmid 28, 130-145.

Lee, G. Y., Haverty, P. M., Li, L., Kljavin, N. M., Bourgon, R., Lee, J., Stern, H., Modrusan, Z., Seshagiri, S., Zhang, Z., et al. (2014). Comparative oncogenomics identifies PSMB4 and SHMT2 as potential cancer driver genes. Cancer Res. 74, 3114-3126.

Li, L., Stoeckert, C. J., and Roos, D. S. (2003). OrthoMCL: identification of ortholog groups for eukaryotic genomes. Genome Res. 13, 2178-2189.

Liu, S.-C., Chuang, S.-M., Hsu, C.-J., Tsai, C.-H., Wang, S.-W., and Tang, C.-H. (2014). CTGF increases vascular endothelial growth factor-dependent angiogenesis in human synovial fibroblasts by increasing miR-210 expression. Cell Death Dis. 5, e1485.

Louis, P., Hold, G. L., and Flint, H. J. (2014). The gut microbiota, bacterial metabolites and colorectal cancer. Nat. Rev. Microbiol. 12, 661-672.

Mazaheri Nezhad Fard, R., Barton, M. D., and Heuzenroeder, M. W. (2010). Novel Bacteriophages in *Enterococcus* spp. Curr. Microbiol. 60, 400-406.

Mazaheri Nezhad Fard, R., Barton, M. D., and Heuzenroeder, M. W. (2011). Bacteriophage-mediated transduction of antibiotic resistance in enterococci. Lett. Appl. Microbiol. 52, 559-564.

Newman, A. M., Liu, C. L., Green, M. R., Gentles, A. J., Feng, W., Xu, Y., Hoang, C. D., Diehn, M., and Alizadeh, A. A. (2015). Robust enumeration of cell subsets from tissue expression profiles. Nat. Methods 12, 453-457.

Palucka, A. K., and Coussens, L. M. (2016). The Basis of Oncoimmunology. Cell 164, 1233-1247.

Paulos, C. M., Wrzesinski, C., Kaiser, A., Hinrichs, C. S., Chieppa, M., Cassard, L., Palmer, D. C., Boni, A., Muranski, P., Yu, Z., et al. (2007). Microbial translocation augments the function of adoptively transferred self/tumor-specific CD8+ T cells via TLR4 signaling. J. Clin. Invest. 117, 2197-2204.

Pedulla, M. L., Ford, M. E., Houtz, J. M., Karthikeyan, T., Wadsworth, C., Lewis, J. A., Jacobs-Sera, D., Falbo, J., Gross, J., Pannunzio, N. R., et al. (2003). Origins of highly mosaic mycobacteriophage genomes. Cell 113, 171-182.

Perez-Muñoz, M. E., Joglekar, P., Shen, Y.-J., Shen, Y.-J., Chang, K. Y., and Peterson, D. A. (2015). Identification and Phylogeny of the First T Cell Epitope Identified from a Human Gut *Bacteroides* Species. PloS One 10, e0144382.

Piuri, M., and Hatfull, G. F. (2006). A peptidoglycan hydrolase motif within the mycobacteriophage TM4 tape measure protein promotes efficient infection of stationary phase cells. Mol. Microbiol. 62, 1569-1585.

Ran, F. A., Hsu, P. D., Wright, J., Agarwala, V., Scott, D. A., and Zhang, F. (2013). Genome engineering using the CRISPR-Cas9 system. Nat. Protoc. 8, 2281-2308.

Ribas, A. (2015). Releasing the Brakes on Cancer Immunotherapy. N. Engl. J. Med. 373, 1490-1492.

Robert, C., Schachter, J., Long, G. V., Arance, A., Grob, J. J., Mortier, L., Daud, A., Carlino, M. S., McNeil, C., Lotem, M., et al. (2015). Pembrolizumab versus Ipilimumab in Advanced Melanoma. N. Engl. J. Med. 372, 2521-2532.

Rong, Y., Dong, Z., Hong, Z., Jin, Y., Zhang, W., Zhang, B., Mao, W., Kong, H., Wang, C., Yang, B., et al. (2017). Reactivity toward *Bifidobacterium longum* and *Enterococcus hirae* demonstrate robust CD8+ T cell response and better prognosis in HBV-related hepatocellular carcinoma. Exp. Cell Res. 358, 352-359.

Rose, N. R. (2017). Negative selection, epitope mimicry and autoimmunity. Curr. Opin. Immunol. 49, 51-55.

Rossini, A., Rumio, C., Sfondrini, L., Tagliabue, E., Morelli, D., Miceli, R., Mariani, L., Palazzo, M., Ménard, S., and Balsari, A. (2006). Influence of antibiotic treatment on breast carcinoma development in proto-neu transgenic mice. Cancer Res. 66, 6219-6224.

Routy, B., Le Chatelier, E., Derosa, L., Duong, C. P. M., Alou, M. T., Daillère, R., Fluckiger, A., Messaoudene, M., Rauber, C., Roberti, M. P., et al. (2018). Gut microbiome influences efficacy of PD-1-based immunotherapy against epithelial tumors. Science 359, 91-97.

Rubio-Godoy, V., Dutoit, V., Zhao, Y., Simon, R., Guillaume, P., Houghten, R., Romero, P., Cerottini, J.-C., Pinilla, C., and Valmori, D. (2002). Positional scanning-synthetic peptide library-based analysis of self-and pathogen-derived peptide cross-reactivity with tumor-reactive Melan-A-specific CTL. J. Immunol. Baltim. Md 1950 169, 5696-5707.

Rusakiewicz, S., Semeraro, M., Sarabi, M., Desbois, M., Locher, C., Mendez, R., Vimond, N., Concha, A., Garrido, F., Isambert, N., et al. (2013). Immune infiltrates are prognostic factors in localized gastrointestinal stromal tumors. Cancer Res. 73, 3499-3510.

Russell-Goldman, E., Xu, J., Wang, X., Chan, J., and Tufariello, J. M. (2008). A *Mycobacterium tuberculosis* Rpf double-knockout strain exhibits profound defects in reactivation from chronic tuberculosis and innate immunity phenotypes. Infect. Immun. 76, 4269-4281.

Rutkowski, M. R., Stephen, T. L., Svoronos, N., Allegrezza, M. J., Tesone, A. J., Perales-Puchalt, A., Brencicova, E., Escovar-Fadul, X., Nguyen, J. M., Cadungog, M. G., et al. (2015). Microbially driven TLR5-dependent signaling governs distal malignant progression through tumor-promoting inflammation. Cancer Cell 27, 27-40.

Samb-Ba, B., Mazenot, C., Gassama-Sow, A., Dubourg, G., Richet, H., Hugon, P., Lagier, J.-C., Raoult, D., and Fenollar, F. (2014). MALDI-TOF identification of the human Gut microbiome in people with and without diarrhea in Senegal. PloS One 9, e87419.

Schreiber, R. D., Old, L. J., and Smyth, M. J. (2011). Cancer immunoediting: integrating immunity's roles in cancer suppression and promotion. Science 331, 1565-1570.

Sears, C. L., and Garrett, W. S. (2014). Microbes, microbiota, and colon cancer. Cell Host Microbe 15, 317-328.

Seemann, T. (2014). Prokka: rapid prokaryotic genome annotation. Bioinforma. Oxf. Engl. 30, 2068-2069.

Senovilla, L., Vitale, I., Martins, I., Tailler, M., Pailleret, C., Michaud, M., Galluzzi, L., Adjemian, S., Kepp, O., Niso-Santano, M., et al. (2012). An immunosurveillance mechanism controls cancer cell ploidy. Science 337, 1678-1684.

Sharma, P., and Allison, J. P. (2015). Immune checkpoint targeting in cancer therapy: toward combination strategies with curative potential. Cell 161, 205-214.

Sivan, A., Corrales, L., Hubert, N., Williams, J. B., Aquino-Michaels, K., Earley, Z. M., Benyamin, F. W., Lei, Y. M., Jabri, B., Alegre, M.-L., et al. (2015). Commensal *Bifidobacterium* promotes antitumor immunity and facilitates anti-P D-L1 efficacy. Science 350, 1084-1089.

Stoll, G., Enot, D., Mlecnik, B., Galon, J., Zitvogel, L., and Kroemer, G. (2014). Immune-related gene signatures predict the outcome of neoadjuvant chemotherapy. Oncoimmunology 3, e27884.

Treangen, T. J., Ondov, B. D., Koren, S., and Phillippy, A. M. (2014). The Harvest suite for rapid core-genome alignment and visualization of thousands of intraspecific microbial genomes. Genome Biol. 15, 524.

Vacchelli, E., Semeraro, M., Enot, D. P., Chaba, K., Poirier Colame, V., Dartigues, P., Perier, A., Villa, I., Rusakiewicz, S., Gronnier, C., et al. (2015). Negative prognostic impact of regulatory T cell infiltration in surgically resected esophageal cancer post-radiochemotherapy. Oncotarget 6, 20840-20850.

Vacchelli, E., Semeraro, M., Adam, J., Dartigues, P., Zitvogel, L., and Kroemer, G. (2016). Immunosurveillance in esophageal carcinoma: The decisive impact of regulatory T cells. Oncoimmunology 5, e1064581.

Vétizou, M., Pitt, J. M., Daillère, R., Lepage, P., Waldschmitt, N., Flament, C., Rusakiewicz, S., Routy, B., Roberti, M. P., Duong, C. P. M., et al. (2015). Anticancer immunotherapy by CTLA-4 blockade relies on the gut microbiota. Science 350, 1079-1084.

Viaud, S., Saccheri, F., Mignot, G., Yamazaki, T., Daillère, R., Hannani, D., Enot, D. P., Pfirschke, C., Engblom, C., Pittet, M. J., et al. (2013). The intestinal microbiota modulates the anticancer immune effects of cyclophosphamide. Science 342, 971-976.

Vujanovic, L., Mandic, M., Olson, W. C., Kirkwood, J. M., and Storkus, W. J. (2007). A *mycoplasma* peptide elicits heteroclitic CD4+ T cell responses against tumor antigen MAGE-A6. Clin. Cancer Res. Off. J. Am. Assoc. Cancer Res. 13, 6796-6806.

Wang, H., He, Z., Xia, L., Zhang, W., Xu, L., Yue, X., Ru, X., and Xu, Y. (2018). PSMB4 overexpression enhances the cell growth and viability of breast cancer cells leading to a poor prognosis. Oncol. Rep. 40, 2343-2352.

Weinbauer, M. G. (2004). Ecology of prokaryotic viruses. FEMS Microbiol. Rev. 28, 127-181.

Wommack, K. E., and Colwell, R. R. (2000). Virioplankton: viruses in aquatic ecosystems. Microbiol. Mol. Biol. Rev. MMBR 64, 69-114.

Yang, Y., Torchinsky, M. B., Gobert, M., Xiong, H., Xu, M., Linehan, J. L., Alonzo, F., Ng, C., Chen, A., Lin, X., et al. (2014). Focused specificity of intestinal TH17 cells towards commensal bacterial antigens. Nature 510, 152-156.

Zhang, X., Lin, D., Lin, Y., Chen, H., Zou, M., Zhong, S., Yi, X., and Han, S. (2017). Proteasome beta-4 subunit contributes to the development of melanoma and is regulated by miR-148b. Tumour Biol. J. Int. Soc. Oncodevelopmental Biol. Med. 39, 1010428317705767.

Zitvogel, L., Galluzzi, L., Viaud, S., Vétizou, M., Daillère, R., Merad, M., and Kroemer, G. (2015). Cancer and the gut microbiota: an unexpected link. Sci. Transl. Med. 7, 271ps1.

Zitvogel, L., Ayyoub, M., Routy, B., and Kroemer, G. (2016). Microbiome and Anticancer Immunosurveillance. Cell 165, 276-287.

Zitvogel, L., Ma, Y., Raoult, D., Kroemer, G., and Gajewski, T. F. (2018). The microbiome in cancer immunotherapy: Diagnostic tools and therapeutic strategies. Science 359, 1366-1370.

The invention claimed is:

1. A method of treating cancer comprising administering a bacterial composition comprising at least one naturally occurring or engineered bacterial strain in combination with an antineoplastic alkylating agent, wherein said at least one bacterial strain expresses the tail tape measure protein of SEQ ID No: 1 or a fragment thereof comprising at least the peptides of SEQ ID Nos: 13 and 14, or a sequence encoding a peptide of at least 9 amino acids comprising at least one epitope selected from the group consisting of SEQ ID No: 55, 56, 62, 63 and 66, with the proviso that said at least one bacterial strain is a different strain from the *Enterococcus hirae* strain 13144 deposited on Nov. 7, 2013 at the CNCM under the number I-4815.

2. The method of claim 1, wherein said administered composition comprises at least one strain harboring a prophage genome with at least 80% identity with the prophage of SEQ ID No: 2, so that the phage encoded by this prophage can in vivo infect the other strains of the composition and/or commensal bacteria of the gut microbiota of a subject in need thereof.

3. The method of claim 1, wherein said composition comprises bacteria selected from the group consisting of:
   (i) *Enterococcus hirae* strain IGR7 deposited on Aug. 31, 2017 at the CNCM under the number 1-5224,
   (ii) *Enterococcus hirae* strain IGR11 deposited on Nov. 27, 2017, at the CNCM under the number I-5261, and
   (iii) mixtures of at least two strains selected from the group consisting of the strains recited in (i) to (iii) (ii) and *Enterococcus hirae* strain CNCM I-4815.

4. The method of claim 1, wherein said composition further comprises *Enterococcus hirae* strain IGR4 deposited on Nov. 27, 2017, at the CNCM under the number 1-5260.

5. A method comprising in vitro introducing, into a bacterial strain, a nucleotide sequence encoding the tail tape measure protein of SEQ ID No: 1 or a fragment thereof comprising at least the peptides of SEQ ID Nos: 13 and 14, or a sequence encoding a peptide of at least 9 amino acids comprising at least one epitope selected from the group consisting of SEQ ID No: 55, 56, 62, 63 and 66 and expressing said tail tape measure protein of SEQ ID No: 1 or fragment thereof.

6. The method of claim 5, comprising in vitro infecting bacteria of said strain with a bacteriophage encoding a tail tape measure protein with at least 80% identity with the tail tape measure protein of SEQ ID No: 1.

7. The method of claim 6, wherein said bacteriophage has a genome comprising a nucleotide sequence of SEQ ID NOs: 2 or a sequence having at least 90% identity thereto.

8. A method of inducing an immune response in a human subject, comprising administering to the human subject an engineered bacterial strain that expresses the tail tape measure protein of SEQ ID No: 1 or a fragment thereof of at least 9 amino acids comprising at least one epitope selected from the group consisting of SEQ ID Nos: 13, 14, 55, 56, 62, 63 and 66, with the proviso that said at least one bacterial strain is a different strain from the *Enterococcus hirae* strain 13144 deposited on Nov. 7, 2013 at the CNCM under the number 1-4815.

9. The method of claim 8, wherein said bacterial strain is selected from the group consisting of *Escherichia coli, Enterococcus gallinarum, Enterococcus faecalis* and *Enterococcus hirae*.

10. The method of claim 8, wherein a HLA-A*0201 patient is treated.

11. A method of inducing an immune response in a human subject, comprising administering to the human subject an immunogenic composition comprising an isolated polypeptide comprising a sequence of at least 9 consecutive amino acids from the tail tape measure protein of SEQ ID No: 1 comprising at least one epitope selected from the group consisting of SEQ ID Nos: 13, 14, 55, 56, 62, 63 and 66, or an isolated polynucleotide encoding the same.

12. The method of claim 11, wherein the sequence of at least 9 consecutive amino acids from the tail tape measure protein of SEQ ID No: 1 is selected from the group consisting of SEQ ID No: 55, 56, 62, 63 and 66.

13. The method of claim 11, wherein a peptide comprising SEQ ID No: 63-or a polynucleotide encoding the same is administered to a HLA-A*0201 patient.

14. A method of inducing an immune response in a human subject, comprising administering to the human subject a bacteriophage composition isolated from bacteria expressing a tail tape measure protein having at least 80% identity with the tail tape measure protein of SEQ ID No: 1.

15. The method of claim 14, wherein said bacteriophage has a genome comprising a nucleotide sequence of SEQ ID No: 2 or a sequence having at least 90% identity thereto.

16. The method of claim 11, wherein said administered composition is administered in combination with a drug blocking an immune checkpoint.

17. The method of claim 15, wherein said administered bacteriophage is administered in combination with a drug blocking an immune checkpoint.

18. The method of claim 1, wherein the antineoplastic alkylating agent is cyclophosphamide.

* * * * *

SEQUENCE LISTING

<160> NUMBER OF SEQ ID NOS: 231

<210> SEQ ID NO 1
<211> LENGTH: 1506
<212> TYPE: PRT
<213> ORGANISM: Enterococcus hirae

<400> SEQUENCE: 1

Met Ala Gln Ser Lys Thr Val Lys Ala Val Leu Thr Ala Ile Asp Lys
1               5                   10                  15

Gly Phe Thr Gln Thr Met Gly Ser Ala Thr Ser Ser Leu Lys Lys Leu
            20                  25                  30

Ser Ser Asn Ala Ser Asp Ile Pro Ser Asn Leu Asn Thr Val Ser Gly
        35                  40                  45

Ala Met Lys Ser Phe Gly Asp Lys Thr Ala Ser Ile Gly Gln Ser Ile
    50                  55                  60

Glu Lys Val Gly Gly Ser Met Thr Lys Gly Ile Thr Leu Pro Ile Ala
65                  70                  75                  80

Gly Ala Val Gly Ala Val Thr Thr Ala Ala Val Lys Trp Glu Ser Ala
                85                  90                  95

Phe Thr Gly Val Lys Lys Thr Asn Asp Glu Met Val Asp Ser Asn Gly
            100                 105                 110

Lys Val Ile Tyr Ser Tyr Asp Asp Leu Glu Lys Gly Leu Arg Asp Leu
        115                 120                 125

Ala Lys Glu Leu Pro Thr Ser His Glu Glu Ile Ala Lys Val Ala Glu
    130                 135                 140

Ala Ala Gly Gln Leu Gly Ile Lys Thr Asp Lys Val Val Gly Phe Thr
145                 150                 155                 160

Lys Thr Met Ile Asp Met Gly Glu Ser Thr Asn Met Ser Ala Asp Thr
                165                 170                 175

Ala Ala Thr Ser Leu Ala Arg Phe Ala Asn Ile Thr Gln Met Ser Gln
            180                 185                 190

Asp Lys Phe Ser Asn Leu Gly Ser Ala Ile Val Asp Leu Gly Asn Asn
        195                 200                 205

Leu Ala Thr Thr Glu Ser Glu Ile Thr Glu Met Gly Leu Arg Leu Ala
    210                 215                 220

Gly Ala Gly Lys Gln Ile Gly Met Thr Glu Gly Asp Ile Val Gly Phe
225                 230                 235                 240

Ala Ala Ala Leu Ser Ser Val Gly Ile Glu Ala Glu Ala Gly Gly Ser
                245                 250                 255

Ala Phe Ser Arg Leu Met Val Gln Met Gln Leu Ala Thr Glu Thr Gly
            260                 265                 270

Val Lys Ala Phe Glu Pro Leu Lys Gln Ala Val Ala Ile Gln Gly Val
        275                 280                 285

Ser Trp Glu Lys Phe Val His Ala Val Asn Trp Gly Gly Lys Glu Leu
    290                 295                 300

Thr Ala Val Ser Lys Gln Met Gly Val Pro Ala Ser Glu Leu Lys Lys
305                 310                 315                 320

Leu Tyr Lys Glu Ala Ser Lys Ala Ser Gly Ser Leu Glu Asp Phe Ala
                325                 330                 335

Asn Val Thr Gly Arg Thr Gly Glu Glu Phe Ala Glu Leu Phe Lys Ser
            340                 345                 350

Asn Pro Ser Gln Ala Met Ile Glu Phe Ile Gln Gly Leu Lys Asp Ser
        355                 360                 365

-continued

```
Glu Lys His Gly Ile Ser Ala Ile Lys Val Leu Asp Met Gly Ile
    370             375                 380

Thr Glu Val Arg Leu Arg Asp Ser Leu Leu Arg Ala Ala Asn Ala Ser
385                 390                 395                 400

Asp Val Phe Glu Gly Ala Val Lys Arg Gly Asn Glu Ala Phe Asn Glu
                405                 410                 415

Asn Thr Ala Leu Ala Glu Glu Ala Gly Lys Arg Tyr Gly Thr Thr Glu
            420                 425                 430

Ser Gln Leu Lys Ile Leu Arg Gly Gln Leu Asn Asp Val Ala Ile Thr
        435                 440                 445

Phe Gly Gly Pro Leu Val Ala Ala Leu Asn Ser Ala Ile Ser Ala Ala
    450                 455                 460

Lys Pro Met Ile Glu Ala Leu Ala Asn Met Ala Glu Ala Phe Ala Ser
465                 470                 475                 480

Ala Asp Pro Lys Thr Gln Glu Phe Ile Leu Lys Met Ala Ala Leu Ala
                485                 490                 495

Ala Ser Ala Gly Pro Val Leu Lys Val Phe Gly Lys Met Thr Ser Val
            500                 505                 510

Phe Gly Lys Thr Ile Ser Thr Met Phe Glu Lys Ala Gly Asn Ile Asp
        515                 520                 525

Ser Lys Trp Lys Gln Phe Ile Val Thr Pro Ile Lys Asn Gly Ser Ser
    530                 535                 540

Ser Ala Leu Gln Ala Val Lys Gly Phe Val Ser Lys Tyr Lys Ser Asn
545                 550                 555                 560

Leu Ala Gly Leu Glu Ser Ala Gly Ile Asn Val Asn Leu Leu Thr Arg
                565                 570                 575

Phe Thr Thr Leu Lys Asp Thr Ile Val Gly Leu Phe Pro Thr Leu Asp
            580                 585                 590

Thr Phe Gly Ala Asn Leu Arg Ala Ser Gln Arg Gln Leu Asn Met Leu
        595                 600                 605

Gly Glu Gly Asn Lys Val Thr Asn Phe Phe Arg Ser Phe Ser Ala Ser
    610                 615                 620

Leu Gln Leu Ser Asn Ser Lys Leu Ala Lys Phe Ala Ser Val Val Ile
625                 630                 635                 640

Asn Pro Ile Gly Ser Leu Arg Asn Leu Ser Ser Ala Ala Gly Lys Ser
                645                 650                 655

Gly Thr Val Leu Ser Gly Leu Gly Val Ala Ala Ser Lys Ala Gly Gly
            660                 665                 670

Gly Phe Arg Thr Phe Ala Ala Thr Gly Ile Arg Ser Ile Ala Ser Leu
        675                 680                 685

Thr Gly Ala Met Leu Ser Asn Pro Ile Thr Ala Ile Leu Val Ala Ile
    690                 695                 700

Thr Thr Thr Ile Val Gly Val Gln Ala Trp Lys Ser Asn Phe Met
705                 710                 715                 720

Asn Ile Gln Gly Tyr Val Lys Thr Ala Phe Ser Gly Ile Val Lys Ser
                725                 730                 735

Phe Lys Ser Val Leu Pro Ser Ser Ala Ser Val Thr Lys Thr Ile Lys
            740                 745                 750

Gly Leu Gly Asn Ile Phe Lys Trp Leu Gly Thr Gly Thr Leu Val Gly
        755                 760                 765

Val Thr Phe Ala Ile Ala Gly Phe Val Asp Gly Leu Arg Ala Ile Ile
    770                 775                 780

Thr Val Gly Lys Thr Ala Val Asn Ala Ile Met Ala Ile Ala Asn Gly
```

```
                    785                 790                795                800
Val Lys Gly Leu Trp Gln Arg Leu Lys Gly Asp Ser Lys Gly Ala Asp
                805                810                815
Lys Ser Phe Lys Asp Val Lys Lys Ser Leu Ala Asp Ile Gly Lys Asp
                820                825                830
Trp Asp Thr Met Phe Ser Asp Ser Ala Leu Lys Lys Ala Ala Lys Ser
                835                840                845
Thr Glu Glu Leu Gly Lys Lys Ser Lys Asp Thr Thr Lys Ala Met Ser
            850                855                860
Met Asn Met Glu Glu Val Ser Asn Ser Val Glu Asn Tyr Ser Ser Lys
865                870                875                880
Leu Asp Glu Ala Lys Gln Ala Met Thr Glu Leu Phe Ser Gln Gln Asn
                885                890                895
Gly Ser Thr Ala Gly Val Glu Ala Tyr Phe Asn His Thr Leu Asp Leu
                900                905                910
Val Thr Asn Leu Lys Glu Gln Gln Lys Lys Ala Val Glu Thr Tyr Asn
                915                920                925
Lys Gln Ile Glu Ala Ala Glu Gly Lys Ser Glu Ala Glu Lys Gln Lys
            930                935                940
Ile Phe Ala Asn Ala Ser Thr Glu Tyr Met Lys Ala Val Gln Ser Asn
945                950                955                960
Asn Ser Asp Leu Leu Lys Val Tyr Thr Asp Tyr Ser Asn Gln Leu Lys
                965                970                975
Asn Asn Lys Thr Val Glu Gly Gln Glu Leu Thr Asp Gln Gln Arg Ala
                980                985                990
Thr Leu Gln Asn Gln Thr Asn Ile  Ile Arg Asp Gln Leu Leu Asp Gln
        995                1000               1005
Gln Lys  Gln Phe Val Glu Ala  Gly Val Asn Lys Leu  Asn Asn Asn
        1010               1015               1020
Gln Ala  Leu Ser Glu Gln Glu  Lys Glu Gln Thr Leu  Ser Ser Leu
        1025               1030               1035
Lys Thr  Phe Gly Glu Ile Gln  Ala Gln Gln Val Gln  Glu Asn Asn
        1040               1045               1050
Ala Gln  Ile Gln Gln Leu Glu  Thr Gln Lys Asn Gln  Ala Lys Thr
        1055               1060               1065
Glu Ser  Glu Lys Ala Ala Phe  Gln Asn Gln Ile Thr  Gln Leu Gln
        1070               1075               1080
Thr Gln  Asn Asp Gln Ile Arg  Gln Ser Glu Leu Glu  Gln Gly Ala
        1085               1090               1095
Gln Leu  Leu Ala Ile Ile Ser  Gln Asn Gly Ala Asn  Lys Ile Ala
        1100               1105               1110
Val Thr  Ala Asp Asn Leu Ala  Gln Leu Lys Gly Val  Thr Asp Gln
        1115               1120               1125
Gln Leu  Leu Gly Ile Tyr Gln  Ser Tyr Val Asn Asn  Gly Ala Ser
        1130               1135               1140
Ile Asp  Gln Gln Met Ala Leu  Leu Ala Gly Met Leu  Arg Gln Arg
        1145               1150               1155
Gly Ile  Asp Gly Ser Asn Gly  Leu Val Gln Gly Leu  Gln Ser Asn
        1160               1165               1170
Asp Pro  Lys Leu Trp Ala Asn  Met Ser Lys Ala Asp  Ile Val Asn
        1175               1180               1185
Thr Leu  Gln Ser Leu Pro Pro  Asp Leu Phe Lys Asn  Gly Gln Asp
        1190               1195               1200
```

Gly Lys Asn Lys Leu Ile Asp Gly Leu Asn Ser Gly Lys Val Glu
1205                1210                1215

Ile Asn Asn Val Gly Gln Glu Leu Met Asn Gln Met Asn Ser Gly
1220                1225                1230

Val Lys Asn Lys Lys Ala Glu Ala Glu Lys Thr Ser Gly Asp Val
1235                1240                1245

Ala Ser Ser Gly Ala Lys Gly Ala Lys Ser Lys Gly Lys Glu Tyr
1250                1255                1260

Asn Ser Gly Gly Asn Ser Asn Ala Gly Glu Tyr Asn Thr Gly Leu
1265                1270                1275

Ala Lys Gln Lys Ser Asn Ala Lys Gln Lys Gly Ala Glu Leu Gly
1280                1285                1290

Ser Ala Pro Val Glu Gly Val Lys Thr Lys Ala Ser Ala Met Arg
1295                1300                1305

Ser Val Gly Glu Gln Leu Gly Arg Ser Phe Val Gln Gly Leu Ala
1310                1315                1320

Ser Gln Val Gly Ser Ala Asn Asn Ala Gly Arg Glu Leu Gly Asn
1325                1330                1335

Ala Val Lys Ser Gly Ala Gly Ser Val Asn Met Thr Ser Val Gly
1340                1345                1350

Ser Asn Met Ala Lys Gly Val Ala Ser Gly Ile Arg Ala Ser Gln
1355                1360                1365

Gly Glu Ala Val Ser Ala Met Gln Asn Leu Val Ala Ala Val Asn
1370                1375                1380

Ala Glu Ala Gln Lys Lys Ala Lys Ile Lys Ser Pro Ser Arg Leu
1385                1390                1395

Leu Lys Tyr Asp Val Gly Val Phe Leu Ala Gln Gly Val Ala Ala
1400                1405                1410

Gly Ile Arg Glu Asp Thr Ser Val Ala Val Gln Ser Ala Lys Asp
1415                1420                1425

Met Ile Ser Ser Ile His Gln Ser Ile Thr Gly Ser Arg Leu Ile
1430                1435                1440

Lys Arg Ser Asn Ala Ile Glu Val Lys His Ser Ile Asp Asn Thr
1445                1450                1455

Pro Met Gly Lys Met Val Glu Ile Leu Glu Glu Ile Arg His Leu
1460                1465                1470

Thr Val Val Met Asp Thr Gly Gln Val Val Gly Ala Leu Gly Ser
1475                1480                1485

Pro Met Asn Leu Asn Leu Ala Glu Gln Gln Lys Gln Asp Gly Arg
1490                1495                1500

Tyr Arg Ser
1505

<210> SEQ ID NO 2
<211> LENGTH: 39290
<212> TYPE: DNA
<213> ORGANISM: Enterococcus hirae

<400> SEQUENCE: 2
atgagtaaaa caactaaaaa tccactcgtc aaaccttttg taaaatgggc aggtggaaaa    60
aggcagctaa tgcctgaaat tattaaatat aagccaaaaa actataaaaa atttattgaa   120
cctttcgttg gcggtggttc agtgtttatg gaacttcaaa ataataacac tgtaattaat   180
gattttaatt ttgaattaat taacacatat attgtaatta gagataattt agatgagtta   240

```
atattggaat tggaaaaaca taaagagaat gattcaaaag attattttta taaattaaga      300
gaatgggata gaaatggaac tttagaagaa aagtcaaatg tagaaagagc ttctcgcttt      360
atatatttga ataaaacttg cttcaatggt ttgtttagag ttaattcgca aaatcaattt      420
aatgttccat atggacatta caaaaatcct aatatagtaa ataaagaagt tttgattgct      480
gatagtaaat ttttaaataa atcgggaatt aaaattatga atgaagactt gaaaaagct       540 gcaaaaactg ctagaaaagg agattttgtg tactttgacc ctccatacgc accactagtt      600
gaagactcac aaagttttgt ggggtatact ttaaatgggt ttgattatga agaacaagta     660
cgattaagaa acttgtttat tgaattagat aaaaaaggtt gttttgtaat gttgtcaaat      720
tcatccagca aaattataca tgatttgtat tctgactata agatactac cgttataata      780 gaagcaagta gaaacataaa ttcaaaggca agtggtagag gtaaagtgga tgaagttctc      840
ataacaaatt acaattacag gcaaagctaa cgtgtaagga agtggtaata gtgaaaaaag      900
gtaaaaatga tgaagcttgg gagaagctgt ttgataaata tgatatctta aataaaatcg      960
ataaaaatga aacatttagc ataagttcta aacaaatcaa tgagttccga gaagccagac     1020
taatgacaaa attcgatcat tccaatcaat tgcctgaaat actttcaaaa aataatatta     1080
ctattcttcc tgattctaga ggtaattata ttcttgggaa attcaaaata tttgaagagt     1140
tgaaacataa aaatctcaaa ccaatttcta tgcaaatacc tgattttata caatctttag     1200
atattacaaa ataacaagt gaaagttctg cattaaatat tgcccatatg agtcaaatga     1260
tagattcggt aatgcaaact aaacacaatg aacctcggtc attacttact ttaagtggaa     1320
gaatgtcaag tggttctctc cagtacaata tactcaatgt tgataagaaa attcataaat     1380
tttcagttga aaatgcacaa attgaaattg atggttctta tgaaaatttg aacaatatac     1440
ttattgtcga agctaaaaat aaaattcctt tagactttaa tatcagacag ctatattatc     1500
cttttcgctt gtatcaaagt ttaaatacta caaaaaatat tactccagtc ttctttacct     1560
atgccgacga tatattttct tttcatgtat ttaaatttac agatattatg aactattcta     1620
gtattaaaaa agttgaacaa attaatttta tcttgaatga ttccttggat ttaaacttag     1680
aagaagtaaa aaaattagt gcaacagcta aagaagtcga agaaccaaaa aatgttccat     1740
ttcctcaagc agacactttt actagaatac ttgatatgat tgattatata tacgaaagaa     1800
aaaacaaata tgaattagca gaagcatatg atttttgattt aagacaaagt gactattatg     1860
cgaatgcatt agtatatttta gggcttgcaa caaagcagaa ccattatttc aagttaaatg     1920
atgaaggaat aaaaattaaa aatatgcaca actcgaataa gagaaatgct ttgcttatct     1980
ctaaaatatt atcgcataag cctttttaaaa ttgcatttga ttccacacta aaaaatggtg     2040
gcaattatga taggaaatat atttctaaaa tcttactgaa taatgtggtg tcgataaaca     2100
gtgaatctac agctaataga agaatgcaga ctgttgttgc atggttaaat tggatattta     2160
gtgtaataga ataacatttta atcattttt agttagatta ttctagctct tttattacag     2220
aaaaatagat tatgtacct gtaggactcg aacctacgac cggacggtta tgagccgtct     2280
gctctgacca actgagctaa gggtacaggt tgttgccact tgttcatac gaattatcca     2340 ttaaagaaag ggttgtggca acaaacctat tatcgcataa ttttggagtg tgactagtaa     2400
tgatagtgaa catatgcgat aataaatata ttttaccgaa catttttag aattgtcaat     2460 acgattatgt acagctcctc aacgaggagc ttttattta taaagttaaa taaatatcct     2520
taatccgaac atcattcact gcaccttcac catttgcttg attacaacga cggaaaatga     2580
```

```
catcgatttt cgtgccttt ttcacccaac ctagatccac tgtgacgtcc atacctagag    2640
catcaccacc tttgtatcca tatgctttct tcacgtcaga gcgtttaatc ccttgtgaag    2700
ctatacgagt gatttccttt gtggtgccat gttccatgat caagacttcc gcatacttac    2760
caattggacc atctggttta tctggtacta gccaaccagc aatattcacc tttttatttc    2820
caacaaattt gaatcgttcc aacttaccat atgcatttcc ctgatggact actttacttg    2880
ctgctactgc tttgtcatga gcagacggtg tttgtggttt tggttgctgt acttgtaccg    2940
attctacttt cacttgatta cttgaagttt gacacttacc tgatgtggca tatgctttcc    3000
aagtattttg atcaccataa aacttatttt ggtcatatgg tgtcgaagta tactgccaca    3060
taaccgcatt tgtccaatgt ttcaaagctg gaaattggaa ttgataagct gctacccata    3120
gaccataatc agctttaaca atcgctgaga aatcttcttc aaataaaaca gaagcggacg    3180
tatacactaa cgctttgata cctgtttttt gttggatacg atctaacatt tgttttaaaa    3240
cgcctgttcc ttgacgtcca tacatttcat aatctaaaac gagaattcct ttaccaatgt    3300
aaccttgaac attattaata agaaatccg tttgtgcttg ccaatttgaa ccgtcaataa     3360
aatgatacac gccaaagggt tttccagact tgatagcttg ttgaacaaac ggatcgcaat    3420
agcgatcaac aaaattacac ccttccgttg ctttaaacat ataagcatct gcgggataat    3480
ctttaatact ttttgaaccg ttattattcg ataaatctac tactttcaat gtcattttc     3540
atcttctcct tcatctaatt ctttgattcc atggttggtt cgtttccata actgatcgcc    3600
atacactgta attcccaccg ctacaatggc tacaaaaaag ttaaatacag tatacccacc    3660
aaataatagt ggtgtaccaa tacaactaat aaccgtaagt gccaaaggaa ttccccagtt    3720
agggaactta ggaatttcct ttaacacttt tcctgctaca tatagtccac acattgcaag    3780
gatcatttca gttgagagtg attccatcca tcttcacctc ttttcagagc ataaaaaaga    3840
agcacaaaat cactttcgta cttcttttc aatctcattt actttgtttt caattcgttt     3900
catatcagag ctcatattca taaacccatt ttttaactca ttcaacgtgg ctaaaaaatc    3960
tcttcgatct tgttttgaac tatttctctc atcttgtaat tctttccgat aggaaaggat    4020
catccgccat gcagcaaaaa tgataatccc tactagaata atggttaatg gtaaaaaaat    4080
aagcccgtct attgcgacta acttagaaaa tacttgatca atgccttca tatcttccca     4140
cctgctttct attcagtgag aatctctttc gcttcttctt ttgtaatact tccttgtgca    4200
acatagctca tgacgtccgc ttttgtatac acacctaaat cataaaaaa ctgaatatct     4260
tctttacttg gatacatttg gcacgcctcc ttctgtaatt actgcctcat ttggaaatac    4320
aacatcttga attctttcca ccatttttt cagttttgtt aattcttca tggtattcgc      4380
tgctacctga ttggagcgaa catactgatc ataaggaact cctttcaccc aaatccactg    4440
attgttttcc caatcaaaac ctgcaatcat cacatctggt cctttaggtg gttctacttc    4500
tgtaaatggt cgtgaagtcg ttgattcttt tggtgcaaac cagacttcat aactttgtcc    4560
gactacttta taaacaactt tcatattttc attcataaat cttcctccta atgtttaaat    4620
acttcattcc ataattgttg aatttgtgtt tgcattcgat caatggtagg gtctctcttg    4680
taataaagca gatctgtcaa ataaattcga taagtaaact gcaacgtagt ttttccatag    4740
tataaagaag tatatgcccc ttttcaccc atcatgagaa tattcactcg tccttgtgaa     4800
tctaagaatt gttcacttcc atttttaca accgaagcgg acattgtttg aaatctttt     4860
tctggatttc gttgatattc tctccattgt tctaaataat tgtcatacca taaacaaccc    4920
attcctcctt gtccgttact ccaactatca gctaccgttc catgataacc atacccatag    4980
```

```
gtacttggag tgatcgaaac tatcccttt tcagtcaatt gaacttgttg ttctaagata   5040
tttataccta atgcttcata gtaatcttct cctaaccatc gtttgatttc ctccactaca   5100
ttccattgga tgcgtaaata aggatagtta ggattattat cggaaccaga tgaactagaa   5160
ttatatgttc tagttccacg tagagcttca taaccaattg cattgactgc acttggataa   5220
gcattaactt caggataacg cgtgtaagga gtaggcattt caaacctgtt ttcagaaaga   5280
aaattgactt gactagcaat attgggattt tcagccatac taccgaccac ttttccttta   5340
aaatcaagtg accgtgatac ctcgaaataa ccttttgtaa atgcctcaat caattctttt   5400
ttcgtgaata attcattttc atcaatgagt tgcaataatc gattggtttc gctttgatta   5460
acttctactt tttgactaag tgattggact tgttcggtca cttgaccaac gctagcctct   5520
aattctggtc ttagtgtttc aatggcttct ttttcacttt ctgctaaatc aaaaatttct   5580
tttttgattt gttcgaagtc tttgatgtat acctcacttg cttcttcaat ttcactttca   5640
atttttgaac ggataactgt aaaagtgaag gctagctcat cactgtgaga gccatcttcg   5700
aaatcaagat acacgtatcc ttttacttcg ccttcataat ttaataactg gtcaggcaga   5760
ggataagtca caatcccact ttcagggtat tcaataatcg gttgactatc gattgcagta   5820
aatttctttt cttggccatc ttgattgatg gttagtaaga ttttaaatgt agtattggtg   5880
agatcgacaa tttgataatc ttgatcacgg aacaaaaatt ctaatactac agaacctttg   5940
tcataactat aaaaaacaaa gcctgtatct tggccatgtc ttccctttac ttttgtattg   6000
acttttattc gaccaatttt tttaaacgtc atttactaca cctccttccc aaataataaa   6060
agctattcta ctcagtcgca tcttgagcta gaatagcttg aactttctt tttagtgttt   6120 ttggcacatc atcaatcgtt ttcttccctt ttctgattaa gtccgcatag atgttttcca   6180
tgttactcac tccctaatga agattcataa atttcggtca ttgctacttg taaatctgtc   6240
acttgattat tcaaggcttc gttactctct ttgaaagctt gattttcttc ttgaactttt   6300
tcaagttgtt gttcagtttt acgatggatt tcttctaaca actccaattt tttagagaaa   6360
tcttgtgtga ctacttcttc ccatttcgc tcccttggat tccaaaattg gcgatctaat   6420
ggaatatctg gtaatggtgg tacagaagta tacggcactc cttctgggaa atcatctggc   6480
atgttttccc agaccttacc ccctactgga taaagatatt catacattgt tttcatcatt   6540 tattcccct attgatttgg ccacgcatca tttgtaaaat agctgacggt tccagaacac   6600
tcttgatttt ctggtaaatt tgtagtagaa accatcacag caattcccga agcatttgcg   6660
taaacagata atgcaagatt tcgattggtt ttattcgcca aagttccacc ccaatccttt   6720
agcgaagttg gagtatatcc ttttggaaaa ggcattaaaa cttccagcc accaaaattt   6780 gctgatttat ttgtgatcga aaaattggct actacacttc gtccatctcg ttcaaatctg   6840
actgaacttt cattggtgaa atctgttgta ttcgtcgttt ttactgtttt tgaaacaaaa   6900
cgatctacag ctactggtac atcattcact gttggtgttt gttgaaaatc tttgaaacca   6960
ccaatgcgtt gattactaga agtatccaca gcttccttaa aattttggtt aatagtttct   7020
gcaccattct ccatacctct ataaatttct tgaaatggca ttaaaatccc tcctatatcg   7080
ataaatcaaa aacgattgat cgattatttt cttcatcaat aataagatat ttattatcat   7140 taatttatt cggtaaatag gttgttttat agtccttcgg tattgtaact acacatttat   7200
tggaactaat ttgcttaaca ctacaaggaa ctgttataga agcgctccct ccaaagaaac   7260
cttcgggttc agtccctaat ggaactacac caatcccata tgtccaagtt ctaaccacaa   7320
```

```
ttaacggatt cgctcctaaa ttatgctcaa tcgttacatc gaatccatct ggaatagaag    7380
acgacaaaat cttttcaata tattctaatc tttcgtccag agttgcaaaa tttccatact    7440
tttcactgct tctagcatta attaactcgc tatctacagt agcattagca atcacacttt    7500
tgaaattttc ttcaatagta gtttgtcgct tttcaatctc tgactgacgt ttctcggtat    7560
tttctgttaa aagtttaatt ttattgaaca atacactggt atattccatc attcttgcta    7620
gtgattctct tacatgtcga cgatacattt tagttcttat ccatgtagca aatgttcttg    7680
aaataggatc aataatccca tactttattt catcttgaac ctcatcaaca tctgttggat    7740
ctcggtaatc tacagacgta ttaggttcat tcgttggttg tgtatcttta aattcttgtg    7800
tcaacaaaat tcacctcact tattttctaa attctcaact cgtttgatta aactagaaat    7860
agtctcatca gactcttctc gagattttt taaatcagtt atttcggagc ttaaattagt    7920
ttcaacttga gctataccat cttttaggga attaatagat tctgaaagtt tttgagttcc    7980
ttcacttaaa tttattattt cgttattttg ctgagacact tcattttta aagattcctg    8040 tttttttatt aaatctgaaa ttgactgtgt tccagccgaa gcatttgctt tgatattaac    8100
taaattagat tgaattgttt ttatttcatt ctggtaatct gttaattttt tcttttaga    8160 acctattgta agtgttactt tttgaggtgc taaaatacta aacttctttt caattacttg    8220
tagcctttct accgcataga gaaattgatt atctactttg taactgtttc ctaaagtgat    8280
taattcatac cgtttatcca atagccctaa ctcaatggct tcaactgtcc aagttaccaa    8340
catcaagctt tggtctttta gccattgcaa ccctcgacgt tttaaaattg atgggtcttt    8400
gacatttgaa aattctacaa tgcccgtgtt taatccaaat tttttgatta acgcttcatc    8460
atcaagataa ttcttaccgc catttacttt ttcgatggta tatttaggtc gtgaaaaatc    8520
tgtccccact tcaatatcag tatttgacgt atcttcaata tcttgaccga cgggcacaat    8580
ccttgtaaac aattcagaaa tatcaatatc tcgagtagca ctttttagat ttttggttaa    8640
ctgtaaagga gtttcactgt tcacaccata attagataga taatctaaat aatttatatt    8700
cccaacgcgt cgaagtgtta acgtaccgcc tagcctatcc aataattttt ctttgatggt    8760
atcagctgtg ctttgatagc ccagccctct caatagatca ccgttatcta aacgtcaac    8820 gttacctaac ttaaaccttt tatagggttc cacttgcttg ttatgaatat caattatttt    8880
ctgcaaataa tctctgacgg gcattcgagt cggcttcata tatgtttgca cagaatcata    8940 taaaaagct ttctcatctt ctataagaaa agattgagaa aagctacccg atgtatccat    9000
tgtgtttgtt attttagcta ctcgaccata aaaaatttct tgttctcgta cagcatctat    9060
aatttgaata aagttaataa taggctctat cttttgatag tatttattgt taatgttgaa    9120
tgtgaattca aacgtagaaa ttcctaatcc gtttaaagat agataaactt cactctcctt    9180
aattttttca ccgtagctat aaggctcgtg aacaattttg ggatttagac gattcggatt    9240
gtcatatagt aatacacgat acattaaacc atcacctcac tagacataaa gaaagagata    9300
tgaccttcgc caaaaatggt taaatgattg attccttttt tcagtttaaa gaagtaatct    9360
tgtgattctc cttttggaac ctttattgtt gttccgtcat ctgtagttaa tttcattgaa    9420
gacgttgcct ttatcgttgg actagaagca tttgctccca tattgataag gaaaatttcc    9480 cttttctat gaatatagta gcctgtccag ttatctacac tatcgtctgt gaaaaagtcc    9540
tcgtcaaaaa tatctgaata agaaatattt tcccttaaag caaaagggta aacatcaaat    9600
tctacagtta acgttaatga gttacttgac gcatcatctt ccgctttcac acttttacat    9660
tttccatacc acctaagacc tgaacgcaac caagagtctt caatataatc aatcccttgt    9720
```

```
aacattagtt cttctttcac ttgggcttcc aacgccttac gttcatcata aggcgtatta    9780
gatcgccaaa aagtaactgt gacaattcga ttactgaaaa ttcgttcacc agtcaacatt    9840
gagaaatcat attgcccttg cataaaagga atttgctcaa taatttctac ttcttccgca    9900
gaaggagcat cgtgttcaat aatgtagaaa ccatgttctt tgctgttaaa cgacctttt    9960 gccatatatt ctacaatttc aatcaactac gatacctccc atcttgcttt tgttgttctg   10020
ctaaattaag attcatcggg ctacctagtg ctcccactac ttggccagta tccatcacaa   10080
cagttaaatg acgtatttct tctaagattt ctaccatttt ccccatcggc gtattatcta   10140
tagaatgttt tacctcaatt gcatttgatc gttttatcaa acgactgcct gtaatagact   10200
ggtgaatgct tgaaatcata tcttttgcac tttgtacggc aactgacgta tcttctcgaa   10260
tacctgctgc cacaccctgt gcaaggaaaa caccaacgtc atatttcaat aggcgtgatg   10320
gagatttaat ctttgctttt ttctgtgctt ctgcattaac tgcagctact aaattttgca   10380
tagcagatac tgcttctcct tggctagctc taataccaga agcaacacct ttagccatat   10440
tagatccaac ggatgtcata ttgactgaac cagcaccact ttttactgcg tttcctaatt   10500
ctctaccagc gttattagct gaaccaacct gtgatgccaa tccttgaacg aaactacgcc   10560
caagctgttc tcctacgctt cgcatagcag aagctttcgt ttttactcct tcaacaggcg   10620
ctgatcctaa ttctgcacct ttttgttttg cgttgctttt ctgttcgct agccctgtgt    10680 tatactctcc agcattagaa ttaccgccgc tattgtattc tttacctttta cttttgcgc   10740 cctttgcacc agatgaagct acatcaccag aagtttttc cgcttctgct ttcttatttt    10800
ttacgcctga gttcatctga ttcattaact cttgaccgac attattgatt tcaacttttc   10860
ctgagttcaa cccgtcgatt aatttgtttt taccatcttg accgttttta aacaaatcag   10920
gcggtaatga ttgcaaggta ttcacaatgt cagcttttga catattcgcc cataatttag   10980
gatcgttgct ttgcaatcct tgaactagtc cgttagaacc atcaattcct cgttgacgta   11040
acattccagc taataaagcc atttgttggt caatgctagc accgttgttt acatacgatt   11100
gataaattcc taataactgt tggtctgtca ctccttttaa ttgagctaaa ttatcagccg   11160
tcaccgcaat tttatttgca ccattttgtg aaataatcgc tagaagctgc gctccttgtt   11220
ctaattcact ttgacgtatc tgatcgttct gtgtttgtaa ttgcgtaatt tggttttgga   11280
aagccgcctt ttctgattca gttttcgctt ggttcttttg tgtttccaat tgctgaattt   11340
gtgcattatt ctcctgcact tgctgtgctt gaatttctcc aaaagttttt aaacttgata   11400
aagtttgttc ttttttcttgt tcacttaacg cttggttgtt attcagctta ttcacaccag   11460
cttcgacaaa ctgtttctgt tgatccaaca attgatcacg aataatattc gtttgatttt   11520
gcaaagttgc tcttttgctga tcggttaact cttgaccttc taccgttttta ttattcttca  11580 actgattaga gtaatctgtg tatactttca acagatcgct attgtttgat tgaacagcct   11640
tcatatactc agttgaagca ttggcaaaaa tcttttgttt ttcagcttcc gatttacctt   11700
ctgccgcttc aatctgctta ttataggttt caacagcctt tttctgttgt tcttttagat   11760
ttgtcactaa atcaagtgta tgattgaaat aagcttctac gccagccgtg ctaccgtttt   11820
gctgtgagaa aagttcagtc attgcctgtt tagcttcatc aagttttgat gagtaatttt   11880
caacactatt tgatacctct tccatattca tggacatggc tttcgtagtg tctttcgatt   11940
tcttccctaa ttcttctgtg cttttagctg cttttttag agcagaatca gaaaacatgg   12000
tatcccagtc ttttccgata tcagctaaac ttttcttcac atctttaaat gatttatcgg   12060
```

```
ctccttttga atcgccttttt aatctttgcc aaagtccttt tactccgtta gcaatggcca    12120
ttattgcatt tactgctgtc tttcctacag taataatggc tcgcaatcca tctacaaaac    12180
ctgcaatagc aaaagtaact ccgacaagag ttcctgttcc taaccattta aaaatatttc    12240
ctaatccttt tattgtttta gtaacactcg cggagctagg aagtacactt ttaaacgatt    12300
ttactattcc gctaaaagcg ttttcacgt agccttgaat gttcataaaa ttggatttcc     12360
aagcttgcac tacaccaact attgtagtgg ttattgctac taaaattgca gttataggat    12420
tgctcaacat agctcctgtt aaactagcta tagatcgtat acccgttgct gcaaatgttc    12480
taaaacctcc acctgctttt gaggcggcta caccaagtcc tgataaaacc gtccctgatt    12540
taccagctgc agaagataaa ttccttagcg acccaatagg attaataaca acggaggcga    12600
atttcgctaa tttgctatta gataattgta aagaagcaga aaaagaacgg aaaaagttag    12660
taacttttatt ccctccccct agcatattta gctgtctttg gcttgctcga agatttgctc    12720
caaaagtgtc caatgtggga aagagaccta caatggtatc ttttagcgta gtaaaacggg    12780
taagcagatt tacatttatc cccgcacttt caagccctgc aagatttgat ttatatttag    12840
aaacaaaccc ttttacagct tgtaatgcgc tactagaacc gttttgata ggagtaacga     12900
taaattgttt ccacttgcta tctatgtttc cagctttctc aaacattgtt gaaattgttt    12960
tgccaaaaac actagtcatt ttcccaaaca cttttaatac aggaccagca gaagcagcta    13020
atgcagccat ttttaaaata aattcttgag tttttggatc agctgatgca aaagcctcgg    13080
ccatatttgc taaagcttca atcataggct tagcagcact tattgcgcta tttaatgcgg    13140
ctactaatgg accgccaaac gtaattgcta catcgtttaa ttgaccacgt aaaatctttta   13200
actgtgattc tgtagttccg tatcgtttgc cagcttcttc tgctagagct gtattttcgt    13260
taaacgcttc gttacctcgt tttacagcac cttcaaagac atcactcgca ttagccgcac    13320
gtagtaaaact atcacgtaat cgaacttcgg taatccccat atcatcaagt actttaatag    13380
ctgagattcc atgcttttct gagtctttca aaccttgaat aaactcaatc atagcttgag    13440
aaggattact cttgaataat tccgcgaact cttcgccagt tcgaccagta acatttgcaa    13500
aatcttccaa acttccagac gccttgcttg cttctttata taattttttc aattctgaag    13560
ctggtactcc catttgttta gaaacagctg ttaattcttt accacccaa ttaacagcat     13620
gaacaaattt tcccaagac actccttgta tagctacagc ttgttttaaa ggttcaaaag     13680
ctttaaccc tgtttcggtg gctaattgca tttgtaccat caacctagaa aaagctgaac    13740
cacccgcttc ggcctctata ccaacagatg ataacgccgc tgcaaaaccg acaatgtctc    13800
cttcagtcat accaatttgt ttcctgcac cagccaaacg gagtcccatt tctgtgattt     13860
ctgattcagt agttgctaag ttattcccta agtcaacaat agctgagcca agattgctaa    13920
atttatcttg agacatttga gtaatattag caaaacgagc taaggaagta gcagctgtat    13980
ctgcagacat atttgttgat cgcccatat cgatcattgt tttagtaaat ccgacaactt     14040
tatcagtttt tattcctaac tgtccagctg cttctgctac ttttgcaatt tcttcatgac    14100
tagtaggtaa ttcttttgct aaatctctaa ggcctttttc taaatcatca taagaataaa    14160
tgactttacc gttagaatcg accatctcat cgttggtctt tttaacacca gtaaatgcac    14220
tttcccattt tacggctgca gttgtgactg ctccaacagc acccgcaatt gggagtgtga    14280
tacctttagt catcgaaccg ccgactttt caatgctttg gccgatactt gcagtttat     14340
caccaaaaact tttcatcgca ccactaactg tgttcaaatt actgggaata tcagaagcat    14400
tcgaactaag ttttttttagc gaagaggtag cactcccat tgtctgagta aacccttttat   14460
```

```
ctattgctgt aagtaccgct ttgactgttt tactttgtgc cacgttgttt cctcctttcc    14520
tcaacaattt ttcttgcttg ttctaatcga cgagcgtttt cttctagctc acttagcttt    14580
tccgcttctc gttgcgaaat ttcccctcgc acatcgcgtt caagcttttc aaagtcgtag    14640
acgtctttca cttcgttaaa aatatagcgt tgtccttttt cgtctggcgt tgtaaaaata    14700
cgtgtagcta acgcgttaac gtatagtttc ctttcttcgt taattgcacg taaatttaca    14760
gcttttatcc gtaaattaaa ttcataaggg gtcatacgct caatttcttt taaagtgata    14820
ttggggaaat gttgaaaaca agtgacaact atttcgtcat aatctaggct gtcgtttctt    14880
gttgattggc ttgcatctgt tccatgtaag ccatgatttt ttggatcgct tctagtgctt    14940
ttttcgttcg aagagccgtt aacggtgctt gctccaagaa agagataaaa ttttcaaaca    15000
acgttaaagc ctcatctgac gtttctaagt agtcgtcaat ttctttcgtt gttaagtcat    15060
cgtaagtaat taacgctgcg tgcattaatt tttgaaaggc aaaagcgtcg ccatcttgta    15120
actctccgat cagttgaacg aagccgtcca attcttcaac gtcaggtttt aatgcgttaa    15180
tttcgtttaa aaatttaaaa ccgaaaacca aaggatattt ttttccatta attgttgcga    15240
ctggttttac gtttgttgac atgtaaaatt cctcctaaaa aagcgacaat gctttcacat    15300
tgtcgcttac ttcttgattt ttaattatgg tactaatgct aataaatctg ttttcgttgt    15360
ttttcctgta aaatcaatac cgtgagcagt taaccattct ttgatttcag gaatagtatt    15420
tgcttctgtt ggtttatttt ccaaagagcg ccctgccaat acagtaaaag ctggaatagc    15480
tactttttca gattcttttt catcttgcac acgtacaaga tgatacgttc ctgctgttac    15540
ttttgctcct gcatcaagtc ctgtgatagt taatggactt gctccttcaa ccacttttc     15600 actacccttta taaatacgat aagtaattgc catgattatt cttcctcctt cacttttaca    15660
acggcaccat ctgctgttgg cgttacactt tcaattttag gtacctcaat tgttttaggt    15720
gcgtattttt ctactggctc ttctggttct gctccagcca ccgtatcata gaagaaagcg    15780
cgtgccagtt cttcattttc agtatcaact gttgcccaac cttctactaa atcaccattt    15840
agcaccaatg ttggtttgat acttgaatta gaatcagatt cagcagaatc tccgaatgaa    15900
tccaataatc ctgtaccaaa ttcagcttcg tatttccctg ttttggatc tttttatca    15960 aaattaatgc gccatacatc aatttctaac ccattacgat acgcatattt caacatgtta    16020
taagtttctg ttcctgttcg taaaaattcc atttcaatag aagctgatgg cattcctgat    16080
gtaggaacat ttccgtcttt tgttgattgg gtatctgttt tgtttctga cttatattcg     16140 tgtgaaattt ctaaagctag caactttgct gctgttgttg cacgttcacg ggttagctga    16200
aacattaatt taattttttt accttgaatt gcttttccaa tttcgagttt ccttctttct    16260
tattcaaatt ctaacgtgat gtcaagtaca ccgtgtgcaa ggctcgtacc aaaattggtt    16320
gtattttcat aaataacttc tgtgctactt tctatcacta accaattaaa gttcttagtc    16380
tgatgcaatt catgaacgat ttttcgcaca tcggctaatg tttgatttaa ttctcgacgt    16440
ttgtcgtcat gattataaac atgaatcata atatttgttg aacctaacgt tcttgttttt    16500
gtttgtctat ccttagacca ttgttcacct aagaaaacaa acggataaga agcctcatca    16560
tctggcaaat gcgcataggt ttcataacct gcttgctcca gtgtgacaaa taatgcttca    16620
taaaattcag aatatggatc tttaaaggtc attttactaa ctcctccata tcgttaagga    16680
atctcttaat agctgccgca tgcccttttt tcatatagaa acgtccatac atgtaacgcg    16740
ttccatactc tacatacgct gaataatcag caaaagctct cacttctcca gtcattccat    16800
```

```
catctttaat aaaagatact tctgttcttt tcaagtaacc acttttaact ggtgtttctt   16860
ctgcaattcg atttgccata taggcagtat cattctttac gattgctttt acatcatcca   16920 gcttttcgc ttcttcaatc gcttcgatta aatcgtccaa ccctgaaatt tctacgcgat    16980
aagtcatcga tactcacttc catacactgt tgtgccttta ctaacacgca aatttttcac   17040
aacagtaaat tttcgatttt tttgttcttc ttcatcgtag tattcaagaa agcctgaacg   17100
aatagttagg cgatctctaa aacgaaaaat gaccatttgc tcctttacag taggaaaaat   17160
ggtcatttgt ttttctgttc caacttcggt tacactgcct atcaagtttt ccgaaatcaa   17220
ttcatgtttt ttattgtaat aattaataca ggttctcata aaaatgatac ctttcttttt   17280
ctggttagtc cttttcttc aagataatcg ttaatttcac tttgaaattc tccaaaatcg    17340
tctaaattat aagaaatggt ttcttctgac tgggaatgtt gttccattcc ttcaaacccc   17400
aaccgattat atcgtttaac aactacggca gacacgatat aatctaattc atcgggaatc   17460
tcgtcagctt taagttttat aagcaactgt ttttcagtca tttctataat ttttctgatt   17520
ttttctttat ctttattaaa tgtttcttct gaaatatcta ataaaaggcg gaaatcatta   17580
aggttcattt tttcacctac tattctactt caataactgc cccatctgcc gttggtgtta   17640
cctttttaac ggtcggggcg cttactttga agtgtatgat acataaatcg ctgggcgtgc   17700 ttttcagtt acgatagcat cgtaatagtt taatcctttg attgtatctc tgtagccgtc    17760
acgatcttgt gaagctggaa ttagatcaat agagttgtat ttttcaactg gcgaacaaac   17820
catcaaaggc acaagaatat aattaatttt cttcgtagaa tctacctgca aacgagattt   17880 tgcaacttt tgaataatag tatctgaacc gtccaactgc gcaactttac gattaatacc    17940
cgaaatttgt tgctcattcg tagtaaatgt ttttgacaca ccttttgcat tttttaatgc   18000
tgaataatag tcagtagatg caaacatgat aaacggaccg acaatttctg catccgtcat   18060
gtaggcttct gccgcatcat aggaagctag agaattttct gtggtaatag tttcttctac   18120
tgttttccct acatatttc cttcagtgtc gtcttcagcg gcttcagcga atgccgcttc    18180
taataatcgt tgtacagcag ttcgatcttt tcaggaatc gcaattaaac gagtatgctc     18240
ttctacaagc gcttgaactt cgtaggaagc attttctgat tgatctaatg tgtctaagtc   18300
ataaccaaac caacgctctt tctccaattt gaacgtttct tttgctacat caattttaga   18360
acgaccatta gcttcattac gtttataatc actagcagta aaacctttca tcttattgat   18420
gcggacttct ttcgctccta caaaatctgc ctcagttact gcagcagctc cacctttta    18480 taagtcccat acttgagaac ctgtggcaaa ttctttgtca attgctttta aatctttgct   18540
atctaaaata attggcataa ttttcatct cctatttctt ttctaaattt ttagctaaat    18600
tactgcgcca atcagtctct tttgttgccg ttgcaatatt tactacttga cctttcagca   18660 attcttttg gatacctct cttgcttttg aaatgatttg ctttaattca tctacagctt     18720
tttttgtatc ctcatccgta tcttttataa gcaataaatc tgcttgggat gcacttacat   18780
aatcagaaag accgttctca gataaatcat tacggacaga ctcggcacga tctaaacgat   18840
caatgcgagc ttgtgcttcc ttttctctct tttctgcttg agcttcttta tcagctgctt   18900
cttgttcctt tgctttcaca cgttcttctg cagtcatttg ctcgtaagat ttttgcttct   18960
cccaatcaga ttttgcttgt tccacagcct ttttagtttc tgctgcaacc atcttggcaa   19020
catcatcacg agtaaaggtt ttccctgtct cttttccgtc tggatttta tcttttggat     19080 tctgagaatc atttgtcgat gaagttccag atccgtttgg attgtcagac tttggatcat   19140
cgggatttgg atcatccgca aaaaattgta aattcatcgg taacaataaa cgtttattag   19200
```

```
ctttcatttt gattcctcca gtcattacgt gaccaatcga aattaatagg ttacgcctat   19260
caatcgaaac agctttctct ttaacgcctg taagcagtaa gaaggcaata aaaaaaagac   19320
taacgtttgt tagactttc atctttatat gctggtgcag tgctacaccg acaccaatta   19380
tgaatagggc ttgcattgct acctggactc atttctgaaa ctttatgtgg atttgcgctt   19440
gctatcccca cacaaatagg acaagcgctt ggctctacga ttaaattgta ttcatcatat   19500
ccgtactttt cgtaactttg cttttgtatc tcactttgaa ttctagaaga ctcactgatc   19560
attaaccttc tagccacata atcagccgtt tcttttcctc tcaaactatc aattactact   19620
aatttgcgta attctctagc tagaatatca gggtgtttgc ctgcaattaa accaactgta   19680
agcaatcgat caatattagc ttttaaaata tcttgattca accacaaacg ctgtgaaaat   19740
gtcgcattat gaaatgatcc atcaataatt gctctagcaa attttcgata gacctcttca   19800
gaaagtattg actcacctaa aattcctgct tgtcgtttga attcttcgat tgcttcgttc   19860
atcaactgat tattgaaata agtttgtagc tggtccgtat tatcggttaa atagatacca   19920
atacttgatt tcaacaattc taagcgattt atcttcattg ttaagttata taaccgtagc   19980
tgatcgtttg cttcttttga aaaatctctt gtttgtacat agagtttttac tttattaaca   20040 aaagcctgaa cttcgtgttt acttacacgc cgttttgctt cttcaataga aatcttttct   20100
cttccagcat aatttgagta gaattgttgt atttccgact ctatctttat ccacaattgt   20160
ttgtaacgtc tgtggatttc ctgttcataa cttatatgtc gacttagcat ttcttcaatg   20220
tgttttgctt ctcgttcagt ccaataatta ctcatgttct tcggtcactt cctccgtagt   20280
ttgagtaatt tccgtaaaat caatttgagg atttaaccga tcttccgttt cttcatcctt   20340
tatacgttcc atttcttggg tcacatcagg aacaatcgat aatacaccta gttgcgtttc   20400
tcttgagaca atcccttcaa gttttttgtgc ggtttctgct tcgtctttaa tattacgcgg   20460
aatgttaaac tcaaaattat attctaaatt aaaccattct ctcgctttag ctgcaggtac   20520
gtttgtaggt aatgaaaaaa tcatttttgta catttgcgca tatcctttttt taaacttcct   20580 tgcttttgct tgtgcgaggt ttctagggtt ttgcatttta aattctaacg agatacctga   20640
ggcattgttg ctgaaacttt cgtcatttgc gttgtaagtc attgacatttt ggtaaatcag   20700 acgttctaat cgatctaata aattttcttg agtagcgtca gaactaggtt tgtctaaaaa   20760
attaatgtct acagtttcac cttcgtttaa aggatctgcg ctgttaatta ctcgattatc   20820
acgcaaaaag gcagcaacat tcttatcagt taaatctaca ccgatcattt ttaagtaagc   20880
atctgcaaag taactcacat catttgcctt ttcagataat gcttcgttgt aattgttaat   20940
cagagaccac accgattcga tacgcccttg tcgttcgtca ttttccataa actcaatcat   21000
aggcacttct ccatatggat tagtgattgc ctcttttccg cctagtaaat aggacaaagc   21060
tttctgaaaa acagttagcc cttgtttagg ctccaatcgt ttagaagtct tggtttgtgt   21120
aaaaataaac gtctcagtgc tattttgagg ataaactgtt gctgttagtt catctcttgt   21180 catttttgtta tataaaactg caaacatagg tgcttttaat aaatcatctg cgtaaacgat   21240
aaacccttgt gtaggtttta aataggtcac acacgtttcg gcttcttcat tttgatataa   21300
aagcttataa gcgtgcccat aaatagcagt tagcttagaa agctctgcat cgttgtcttc   21360
ttcctcgttt cttttacgaa aatcttggac aaattctttt atctcttcat ctggatgagt   21420
aatctttgtt ggcttaccgt taagaaaagc tgcagaacta tctacaacat agcgagcaaa   21480
atttacagct atacgatgat ctggttttcc aattcctta tttttttgat aataaatgtc   21540
```

```
atgttggcca ttgtagagct tctctagctc ttcgtaaaac ccgattagtt ttcgatgttt    21600
attaatatat ttgtctacta actgttcatt aatctctgca tttttatcac aataaaatac    21660
acgatttccc aaaaggtcaa cgaactctcg tattttactt tcagtgtttg ttctacttac    21720
ttcatccgtc atcaaataac ccccttcaca ctttgtaatt taatcccacg tgttttctta    21780
ctacgatgtt ctactgcata tcgtaaggca tctatcacgt gattatagct atcaataggc    21840
tcattggtgt attccctgt tttcttatct ttagcccacg tatagttttc caattcctca    21900
atcagtttga cacagcgatc atctactatt agctcgtact gcaataaaaa agaaagcccc    21960
tgacgtatcg aatcaggacc tttcttagct gcacgtattc tagtaattcc gttcttcttg    22020
atttctgcaa tagatttctt ttctgctgag tcagcagtaa taatttcttt tgaatagcct    22080
aaatctttaa taactgttgc aatctcatcg ttcaacattc ctttttttaac atactcttca    22140 agaacatata tttctttgtt cttctcgtct actttaacgt gaataaaagc agatggatca    22200
tttacatacc caaagtctag gccgaaatcc gaatcaagct gccttagctt ttcatcgtgc    22260
ttgtccaatc ttttttcttg gtaagttgga aacacaagct tatctagcgt agcaaattct    22320
cctaaagcgt atatgcgata atacgctggg tttcgcttag ctaaatcctc aattaccttt    22380
ttattttcac tatcaagaaa ccgattgtct ttatatgtgc tgtgataaat ccctgttctt    22440
tgttgatcga cttctgcttc ctcaccaaag aaagatttat atacccaatt tagtttagaa    22500
actgggttaa acattaaaaa gatttgacgt ttcacatgcc tacgctcacg taaacgtaaa    22560
gtaagttgtg tataatcttc tagcgtaaat tctgttgctt cttccatcac tacatcagac    22620
agacctttga tagattttat tttctctggg tcgtccattc ccttgaaaag gaactccgcc    22680
ccatttggta aagtaatcct aaaatcggtg ttgtttactt tacacttgtc tagcagtccc    22740
caatccgaaa gacacgcttt cacatcctcg aaaatagagt cttttaagct acgccctact    22800
tttcttgtaa ataaaatctt tcttggtttc ttccacttct gacaggcttt aaaaacaacc    22860
ttttgaacaa ctccgtgact cttgccagat gaagcgccgc cccaataaac ctcagtaaat    22920
ttagaatagt caactaatcg atcataaaat gatttgttaa aaactcttga cgggaaatta    22980
aactctaaaa taatgttacg tttcttcgtc tgcatcccat tcaccaacct taattacaat    23040
atctcctgtt tgtaaatcga cttttatcagt gaacagtgca tgacgtttac caagaagttc    23100
tgcagctttt aatcgatctt ttgcacccac atcaatatct acgattgttt gttcgccttc    23160
tcctaaaccg attatcgttt cttctttgta ctcaccacgc ataacagccg ttaaatactc    23220
caaaacttct tgagcatcgg ctgttcgttc gttttttcatt tctgcaaggc gtttgtctat    23280
ataagattta attgtagtat tttgtagtaa tttagaagca tttgtgtttg cgtattttga    23340
actataaccc gctttaattg ctgcctgtgt agcatttcct gtctcaatgt agaagtcgca    23400
aaatcgtttc tgtttctcgg tcatcctcat aatattcacc tcctcaaaat aaaaagacca    23460
ctcaatgagt gatctaatat gtactacagg acccactatc cttcgaggga atgtggatta    23520
cagaaacatc agcgcgctat agtttccaac ctgtatattc ggttttactg acaggcagtt    23580
atggattacc gtaaaccaaa gtcactggca aggaatcgaa cctggcatgg tcaaatcata    23640
aaacgttaag gctatccctc gacgtattga ccttatttt aagcgtctac cctttccgcc    23700
acagtgacat aaaaaaacgg aatacctact atacaataat tttataatag atatccccgt    23760
acgaaacagt attcattgct ataattcatt tatcagcgat ggaagcgctg aaataactat    23820
tagcgaggta tactttatgc acaaaacagg atcaaaacca ggcaaaggcg agtactattg    23880
cctaaattgc ggacaaaacg tcacacttga ccaatctact gacaaattac caccatgtcc    23940
```

```
acgatgtacc aacacaacct ttagaaaagg atagccagtg aagaggtcga tgttcgacct   24000
cttttaaatt gcaatttctc ttttgaaaaa acaataaggt tttccgaaaa gattaatttg   24060
aaaccatgcc actgcttttc gctcattgtt ttcgtttctg tactttgtaa taaaatgatg   24120
cataattgaa tcctcccact tatttatttt ttagtaattt gctactgatt tcccacgata   24180
tgtgtttccg tcactatctt gaggagcagt cccatctgct tctctatttt tttgtacagc   24240
tgatctatac ttttctactg agtaacactc aattactctc tctaaatgat tttgataaac   24300
ttttagagtc tctttcaaat gcttgttttc ttctagcaaa aattgatttt ctttttttaa   24360
atccatatta atctctccat ttatataata aacagacagc aaccagttga tatagataaa   24420
caatggaaag taaaggaggt tttcacttcc ttttgttatt ttttgtttta gttgctgcct   24480
atcgaagctc aataaaacga tgagggagat ttcctcccctt acattttatt ttgtcgaatt   24540
cctgtttcct aatctttcga cactatcata atatcacgtt aaatcgtata atttgtgcca   24600
aatctacgcc aaaaaggcca aaattgcgcc aaaaacgcca tttacgccaa aattatcgat   24660
aagcaactac tccgaaaaca tctgcaaatt ctagtaaagc ttctgatttc attcgattaa   24720
atgttcgagt agctacaccc aaaattatctg caatttcatc atttgtcata gaatctcgta   24780
cacaatacgt atagtacaga gtttgtctac taattaaacc tagtctgctt agagcatatt   24840
caattgattt caatttctct tttgattcca tattctggat aatggcatcc tctaataaat   24900
ttcctttact tggtgcctta ggcatatcat cgataaatgg agaacgaata tcaattggac   24960
ttcgatctgc ttttctttgt aagcttctat attgtcttaa aatagctctt gcatttttctt   25020 tggtttgttt tatgtcagct tctttaatca ttacaaatca ctccaagata tgttataatg   25080
aaaaagaact tgttacaat tcaccatact atgtagagac agccaattac tggctgtcta    25140
ttttttataa aaatttttt attaattata atttttata aaaaataaaa atattaacat     25200
ctgttatcat ataaatgaac attgttttt atcttatatc atttaggagg aaactatgcc   25260
atttatcgtt tatttttta tgacatttgt tattatttat attcctgtac caacaattat   25320
tttttatttt tttagattta cagagcagct tactggaatt gtaattatat ataaattgct   25380
tcttttaatt ttattaatac ttgatatcaa gttaggatat aacttattct ataatcaaaa   25440
aattaaaaaa cgaagttacc ttcttttct ctttctcaat acaatagaag aactaatgca   25500
catttacttc ttctttacgt atcataatgt ttttctcttt atttttatgca ttgcccaagt   25560 actcttattg aactgtgctt ttttatttcc tttatctaaa agttttcgca aattttttatt   25620 ttaataaaaa atataatgaa tttagacagc tgaaaaatga ctgtctattt tttatgttct   25680
aaatatcaac tccataagtg gtcatccgtt taaactaatc tgtgtaattg tcctttactt   25740
ctaaaacatc atataagtct ctacctctta ctaactgttc attattttca ttaatgataa    25800
tcggtattaa ttccatttg ttgctctcct ttcttcaaat gctttgcatt agccgttcca   25860
ttctgaacag ccttttgttc caaacggcgt ttttcttct tgattttttga ttttgtttta   25920 cccatttta tctcctaata actttgtagc catacaaata atttcgttaa taaatagcgt   25980
aataacacct atacattgca atctaaccct accgtttctg tctaacattg tgactttcgg   26040
accgaacaac gtaataatga acaatacccca ttctagtttc gtcatttctt attccctct   26100 tgaataatta ctaacataac aataaaaagt acaataaata taaaggata aatcattccg   26160 cttcccctc agcacaaaac gcatttctta taaatattac attcagttct tgttttttta   26220
tttttgctac tctatgtttt ctgttattca ttatgattcc tccttatcca ccccatcttg   26280
```

```
cgcaaagaat tattcactac aaaacacatc agcaaagtat tcgccattct tgtaaatatt    26340
aagaaaatat ttgtgactcg gttctctata ctcattgata ttagctattt ctgctacaaa    26400
cacatcatca gtcttgctag ctagattgaa tctatctttt acttccattc ttctatcacc    26460
tcttccactg ttccaccgat ttgtatagca tccatttcgg cttcttcttt agaatcgtat    26520
tttattcgtt gagcaagcgc accaggagca tcgtcaataa tataagtcac tttagtttca    26580
tcgaaaccag aaaatatcc tttgccaatt tttacgcaat acaaagcata ctccgaaaat    26640
tttaagcatt ctgccgctgc tttactaaaa tttattccat actttgaaat agtaacttct    26700
ggctctcttg cctgagaatt caatgcaatc aatttaaagt cttctgttag tttcataaaa    26760
ttaactcctt gctactttt catccaagcc tgattaggtt tagcttgttt cgttttttc    26820 tgtacaaatt tcttagaatg gttgttagca tttggattct tagaataatc tttcacttct    26880
accacttcac cattactcac ataagcggct agttcagcca tttcttttgt gttatatcgc    26940
tttgcctttt tcaaatcagg gactccatat ccttctgagt cgacataaca catcgctttt    27000
acaacgtatg tcacgctcaa acctccaata cctaatttct aaatgctcta cgtattgtgt    27060
acgcttcgtt aattattttc ttcaatgtat ccgacggata gattcgatgg cttgctttct    27120
tggtatcttg ttcatataac caagcaagct gtgctagagt atcatcgtca agagaaaatc    27180
tcggtctttt cttaggtgtc ccacctgttt gttttggctg tcccacctac acagtcgctc    27240
cttctatttc ttttgaataa agtgatacct ctactcttgg ttgtttcgca tctactacga    27300
aatgatgtgt gatttccacg atttcattcc agccatcgtt tggtaacgct cctgcattga    27360
ctaaaccatc aagaataaac ttaacggcaa acgcaatgtt atcaggatct ttccgtctat    27420
ttttcatgta ccaagtaatc gacaagcaca caggtagctc gaaagataag ccttgttgaa    27480
tagcctctaa cacggctcgt ttacaccgat tggtgttttt ctgttttact tgatttccct    27540
tcatcggatg cgttcgttga atattgataa attcgtttaa actcatcaat tctccaggaa    27600
tataaaacgt gttcatgcga ttgctccttt tactggtttt aatcgtttat cggttgtttg    27660
agaaaagacc atcgtaaatc catcagaatt gacaaacatt cttgatgtcg tcctcgtacc    27720
gtaggcttct ttcagttctt taccaagcaa gttcgttgtg ataatcgttg gtaagttctg    27780
tcgtgcatcc aagaacgaat tcaatgtgtt tacgccaaac gttcgactat ctgatgcatc    27840 tttttcctagc tccgaaccaa catcatcaat gacaactaaa tccgctgttt tgatatctgc    27900
aatcaacgac ccctcgatcg ttttttctgag ttcaggattg ttgtacgaaa acttgatttg    27960
atccagcatt tcctgtaatc cgataaacaa gattttcttg tcgtagtttg agcgcttcaa    28020
aacttcccaa gccgctgcca tcgctaggtg acttttacct gctccctgtt tgccacttaa    28080
aacaaggtga cttggatttc ctagcaagac tgaattaaca aagcgtttgg ttacttcaac    28140
tgcttgtctt gtttcttgat cgacaatttg ataattctgt aatgtacaat caaacaacgc    28200
tttgtttggc acgacagaac cacctttgaa aaaattgatg gctcttgctt tcagactttc    28260
gttgtacatt cgctctgtct gtaaatcttc ctgaactcgc aatgctttat aaccacactg    28320
catacaggtt ggtttacagc gctctgagcc atcggggttc ttcgtacgcc atccatacaa    28380
aggctgtcca cattcaggac attcaccacg ttggacaagc accttctgta tcagcttttc    28440
catgatttct ccaacggttt ccatgtccac gcctcctctc aaataggcaa ctcatctgtg    28500
ctaaatttct cgtattcaag cgttttggtt tgttttgttt tataatcacg attcgcttgc    28560
gctgccattg tgtcatattt ttctcgcaat ttttagcag ataaaatatt cgatgcccaa    28620
aacacattgt gctgactcca ttcaatcatt ccccgtacct ggttttcggt ccgcttgtcg    28680
```

```
atctcgatca ttttccgaat gtcatctgcc caactttgca gattcggctt tttgatttcc    28740
tgattctgac aaatctgttt gaataactcc tccgcgagaa tgtaataaac tgagtcggtg    28800
tcgtaaacac gcttttttgcg tggttgcgac gatgatgttt tattattctt ttcattctta    28860
taattctttt cattcttgtt tgtgtgcact tgttgttcac ttgttgtgcg tttgatgttc    28920
atttgatgtt cattgctttg gtacaaagac cagttttgta ttgatataac gctgtatttc    28980
gtagttgatt tgatgttcaa cattccgttt ttttcaaatt gctttagcca tctccataca    29040
gaaccgctgt tcacttgatg ttcacgtttc acgccttcgt tcatctcaga tgtgatagca    29100
tcgcgccctg tgacgaattc cccgctgttc acttgtatct cttttccatt aaaaagtatc    29160
ttgcgattct catgactcgc tttcatcaaa cacaagctcc ataatttata catataagga    29220
ttggtccaaa cgaatgaatt catcacttt cgatgtaatt tgacatatcc tgtgttcatt    29280
cgtatttctc ctctagacaa gcgaggggaa actccctcgc tatagtggtg gattcagtga    29340
atcaaataat gtcgtttgtt gattaaaagg gaaggtcatc atctgaaata tcaattgcag    29400
aactacctgc aaatggatcg tttgaatgtt gctgtgcaaa tgtgttttta tttgcttcat    29460
tactgatagg acgttccacg ccgttaggct tacttccttc ttcatcaagt ttgttataag    29520
ctttcacaga taaattccat ctgtcgttat aatcactatg tttccaatca acagtaatat    29580
ttaatgtttt accttttgcg gcagtgacta attgttgaat actatcaatt gctgttccgt    29640
ccggtactcc aattgctgtt aaaatcgtat taaatcgttt agtagaaaat tcaatatcgt    29700
tgttatccca cacaatattg tcgtaaagaa ttttccacc tttatatttg ccgtcgatca    29760
cttcataatt gaagacagcc atatcattat ttgtttcttt tgttttttg cactcagaat    29820 caggaagaat ttttacattg taacttcctg cttcttttac tgatttgcct aaaacatttt    29880
gtgaatctac tacaaatagt gccatattaa attccttctt cctgatgatt atttattagt    29940
tcctttgctt cgataagctt gcgatcatcg attctatttt ttgcatgatt cccgtttct    30000 ggatttaaat caatcaaacg tttatcatca tcaatataga tacgaccgac taaatcaaac    30060
attgatgtaa aagcattaaa ggtcttttcg ttcatatctg gactaaaacg tcctttgcca    30120
tctaatccgc tagcaccatt gtcaacttgg tgtgcagttg cataaatagt tttgttgctc    30180
tctcttaatt ttgttcctaa ttgtctgaac catagttgca atttctgata attttgacgt    30240
ccgtctcgtg aagctccgtc aatattttct agtactaaat tttgtaaggc agtcatgttg    30300
tctaagataa tgacttcgta ttctggtttg ctcaatgctc ctagtaccca cttatctatt    30360
aatgattgga tattaggcgc atctccactt tctaactgaa caacagagat atcttttttcc    30420 ccaattaata cgttcgttga taaatcaaaa ctaaaaagta ttttatttcc ttcaaactgt    30480
ttagctagtg aagttttttcc tgtacctcca tcaccgtaaa taaatacat attcgcttgt    30540 tttggtactg ttccatttgg atagaatttc atacctgctt caccttcact tttacttctg    30600
gctctttgat accaactgtt agattcggaa tataacaacc attctcatct attactcgaa    30660
gatcatccgt tagttgaaac acaccgtcag caatcaactt cttgatgtct agttgctttg    30720
gtttgtattc agttgattct ttgaccaatt caggatgttc gtttcgaagg tattgaataa    30780
attgttcttt ctcttctttt actttggatg gttgtaattt aaaatgcgat ggcttacgca    30840
aatctacagg cttcatcgtc aaaacaaagc ttttggtttc gactaattct gcattgccca    30900
tcaactgtct ttgataaact actgcttcat caatttcttt ttgtaaatct gcacatacac    30960
gattctttct ttccgttatc tgtgcaattt caatatcgta ttgattaagc cgatgtttct    31020
```

```
ttgcttgttc taattcctcg attttttcg tgatccattc caaatcatat ccttcaaaat    31080
gactcatctt cgtcctcctc atcgattggt gcttcatatg gtggtttagc ataatcagga   31140
tcagttaaat agttgtcaag atttgctaac tcgttcatat ttcccctctt ttcctcttgc   31200
tagcacgcaa agcacaagca tggcaattgc gaataacaag ccaaagatta cgtacctttt   31260
cgctacaatc actaacgtga aaataaaat aatgaataga tcaattgttt tttcgttcat    31320
gtgtgataac atcctttact gtaattcttc ttctgaaaaa gaacttttgt tgctcaaata   31380
cgttgatggc gtactcgtag ttgtcttctg ttaagtcgtt gatacgctca atttctaaac   31440
aagcttttac agcttcataa atagcattct tttgatttag aataattctt cgattgtctc   31500
gttgattttc aagccatgcc tcgactacct taccgaattt atatccgtaa ttgattctcg   31560
gtttatttcg ttcagctaat tgcttttcaa cctcttcggc aatacgttta ctcaattctt   31620
ctgtcgtcat tgtcaccatt tctgccattg ttgttcctcc gttatcatgg tatactttag   31680
ctaaaatgat ttttaaaaag tgcatcaaca cttgtgccga gtatttcggc tagtttgaat   31740
gcggtactca agcttggtag gcgtgtaccg tattcaaatc tttggtatga agttagcgtt   31800
attcctaatt tttttgctac ttcatgttgc tttagacctg cattttcgcg ggctttttt    31860
agttttcgt tattcaaatc acatcccact ttctttattg attacatcca attaggttgt   31920
aacctaattt tattatacat ccacattggt tgtagtcaag tatttttatt ttggaggttt   31980
tctcatggaa acaaacattc ctgacagatt aaaacaactt agggaaacag ccaatttgac   32040
tcaatcagat atggcagaaa tacttgatgt aaaactgcaa agttatcaac gtttcgaata   32100
cggtagtaga cgccccagtc tcgatgtatt aatcgccctc gccgactact tcgatgtatc   32160
gcttgattat ttagtcggta gaacagacga gaaatgatcg cttaggcggt cttttttgt    32220
ttccgcagtc tttgatataa tcttcttatc aggatgacga actgaaatat ctgataagga   32280
ggtaaagcta tggactatga taattttttat caagttgaaa gttttctagt tactcgcaaa   32340
gaagaaaaat atgtcaacga actattaaaa tttggatgga aattgatttc tgtgattcag   32400
tacaaagatg actatgacgc atatggtaaa tatgtgttag gtgctgacaa aaatactttt   32460
gaaaaacgta attttcaaat gattcttaat gaagaaaacg aacaagatcc attgccattt   32520
tagtttcttg cttcaggatg tttcatctca aaattcttta attgctcctt gctatttctg   32580
atagcttgga gctcttttttt tatttcttct tgcgattcaa taattttttg ctgttgctta   32640
agaagctcat tgagtgctac catttgtaat tcttccattt gactacctcc gtttctaagt   32700
gataaactta acttactagt tatgattttt taccaattag cgaccctcat cgctagttgg   32760
tctttttta cttctcgcca cttcttctgg cgttcacgcc attgttcccc taacaatcta   32820
ggtttcattt cttcgtggta ttcctgattt agttttcgca tcaagtgttg atgctcttgt   32880
aaggtcattt gatccctcct tcgtttctca ccgtcaccac ctccggaaag aggagttgcc   32940
catgccaacg tgtatatgcg aacttgattt ttaaggagaa aactcgcaac tcctcttttc   33000
ggaagtggtg cgtgtgtgat ataatattat tgttctatgg tgcccactac ttgcttgccg   33060
gctgtgtggg cttttcttt tgttcaatta tggttgccac cacagtaact ccccaatgtc    33120
tagaacgtat tctagccatt tcatctgcta atctttgaag attaggtgtg ccattcaaag   33180
tgatttttgg cttgttactc acaatctcac atcctacact gttgattttc gttcatttct   33240
tttgctaaaa tttcattatc agtgagtggt ccactgaaat aactgataag gcggtgataa   33300
atatgggat gactgataaa gagatcgctt tggagattac gaagtcttat ttaaatcatt    33360
tatctgatag ggctagaagc aacaatatta acgaatctca tgctacagcc caaaatgttt   33420
```

```
gcaacatgta caaagtattt tatgatgtgg tgtcttctgt aggaaagtct tctagtggta   33480
aagaatagtt atttttttca atacaaaagt taacatcata cttttcattt agaacttcta   33540
ggtcggctag gagttctttg gcgttttcaa tactttctac ttgtgctgat acttcaatta   33600
tttgtttctt catccttctc acctcacgct ggttgattaa cgttcgcata ctttcggtca   33660
atccctaaaa agtctgcgat tttcaacttg taaaagtccg ctttattgtc ttgttatcca   33720
cctcttgata aaattagttt gaaagcgagg tgaataataa atggataata tccctaaaaa   33780
cttaagtaaa gaagaacttg agcttgtaac tgatatgctt tatactttac gagattttct   33840
aaaaaagaaa tctattagaa gtaattctaa aacaggtcaa atgatgaatg aattagagat   33900
agaacttcag aacatagctc ttaaacattt attcaatcag cgcagataac tcgttggcag   33960
ctttaactct ttcatccaag ccttcatgtc gatttcctcg taatatactt gataattctt   34020
tttctctgcc tttggtaaat gaatcttgaa gtcttttttt aaagacttct ttattttcga   34080 tttttttgaga agttaaatta tcttgaaaac ttctatcaac aatttctttg attttttgcc   34140
actcataaaa tttcaattct gacaagacat taaacaactc gttttttttgt ttttccactt   34200 gcttcacctc ctacattgat tgctcactca cctcttggta gaattattaa tatagaaagg   34260
cggtgatttt tttatggcta ttgctaatac agatactttt gctcttgctg tcgttcaatc   34320
atctgatcca aaattaacag ttgaagaaaa aatctctctt tacattgaag caagagacaa   34380
agcaaaagaa tacaataaaa aacatcctaa taaggagtc aaccttaaaa aaatttaacc   34440
gtaccaatgt gttaaaacct gtaaaagctc tgcaatggaa gccgccattt cagggctttt   34500
atcatctaaa tcaatcaatt cagaggtata agctattgct ttttcatata attcgtccat   34560
ctccctacac ctcctacgct ggttgttggt taccttcaag tcgcacaaac gcgactttt   34620 gctaaaaaaa atttcaactg cttcagaatc tgttaatgga acttcttctt taattttttt   34680
agcttcagct atagtaaaat ctccaccgtt tttcatttt ctatagaatg tacttctgtt   34740
aattccgatt gaatcggcaa ctgcttgttg agtagttcca cgctcaacta ttaatccttt   34800
taatttagct acatcaatca taaataacac ctctctttt gtcgcattta tgcgacttga   34860 tatttttaaat atacatcaat atctcaaaac agtcaacaca aaagttgcat ttttgcgatt   34920
gtttttgttg caaatttgca acataattta tataatagtg attggaggtg atggaatgac   34980
tgtaggagaa aaaatgaagt ttagaagaaa agaactaaaa ataagtgcgg atgaaatagc   35040
aaaagcctta ggtgtttcca gatcaaccat atttagatat gaaaaagggg aaatagaaaa   35100
actaccaaca gaaaatttac gaaaaatagc cgaagttttg aaaacaactc ctgaagaatt   35160
aatgggatgg actgaaactg aaaataattt ttctatagtg tctatttaca accaacttgt   35220
ttcacctcga caacaaaaag tatatgactt tgctaaacat gagttagaag aacagcaaga   35280
gtcagaacga agaaataaaa ttcagtctct tcaaaaatat agagaaatga aagagcaaaa   35340
agaagaattt gccgatatag aatggtacgg atgtgcttca gcaggtactg gagaattcat   35400
gtttgataat aaagaagtga tttcacttcc taaaaaacaa attcctttag aagctgattt   35460
ttgcttaact gtcaatggtg actctatgga accattaatt caccatcatg attatatttt   35520
cgtttctaaa caagatactt tatttaacgg aaacattggc gttgttatcg tagacggaga   35580
agcattcatt aaaaaagttt tttttgaaaa tgataaagct cgtttacaat catttaataa   35640
aaaatataaa gacattattg ttgatgattc taacgatttt aggattattg gcaaagtggt   35700
tttataaaaa aagaaccacc taccaatttg gctaggtggt tttatataa atattttaa   35760
```

-continued

```
agtaaggagt tttagtttta tgaaaaaaat tattattagt atatcaatta tcgcaattat   35820
tatttttgga ggaattttct actacacaca agtgaaacgt ccacatgacg aagccgtgga   35880
gaaatatgaa caagttattt cagaacgaaa aaacaaaat aacaatttac aagatttaat    35940
taaccaatct gaaatatta ttaaaggaaa aaacaaaccg tataagcaag aaactttcga    36000
ttctttaaaa aagaaatag atattgctaa aaagaatta attaatatac ctaacatacc     36060
ttcaaaaact aaagatattt tagaagatgt tgaaaaattc acacatccat tcaactattc   36120
agatattgaa agtaagttaa agaaaaaat ggaagctgca caaaatagca taaaacaatt    36180
aaaacaagta acagctcctt cacaagattt cattttaaat agaattaaag aagttaagaa   36240
tatcgatgct gtcgaacctg caacagaagc aaacgatccg aacgaactcc tcaataaagc   36300
aggaggatat actgcagcta ttttctttag ttctcccttta gtaaatcaat ctgaagtcta  36360
cggtgaatca attattgata aaggtacaga cggaggagga tgcatagaag tatatgctaa   36420
tacagaagat gcagaaaaaa gagataaata tttagcagca tttgatggag gatctctcag   36480
cccaggttct cataaagttt taggtacttt agttattcgt acatcagcaa agttgacagc   36540
tactcaacaa aatgaattaa ctaatgacat tatcaatagt ttaattaagt tataaaagtt   36600
tagccttcgg gcttttcttt tacaatcaat aagaacgtac attcgaaagg ataacatg    36660 aaacgagtag cattatatat gagagtatca actgaacaac aagccaaaca tggagatagt   36720
cttagagaac aaaaagaaac cctctatgaa tatatcgaac aacacaagga tttgaaagta   36780
gttaatgaat atgtagacgg tggtatttct ggtcaaaaaa taaatcgtga tgaatttcaa   36840
aaactattac aagatgtaaa agaaaataaa atagatctaa ttttatttac aaaattagat   36900
agatggttta gaaatctacg acattattta aacactcaag aaattttaga aaaacacaac   36960
gtttcttgga atgctgtttc gcaacaatat tatgatacaa ctacagcgta tggcagaact   37020
ttcattgcac aagtaatgag ttttgctgaa ttggaagccc aaattgattc ggaacgcatc   37080
aaagctgtta tggcaaataa aattgcacaa ggtgaagtag taagcgggaa aactccgtta   37140
ggctactcta tagaaaataa gaaattagta ataaatgatg atgctcctat cgtgatagat   37200
atattcaact actttcttc tagtggtagt ttaagaaaaa ctgtttatta tttaggctct    37260
cagtatggaa tcgttagaga ttatcaaagt gttaaaaata tgttgacgaa caaaaaatac   37320
attggtgaat taagaaataa taaaaattac tgtcctccta ttattgataa aaaacttttt   37380
tatgctgttc aaaaagcatt acctaaaaat ttaaaaacaa atgcaaaacg cgattacatt   37440
tttaaaggtt tattaaaatg ttctgactgt cagggatcag tagctggtca aactattaaa   37500
gcaagatata agaaaaaaga cggtacagaa tcaatatacg aaagaacttg ttatagatgt   37560
gtaaaacgaa gaaataataa attacgttgt acaaataagc gcgcttttta cgaaaaaaat   37620
ttagaacgtt atattttga agctactaaa caaaaatttg aacaaataca aataaactat   37680
tcaaaaaaac aaccaagat tattaaaaag aaaaatagta agaaaatat tgagaataaa    37740 ttagatagat tgaagaaagc ctacttgaat gaagttatag acttagagga atacaaaaaa   37800
gatcgagaag ctttaatgaa agaattaaat gaaattgaag tagagccagc taaaatagat   37860
ataaaaaatg tcgaatttat tctatcaaaa gaattcgatg aaatttataa agaatcttct   37920
aaagaagaaa aaaatgcatt atggcgttca attatcgata acataatagt atttccagat   37980
ggcaatataa cagtaaattt ccttttataa tttatgtgta ctaacttata tattccagat   38040
ggatgattat gaactaaaat aattctcgct gcagaatatc gaacagcata atggaacact   38100
tctcttggat gtgcgatcgt ttgatccagg gaaccaataa atagcgtttt tttcaacaat   38160
```

```
acttgattct tagtatccaa ataaatacaa atcaaatgtt cttgtttgtg atcctttaat    38220
tctatgatta attgatgcgc taattcatag ctggcatgga tcgtgggttg taccgctaca    38280
tgctgtgttt ggattctttt tcctagctcg atcagtgctt tgatttcaag agccttaacc    38340
tgaccaattc ctcgtatttt ttccagctca gacagcgttg cctgtcttaa cagtgcaagt    38400
ccaccaaatg ttttcaacaa attacctgct agttccaaga cattataggg atgctgtccc    38460
gtgcgtaata aaatagcaag taattcttga tcagagagtg ctttctctcc gtaaagcaac    38520
attcgctccc ttggaagtga ggttgctggc acagcatcca gcaattttt tccataaaa     38580
tcccccttt cttcttctca ctaataagat acgaaaaaag gggggagcta tttttatttt    38640
tttagatatc ctggtacttc gtgtagagaa gataaaactg ctaacgtttt tgttgcaag    38700
tcttctgaag gagccaacaa atctgggatc atgatcactg gatctccgc acttgctgct    38760
gcaagtatcc cgtttttaga atcttccaga accaatgttt cttgttttt cgttcctaga    38820
tattcatggg caagcaaaaa gatttctgga tcaggtttag cacgtttgac attttctgct    38880
gaaacaatcg tttcaaaata gtttgtcagt tggttctttt ccaataatag ctcaataata    38940
tgacgttggt tactagaagc gacaacttta ggtattcgt gttcttctaa aaagtccagt    39000
aattcgatta ctcctggttt taattgcact gcacctaagg aaaaccgtct gatcgtttct    39060
tcataagcat cattaatgaa ttttgaaca ttgttttcc caaaacttgc aaagatctga    39120
tgataatttg cccaaacctc ttcatctgat acacctagat attttaaata caattctttg    39180
tcgtaaggaa agcccatttg atcagcaacc atttgcgagg cttcatagta gacgatttct    39240
gtgtcaaaga gtaacccatc catgtcaaaa atgacagctt tataattcat                39290
```

<210> SEQ ID NO 3
<211> LENGTH: 9
<212> TYPE: PRT
<213> ORGANISM: Enterococcus hirae

<400> SEQUENCE: 3

Ser Ala Phe Pro Tyr Glu Gln Glu Leu
1               5

<210> SEQ ID NO 4
<211> LENGTH: 9
<212> TYPE: PRT
<213> ORGANISM: Enterococcus hirae

<400> SEQUENCE: 4

Tyr Asn Tyr Ser Lys Ser Tyr Pro Val
1               5

<210> SEQ ID NO 5
<211> LENGTH: 9
<212> TYPE: PRT
<213> ORGANISM: Enterococcus hirae

<400> SEQUENCE: 5

Val Ser Phe Ser His Tyr Arg Pro Gly
1               5

<210> SEQ ID NO 6
<211> LENGTH: 9
<212> TYPE: PRT
<213> ORGANISM: Enterococcus hirae

<400> SEQUENCE: 6

Val Thr Phe Leu Gly Tyr Asn Ala Phe
1               5

<210> SEQ ID NO 7
<211> LENGTH: 9
<212> TYPE: PRT
<213> ORGANISM: Enterococcus hirae

<400> SEQUENCE: 7

Thr Val Tyr Thr Phe His Val Asn Ile
1               5

<210> SEQ ID NO 8
<211> LENGTH: 9
<212> TYPE: PRT
<213> ORGANISM: Enterococcus hirae

<400> SEQUENCE: 8

Thr Ser Tyr Ser Pro Leu Phe Leu Leu
1               5

<210> SEQ ID NO 9
<211> LENGTH: 9
<212> TYPE: PRT
<213> ORGANISM: Enterococcus hirae

<400> SEQUENCE: 9

Thr Asn Tyr Ile Tyr Pro Asn Ile Leu
1               5

<210> SEQ ID NO 10
<211> LENGTH: 9
<212> TYPE: PRT
<213> ORGANISM: Enterococcus hirae

<400> SEQUENCE: 10

Val Val Pro Ile Leu Phe Leu Gly Leu
1               5

<210> SEQ ID NO 11
<211> LENGTH: 9
<212> TYPE: PRT
<213> ORGANISM: Enterococcus hirae

<400> SEQUENCE: 11

Lys Asn Tyr Lys Ala Tyr Val Glu Leu
1               5

<210> SEQ ID NO 12
<211> LENGTH: 9
<212> TYPE: PRT
<213> ORGANISM: Enterococcus hirae

<400> SEQUENCE: 12

Ser Ala Met Lys Tyr Gly Ile Pro Leu
1               5

<210> SEQ ID NO 13
<211> LENGTH: 9
<212> TYPE: PRT
<213> ORGANISM: Enterococcus hirae

<400> SEQUENCE: 13

Thr Ser Leu Ala Arg Phe Ala Asn Ile

```
<210> SEQ ID NO 14
<211> LENGTH: 9
<212> TYPE: PRT
<213> ORGANISM: Enterococcus hirae

<400> SEQUENCE: 14

Ala Met Ile Glu Phe Ile Gln Gly Leu
1               5

<210> SEQ ID NO 15
<211> LENGTH: 9
<212> TYPE: PRT
<213> ORGANISM: Enterococcus hirae

<400> SEQUENCE: 15

Val Ala Ile Thr Phe Gly Gly Pro Leu
1               5

<210> SEQ ID NO 16
<211> LENGTH: 9
<212> TYPE: PRT
<213> ORGANISM: Enterococcus hirae

<400> SEQUENCE: 16

Val Ser Thr Asn His Tyr Gly Leu Leu
1               5

<210> SEQ ID NO 17
<211> LENGTH: 9
<212> TYPE: PRT
<213> ORGANISM: Enterococcus hirae

<400> SEQUENCE: 17

Val Met Phe Gly Leu Phe Ile Thr Ile
1               5

<210> SEQ ID NO 18
<211> LENGTH: 9
<212> TYPE: PRT
<213> ORGANISM: Enterococcus hirae

<400> SEQUENCE: 18

Thr Val Phe Ser Leu Val Ser Leu Leu
1               5

<210> SEQ ID NO 19
<211> LENGTH: 9
<212> TYPE: PRT
<213> ORGANISM: Enterococcus hirae

<400> SEQUENCE: 19

Ser Ile Tyr Asn Leu Glu Lys Pro Leu
1               5

<210> SEQ ID NO 20
<211> LENGTH: 9
<212> TYPE: PRT
<213> ORGANISM: Enterococcus hirae

<400> SEQUENCE: 20

Tyr Thr Ile Ile Arg Tyr Gly Asn Leu
1               5
```

```
<210> SEQ ID NO 21
<211> LENGTH: 9
<212> TYPE: PRT
<213> ORGANISM: Enterococcus hirae

<400> SEQUENCE: 21

Ser Asn Gly Leu Leu Tyr Thr Pro Met
1               5

<210> SEQ ID NO 22
<211> LENGTH: 9
<212> TYPE: PRT
<213> ORGANISM: Enterococcus hirae

<400> SEQUENCE: 22

Asn Asn Tyr His Tyr Val Gly Gly Leu
1               5

<210> SEQ ID NO 23
<211> LENGTH: 9
<212> TYPE: PRT
<213> ORGANISM: Enterococcus hirae

<400> SEQUENCE: 23

Ser Met Phe Leu Asn Cys Asn Asn Leu
1               5

<210> SEQ ID NO 24
<211> LENGTH: 9
<212> TYPE: PRT
<213> ORGANISM: Enterococcus hirae

<400> SEQUENCE: 24

Ile Ala Phe Gln Gly Tyr Ser Ser Leu
1               5

<210> SEQ ID NO 25
<211> LENGTH: 9
<212> TYPE: PRT
<213> ORGANISM: Enterococcus hirae

<400> SEQUENCE: 25

Gln Val Thr Asn Phe Phe Asn Met Phe
1               5

<210> SEQ ID NO 26
<211> LENGTH: 9
<212> TYPE: PRT
<213> ORGANISM: Enterococcus hirae

<400> SEQUENCE: 26

Ile Met Leu Gly Leu Phe Met Thr Met
1               5

<210> SEQ ID NO 27
<211> LENGTH: 9
<212> TYPE: PRT
<213> ORGANISM: Enterococcus hirae

<400> SEQUENCE: 27

Ile Asn Ala Lys Phe Ser Ser Gln Leu
1               5

<210> SEQ ID NO 28
```

```
<211> LENGTH: 9
<212> TYPE: PRT
<213> ORGANISM: Enterococcus hirae

<400> SEQUENCE: 28

Tyr Ile Tyr Asn His Tyr Lys Asp Met
1               5

<210> SEQ ID NO 29
<211> LENGTH: 9
<212> TYPE: PRT
<213> ORGANISM: Enterococcus hirae

<400> SEQUENCE: 29

Tyr Val Tyr Gly Lys Ser Arg Thr Met
1               5

<210> SEQ ID NO 30
<211> LENGTH: 9
<212> TYPE: PRT
<213> ORGANISM: Enterococcus hirae

<400> SEQUENCE: 30

Ile Ala Phe Leu Ser Tyr Lys Leu Phe
1               5

<210> SEQ ID NO 31
<211> LENGTH: 9
<212> TYPE: PRT
<213> ORGANISM: Enterococcus hirae

<400> SEQUENCE: 31

Ile Met Tyr Glu Tyr Met Tyr Pro Val
1               5

<210> SEQ ID NO 32
<211> LENGTH: 9
<212> TYPE: PRT
<213> ORGANISM: Enterococcus hirae

<400> SEQUENCE: 32

Ser Ser Met Glu Tyr Phe Leu Lys Val
1               5

<210> SEQ ID NO 33
<211> LENGTH: 9
<212> TYPE: PRT
<213> ORGANISM: Enterococcus hirae

<400> SEQUENCE: 33

Ile Ser Phe Phe Gln Glu Asn Gln Leu
1               5

<210> SEQ ID NO 34
<211> LENGTH: 9
<212> TYPE: PRT
<213> ORGANISM: Enterococcus hirae

<400> SEQUENCE: 34

Thr Asn Leu Leu Phe Met Thr Ser Leu
1               5

<210> SEQ ID NO 35
<211> LENGTH: 9
<212> TYPE: PRT
```

<213> ORGANISM: Enterococcus hirae

<400> SEQUENCE: 35

Lys Ile Phe Ser Ile Phe Met Leu Leu
1               5

<210> SEQ ID NO 36
<211> LENGTH: 9
<212> TYPE: PRT
<213> ORGANISM: Enterococcus hirae

<400> SEQUENCE: 36

Leu Asn Ile Phe Lys Phe Asn Arg Phe
1               5

<210> SEQ ID NO 37
<211> LENGTH: 9
<212> TYPE: PRT
<213> ORGANISM: Enterococcus hirae

<400> SEQUENCE: 37

Met Thr Tyr Asp Tyr Arg Gly Gly Phe
1               5

<210> SEQ ID NO 38
<211> LENGTH: 9
<212> TYPE: PRT
<213> ORGANISM: Enterococcus hirae

<400> SEQUENCE: 38

Pro Ser Tyr Met Phe Arg Thr Ser Phe
1               5

<210> SEQ ID NO 39
<211> LENGTH: 9
<212> TYPE: PRT
<213> ORGANISM: Enterococcus hirae

<400> SEQUENCE: 39

Gln Ser Tyr Thr Tyr Tyr Met Thr Ala
1               5

<210> SEQ ID NO 40
<211> LENGTH: 9
<212> TYPE: PRT
<213> ORGANISM: Enterococcus hirae

<400> SEQUENCE: 40

Ile Thr Phe Ser His Tyr Glu Pro Thr
1               5

<210> SEQ ID NO 41
<211> LENGTH: 9
<212> TYPE: PRT
<213> ORGANISM: Enterococcus hirae

<400> SEQUENCE: 41

Met Ser Phe Thr Phe Phe Ser Ser Thr
1               5

<210> SEQ ID NO 42
<211> LENGTH: 9
<212> TYPE: PRT
<213> ORGANISM: Enterococcus hirae

```
<400> SEQUENCE: 42

Ile Ala Phe Gln Asn Phe Val Asn Leu
1               5

<210> SEQ ID NO 43
<211> LENGTH: 9
<212> TYPE: PRT
<213> ORGANISM: Enterococcus hirae

<400> SEQUENCE: 43

Ser Met Phe Ile Ala Phe Gln Asn Phe
1               5

<210> SEQ ID NO 44
<211> LENGTH: 9
<212> TYPE: PRT
<213> ORGANISM: Enterococcus hirae

<400> SEQUENCE: 44

Leu Asn Tyr Asp Tyr Gly Asn Arg Ile
1               5

<210> SEQ ID NO 45
<211> LENGTH: 9
<212> TYPE: PRT
<213> ORGANISM: Enterococcus hirae

<400> SEQUENCE: 45

Ala Gly Ile Cys Phe Phe Thr Gly Val
1               5

<210> SEQ ID NO 46
<211> LENGTH: 9
<212> TYPE: PRT
<213> ORGANISM: Enterococcus hirae

<400> SEQUENCE: 46

Val Glu Tyr Thr Tyr Phe Pro Thr Leu
1               5

<210> SEQ ID NO 47
<211> LENGTH: 9
<212> TYPE: PRT
<213> ORGANISM: Enterococcus hirae

<400> SEQUENCE: 47

Ala Ala Tyr Val Phe Glu Met Asn Phe
1               5

<210> SEQ ID NO 48
<211> LENGTH: 9
<212> TYPE: PRT
<213> ORGANISM: Enterococcus hirae

<400> SEQUENCE: 48

Glu Met Tyr Arg Lys Leu Ser Thr Leu
1               5

<210> SEQ ID NO 49
<211> LENGTH: 9
<212> TYPE: PRT
<213> ORGANISM: Enterococcus hirae

<400> SEQUENCE: 49
```

```
Tyr Asn Tyr Gly Tyr Lys Ser Val Leu
1               5

<210> SEQ ID NO 50
<211> LENGTH: 9
<212> TYPE: PRT
<213> ORGANISM: Enterococcus hirae

<400> SEQUENCE: 50

Val Ile His Glu Leu Tyr Asn Ser Leu
1               5

<210> SEQ ID NO 51
<211> LENGTH: 9
<212> TYPE: PRT
<213> ORGANISM: Enterococcus hirae

<400> SEQUENCE: 51

Thr Asn Tyr Val Lys Leu Arg Pro Leu
1               5

<210> SEQ ID NO 52
<211> LENGTH: 9
<212> TYPE: PRT
<213> ORGANISM: Enterococcus hirae

<400> SEQUENCE: 52

Gln Ala Val Asn His Phe Thr Gly Ile
1               5

<210> SEQ ID NO 53
<211> LENGTH: 9
<212> TYPE: PRT
<213> ORGANISM: Enterococcus hirae

<400> SEQUENCE: 53

Tyr Thr Asp Tyr Ser Asn Gln Leu Lys
1               5

<210> SEQ ID NO 54
<211> LENGTH: 9
<212> TYPE: PRT
<213> ORGANISM: Enterococcus hirae

<400> SEQUENCE: 54

Ala Met Ile Glu Phe Ile Gln Gly Leu
1               5

<210> SEQ ID NO 55
<211> LENGTH: 9
<212> TYPE: PRT
<213> ORGANISM: Enterococcus hirae

<400> SEQUENCE: 55

Lys Met Val Glu Ile Leu Glu Glu Ile
1               5

<210> SEQ ID NO 56
<211> LENGTH: 9
<212> TYPE: PRT
<213> ORGANISM: Enterococcus hirae

<400> SEQUENCE: 56

Arg Leu Leu Lys Tyr Asp Val Gly Val
1               5
```

<210> SEQ ID NO 57
<211> LENGTH: 9
<212> TYPE: PRT
<213> ORGANISM: Enterococcus hirae

<400> SEQUENCE: 57

Thr Leu Val Gly Val Thr Phe Ala Ile
1               5

<210> SEQ ID NO 58
<211> LENGTH: 9
<212> TYPE: PRT
<213> ORGANISM: Enterococcus hirae

<400> SEQUENCE: 58

Ala Met Gln Asn Leu Val Ala Ala Val
1               5

<210> SEQ ID NO 59
<211> LENGTH: 9
<212> TYPE: PRT
<213> ORGANISM: Enterococcus hirae

<400> SEQUENCE: 59

Ala Ile Met Ala Ile Ala Asn Gly Val
1               5

<210> SEQ ID NO 60
<211> LENGTH: 9
<212> TYPE: PRT
<213> ORGANISM: Enterococcus hirae

<400> SEQUENCE: 60

Ala Met Ser Met Asn Met Glu Glu Val
1               5

<210> SEQ ID NO 61
<211> LENGTH: 9
<212> TYPE: PRT
<213> ORGANISM: Enterococcus hirae

<400> SEQUENCE: 61

Lys Val Phe Gly Lys Met Thr Ser Val
1               5

<210> SEQ ID NO 62
<211> LENGTH: 9
<212> TYPE: PRT
<213> ORGANISM: Enterococcus hirae

<400> SEQUENCE: 62

Leu Leu Gly Ile Tyr Gln Ser Tyr Val
1               5

<210> SEQ ID NO 63
<211> LENGTH: 9
<212> TYPE: PRT
<213> ORGANISM: Enterococcus hirae

<400> SEQUENCE: 63

Lys Leu Ala Lys Phe Ala Ser Val Val
1               5

```
<210> SEQ ID NO 64
<211> LENGTH: 9
<212> TYPE: PRT
<213> ORGANISM: Enterococcus hirae

<400> SEQUENCE: 64

Lys Leu Trp Ala Asn Met Ser Lys Ala
1               5

<210> SEQ ID NO 65
<211> LENGTH: 9
<212> TYPE: PRT
<213> ORGANISM: Enterococcus hirae

<400> SEQUENCE: 65

Met Leu Ser Asn Pro Ile Thr Ala Ile
1               5

<210> SEQ ID NO 66
<211> LENGTH: 9
<212> TYPE: PRT
<213> ORGANISM: Enterococcus hirae

<400> SEQUENCE: 66

Ile Leu Val Ala Ile Thr Thr Thr Ile
1               5

<210> SEQ ID NO 67
<211> LENGTH: 9
<212> TYPE: PRT
<213> ORGANISM: Enterococcus hirae

<400> SEQUENCE: 67

Lys Met Ala Ala Leu Ala Ala Ser Ala
1               5

<210> SEQ ID NO 68
<211> LENGTH: 9
<212> TYPE: PRT
<213> ORGANISM: Enterococcus hirae

<400> SEQUENCE: 68

Ala Met Leu Ser Asn Pro Ile Thr Ala
1               5

<210> SEQ ID NO 69
<211> LENGTH: 9
<212> TYPE: PRT
<213> ORGANISM: Enterococcus hirae

<400> SEQUENCE: 69

Asn Met Ala Glu Ala Phe Ala Ser Ala
1               5

<210> SEQ ID NO 70
<211> LENGTH: 9
<212> TYPE: PRT
<213> ORGANISM: Enterococcus hirae

<400> SEQUENCE: 70

Thr Met Phe Ser Asp Ser Ala Leu Lys
1               5

<210> SEQ ID NO 71
<211> LENGTH: 9
```

```
<212> TYPE: PRT
<213> ORGANISM: Enterococcus hirae

<400> SEQUENCE: 71

Leu Leu Thr Arg Phe Thr Thr Leu Lys
1               5

<210> SEQ ID NO 72
<211> LENGTH: 9
<212> TYPE: PRT
<213> ORGANISM: Enterococcus hirae

<400> SEQUENCE: 72

Lys Thr Ala Phe Ser Gly Ile Val Lys
1               5

<210> SEQ ID NO 73
<211> LENGTH: 9
<212> TYPE: PRT
<213> ORGANISM: Enterococcus hirae

<400> SEQUENCE: 73

Lys Thr Ile Ser Thr Met Phe Glu Lys
1               5

<210> SEQ ID NO 74
<211> LENGTH: 9
<212> TYPE: PRT
<213> ORGANISM: Enterococcus hirae

<400> SEQUENCE: 74

Val Phe Gly Lys Met Thr Ser Val Phe
1               5

<210> SEQ ID NO 75
<211> LENGTH: 9
<212> TYPE: PRT
<213> ORGANISM: Enterococcus hirae

<400> SEQUENCE: 75

Ala Tyr Phe Asn His Thr Leu Asp Leu
1               5

<210> SEQ ID NO 76
<211> LENGTH: 9
<212> TYPE: PRT
<213> ORGANISM: Enterococcus hirae

<400> SEQUENCE: 76

Ala Trp Lys Ser Asn Phe Met Asn Ile
1               5

<210> SEQ ID NO 77
<211> LENGTH: 9
<212> TYPE: PRT
<213> ORGANISM: Enterococcus hirae

<400> SEQUENCE: 77

Arg Tyr Gly Thr Thr Glu Ser Gln Leu
1               5

<210> SEQ ID NO 78
<211> LENGTH: 9
<212> TYPE: PRT
<213> ORGANISM: Enterococcus hirae
```

<400> SEQUENCE: 78

Ser Tyr Val Asn Asn Gly Ala Ser Ile
1               5

<210> SEQ ID NO 79
<211> LENGTH: 9
<212> TYPE: PRT
<213> ORGANISM: Enterococcus hirae

<400> SEQUENCE: 79

Lys Tyr Lys Ser Asn Leu Ala Gly Leu
1               5

<210> SEQ ID NO 80
<211> LENGTH: 9
<212> TYPE: PRT
<213> ORGANISM: Enterococcus hirae

<400> SEQUENCE: 80

Val Phe Gly Lys Met Thr Ser Val Phe
1               5

<210> SEQ ID NO 81
<211> LENGTH: 9
<212> TYPE: PRT
<213> ORGANISM: Enterococcus hirae

<400> SEQUENCE: 81

Ala Phe Ser Gly Ile Val Lys Ser Phe
1               5

<210> SEQ ID NO 82
<211> LENGTH: 9
<212> TYPE: PRT
<213> ORGANISM: Enterococcus hirae

<400> SEQUENCE: 82

Val Tyr Thr Asp Tyr Ser Asn Gln Leu
1               5

<210> SEQ ID NO 83
<211> LENGTH: 9
<212> TYPE: PRT
<213> ORGANISM: Enterococcus hirae

<400> SEQUENCE: 83

Ala Phe Gln Asn Gln Ile Thr Gln Leu
1               5

<210> SEQ ID NO 84
<211> LENGTH: 9
<212> TYPE: PRT
<213> ORGANISM: Enterococcus hirae

<400> SEQUENCE: 84

Val Ile Asn Pro Ile Gly Ser Leu Arg
1               5

<210> SEQ ID NO 85
<211> LENGTH: 9
<212> TYPE: PRT
<213> ORGANISM: Enterococcus hirae

<400> SEQUENCE: 85

```
Lys Ala Lys Ile Lys Ser Pro Ser Arg
1               5

<210> SEQ ID NO 86
<211> LENGTH: 9
<212> TYPE: PRT
<213> ORGANISM: Enterococcus hirae

<400> SEQUENCE: 86

Lys Thr Ile Ser Thr Met Phe Glu Lys
1               5

<210> SEQ ID NO 87
<211> LENGTH: 9
<212> TYPE: PRT
<213> ORGANISM: Enterococcus hirae

<400> SEQUENCE: 87

Ala Ser Lys Ala Gly Gly Gly Phe Arg
1               5

<210> SEQ ID NO 88
<211> LENGTH: 9
<212> TYPE: PRT
<213> ORGANISM: Enterococcus hirae

<400> SEQUENCE: 88

Arg Thr Phe Ala Ala Thr Gly Ile Arg
1               5

<210> SEQ ID NO 89
<211> LENGTH: 9
<212> TYPE: PRT
<213> ORGANISM: Enterococcus hirae

<400> SEQUENCE: 89

Gly Asn Lys Val Thr Asn Phe Phe Arg
1               5

<210> SEQ ID NO 90
<211> LENGTH: 9
<212> TYPE: PRT
<213> ORGANISM: Enterococcus hirae

<400> SEQUENCE: 90

Ile Thr Gly Ser Arg Leu Ile Lys Arg
1               5

<210> SEQ ID NO 91
<211> LENGTH: 9
<212> TYPE: PRT
<213> ORGANISM: Enterococcus hirae

<400> SEQUENCE: 91

Asp Val Phe Glu Gly Ala Val Lys Arg
1               5

<210> SEQ ID NO 92
<211> LENGTH: 9
<212> TYPE: PRT
<213> ORGANISM: Enterococcus hirae

<400> SEQUENCE: 92

Glu Ala Phe Ala Ser Ala Asp Pro Lys
```

```
<210> SEQ ID NO 93
<211> LENGTH: 9
<212> TYPE: PRT
<213> ORGANISM: Enterococcus hirae

<400> SEQUENCE: 93

Asp Val Phe Glu Gly Ala Val Lys Arg
1               5

<210> SEQ ID NO 94
<211> LENGTH: 9
<212> TYPE: PRT
<213> ORGANISM: Enterococcus hirae

<400> SEQUENCE: 94

Thr Met Phe Ser Asp Ser Ala Leu Lys
1               5

<210> SEQ ID NO 95
<211> LENGTH: 9
<212> TYPE: PRT
<213> ORGANISM: Enterococcus hirae

<400> SEQUENCE: 95

Glu Ser Ala Phe Thr Gly Val Lys Lys
1               5

<210> SEQ ID NO 96
<211> LENGTH: 9
<212> TYPE: PRT
<213> ORGANISM: Enterococcus hirae

<400> SEQUENCE: 96

Thr Ser Val Ala Val Gln Ser Ala Lys
1               5

<210> SEQ ID NO 97
<211> LENGTH: 9
<212> TYPE: PRT
<213> ORGANISM: Enterococcus hirae

<400> SEQUENCE: 97

Asp Thr Ala Ala Thr Ser Leu Ala Arg
1               5

<210> SEQ ID NO 98
<211> LENGTH: 9
<212> TYPE: PRT
<213> ORGANISM: Enterococcus hirae

<400> SEQUENCE: 98

Met Ile Glu Phe Ile Gln Gly Leu Lys
1               5

<210> SEQ ID NO 99
<211> LENGTH: 9
<212> TYPE: PRT
<213> ORGANISM: Enterococcus hirae

<400> SEQUENCE: 99

Met Ala Leu Leu Ala Gly Met Leu Arg
1               5
```

```
<210> SEQ ID NO 100
<211> LENGTH: 9
<212> TYPE: PRT
<213> ORGANISM: Enterococcus hirae

<400> SEQUENCE: 100

Arg Thr Phe Ala Ala Thr Gly Ile Arg
1               5

<210> SEQ ID NO 101
<211> LENGTH: 9
<212> TYPE: PRT
<213> ORGANISM: Enterococcus hirae

<400> SEQUENCE: 101

Phe Ser Gly Ile Val Lys Ser Phe Lys
1               5

<210> SEQ ID NO 102
<211> LENGTH: 9
<212> TYPE: PRT
<213> ORGANISM: Enterococcus hirae

<400> SEQUENCE: 102

Glu Ala Gly Gly Ser Ala Phe Ser Arg
1               5

<210> SEQ ID NO 103
<211> LENGTH: 9
<212> TYPE: PRT
<213> ORGANISM: Enterococcus hirae

<400> SEQUENCE: 103

Thr Ser Val Gly Ser Asn Met Ala Lys
1               5

<210> SEQ ID NO 104
<211> LENGTH: 9
<212> TYPE: PRT
<213> ORGANISM: Enterococcus hirae

<400> SEQUENCE: 104

Lys Thr Ile Ser Thr Met Phe Glu Lys
1               5

<210> SEQ ID NO 105
<211> LENGTH: 9
<212> TYPE: PRT
<213> ORGANISM: Enterococcus hirae

<400> SEQUENCE: 105

Tyr Thr Asp Tyr Ser Asn Gln Leu Lys
1               5

<210> SEQ ID NO 106
<211> LENGTH: 9
<212> TYPE: PRT
<213> ORGANISM: Enterococcus hirae

<400> SEQUENCE: 106

Met Val Glu Ile Leu Glu Glu Ile Arg
1               5

<210> SEQ ID NO 107
```

-continued

```
<211> LENGTH: 9
<212> TYPE: PRT
<213> ORGANISM: Enterococcus hirae

<400> SEQUENCE: 107

Val Ile Asn Pro Ile Gly Ser Leu Arg
1               5

<210> SEQ ID NO 108
<211> LENGTH: 9
<212> TYPE: PRT
<213> ORGANISM: Enterococcus hirae

<400> SEQUENCE: 108

Glu Asp Phe Ala Asn Val Thr Gly Arg
1               5

<210> SEQ ID NO 109
<211> LENGTH: 9
<212> TYPE: PRT
<213> ORGANISM: Enterococcus hirae

<400> SEQUENCE: 109

Ile Ala Gly Phe Val Asp Gly Leu Arg
1               5

<210> SEQ ID NO 110
<211> LENGTH: 9
<212> TYPE: PRT
<213> ORGANISM: Enterococcus hirae

<400> SEQUENCE: 110

Thr Pro Met Gly Lys Met Val Glu Ile
1               5

<210> SEQ ID NO 111
<211> LENGTH: 9
<212> TYPE: PRT
<213> ORGANISM: Enterococcus hirae

<400> SEQUENCE: 111

Asn Leu Leu Thr Arg Phe Thr Thr Leu
1               5

<210> SEQ ID NO 112
<211> LENGTH: 9
<212> TYPE: PRT
<213> ORGANISM: Enterococcus hirae

<400> SEQUENCE: 112

Arg Leu Ile Lys Arg Ser Asn Ala Ile
1               5

<210> SEQ ID NO 113
<211> LENGTH: 9
<212> TYPE: PRT
<213> ORGANISM: Enterococcus hirae

<400> SEQUENCE: 113

Ala Arg Phe Ala Asn Ile Thr Gln Met
1               5

<210> SEQ ID NO 114
<211> LENGTH: 9
<212> TYPE: PRT
```

<213> ORGANISM: Enterococcus hirae

<400> SEQUENCE: 114

Phe Arg Thr Phe Ala Ala Thr Gly Ile
1               5

<210> SEQ ID NO 115
<211> LENGTH: 9
<212> TYPE: PRT
<213> ORGANISM: Enterococcus hirae

<400> SEQUENCE: 115

Leu Arg Ala Ile Ile Thr Val Gly Lys
1               5

<210> SEQ ID NO 116
<211> LENGTH: 9
<212> TYPE: PRT
<213> ORGANISM: Enterococcus hirae

<400> SEQUENCE: 116

Ala Arg Phe Ala Asn Ile Thr Gln Met
1               5

<210> SEQ ID NO 117
<211> LENGTH: 9
<212> TYPE: PRT
<213> ORGANISM: Enterococcus hirae

<400> SEQUENCE: 117

Gln Gln Met Ala Leu Leu Ala Gly Met
1               5

<210> SEQ ID NO 118
<211> LENGTH: 9
<212> TYPE: PRT
<213> ORGANISM: Enterococcus hirae

<400> SEQUENCE: 118

Arg Leu Ile Lys Arg Ser Asn Ala Ile
1               5

<210> SEQ ID NO 119
<211> LENGTH: 9
<212> TYPE: PRT
<213> ORGANISM: Enterococcus hirae

<400> SEQUENCE: 119

Asn Pro Ser Gln Ala Met Ile Glu Phe
1               5

<210> SEQ ID NO 120
<211> LENGTH: 9
<212> TYPE: PRT
<213> ORGANISM: Enterococcus hirae

<400> SEQUENCE: 120

Phe Ala Asn Ala Ser Thr Glu Tyr Met
1               5

<210> SEQ ID NO 121
<211> LENGTH: 9
<212> TYPE: PRT
<213> ORGANISM: Enterococcus hirae

```
<400> SEQUENCE: 121

Glu Ala Glu Ala Gly Gly Ser Ala Phe
1               5

<210> SEQ ID NO 122
<211> LENGTH: 9
<212> TYPE: PRT
<213> ORGANISM: Enterococcus hirae

<400> SEQUENCE: 122

Met Ala Ala Leu Ala Ala Ser Ala Gly
1               5

<210> SEQ ID NO 123
<211> LENGTH: 9
<212> TYPE: PRT
<213> ORGANISM: Enterococcus hirae

<400> SEQUENCE: 123

Phe Ala Ala Ala Leu Ser Ser Val Gly
1               5

<210> SEQ ID NO 124
<211> LENGTH: 9
<212> TYPE: PRT
<213> ORGANISM: Enterococcus hirae

<400> SEQUENCE: 124

Leu Ala Ala Ser Ala Gly Pro Val Leu
1               5

<210> SEQ ID NO 125
<211> LENGTH: 9
<212> TYPE: PRT
<213> ORGANISM: Enterococcus hirae

<400> SEQUENCE: 125

Ala Ala Val Lys Trp Glu Ser Ala Phe
1               5

<210> SEQ ID NO 126
<211> LENGTH: 9
<212> TYPE: PRT
<213> ORGANISM: Enterococcus hirae

<400> SEQUENCE: 126

Ser Lys Ala Asp Ile Val Asn Thr Leu
1               5

<210> SEQ ID NO 127
<211> LENGTH: 9
<212> TYPE: PRT
<213> ORGANISM: Enterococcus hirae

<400> SEQUENCE: 127

Ile Lys Asn Gly Ser Ser Ser Ala Leu
1               5

<210> SEQ ID NO 128
<211> LENGTH: 9
<212> TYPE: PRT
<213> ORGANISM: Enterococcus hirae

<400> SEQUENCE: 128
```

Asn Lys Leu Asn Asn Gln Ala Leu
1               5

<210> SEQ ID NO 129
<211> LENGTH: 9
<212> TYPE: PRT
<213> ORGANISM: Enterococcus hirae

<400> SEQUENCE: 129

Val Glu Ala Tyr Phe Asn His Thr Leu
1               5

<210> SEQ ID NO 130
<211> LENGTH: 9
<212> TYPE: PRT
<213> ORGANISM: Enterococcus hirae

<400> SEQUENCE: 130

Thr Glu Val Arg Leu Arg Asp Ser Leu
1               5

<210> SEQ ID NO 131
<211> LENGTH: 9
<212> TYPE: PRT
<213> ORGANISM: Enterococcus hirae

<400> SEQUENCE: 131

Ser Glu Leu Glu Gln Gly Ala Gln Leu
1               5

<210> SEQ ID NO 132
<211> LENGTH: 9
<212> TYPE: PRT
<213> ORGANISM: Enterococcus hirae

<400> SEQUENCE: 132

Thr Glu Val Arg Leu Arg Asp Ser Leu
1               5

<210> SEQ ID NO 133
<211> LENGTH: 9
<212> TYPE: PRT
<213> ORGANISM: Enterococcus hirae

<400> SEQUENCE: 133

Ala Glu Ala Ala Gly Gln Leu Gly Ile
1               5

<210> SEQ ID NO 134
<211> LENGTH: 9
<212> TYPE: PRT
<213> ORGANISM: Enterococcus hirae

<400> SEQUENCE: 134

Lys Gly Leu Gly Asn Ile Phe Lys Trp
1               5

<210> SEQ ID NO 135
<211> LENGTH: 9
<212> TYPE: PRT
<213> ORGANISM: Enterococcus hirae

<400> SEQUENCE: 135

Ile Ala Asn Gly Val Lys Gly Leu Trp
1               5

```
<210> SEQ ID NO 136
<211> LENGTH: 9
<212> TYPE: PRT
<213> ORGANISM: Enterococcus hirae

<400> SEQUENCE: 136

Lys Ala Gly Asn Ile Asp Ser Lys Trp
1               5

<210> SEQ ID NO 137
<211> LENGTH: 9
<212> TYPE: PRT
<213> ORGANISM: Enterococcus hirae

<400> SEQUENCE: 137

Lys Ser Asn Pro Ser Gln Ala Met Ile
1               5

<210> SEQ ID NO 138
<211> LENGTH: 9
<212> TYPE: PRT
<213> ORGANISM: Enterococcus hirae

<400> SEQUENCE: 138

Arg Ser Phe Ser Ala Ser Leu Gln Leu
1               5

<210> SEQ ID NO 139
<211> LENGTH: 9
<212> TYPE: PRT
<213> ORGANISM: Enterococcus hirae

<400> SEQUENCE: 139

Arg Ala Ala Asn Ala Ser Asp Val Phe
1               5

<210> SEQ ID NO 140
<211> LENGTH: 9
<212> TYPE: PRT
<213> ORGANISM: Enterococcus hirae

<400> SEQUENCE: 140

Ser Thr Ala Gly Val Glu Ala Tyr Phe
1               5

<210> SEQ ID NO 141
<211> LENGTH: 9
<212> TYPE: PRT
<213> ORGANISM: Enterococcus hirae

<400> SEQUENCE: 141

Leu Ser Asn Pro Ile Thr Ala Ile Leu
1               5

<210> SEQ ID NO 142
<211> LENGTH: 9
<212> TYPE: PRT
<213> ORGANISM: Enterococcus hirae

<400> SEQUENCE: 142

Leu Ser Asn Ser Lys Leu Ala Lys Phe
1               5
```

<210> SEQ ID NO 143
<211> LENGTH: 9
<212> TYPE: PRT
<213> ORGANISM: Enterococcus hirae

<400> SEQUENCE: 143

Phe Ala Asn Ala Ser Thr Glu Tyr Met
1               5

<210> SEQ ID NO 144
<211> LENGTH: 9
<212> TYPE: PRT
<213> ORGANISM: Enterococcus hirae

<400> SEQUENCE: 144

Phe Lys Ser Asn Pro Ser Gln Ala Met
1               5

<210> SEQ ID NO 145
<211> LENGTH: 9
<212> TYPE: PRT
<213> ORGANISM: Enterococcus hirae

<400> SEQUENCE: 145

Leu Ala Ala Ser Ala Gly Pro Val Leu
1               5

<210> SEQ ID NO 146
<211> LENGTH: 9
<212> TYPE: PRT
<213> ORGANISM: Enterococcus hirae

<400> SEQUENCE: 146

Glu Ala Ser Lys Ala Ser Gly Ser Leu
1               5

<210> SEQ ID NO 147
<211> LENGTH: 9
<212> TYPE: PRT
<213> ORGANISM: Enterococcus hirae

<400> SEQUENCE: 147

Val Ala Ile Thr Phe Gly Gly Pro Leu
1               5

<210> SEQ ID NO 148
<211> LENGTH: 9
<212> TYPE: PRT
<213> ORGANISM: Enterococcus hirae

<400> SEQUENCE: 148

Ser Ala Ile Ser Ala Ala Lys Pro Met
1               5

<210> SEQ ID NO 149
<211> LENGTH: 9
<212> TYPE: PRT
<213> ORGANISM: Enterococcus hirae

<400> SEQUENCE: 149

Glu Ala Phe Asn Glu Asn Thr Ala Leu
1               5

<210> SEQ ID NO 150
<211> LENGTH: 9

```
<212> TYPE: PRT
<213> ORGANISM: Enterococcus hirae

<400> SEQUENCE: 150

Ser Ala Asn Asn Ala Gly Arg Glu Leu
1               5

<210> SEQ ID NO 151
<211> LENGTH: 9
<212> TYPE: PRT
<213> ORGANISM: Enterococcus hirae

<400> SEQUENCE: 151

Ala Ala Gly Lys Ser Gly Thr Val Leu
1               5

<210> SEQ ID NO 152
<211> LENGTH: 9
<212> TYPE: PRT
<213> ORGANISM: Enterococcus hirae

<400> SEQUENCE: 152

Lys Ala Ala Lys Ser Thr Glu Glu Leu
1               5

<210> SEQ ID NO 153
<211> LENGTH: 9
<212> TYPE: PRT
<213> ORGANISM: Enterococcus hirae

<400> SEQUENCE: 153

Phe Ala Ser Val Val Ile Asn Pro Ile
1               5

<210> SEQ ID NO 154
<211> LENGTH: 9
<212> TYPE: PRT
<213> ORGANISM: Enterococcus hirae

<400> SEQUENCE: 154

Phe Ala Ala Thr Gly Ile Arg Ser Ile
1               5

<210> SEQ ID NO 155
<211> LENGTH: 9
<212> TYPE: PRT
<213> ORGANISM: Enterococcus hirae

<400> SEQUENCE: 155

Arg Ala Ala Asn Ala Ser Asp Val Phe
1               5

<210> SEQ ID NO 156
<211> LENGTH: 9
<212> TYPE: PRT
<213> ORGANISM: Enterococcus hirae

<400> SEQUENCE: 156

Ala Ser Ile Asp Gln Gln Met Ala Leu
1               5

<210> SEQ ID NO 157
<211> LENGTH: 9
<212> TYPE: PRT
<213> ORGANISM: Enterococcus hirae
```

<400> SEQUENCE: 157

Ala Ala Lys Pro Met Ile Glu Ala Leu
1               5

<210> SEQ ID NO 158
<211> LENGTH: 9
<212> TYPE: PRT
<213> ORGANISM: Enterococcus hirae

<400> SEQUENCE: 158

Asn Ala Lys Gln Lys Gly Ala Glu Leu
1               5

<210> SEQ ID NO 159
<211> LENGTH: 9
<212> TYPE: PRT
<213> ORGANISM: Enterococcus hirae

<400> SEQUENCE: 159

Thr Ala Val Asn Ala Ile Met Ala Ile
1               5

<210> SEQ ID NO 160
<211> LENGTH: 9
<212> TYPE: PRT
<213> ORGANISM: Enterococcus hirae

<400> SEQUENCE: 160

Ser Ala Asp Pro Lys Thr Gln Glu Phe
1               5

<210> SEQ ID NO 161
<211> LENGTH: 9
<212> TYPE: PRT
<213> ORGANISM: Enterococcus hirae

<400> SEQUENCE: 161

Asn Ala Ser Asp Ile Pro Ser Asn Leu
1               5

<210> SEQ ID NO 162
<211> LENGTH: 9
<212> TYPE: PRT
<213> ORGANISM: Enterococcus hirae

<400> SEQUENCE: 162

Ser Ala Asp Thr Ala Ala Thr Ser Leu
1               5

<210> SEQ ID NO 163
<211> LENGTH: 9
<212> TYPE: PRT
<213> ORGANISM: Enterococcus hirae

<400> SEQUENCE: 163

Phe Ala Ser Ala Asp Pro Lys Thr Gln
1               5

<210> SEQ ID NO 164
<211> LENGTH: 9
<212> TYPE: PRT
<213> ORGANISM: Enterococcus hirae

<400> SEQUENCE: 164

```
Glu Ala Glu Ala Gly Gly Ser Ala Phe
1               5

<210> SEQ ID NO 165
<211> LENGTH: 9
<212> TYPE: PRT
<213> ORGANISM: Enterococcus hirae

<400> SEQUENCE: 165

Phe Val Ser Lys Tyr Lys Ser Asn Leu
1               5

<210> SEQ ID NO 166
<211> LENGTH: 9
<212> TYPE: PRT
<213> ORGANISM: Enterococcus hirae

<400> SEQUENCE: 166

Ala Ala Val Lys Trp Glu Ser Ala Phe
1               5

<210> SEQ ID NO 167
<211> LENGTH: 9
<212> TYPE: PRT
<213> ORGANISM: Enterococcus hirae

<400> SEQUENCE: 167

Ile Ala Ser Leu Thr Gly Ala Met Leu
1               5

<210> SEQ ID NO 168
<211> LENGTH: 9
<212> TYPE: PRT
<213> ORGANISM: Enterococcus hirae

<400> SEQUENCE: 168

Ser Ala Ala Gly Lys Ser Gly Thr Val
1               5

<210> SEQ ID NO 169
<211> LENGTH: 9
<212> TYPE: PRT
<213> ORGANISM: Enterococcus hirae

<400> SEQUENCE: 169

Phe Gly Gly Pro Leu Val Ala Ala Leu
1               5

<210> SEQ ID NO 170
<211> LENGTH: 9
<212> TYPE: PRT
<213> ORGANISM: Enterococcus hirae

<400> SEQUENCE: 170

Ile Lys Asn Gly Ser Ser Ser Ala Leu
1               5

<210> SEQ ID NO 171
<211> LENGTH: 9
<212> TYPE: PRT
<213> ORGANISM: Enterococcus hirae

<400> SEQUENCE: 171

Ser Ala Asp Pro Lys Thr Gln Glu Phe
```

```
1               5

<210> SEQ ID NO 172
<211> LENGTH: 9
<212> TYPE: PRT
<213> ORGANISM: Enterococcus hirae

<400> SEQUENCE: 172

Met Val Asp Ser Asn Gly Lys Val Ile
1               5

<210> SEQ ID NO 173
<211> LENGTH: 9
<212> TYPE: PRT
<213> ORGANISM: Enterococcus hirae

<400> SEQUENCE: 173

Ser Ala Asp Thr Ala Ala Thr Ser Leu
1               5

<210> SEQ ID NO 174
<211> LENGTH: 9
<212> TYPE: PRT
<213> ORGANISM: Enterococcus hirae

<400> SEQUENCE: 174

Leu Lys Asp Thr Ile Val Gly Leu Phe
1               5

<210> SEQ ID NO 175
<211> LENGTH: 9
<212> TYPE: PRT
<213> ORGANISM: Enterococcus hirae

<400> SEQUENCE: 175

Ala Arg Phe Ala Asn Ile Thr Gln Met
1               5

<210> SEQ ID NO 176
<211> LENGTH: 9
<212> TYPE: PRT
<213> ORGANISM: Enterococcus hirae

<400> SEQUENCE: 176

Ala Arg Phe Ala Asn Ile Thr Gln Met
1               5

<210> SEQ ID NO 177
<211> LENGTH: 9
<212> TYPE: PRT
<213> ORGANISM: Enterococcus hirae

<400> SEQUENCE: 177

Phe Ala Ala Thr Gly Ile Arg Ser Ile
1               5

<210> SEQ ID NO 178
<211> LENGTH: 9
<212> TYPE: PRT
<213> ORGANISM: Enterococcus hirae

<400> SEQUENCE: 178

Phe Ala Ser Val Val Ile Asn Pro Ile
1               5
```

<210> SEQ ID NO 179
<211> LENGTH: 9
<212> TYPE: PRT
<213> ORGANISM: Enterococcus hirae

<400> SEQUENCE: 179

Phe Val Glu Ala Gly Val Asn Lys Leu
1               5

<210> SEQ ID NO 180
<211> LENGTH: 9
<212> TYPE: PRT
<213> ORGANISM: Enterococcus hirae

<400> SEQUENCE: 180

Phe Ala Asn Ala Ser Thr Glu Tyr Met
1               5

<210> SEQ ID NO 181
<211> LENGTH: 9
<212> TYPE: PRT
<213> ORGANISM: Enterococcus hirae

<400> SEQUENCE: 181

Val Val Met Asp Thr Gly Gln Val Val
1               5

<210> SEQ ID NO 182
<211> LENGTH: 9
<212> TYPE: PRT
<213> ORGANISM: Enterococcus hirae

<400> SEQUENCE: 182

Lys Val Phe Gly Lys Met Thr Ser Val
1               5

<210> SEQ ID NO 183
<211> LENGTH: 9
<212> TYPE: PRT
<213> ORGANISM: Enterococcus hirae

<400> SEQUENCE: 183

Ala Tyr Phe Asn His Thr Leu Asp Leu
1               5

<210> SEQ ID NO 184
<211> LENGTH: 9
<212> TYPE: PRT
<213> ORGANISM: Enterococcus hirae

<400> SEQUENCE: 184

Ser Tyr Val Asn Asn Gly Ala Ser Ile
1               5

<210> SEQ ID NO 185
<211> LENGTH: 9
<212> TYPE: PRT
<213> ORGANISM: Enterococcus hirae

<400> SEQUENCE: 185

Val Tyr Thr Asp Tyr Ser Asn Gln Leu
1               5

<210> SEQ ID NO 186

```
<211> LENGTH: 9
<212> TYPE: PRT
<213> ORGANISM: Enterococcus hirae

<400> SEQUENCE: 186

Phe Phe Arg Ser Phe Ser Ala Ser Leu
1               5

<210> SEQ ID NO 187
<211> LENGTH: 9
<212> TYPE: PRT
<213> ORGANISM: Enterococcus hirae

<400> SEQUENCE: 187

Arg Ser Phe Ser Ala Ser Leu Gln Leu
1               5

<210> SEQ ID NO 188
<211> LENGTH: 9
<212> TYPE: PRT
<213> ORGANISM: human

<400> SEQUENCE: 188

Lys Leu Gln Lys Phe Ala Ser Thr Val
1               5

<210> SEQ ID NO 189
<211> LENGTH: 9
<212> TYPE: PRT
<213> ORGANISM: mouse

<400> SEQUENCE: 189

Gly Ser Leu Ala Arg Phe Arg Asn Ile
1               5

<210> SEQ ID NO 190
<211> LENGTH: 9
<212> TYPE: PRT
<213> ORGANISM: artificial sequence
<220> FEATURE:
<223> OTHER INFORMATION: mutated peptide

<400> SEQUENCE: 190

Gly Ser Phe Ala Arg Phe Arg Asn Ile
1               5

<210> SEQ ID NO 191
<211> LENGTH: 20
<212> TYPE: DNA
<213> ORGANISM: Artificial Sequence
<220> FEATURE:
<223> OTHER INFORMATION: primer

<400> SEQUENCE: 191
actgcagccg taaaatggga                                          20

<210> SEQ ID NO 192
<211> LENGTH: 20
<212> TYPE: DNA
<213> ORGANISM: Artificial Sequence
<220> FEATURE:
<223> OTHER INFORMATION: primer

<400> SEQUENCE: 192
tccgtatcgt ttgccagctt                                          20
```

```
<210> SEQ ID NO 193
<211> LENGTH: 92
<212> TYPE: DNA
<213> ORGANISM: Artificial Sequence
<220> FEATURE:
<223> OTHER INFORMATION: primer

<400> SEQUENCE: 193
caataaaaaa tcagacctaa gactgatgac aaaaagagca aatttttgata aaatagtatt    60 agaattaaat taaaaaggga ggccaaatat ag                                  92

<210> SEQ ID NO 194
<211> LENGTH: 100
<212> TYPE: DNA
<213> ORGANISM: Artificial Sequence
<220> FEATURE:
<223> OTHER INFORMATION: primer

<400> SEQUENCE: 194
gatcctatat ttggcctccc tttttaattt aattctaata ctatttttatc aaaatttgct   60 cttttttgtca tcagtcttag gtctgatttt ttattgcatg                         100

<210> SEQ ID NO 195
<211> LENGTH: 36
<212> TYPE: DNA
<213> ORGANISM: Artificial Sequence
<220> FEATURE:
<223> OTHER INFORMATION: primer

<400> SEQUENCE: 195
tccggatcca tggcacaaag taaaacagtc aaagcg                              36

<210> SEQ ID NO 196
<211> LENGTH: 66
<212> TYPE: DNA
<213> ORGANISM: Artificial Sequence
<220> FEATURE:
<223> OTHER INFORMATION: primer

<400> SEQUENCE: 196
caggaattct tacttgtcgt catcgtcttt gtagtcacgt agtaaactat cacgtaatcg    60
aacttc                                                               66

<210> SEQ ID NO 197
<211> LENGTH: 35
<212> TYPE: DNA
<213> ORGANISM: Artificial Sequence
<220> FEATURE:
<223> OTHER INFORMATION: primer

<400> SEQUENCE: 197
aacgagctaa ggcagtagca gctgtatctg cagac                               35

<210> SEQ ID NO 198
<211> LENGTH: 35
<212> TYPE: DNA
<213> ORGANISM: Artificial Sequence
<220> FEATURE:
<223> OTHER INFORMATION: primer

<400> SEQUENCE: 198
gtctgcagat acagctgcta ctgccttagc tcgtt                               35
```

```
<210> SEQ ID NO 199
<211> LENGTH: 38
<212> TYPE: DNA
<213> ORGANISM: Artificial Sequence
<220> FEATURE:
<223> OTHER INFORMATION: primer

<400> SEQUENCE: 199
attagcaaaa cgagcgaagg aagtagcagc tgtatctg                              38

<210> SEQ ID NO 200
<211> LENGTH: 38
<212> TYPE: DNA
<213> ORGANISM: Artificial Sequence
<220> FEATURE:
<223> OTHER INFORMATION: primer

<400> SEQUENCE: 200
cagatacagc tgctacttcc ttcgctcgtt ttgctaat                              38

<210> SEQ ID NO 201
<211> LENGTH: 27
<212> TYPE: DNA
<213> ORGANISM: Artificial Sequence
<220> FEATURE:
<223> OTHER INFORMATION: primer

<400> SEQUENCE: 201
cttggatcca tggtgagcaa gggcgag                                         27

<210> SEQ ID NO 202
<211> LENGTH: 31
<212> TYPE: DNA
<213> ORGANISM: Artificial Sequence
<220> FEATURE:
<223> OTHER INFORMATION: primer

<400> SEQUENCE: 202
caggaattcc tacataatta cacactttgt c                                    31

<210> SEQ ID NO 203
<211> LENGTH: 23
<212> TYPE: DNA
<213> ORGANISM: Artificial Sequence
<220> FEATURE:
<223> OTHER INFORMATION: primer

<400> SEQUENCE: 203
cccagtcacg acgttgtaaa acg                                             23

<210> SEQ ID NO 204
<211> LENGTH: 24
<212> TYPE: DNA
<213> ORGANISM: Artificial Sequence
<220> FEATURE:
<223> OTHER INFORMATION: primer

<400> SEQUENCE: 204
gagcggataa caatttcaca cagg                                            24

<210> SEQ ID NO 205
<211> LENGTH: 20
<212> TYPE: DNA
<213> ORGANISM: Artificial Sequence
<220> FEATURE:
<223> OTHER INFORMATION: gRNA
```

```
<400> SEQUENCE: 205
agatattgcg gaaacgagcc                                          20

<210> SEQ ID NO 206
<211> LENGTH: 20
<212> TYPE: DNA
<213> ORGANISM: Artificial Sequence
<220> FEATURE:
<223> OTHER INFORMATION: primer

<400> SEQUENCE: 206
ctcagggacc cttttcacga                                          20

<210> SEQ ID NO 207
<211> LENGTH: 20
<212> TYPE: DNA
<213> ORGANISM: Artificial Sequence
<220> FEATURE:
<223> OTHER INFORMATION: primer

<400> SEQUENCE: 207
cccactccct gttctacaca                                          20

<210> SEQ ID NO 208
<211> LENGTH: 21
<212> TYPE: DNA
<213> ORGANISM: Artificial Sequence
<220> FEATURE:
<223> OTHER INFORMATION: primer

<400> SEQUENCE: 208
ggaccctttt cacgattcag g                                        21

<210> SEQ ID NO 209
<211> LENGTH: 9
<212> TYPE: PRT
<213> ORGANISM: artificial sequence
<220> FEATURE:
<223> OTHER INFORMATION: peptide with variable positions
<220> FEATURE:
<221> NAME/KEY: X=AorQ
<222> LOCATION: (3)..(3)
<220> FEATURE:
<221> NAME/KEY: X=VorT
<222> LOCATION: (8)..(8)

<400> SEQUENCE: 209

Lys Leu Xaa Lys Phe Ala Ser Xaa Val
1               5

<210> SEQ ID NO 210
<211> LENGTH: 9
<212> TYPE: PRT
<213> ORGANISM: Artificial Sequence
<220> FEATURE:
<223> OTHER INFORMATION: hybrid

<400> SEQUENCE: 210

Lys Leu Ala Lys Phe Ala Ser Thr Val
1               5

<210> SEQ ID NO 211
<211> LENGTH: 9
<212> TYPE: PRT
<213> ORGANISM: artificial sequence
<220> FEATURE:
<223> OTHER INFORMATION: hybrid
```

<400> SEQUENCE: 211

Lys Leu Gln Lys Phe Ala Ser Val Val
1               5

<210> SEQ ID NO 212
<211> LENGTH: 49
<212> TYPE: PRT
<213> ORGANISM: Homo sapiens

<400> SEQUENCE: 212

Asn Gly Ser Ala Val Ala Lys Ile Ile Gly Asn Asn Val Lys Lys Leu
1               5                   10                  15

Gln Lys Phe Ala Ser Thr Val Lys Met Trp Val Phe Glu Glu Thr Val
            20                  25                  30

Asn Gly Arg Lys Leu Thr Asp Ile Ile Asn Asn Asp His Glu Asn Val
        35                  40                  45

Lys

<210> SEQ ID NO 213
<211> LENGTH: 402
<212> TYPE: PRT
<213> ORGANISM: Enterococcus hirae

<400> SEQUENCE: 213

Met Ala Gln Ser Lys Thr Val Lys Ala Val Leu Thr Ala Ile Asp Lys
1               5                   10                  15

Gly Phe Thr Gln Thr Met Gly Ser Ala Thr Ser Ser Leu Lys Lys Leu
            20                  25                  30

Ser Ser Asn Ala Ser Asp Ile Pro Ser Asn Leu Asn Thr Val Ser Gly
        35                  40                  45

Ala Met Lys Ser Phe Gly Asp Lys Thr Ala Ser Ile Gly Gln Ser Ile
    50                  55                  60

Glu Lys Val Gly Gly Ser Met Thr Lys Gly Ile Thr Leu Pro Ile Ala
65                  70                  75                  80

Gly Ala Val Gly Ala Val Thr Thr Ala Ala Val Lys Trp Glu Ser Ala
                85                  90                  95

Phe Thr Gly Val Lys Lys Thr Asn Asp Glu Met Val Asp Ser Asn Gly
            100                 105                 110

Lys Val Ile Tyr Ser Tyr Asp Asp Leu Glu Lys Gly Leu Arg Asp Leu
        115                 120                 125

Ala Lys Glu Leu Pro Thr Ser His Glu Glu Ile Ala Lys Val Ala Glu
    130                 135                 140

Ala Ala Gly Gln Leu Gly Ile Lys Thr Asp Lys Val Val Gly Phe Thr
145                 150                 155                 160

Lys Thr Met Ile Asp Met Gly Glu Ser Thr Asn Met Ser Ala Asp Thr
                165                 170                 175

Ala Ala Thr Ser Leu Ala Arg Phe Ala Asn Ile Thr Gln Met Ser Gln
            180                 185                 190

Asp Lys Phe Ser Asn Leu Gly Ser Ala Ile Val Asp Leu Gly Asn Asn
        195                 200                 205

Leu Ala Thr Thr Glu Ser Glu Ile Thr Glu Met Gly Leu Arg Leu Ala
    210                 215                 220

Gly Ala Gly Lys Gln Ile Gly Met Thr Glu Gly Asp Ile Val Gly Phe
225                 230                 235                 240

Ala Ala Ala Leu Ser Ser Val Gly Ile Glu Ala Glu Ala Gly Gly Ser

```
            245                 250                 255
Ala Phe Ser Arg Leu Met Val Gln Met Gln Leu Ala Thr Glu Thr Gly
            260                 265                 270

Val Lys Ala Phe Glu Pro Leu Lys Gln Ala Val Ala Ile Gln Gly Val
            275                 280                 285

Ser Trp Glu Lys Phe Val His Ala Val Asn Trp Gly Gly Lys Glu Leu
            290                 295                 300

Thr Ala Val Ser Lys Gln Met Gly Val Pro Ala Ser Glu Leu Lys Lys
305                 310                 315                 320

Leu Tyr Lys Glu Ala Ser Lys Ala Ser Gly Ser Leu Glu Asp Phe Ala
                325                 330                 335

Asn Val Thr Gly Arg Thr Gly Glu Glu Phe Ala Glu Leu Phe Lys Ser
                340                 345                 350

Asn Pro Ser Gln Ala Met Ile Glu Phe Ile Gln Gly Leu Lys Asp Ser
                355                 360                 365

Glu Lys His Gly Ile Ser Ala Ile Lys Val Leu Asp Met Gly Ile Thr
                370                 375                 380

Glu Val Arg Leu Arg Asp Ser Leu Leu Arg Asp Tyr Lys Asp Asp Asp
385                 390                 395                 400

Asp Lys

<210> SEQ ID NO 214
<211> LENGTH: 402
<212> TYPE: PRT
<213> ORGANISM: Enterococcus hirae

<400> SEQUENCE: 214

Met Ala Gln Ser Lys Thr Val Lys Ala Val Leu Thr Ala Ile Asp Lys
1               5                   10                  15

Gly Phe Thr Gln Thr Met Gly Ser Ala Thr Ser Ser Leu Lys Lys Leu
            20                  25                  30

Ser Ser Asn Ala Ser Asp Ile Pro Ser Asn Leu Asn Thr Val Ser Gly
        35                  40                  45

Ala Met Lys Ser Phe Gly Asp Lys Thr Ala Ser Ile Gly Gln Ser Ile
50                  55                  60

Glu Lys Val Gly Gly Ser Met Thr Lys Gly Ile Thr Leu Pro Ile Ala
65                  70                  75                  80

Gly Ala Val Gly Ala Val Thr Thr Ala Ala Val Lys Trp Glu Ser Ala
                85                  90                  95

Phe Thr Gly Val Lys Lys Thr Asn Asp Glu Met Val Asp Ser Asn Gly
            100                 105                 110

Lys Val Ile Tyr Ser Tyr Asp Asp Leu Glu Lys Gly Leu Arg Asp Leu
        115                 120                 125

Ala Lys Glu Leu Pro Thr Ser His Glu Glu Ile Ala Lys Val Ala Glu
130                 135                 140

Ala Ala Gly Gln Leu Gly Ile Lys Thr Asp Lys Val Val Gly Phe Thr
145                 150                 155                 160

Lys Thr Met Ile Asp Met Gly Glu Ser Thr Asn Met Ser Ala Asp Thr
                165                 170                 175

Ala Ala Thr Ala Leu Ala Arg Phe Ala Asn Ile Thr Gln Met Ser Gln
                180                 185                 190

Asp Lys Phe Ser Asn Leu Gly Ser Ala Ile Val Asp Leu Gly Asn Asn
            195                 200                 205

Leu Ala Thr Thr Glu Ser Glu Ile Thr Glu Met Gly Leu Arg Leu Ala
```

```
            210                 215                 220
Gly Ala Gly Lys Gln Ile Gly Met Thr Glu Gly Asp Ile Val Gly Phe
225                 230                 235                 240

Ala Ala Ala Leu Ser Ser Val Gly Ile Glu Ala Glu Ala Gly Gly Ser
                245                 250                 255

Ala Phe Ser Arg Leu Met Val Gln Met Gln Leu Ala Thr Glu Thr Gly
                260                 265                 270

Val Lys Ala Phe Glu Pro Leu Lys Gln Ala Val Ala Ile Gln Gly Val
            275                 280                 285

Ser Trp Glu Lys Phe Val His Ala Val Asn Trp Gly Gly Lys Glu Leu
        290                 295                 300

Thr Ala Val Ser Lys Gln Met Gly Val Pro Ala Ser Glu Leu Lys Lys
305                 310                 315                 320

Leu Tyr Lys Glu Ala Ser Lys Ala Ser Gly Ser Leu Glu Asp Phe Ala
                325                 330                 335

Asn Val Thr Gly Arg Thr Gly Glu Glu Phe Ala Glu Leu Phe Lys Ser
                340                 345                 350

Asn Pro Ser Gln Ala Met Ile Glu Phe Ile Gln Gly Leu Lys Asp Ser
            355                 360                 365

Glu Lys His Gly Ile Ser Ala Ile Lys Val Leu Asp Met Gly Ile Thr
        370                 375                 380

Glu Val Arg Leu Arg Asp Ser Leu Leu Arg Asp Tyr Lys Asp Asp Asp
385                 390                 395                 400

Asp Lys

<210> SEQ ID NO 215
<211> LENGTH: 402
<212> TYPE: PRT
<213> ORGANISM: Enterococcus hirae

<400> SEQUENCE: 215

Met Ala Gln Ser Lys Thr Val Lys Ala Val Leu Thr Ala Ile Asp Lys
1               5                   10                  15

Gly Phe Thr Gln Thr Met Gly Ser Ala Thr Ser Ser Leu Lys Lys Leu
                20                  25                  30

Ser Ser Asn Ala Ser Asp Ile Pro Ser Asn Leu Asn Thr Val Ser Gly
            35                  40                  45

Ala Met Lys Ser Phe Gly Asp Lys Thr Ala Ser Ile Gly Gln Ser Ile
        50                  55                  60

Glu Lys Val Gly Gly Ser Met Thr Lys Gly Ile Thr Leu Pro Ile Ala
65                  70                  75                  80

Gly Ala Val Gly Ala Val Thr Thr Ala Ala Val Lys Trp Glu Ser Ala
                85                  90                  95

Phe Thr Gly Val Lys Lys Thr Asn Asp Glu Met Val Asp Ser Asn Gly
                100                 105                 110

Lys Val Ile Tyr Ser Tyr Asp Asp Leu Glu Lys Gly Leu Arg Asp Leu
            115                 120                 125

Ala Lys Glu Leu Pro Thr Ser His Glu Glu Ile Ala Lys Val Ala Glu
        130                 135                 140

Ala Ala Gly Gln Leu Gly Ile Lys Thr Asp Lys Val Val Gly Phe Thr
145                 150                 155                 160

Lys Thr Met Ile Asp Met Gly Glu Ser Thr Asn Met Ser Ala Asp Thr
                165                 170                 175

Ala Ala Thr Ser Phe Ala Arg Phe Ala Asn Ile Thr Gln Met Ser Gln
```

```
                180             185                 190
Asp Lys Phe Ser Asn Leu Gly Ser Ala Ile Val Asp Leu Gly Asn Asn
            195                 200                 205
Leu Ala Thr Thr Glu Ser Glu Ile Thr Glu Met Gly Leu Arg Leu Ala
            210                 215                 220
Gly Ala Gly Lys Gln Ile Gly Met Thr Glu Gly Asp Ile Val Gly Phe
225                 230                 235                 240
Ala Ala Ala Leu Ser Ser Val Gly Ile Glu Ala Glu Ala Gly Gly Ser
                245                 250                 255
Ala Phe Ser Arg Leu Met Val Gln Met Gln Leu Ala Thr Glu Thr Gly
                260                 265                 270
Val Lys Ala Phe Glu Pro Leu Lys Gln Ala Val Ala Ile Gln Gly Val
            275                 280                 285
Ser Trp Glu Lys Phe Val His Ala Val Asn Trp Gly Gly Lys Glu Leu
            290                 295                 300
Thr Ala Val Ser Lys Gln Met Gly Val Pro Ala Ser Glu Leu Lys Lys
305                 310                 315                 320
Leu Tyr Lys Glu Ala Ser Lys Ala Ser Gly Ser Leu Glu Asp Phe Ala
                325                 330                 335
Asn Val Thr Gly Arg Thr Gly Glu Glu Phe Ala Glu Leu Phe Lys Ser
                340                 345                 350
Asn Pro Ser Gln Ala Met Ile Glu Phe Ile Gln Gly Leu Lys Asp Ser
                355                 360                 365
Glu Lys His Gly Ile Ser Ala Ile Lys Val Leu Asp Met Gly Ile Thr
            370                 375                 380
Glu Val Arg Leu Arg Asp Ser Leu Leu Arg Asp Tyr Lys Asp Asp Asp
385                 390                 395                 400
Asp Lys

<210> SEQ ID NO 216
<211> LENGTH: 9
<212> TYPE: PRT
<213> ORGANISM: Enterococcus hirae

<400> SEQUENCE: 216

Thr Ala Leu Ala Arg Phe Ala Asn Ile
1               5

<210> SEQ ID NO 217
<211> LENGTH: 9
<212> TYPE: PRT
<213> ORGANISM: Enterococcus hirae

<400> SEQUENCE: 217

Thr Ser Phe Ala Arg Phe Ala Asn Ile
1               5

<210> SEQ ID NO 218
<211> LENGTH: 9
<212> TYPE: PRT
<213> ORGANISM: Artificial Sequence
<220> FEATURE:
<223> OTHER INFORMATION: synthetic construct

<400> SEQUENCE: 218

Ala Ile Ile Glu Phe Ile Lys Gly Leu
1               5
```

```
<210> SEQ ID NO 219
<211> LENGTH: 6
<212> TYPE: PRT
<213> ORGANISM: Artificial Sequence
<220> FEATURE:
<223> OTHER INFORMATION: synthetic construct

<400> SEQUENCE: 219

Ser Ser Gly Ser Leu Ala
1               5

<210> SEQ ID NO 220
<211> LENGTH: 22
<212> TYPE: DNA
<213> ORGANISM: Artificial Sequence
<220> FEATURE:
<223> OTHER INFORMATION: synthetic construct

<400> SEQUENCE: 220
gctcctacgg ctccctggct cg                                              22

<210> SEQ ID NO 221
<211> LENGTH: 6
<212> TYPE: PRT
<213> ORGANISM: Artificial Sequence
<220> FEATURE:
<223> OTHER INFORMATION: synthetic construct

<400> SEQUENCE: 221

Ser Ser Gly Ala Leu Ala
1               5

<210> SEQ ID NO 222
<211> LENGTH: 22
<212> TYPE: DNA
<213> ORGANISM: Artificial Sequence
<220> FEATURE:
<223> OTHER INFORMATION: synthetic construct

<400> SEQUENCE: 222
gctcctacgg cgcactagct cg                                              22

<210> SEQ ID NO 223
<211> LENGTH: 6
<212> TYPE: PRT
<213> ORGANISM: Artificial Sequence
<220> FEATURE:
<223> OTHER INFORMATION: synthetic construct

<400> SEQUENCE: 223

Ser Ser Gly Ser Phe Ala
1               5

<210> SEQ ID NO 224
<211> LENGTH: 22
<212> TYPE: DNA
<213> ORGANISM: Artificial Sequence
<220> FEATURE:
<223> OTHER INFORMATION: synthetic construct

<400> SEQUENCE: 224
gctcctacgg ctccttcgct cg                                              22

<210> SEQ ID NO 225
<211> LENGTH: 264
<212> TYPE: PRT
<213> ORGANISM: Mus musculus
```

<400> SEQUENCE: 225

```
Met Glu Ala Phe Trp Glu Ser Arg Ala Gly His Trp Ala Gly Gly Pro
1               5                   10                  15

Ala Pro Gly Gln Phe Tyr Arg Ile Pro Ala Thr Pro Ser Gly Leu Met
            20                  25                  30

Asp Pro Ala Ser Ala Pro Cys Glu Gly Pro Ile Thr Arg Thr Gln Asn
        35                  40                  45

Pro Met Val Thr Gly Thr Ser Val Leu Gly Val Lys Phe Asp Gly Gly
    50                  55                  60

Val Val Ile Ala Ala Asp Met Leu Gly Ser Tyr Gly Ser Leu Ala Arg
65                  70                  75                  80

Phe Arg Asn Ile Ser Arg Ile Met Arg Val Asn Asp Ser Thr Met Leu
                85                  90                  95

Gly Ala Ser Gly Asp Tyr Ala Asp Phe Gln Tyr Leu Lys Gln Val Leu
            100                 105                 110

Gly Gln Met Val Ile Asp Glu Leu Leu Gly Asp Gly His Ser Tyr
        115                 120                 125

Ser Pro Arg Ala Ile His Ser Trp Leu Thr Arg Ala Met Tyr Ser Arg
130                 135                 140

Arg Ser Lys Met Asn Pro Leu Trp Asn Thr Met Val Ile Gly Gly Tyr
145                 150                 155                 160

Ala Asp Gly Glu Ser Phe Leu Gly Tyr Val Asp Met Leu Gly Val Ala
                165                 170                 175

Tyr Glu Ala Pro Ser Leu Ala Thr Gly Tyr Gly Ala Tyr Leu Ala Gln
            180                 185                 190

Pro Leu Leu Arg Glu Val Leu Glu Lys Gln Pro Val Leu Ser Gln Thr
        195                 200                 205

Glu Ala Arg Glu Leu Val Glu Arg Cys Met Arg Val Leu Tyr Tyr Arg
    210                 215                 220

Asp Ala Arg Ser Tyr Asn Arg Phe Gln Ile Ala Thr Val Thr Glu Lys
225                 230                 235                 240

Gly Val Glu Ile Glu Gly Pro Leu Ser Ala Gln Thr Asn Trp Asp Ile
                245                 250                 255

Ala His Met Ile Ser Gly Phe Glu
            260

<210> SEQ ID NO 226
<211> LENGTH: 55
<212> TYPE: PRT
<213> ORGANISM: Enterococcus hirae

<400> SEQUENCE: 226

Met Val Asp Met Gly Glu Ser Thr Asn Met Ser Ala Glu Thr Ala Ala
1               5                   10                  15

Thr Ser Leu Ala Arg Phe Ala Asn Ile Thr Gln Met Ser Gln Lys Asp
            20                  25                  30

Phe Asp Lys Leu Gly Ser Val Ile Val Asp Leu Gly Asn Asn Phe Ala
        35                  40                  45

Thr Thr Glu Ser Glu Ile Thr
    50                  55

<210> SEQ ID NO 227
<211> LENGTH: 52
<212> TYPE: PRT
<213> ORGANISM: Enterococcus hirae
```

-continued

<400> SEQUENCE: 227

Ala Asn Val Ala Gly Val Thr Ser Glu Gln Phe Gln Lys Leu Phe Lys
1               5                   10                  15

Ser Asp Pro Ser Glu Ala Ile Ile Lys Phe Ile Gln Gly Leu Lys Asp
            20                  25                  30

Ser Glu Lys His Gly Thr Ser Ala Ile Lys Val Leu Asp Asp Met Asp
        35                  40                  45

Ile Lys Glu Val
    50

<210> SEQ ID NO 228
<211> LENGTH: 55
<212> TYPE: PRT
<213> ORGANISM: Enterococcus hirae

<400> SEQUENCE: 228

Met Ile Asp Leu Gly Glu Ser Thr Asn Met Ser Ala Glu Thr Ala Ala
1               5                   10                  15

Thr Ser Phe Ala Arg Phe Ala Asn Ile Thr Gln Met Ser Gln Lys Asp
            20                  25                  30

Phe Asp Lys Leu Gly Ser Val Val Asp Leu Gly Asn Asn Leu Ala
        35                  40                  45

Thr Thr Glu Ser Glu Ile Thr
    50              55

<210> SEQ ID NO 229
<211> LENGTH: 52
<212> TYPE: PRT
<213> ORGANISM: Enterococcus hirae

<400> SEQUENCE: 229

Ala Asp Val Thr Gly Arg Thr Ser Asp Glu Phe Ala Glu Leu Phe Lys
1               5                   10                  15

Ser Asn Pro Ser Gln Ala Ile Ile Glu Phe Ile Lys Gly Leu Gly Asn
            20                  25                  30

Ala Glu Lys His Gly Thr Ser Ala Ile Lys Val Leu Asn Asp Met Glu
        35                  40                  45

Ile Lys Glu Val
    50

<210> SEQ ID NO 230
<211> LENGTH: 55
<212> TYPE: PRT
<213> ORGANISM: Enterococcus hirae

<400> SEQUENCE: 230

Leu Leu Gln Tyr Ala Glu Ile Asn Asp Thr Asp Val Ser Gln Ser Ala
1               5                   10                  15

Ile Phe Ala Arg Gln Ala Ile Glu Ala Tyr Asn Met Ser Tyr Asp Asp
            20                  25                  30

Leu Asn Ser Val Leu Asp Val Thr Thr Lys Thr Ala Gln Asn Thr Gly
        35                  40                  45

Gln Ser Asn Asp Asp Leu Met
    50              55

<210> SEQ ID NO 231
<211> LENGTH: 48
<212> TYPE: PRT

-continued

```
<213> ORGANISM: Enterococcus hirae

<400> SEQUENCE: 231

Ile Leu Gly Phe Gly Gly Ser Thr Asp Gln Val Asn Glu Ala Val Ile
1               5                   10                  15

Gln Leu Ser Gln Ser Phe Ser Asn Gly Lys Val Asp Ala Gln Thr Trp
            20                  25                  30

Asn Ser Met Ile Asn Ala Gln Leu Gly Pro Thr Leu Ser Ala Ile Ala
        35                  40                  45
```